(12) United States Patent
Blanco-Pillado et al.

(10) Patent No.: US 7,608,629 B2
(45) Date of Patent: Oct. 27, 2009

(54) (PIPERIDINYLOXY)PHENYL, (PIPERIDINYLOXY)PYRIDINYL, (PIPERIDINYLSULFANYL)PHENYL AND (PIPERIDINYLSULFANYL)PYRIDINYL COMPOUNDS AS 5-HT$_{1F}$ AGONISTS

(75) Inventors: Maria-Jesus Blanco-Pillado, Indianapolis, IN (US); Dana Rae Benesh, Westfield, IN (US); Sandra Ann Filla, Brownsburg, IN (US); Kevin John Hudziak, Indianapolis, IN (US); Brian Michael Mathes, Indianapolis, IN (US); Daniel Timothy Kohlman, Camby, IN (US); Bai-Ping Ying, Fishers, IN (US); Deyi Zhang, Carmel, IN (US); Yao-Chang Xu, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 290 days.

(21) Appl. No.: 10/552,131

(22) PCT Filed: Apr. 14, 2004

(86) PCT No.: PCT/US2004/009283

§ 371 (c)(1),
(2), (4) Date: Oct. 11, 2005

(87) PCT Pub. No.: WO2004/094380

PCT Pub. Date: Nov. 4, 2004

(65) Prior Publication Data

US 2006/0211734 A1    Sep. 21, 2006

Related U.S. Application Data

(60) Provisional application No. 60/464,396, filed on Apr. 18, 2003.

(51) Int. Cl.
*A61K 31/4545* (2006.01)
*C07D 401/14* (2006.01)

(52) U.S. Cl. .................. 514/318; 514/326; 546/189; 546/193; 546/208; 546/209; 546/210

(58) Field of Classification Search ................ 514/318; 546/189, 193, 208, 209, 210
See application file for complete search history.

(56) References Cited

U.S. PATENT DOCUMENTS

| 4,110,459 | A | 8/1978 | Helsley et al. |
|---|---|---|---|
| 5,118,689 | A | 6/1992 | Oinuma et al. |
| 5,254,689 | A | 10/1993 | Butera et al. |
| 5,286,866 | A | 2/1994 | Carr et al. |
| 5,521,196 | A | 5/1996 | Audia et al. |
| 5,521,197 | A | 5/1996 | Audia |
| 5,708,008 | A | 1/1998 | Audia et al. |
| 5,708,187 | A | 1/1998 | Flaugh et al. |
| 5,721,252 | A | 2/1998 | Audia et al. |
| 5,814,653 | A | 9/1998 | Flaugh et al. |
| 5,942,536 | A | 8/1999 | Fritz et al. |
| 5,962,474 | A | 10/1999 | Audia et al. |
| 5,965,562 | A | 10/1999 | Ofner et al. |
| 6,001,849 | A | 12/1999 | Elliott et al. |
| 6,133,290 | A | 10/2000 | Krushinski et al. |
| 6,358,972 | B1 | 3/2002 | Filla et al. |
| 6,878,714 | B2 * | 4/2005 | Askew et al. ............... 514/256 |
| 7,105,682 | B2 * | 9/2006 | Chen et al. ............... 546/277.1 |

FOREIGN PATENT DOCUMENTS

| AU | 705851 | 4/1996 |
|---|---|---|
| AU | A-33174/95 | 4/1996 |
| EP | 0 733 628 A | 9/1996 |
| EP | 0 832 650 A2 | 4/1998 |
| EP | 0 832 650 A3 | 4/1998 |
| WO | WO 95 00131 A | 1/1995 |
| WO | WO 96 29075 | 9/1996 |
| WO | WO-97/08144 | 3/1997 |
| WO | WO 97 13512 | 4/1997 |
| WO | WO 97/08144 | 6/1997 |
| WO | WO 98 08502 | 3/1998 |
| WO | WO 98 15545 | 4/1998 |
| WO | WO 98 20875 | 5/1998 |
| WO | WO 98 46570 | 10/1998 |
| WO | WO 98 55115 | 12/1998 |
| WO | WO 99 25348 | 5/1999 |
| WO | WO 00 00490 | 1/2000 |
| WO | WO 00 34266 | 6/2000 |
| WO | WO 00 47559 | 8/2000 |
| WO | WO 00 50426 | 8/2000 |
| WO | WO 00/00487 | 10/2000 |
| WO | WO 03/084949 | 10/2003 |
| WO | WO 2004/094380 | 4/2004 |

OTHER PUBLICATIONS

Phebus et al. "Characterization of LY344864 . . . " CA 128:18603 (1997).*

(Continued)

*Primary Examiner*—Celia Chang
(74) *Attorney, Agent, or Firm*—R. Craig Tucker

(57) ABSTRACT

The present invention relates to compounds of formula 1: and pharmaceutically acceptable acid addition sails thereof. The compounds of the present invention are useful for activating 5-HT$_{1F}$ receptors, inhibiting neuronal protein extravasation, and for the treatment or preverition of migraine in mammals, particularly humans.

(I)

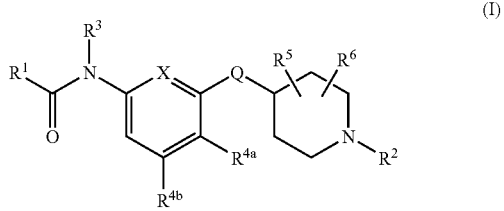

8 Claims, No Drawings

OTHER PUBLICATIONS

Pruecher et al. "Preparation of 3-aryl . . . " CA 122:265361 (1995).*
Gaster et al. "Preparation of arylacetamide . . . " CA 130:13850 (1998).*
Cohen et al. "5-hydroxytryptamine1F . . . " CA 131:266942 (1999).*
Chen et al. "Preparation fo substituted2-(1H-indazol . . . "CA 137:216945 (2002).*
Eriksson et al. "Preparation of 5-substituted imidazolidine . . . " CA 137:247696 (2002).*
Askew et al. "Preparation of 2-aminopyridine . . . " CA 140:16647 (2003).*
King "Bioisosteres, conformational . . . " Med. Chem. Principle and Practice. p. 206-208 (1994).*
Wainscott et al. "Human 5-HT1F receptor stimulated . . . " European J. Pharm. 352 p. 117-124 (1998).*
Blanco et al. "Preparation of N-piperidinyloxy . . . " CA 141:395422 (2004); and sample structure delineation.*
Blanco et al. "Novel stubstituted N-3-1-methyl-piperidinyl . . . " CASPLUS AN 2004:226622 (2004).*
Migraine National headache foundation (2009) (one page from internet).*
MayoClinic "migraine" (2009) (twelve pages from internet).*
Widipedia "headache" (2009) (six pages from internet).*

Parsons et al. "the neuronal verss vascular hypothesis of migraine . . . " Curr. Opin. Pharm. v.3, p. 73-77 (2003).*
Adham N et al: "Cloning of Another Human Serotonin Receptor (5-HT1F): A Fifth 5-HT1Receptor Subtype Coupled to the Inhibition of Adenylate Cyclase" Proceedings of the National Academy of Sciences of USA, *US. National Academy of Science*. Washington, vol. 9, No. 2, 408-412, (1993).
Johnson K, "5-$HT_{1F}$ receptor agonists inhibit neurogenic dural inflammation in guinea pigs" *NeuroReport* 8, 2237-2240 (1997).
Streitwiser, et al, "Introduction to Organic Chemistry" MacMillian Publishing Co. Inc., 586-587 (1976).
Graham, et al, "Mechanism of Migraine Headache and Action of Ergotamine Tartrate" *Archives of Neurol. Psychiatry*, 39:737-63, (1938).
Humphrey, et al., "Serotonin and Migraine" *Ann. NY Acad. Sci.*, 600:587-600, (1900).
Moskowitz, M, "Interpreting vessel diameter changes in vascular headaches" Cephalalgia, 12:5-7, (1992).
Moskowitz, A. "Neurogenic inflammation in the pathophysiology and treatment of migraine" *Neurology*, 43 (suppl. 3) :S16-S20 (1993).
Johnson, K, et al. "A fluorescence-based method for assessing dural protein extravasation induced by trigeminal ganglion stimulation". *Neurosciences Methods* 81, 19-24 (1998).

* cited by examiner

(PIPERIDINYLOXY)PHENYL, (PIPERIDINYLOXY)PYRIDINYL, (PIPERIDINYLSULFANYL)PHENYL AND (PIPERIDINYLSULFANYL)PYRIDINYL COMPOUNDS AS 5-HT$_{1F}$ AGONISTS

This U.S. national stage application of International Application PCT/US2004/009283, filed Apr. 14, 2004, claims priority to U.S. provisional application Ser. No. 60/464,396, filed Apr. 18, 2003.

BACKGROUND OF THE INVENTION

Until recently, theories regarding the pathophysiology of migraine have been dominated since 1938 by the work of Graham and Wolff. *Arch. Neurol. Psychiatry,* 39:737-63, 1938. They proposed that the cause of migraine headache was vasodilatation of extracranial vessels. This view was supported by knowledge that ergot alkaloids and sumatriptan, a hydrophilic 5-HT$_1$ agonist which does not cross the blood-brain barrier, induce contraction of cephalic vascular smooth muscle and are effective in the treatment of migraine. Humphrey, et al., *Ann. NY Acad. Sci.,* 600:587-600, 1990. Recent work by Moskowitz has shown, however, that the occurrence of migraine headaches is independent of changes in vessel diameter. *Cephalalgia,* 12:5-7, 1992.

Moskowitz has proposed that currently unknown triggers for pain stimulate trigeminal ganglia that innervate vasculature within the cephalic tissue, giving rise to release of vasoactive neuropeptides from axons on the vasculature. These released neuropeptides then activate a series of events, a consequence of which is pain. This neurogenic inflammation is blocked by sumatriptan and ergot alkaloids by mechanisms involving 5-HT receptors, believed to be closely related to the 5-HT$_{1D}$ subtype, located on the trigeminovascular fibers. *Neurology,* 43(suppl. 3):S16-S20 1993. Sumatriptan, in fact, has high affinity for the 5-HT$_{1B}$ and 5-HT$_{1D}$ receptors, $K_i$=10.3 nM and 5.1 nM, respectively, which activity may be indicative of vasoconstrictive activity. Sumatriptan and similar compounds previously advanced for the treatment of migraine had tended to be selected on the basis of this vasoconstrictive activity under the premises of the prior art models for migraine.

Serotonin (5-HT) exhibits diverse physiological activity mediated by at least seven receptor classes, the most heterogeneous of which appears to be 5-HT$_1$. A human gene which expresses one of these 5-HT$_1$ receptor subtypes, named 5-HT$_{1F}$, was isolated by Kao and coworkers. *Proc. Natl. Acad. Sci. USA,* 90:408-412, 1993. This 5-HT$_{1F}$ receptor exhibits a pharmacological profile distinct from any serotonergic receptor yet described. It was found that sumatriptan, in addition to the above mentioned strong affinities for the 5-HT$_{1B}$ and 5-HT$_{1D}$ receptors, also has affinity for the 5-HT$_{1F}$ receptor subtype, with a $K_i$ of about 23 nM. This suggests a possible role for the 5-HT$_{1F}$ receptor in migraine.

Various 5-HT$_{1F}$ receptor agonists have subsequently been developed which have shown relative selectivity for the 5-HT$_{1F}$ receptor subclass and it has been shown that such selectivity generally reduces the vasoconstrictive activity characteristic of other compounds advanced as potential agents for the treatment of migraine and associated disorders.

Included among these 5-HT$_{1F}$ receptor agonists are compounds disclosed in the following:

U.S. Pat. Nos. 5,708,187 and 5,814,653, describing a family of 6-substituted-3-amino(alkyl)-tetrahydrocarbazoles and 7-substituted-4-amino(alkyl)cyclohepta[7,6b]indoles;

U.S. Pat. No. 5,521,196, U.S. Pat. No. 5,721,252, U.S. Pat. No. 5,521,197, and WO 96/29075, describing 15, various families of 5-substituted piperidin-3-yl-indoles and 5-substituted 1,2,3,6 tetrahydropyridin-3-yl-indoles;

WO 97/13512 describing a family of 5-substituted 3-aminoethylindoles;

WO 98/46570 describing a family of 5-substituted indoles, pyrrolo[3,2-b]pyridines, benzofurans, and benzothiophenes, having the 3-position substituted with octahydroindolizinyl, octahydro-2H-quinolizinyl, decahydropyrido[1,2-a]azepinyl, 1,2,3,5,8,8a-hexahydroindolizinyl, 1,3,4,6,9,9a-hexahydro-2H-quinolizinyl, or 1,4,6,7,8,9,10,10a-octahydropyrido[1,2-a]azepinyl;

WO 98/20875 and WO 99/25348 describing two families of 5-substituted piperidin-3-yl-azaindoles and 5-substituted 1,2,3,6-tetrahydropyridin-3-yl-azaindoles;

WO 00/00487 describing a family of 5-substituted (piperidin-3-yl or 1,2,3,6-tetrahydropyridin-3-yl)indoles, azaindoles, benzofurans, and benzothiophenes;

WO 98/08502 describing a family of 8-substituted-1,2,3,4-tetrahydro-2-dibenzofuranamines and 9-substituted-2-aminocyclohepta[b]benzofurans;

WO 98/55115 describing a family of 3-amino-1,2,3,4-tetrahydro-9H-carbazole-6-carboxamides and 4-amino-10H-cyclohepta[7,6-b]indole-7-carboxamides;

WO 98/15545 describing a select family of 3,5-disubstituted indoles and benzofurans;

WO 00/00490 describing a family of 5-allyl-substituted (piperidin-3-yl or 1,2,3,6-tetrahydropyridin-3-yl)indoles, azaindoles, benzofurans, and benzothiophenes;

WO 00/47559 describing a family of 4-(3-substituted-benzoyl)piperidines;

WO 00/50426 describing a family of 3,5-disubstituted azabenzofurans; and

WO 00/34266 describing a family of 3-heteroaryl-5-[2-(aryl or heteroaryl)-2-oxoethyl]indoles.

Continued research has now surprisingly yielded a new and unexpected class of novel selective 5-HT$_{1F}$ agonists having distinct chemical and receptor binding properties, which inhibit peptide extravasation, while avoiding significant vasoconstrictive activity, and are therefore useful for the treatment of migraine and other 5-HT$_{1F}$ receptor associated disorders.

SUMMARY OF THE INVENTION

The present invention relates to N-[3-(4-piperidinyloxy) phenyl]amide, N-[3-(4-piperidinyloxy)pyridinyl]amide, N-[3-(4-piperidinylthio)phenyl]amide and 3-N-[3-(4-piperidinylthio)pyridinyl]amide compounds of the general formula I:

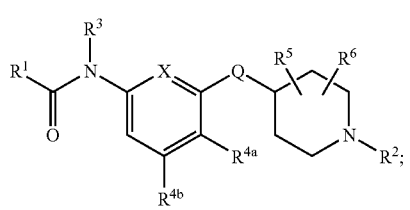

and pharmaceutically acceptable acid addition salts thereof, where:

Q is oxygen or sulfur;

X is —C(R$^{4c}$)= or —N=;

$R^1$ is $C_1$-$C_6$ alkyl, substituted $C_1$-$C_6$ alkyl, $C_3$-$C_7$ cycloalkyl, substituted $C_3$-$C_7$ cycloalkyl, $C_3$-$C_7$ cycloalkyl-$C_1$-$C_3$ alkyl, substituted $C_3$-$C_7$ cycloalkyl-$C_1$-$C_3$ alkyl, phenyl, substituted phenyl, heterocycle, or substituted heterocycle;

$R^2$ is hydrogen, $C_1$-$C_3$ alkyl optionally substituted with one to three fluoro, $C_3$-$C_6$ cycloalkyl-$C_1$-$C_3$ alkyl, or a group of formula II

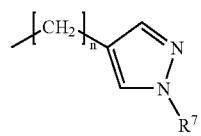

$R^3$ is hydrogen or $C_1$-$C_3$ alkyl;

$R^{4a}$ and $R^{4b}$ are independently hydrogen, halo, or $C_1$-$C_4$ alkyl optionally substituted with one to three fluoro substituents;

When X is —C($R^{4c}$)═, $R^{4c}$ is hydrogen, halo, or $C_1$-$C_4$ alkyl optionally substituted with one to three fluoro substituents;

$R^5$ is hydrogen or $C_1$-$C_3$ alkyl optionally substituted with one to three fluoro substituents;

$R^6$ is hydrogen or $C_1$-$C_3$ alkyl optionally substituted with one to three fluoro substituents, provided that $R^6$ may be $C_1$-$C_3$ alkyl only when $R^5$ is other than hydrogen;

$R^7$ is hydrogen or $C_1$-$C_6$ alkyl optionally substituted with one to three halo substituents; and n is an integer from 1 to 6 inclusively.

The present invention also relates to pharmaceutical compositions comprising a compound of formula I, or a pharmaceutically acceptable acid addition salt thereof, and a pharmaceutically acceptable carrier, diluent, or excipient. In another embodiment, the present invention relates to pharmaceutical compositions adapted for the activation of 5-HT$_{1F}$ receptors, for the inhibition of neuronal protein extravasation, and/or for the treatment or prevention of migraine in mammals, particularly humans, containing a compound of formula I, or a pharmaceutically acceptable acid addition salt thereof, and a pharmaceutically acceptable carrier, diluent, or excipient.

In addition, the present invention relates to a method for activating 5-HT$_{1F}$ receptors in mammals, particularly humans, comprising administering to a mammal in need of such activation an effective amount of a compound of formula I, or a pharmaceutically acceptable acid addition salt thereof.

Moreover, the present invention relates to a method for inhibiting neuronal protein extravasation in mammals, particularly humans, comprising administering to a mammal in need of such inhibition an effective amount of a compound of formula I, or a pharmaceutically acceptable acid addition salt thereof.

Additionally, the present invention relates to a method for treating or preventing migraine in mammals, particularly humans, comprising administering to a mammal in need of such treatment or prevention, an effective amount of a compound of formula I, or a pharmaceutically acceptable acid addition salt thereof.

Another aspect of the present invention relates to the use of a compound of formula I as a medicament, and in particular a medicament adapted for the activation of 5-HT$_{1F}$ receptors, for the inhibition of neuronal protein extravasation, and/or for the treatment or prevention of migraine in mammals, particularly humans. That is to say, the present invention relates to the use of a compound of formula I for the activation of 5-HT$_{1F}$ receptors, for the inhibition of neuronal protein extravasation, and/or for the treatment or prevention of migraine in mammals, particularly in humans.

Additionally, the present invention relates to the use of one or more compounds of formula I in the manufacture of a medicament for the activation of 5-HT$_{1F}$ receptors, for the inhibition of neuronal protein extravasation, and/or for the treatment or prevention of migraine in mammals, particularly in humans.

Furthermore, the present invention provides for methods for the treatment and/or prevention of 5-HT$_{1F}$-mediated disorders comprising administering to a mammal in need of such treatment or prevention, particularly a human, an effective amount of a compound of formula I, or a pharmaceutically acceptable acid addition salt thereof. In preferred embodiments, the 5-HT$_{1F}$-mediated disorder is neuronal protein extravasation and/or migraine.

DETAILED DESCRIPTION OF THE INVENTION

One embodiment of the present invention is a method for increasing activation of 5-HT$_{1F}$ receptors, while avoiding vasoconstrictive activity, for treating a variety of disorders that have been linked to decreased neurotransmission of serotonin in mammals. In preferred embodiments, the mammal to be treated by the administration of compounds of this invention is human. Included among these disorders are migraine, general pain, trigeminal neuralgia, dental pain or temperomandibular joint dysfunction pain, anxiety, general anxiety disorder, panic disorder, depression, disorders of sleep, chronic fatigue syndrome, premenstrual syndrome or late luteal phase syndrome, post-traumatic syndrome, memory loss, dementia including dementia of aging, social phobia, autism, attention deficit hyperactivity disorder, disruptive behavior disorders, impulse control disorders, borderline personality disorder, obsessive compulsive disorder, premature ejaculation, erectile dysfunction, bulimia, anorexia nervosa, alcoholism, tobacco abuse, mutism, and trichotillomania. The compounds of this invention are also useful as a prophylactic treatment for migraine. Any of these methods employ a compound of formula I.

In those instances where the disorders which can be treated by serotonin agonists are known by established and accepted classifications, their classifications can be found in various sources. For example, at present, the fourth edition of the Diagnostic and Statistical Manual of Mental Disorders (DSM-IV™) (1994, American Psychiatric Association, Washington, D.C.), provides a diagnostic tool for identifying many of the disorders described herein. Also, the International Classification of Diseases, Tenth Revision (ICD-10), provides classifications for many of the disorders described herein. The skilled artisan will recognize that there are alternative nomenclatures, nosologies, and classification systems for disorders described herein, including those as described in the DSM-IV and ICD-10, and that terminology and classification systems evolve with medical scientific progress.

The use of a compound of formula I for the activation of the 5-HT$_{1F}$ receptor, for the inhibition of neuronal peptide extravasation, in general or due to stimulation of the trigeminal ganglia specifically, and/or for the treatment of any of the disorders described above, are all embodiments of the present invention.

Likewise, the use of a compound of formula I, or a combination of more than one compound of formula I, in the manufacture of a medicament for the activation of the 5-HT$_{1F}$ receptor, for the inhibition of neuronal peptide extravasation, in general or due to stimulation of the trigeminal ganglia specifically, and/or for the treatment of any of the disorders described above, are also all embodiments of the present invention.

The general chemical terms used throughout have their usual meanings. For example, the term alkyl refers to a branched or unbranched saturated hydrocarbon group. The term "n-alkyl" refers to an unbranched alkyl group. By way of illustration, but without limitation, the term "$C_1$-$C_2$ alkyl" refers to methyl and ethyl. The term "$C_1$-$C_3$ n-alkyl" refers to methyl, ethyl, and propyl. The term "$C_1$-$C_3$ alkyl" refers to methyl, ethyl, propyl, and isopropyl. The term "$C_1$-$C_4$ n-alkyl" refers to methyl, ethyl, n-propyl, and n-butyl. The term "$C_1$-$C_4$ alkyl" refers to methyl, ethyl, propyl, isopropyl, n-butyl, isobutyl, sec-butyl, and tert-butyl. The term "$C_1$-$C_6$ alkyl" refers to all branched and unbranched alkyl groups having from one to six carbon atoms. The term "$C_3$-$C_6$ alkyl" refers to all branched and unbranched alkyl groups having from three to six carbon atoms. The term "$C_3$-$C_6$ cycloalkyl" refers to cyclopropyl, cyclobutyl, cyclopentyl, and cyclohexyl. The term "$C_3$-$C_7$ cycloalkyl" also includes cycloheptyl. Cycloalkylalkyl refers to a cycloalkyl moiety linked through an alkyl linker chain, as for example, but without limitation, cyclopropylmethyl, cyclopropylethyl, cyclopropylpropyl, cyclobutylmethyl, cyclobutylethyl, cyclobutylpropyl, cyclopentylmethyl, cyclopentylethyl, cyclopentylpropyl, cyclohexylmethyl, cyclohexylethyl, and cyclohexylpropyl, all of which may be referred to as $C_3$-$C_6$ cycloalkyl $C_1$-$C_3$ alkyl. $C_3$-$C_7$ cycloalkyl $C_1$-$C_3$ alkyl would also include cycloheptylmethyl, cycloheptylethyl, and cycloheptylpropyl. Each alkyl, cycloalkyl, and cycloalkylalkyl group may be optionally substituted as provided for herein.

The terms "alkoxy", "phenyloxy", "benzoxy" and "pyrimidinyloxy" refer to an alkyl group, phenyl group, benzyl group, or pyrimidinyl group, respectively, each optionally substituted as provided for herein, that is bonded through an oxygen atom.

The terms "alkylthio", "phenylthio", and "benzylthio" refer to an alkyl group, phenyl group, or benzyl group, respectively, each optionally substituted as provided for herein, that is bonded through a sulfur atom.

The term "$C_1$-$C_4$ acyl" refers to a formyl group or a $C_1$-$C_3$ alkyl group bonded through a carbonyl moiety. The term "$C_1$-$C_4$ alkoxycarbonyl" refers to a $C_1$-$C_4$ alkoxy group bonded through a carbonyl moiety.

The term "halo" refers to fluoro, chloro, bromo, or iodo. Preferred halo groups are fluoro, chloro, and bromo. More preferred halo groups are fluoro and chloro.

The term "heterocycle" is taken to mean a saturated or unsaturated 5- or 6-membered ring containing from 1 to 3 heteroatoms selected from nitrogen, oxygen and sulfur, said ring optionally being benzofused. Exemplary heterocycles, for the purposes of the present invention, include furanyl, thiophenyl, pyrrolyl, pyrrolidinyl, pyridinyl, N-methylpyrrolyl, oxazolyl, isoxazolyl, pyrazolyl, imidazolyl, triazolyl, oxadiazolyl, thiadiazolyl, thiazolyl, thiazolidinyl, N-acetylthiazolidinyl, pyrimidinyl, pyrazinyl, pyridazinyl, and the like. Benzofused heterocyclic rings include isoquinolinyl, benzoxazolyl, benzodioxolyl, benzothiazolyl, quinolinyl, benzofuranyl, benzothiophenyl, indolyl, and the like, all of which may be optionally substituted which also includes optionally substituted on the benzo ring when the heterocycle is benzofused.

In one embodiment, preferred heterocycles include pyridinyl, indolyl, furanyl, benzofuranyl, thiophenyl, benzodioxolyl, and thiazolidinyl, all of which may be optionally substituted.

In yet another embodiment, preferred heterocycles include pyridinyl and thiophenyl.

Substituted alkyl, cycloalkyl, cycloalkylalkyl, alkoxy, or alkylthio, means an alkyl, cycloalkyl, cycloalkylalkyl, alkoxy, or alkylthio group, respectively, substituted one or more times independently with a substituent selected from the group consisting of halo, hydroxy, and $C_1$-$C_3$ alkoxy. By way of illustration, but without limitation, examples include trifluoromethyl, pentafluoroethyl, 5-fluoro-2-bromopentyl, 3-hydroxypropyloxy, 4-hydroxycyclohexyloxy, 2-bromoethylthio, 3-ethoxypropyloxy, 3-ethoxy-4-chlorocyclohexyl, and the like. Preferred substitutions include substitution 1-5 times with halo, each independently selected, or substituted 1-3 times with halo and 1-2 times independently with a group selected from hydroxy and $C_1$-$C_3$ alkoxy, or substituted 1-3 times independently with a group selected from hydroxy and $C_1$-$C_3$ alkoxy, provided that no more than one hydroxy and/or alkoxy substituent may be attached through the same carbon.

The terms "substituted phenyl" and "substituted heterocycle" are taken to mean that the cyclic moiety in either case is substituted with one or more halo substituents, preferably one to five, each independently selected; or substituted with one or more substituents, preferably one to two substituents, independently selected from the group consisting of halo, $C_1$-$C_4$ alkyl, $C_1$-$C_4$ alkoxy, $C_1$-$C_4$ alkylthio, cyano, and nitro, wherein each alkyl, alkoxy and alkylthio substituent can be further substituted independently with $C_1$-$C_2$ alkoxy or with one to five halo groups selected from fluoro and chloro; or substituted with one substituent selected from the group consisting of phenyloxy, benzyloxy, phenylthio, benzylthio, and pyrimidinyloxy, wherein the phenyloxy, benzyloxy, phenylthio, benzylthio, and pyrimidinyloxy moiety can be further substituted with one to two substituents selected from the group consisting of halo, $C_1$-$C_2$ alkyl, and $C_1$-$C_2$ alkoxy; or substituted with one substituent selected from the group consisting of $C_1$-$C_4$ acyl and $C_1$-$C_4$ alkoxycarbonyl, and further substituted with zero to one substituent selected from the group consisting of halo, $C_1$-$C_4$ alkyl, $C_1$-$C_4$ alkoxy, and $C_1$-$C_4$ alkylthio. When a substituent is halo, preferred halo groups are fluoro, chloro, and bromo.

In another embodiment, preferred substitutions for "substituted phenyl" and "substituted heterocycle" include substitution with one or more halo substituents, preferably one to five, each independently selected; or substituted with one or more substituents, preferably one to two substituents, independently selected from the group consisting of halo, $C_1$-$C_4$ alkyl, $C_1$-$C_4$ alkoxy, cyano, and nitro, wherein each alkyl and alkoxy substituent can be further substituted independently with one to five halo groups selected from fluoro and chloro.

The terms "gem-", "geminal", or "geminate" refer to two identical substituents bonded to a common carbon atom, as for example, but without limitation, gem-methyl, meaning two methyl groups bound to a common, carbon atom, as for instance in a 2,2-dimethylpiperinyl group or a 3,3-dimethylpiperinyl group. Abbreviations used herein are defined as follows:

BINAP means 2,2'-bis(diphenylphosphino)-1,1'binaphthyl.

Collidine means trimethylpyridine.

DMF means N,N-dimethylformamide.

DMSO means dimethylsulfoxide.

FMOC means a 9-fluorenylmethoxycarbonyl moiety.

HATU means O-(7-Azabenzotriazol-1-yl)-N,N,N',N'-tetramethyluronium hexafluorophosphate.

MTBE means methyl t-butyl ether.

NMP means N-methyl-2-pyrrolidinone

Pd$_2$(dba)$_3$ means tris(dibenzylidineacetone)-dipalladium (0).

SCX column or cartridge, as used herein, refers to a Varian Bond Elute® silica based strong cation exchange resin column or disposable cartridge.

t-Boc means a tert-butoxycarbonyl moiety.

THF means tetrahydrofuran.

The term "amino protecting group" as used in this specification refers to a substituent commonly employed to block or protect the amino functionality while reacting other functional groups on the compound. Examples of such amino-protecting groups include the formyl group, the trityl group, the phthalimido group, the acetyl group, the trichloroacetyl group, the chloroacetyl, bromoacetyl, and iodoacetyl groups, urethane-type blocking groups such as benzyloxycarbonyl, 9-fluorenylmethoxycarbonyl ("FMOC"), t-butoxycarbonyl (t-BOC), and the like; and like amino protecting groups. The species of amino protecting group employed is not critical so long as the derivatized amino group is stable to the conditions of subsequent reactions on other positions of the molecule and can be removed at the appropriate point without disrupting the remainder of the molecule. The selection and use (addition and subsequent removal) of amino protecting groups is well within the ordinary skill of the art. Further examples of groups referred to by the above terms are described by T. W. Greene and P. G. M. Wuts, "Protective Groups in Organic Synthesis", 3$^{rd}$ edition, John Wiley and Sons, New York, N.Y., 1999, chapter 7, hereafter referred to as "Greene".

The term "pharmaceutical" or "pharmaceutically acceptable" when used herein as an adjective, means substantially non-toxic and substantially non-deleterious to the recipient.

By "pharmaceutical composition" it is further meant that the carrier, solvent, excipients and salt must be compatible with the active ingredient of the composition (e.g. a compound of formula I). It is understood by those of ordinary skill in this art that the terms "pharmaceutical formulation" and "pharmaceutical composition" are generally interchangeable, and they are so used for the purposes of this application.

The term "acid addition salt" refers to a salt of a compound prepared by reaction of the compound with a mineral or organic acid. The compounds of the present invention form pharmaceutically acceptable acid addition salts with a wide variety of organic and inorganic acids and include the physiologically acceptable salts which are often used in pharmaceutical chemistry. Such salts are also part of this invention. A "pharmaceutically-acceptable (acid) addition salt" is formed from a pharmaceutically-acceptable acid as is well known in the art. Such salts include the pharmaceutically acceptable salts exemplified in Berge, S. M, Bighley, L. D., and Monkhouse, D. C., *J. Pharm. Sci.*, 66:1, (1977), which are well known to those skilled in the art.

The pharmaceutically acceptable acid addition salts of the invention are typically formed by reacting a compound of formula I with an equimolar or excess amount of acid. Alternatively, some compounds may form hemi-salts by reacting the compound with the desired acid in a 2:1 ratio, compound to acid.

Inorganic acids commonly employed to form such salts include hydrochloric acid, hydrobromic acid, hydroiodic acid, sulfuric acid, phosphoric acid, and the like. Organic acids commonly employed to form such salts include p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, hemisuccinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like.

The term "effective amount" means an amount of a compound of formula I which is capable of activating 5-HT$_{1F}$ receptors and/or inhibiting neuronal protein extravasation. It is understood that compounds of the present invention may exist as stereoisomers. As such, all enantiomers, diastereomers, and mixtures thereof, are included within the scope of the present invention. Where specific stereochemistries are identified in this application, the Cahn-Prelog-Ingold designations of (R)- and (S)- and the cis and trans designation of relative stereochemistry are used to refer to specific isomers and relative stereochemistry. In addition, arbitrary designations of "cis isomer 1", "cis isomer 2", "trans isomer 1", or "trans isomer 2" are used to distinguish resolved stereoisomers of compounds having two chiral centers with known cis or trans configurations, but for which the absolute stereochemistry has not been determined (i.e. it is unknown whether the specific compound is the (R,R) or (S,S) cis isomer, or the (R,S) or (S,R) trans isomer). While all enantiomers, diastereomers, and mixtures thereof, are contemplated within the present invention, preferred embodiments are single enantiomers and single diastereomers.

While all of the compounds of the present invention are useful as 5-HT$_{1F}$ agonists, certain classes are preferred, as for example, compounds having any of the following enumerated selections of substituents: Compounds wherein 1) R$^1$ is phenyl, substituted phenyl, heterocycle, or substituted heterocycle;
2) R$^1$ is substituted phenyl;
3) R$^1$ is mono- or di-substituted phenyl wherein the substituents are independently selected from halo, C$_1$-C$_4$ alkyl, C$_1$-C$_4$ alkoxy, trifluoromethyl, trifluoromethoxy, trifluoroethoxy, phenyloxy, benzyloxy, cyano, and nitro;
4) R$^1$ is mono- or di-substituted phenyl wherein the substituents are independently selected from halo, C$_1$-C$_2$ alkoxy, trifluoromethyl, trifluoromethoxy, and trifluoroethoxy;
5) R$^1$ is mono- or di-substituted phenyl wherein the substituents are independently selected from halo, trifluoromethyl, and trifluoromethoxy;
6) R$^1$ is mono-, di- or tri-halo substituted phenyl;
7) R$^1$ is heterocycle or substituted heterocycle;
8) R$^1$ is heterocycle or substituted heterocycle wherein the heterocycle is selected from the group consisting of furanyl, thiophenyl, pyrrolyl, pyrrolidinyl, pyridinyl, N-methylpyrrolyl, oxazolyl, isoxazolyl, pyrazolyl, imidazolyl, triazolyl, oxadiazolyl, thiadiazolyl, thiazolyl, thiazolidinyl, N-acetylthiazolidinyl, pyrimidinyl, pyrazinyl, pyridazinyl, isoquinolinyl, benzoxazolyl, benzodioxolyl, benzothiazolyl, quinolinyl, benzofuranyl, benzothiophenyl, indolyl;
9) R$^1$ is a substituted or unsubstituted heterocycle wherein the heterocycle is selected from the group consisting of pyridinyl, indolyl, benzofuranyl, furanyl, thiophenyl, benzodioxolyl, and thiazolidinyl;

10) $R^1$ is a substituted or unsubstituted heterocycle wherein the heterocycle is selected from the group consisting of pyridinyl and thiophenyl;
11) $R^1$ is mono-, di-, or tri-halo-substituted heterocycle, each halo group being independently selected;
12) $R^1$ is mono- or di-substituted heterocycle, wherein one of the substituents is selected from the group consisting of $C_1$-$C_2$ alkoxy, phenoxy, and phenylthio;
13) $R^1$ is mono-substituted heterocycle, wherein the substituents is halo or nitro;
14) $R^1$ is mono-halo substituted heterocycle;
15) $R^1$ is unsubstituted heterocycle;
16) $R^2$ is hydrogen or $C_1$-$C_3$ alkyl;
17) $R^2$ is hydrogen or methyl;
18) $R^2$ is pyrazolylalkyl or N-substituted pyrazolylalkyl;
19) $R^2$ is pyrazol-4-yl-ethyl;
20) $R^2$ is 1-($C_1$-$C_3$ alkyl)pyrazol-4-yl-ethyl;
21) $R^3$ is hydrogen;
22) $R^3$ is methyl;
23) $R^3$ is ethyl;
24) $R^{4a}$, $R^{4b}$, and $R^{4c}$ if present, are each hydrogen;
25) One of $R^{4a}$, $R^{4b}$, or $R^{4c}$ if present, is halo;
26) One of $R^{4a}$, $R^{4b}$, or $R^{4c}$ if present, is fluoro or chloro;
27) One of $R^{4a}$, $R^{4b}$, or $R^{4c}$ if present, is $C_1$-$C_3$ alkyl;
28) $R^5$ is hydrogen;
29) $R^5$ is $C_1$-$C_3$ alkyl;
30) $R^5$ is methyl;
31) $R^6$ is hydrogen;
32) $R^6$ is methyl;
33) $R^6$ is gem relative to $R^5$;
34) $R^6$ is gem-methyl relative to $R^5$;
35) $R^5$ is methyl and $R^6$ are gem-methyl relative to $R^5$;
36) $R^3$ is hydrogen or methyl, $R^{4a}$, $R^{4b}$, and $R^{4c}$ if present, are hydrogen or halogen, $R^5$ is hydrogen or methyl, and $R^6$ is hydrogen or gem-methyl with to $R^5$;
37) $R^3$ is hydrogen or methyl, $R^{4a}$, $R^{4b}$, and $R^{4c}$ if present, are each hydrogen, $R^5$ is hydrogen or methyl, and $R^6$ is hydrogen;
38) $R^2$ is hydrogen or $C_1$-$C_3$ alkyl, $R^3$ is hydrogen or methyl, $R^{4a}$, $R^{4b}$, and $R^{4c}$ if present, are each hydrogen or halogen, $R^5$ is hydrogen or methyl, and $R^6$ is hydrogen or gem-methyl with to $R^5$;
39) $R^2$ is hydrogen or $C_1$-$C_3$ alkyl, $R^3$ is hydrogen or methyl, $R^{4a}$, $R^{4b}$, and $R^{4c}$ if present, are each hydrogen, $R^5$ is hydrogen or methyl, and $R^6$ is hydrogen;
40) $R^2$ is hydrogen or methyl, and $R^3$, $R^{4a}$, $R^{4b}$, $R^{4c}$ if present, and $R^5$ are each hydrogen;
41) $R^2$ is hydrogen or methyl, and $R^3$ is methyl, and $R^{4a}$, $R^{4b}$, $R^{4c}$ if present, and $R^5$ are each hydrogen
42) $R^1$ is mono-, di-, or tri-substituted phenyl wherein the substituents are independently selected from halo, $C_1$-$C_2$ alkoxy, trifluoromethyl, trifluoromethoxy, and trifluoroethoxy, $R^2$ is hydrogen or methyl, and $R^3$, $R^{4a}$, $R^{4b}$, $R^{4c}$ if present, and $R^5$ are each hydrogen;
43) $R^1$ is a substituted or unsubstituted heterocycle selected from the group consisting of pyridinyl, indolyl, benzofuranyl, furanyl, thiophenyl, benzodioxolyl, and thiazolidinyl, $R^2$ is hydrogen or methyl, and $R^3$, $R^{4a}$, $R^{4b}$, $R^{4c}$ if present, and $R^5$ are each hydrogen;
44) $R^1$ is mono-, di-, or tri-substituted phenyl wherein the substituents are independently selected from halo, $R^2$ is hydrogen or methyl, and $R^3$, $R^{4a}$, $R^{4b}$, $R^{4c}$ if present, and $R^5$ are each hydrogen;
45) the compound is an acid addition salt;

It will be understood that the above classes may be combined to form additional preferred classes, as for example the combination of preferred selections for two or more substituents. Illustrative examples of combinations of preferred classes forming additional preferred classes are:

46) the combination of any one of preferred classes 10) through 15) with preferred class 8);
47) the combination of any one of preferred classes 10) through 15) with preferred class 9);
48) the combination of any one of preferred classes 1) through 15), 46), or 47) with preferred class 16);
49) the combination of any one of preferred classes 1) through 15), 46), or 47) with preferred class 17);
50) the combination of any one of preferred classes 1) through 15), 46), or 47) with preferred class 21);
51) the combination of any one of preferred classes 1) through 15), 46), or 47) with preferred class 22);
52) the combination of any one of preferred classes 1) through 15), 46), or 47) with preferred class 24);
53) the combination of any one of preferred classes 1) through 15), 46), or 47) with preferred class 26);
54) the combination of any one of preferred classes 1) through 15), 46), or 47) with preferred class 27);
55) the combination of any one of preferred classes 1) through 15), 46), or 47) with preferred class 28);
56) the combination of any one of preferred classes 1) through 15), 46), or 47) with preferred class 30) and 31);
57) the combination of any one of preferred classes 1) through 15), 46), or 47) with preferred class 30) and 32);
58) the combination of any one of preferred classes 1) through 15), 46), or 47) with preferred class 30) and 34);
59) the combination of preferred classes 48) with preferred class 21);
60) the combination of preferred classes 48) with preferred class 22);
61) the combination of preferred classes 49) with preferred class 21);
62) the combination of preferred classes 49) with preferred class 22);
63) the combination of any one of preferred classes 59) through 62) with preferred class 24) and 28);
64) the combination of any one of preferred classes 59) through 62) with preferred class 26) and 28);
65) the combination of any one of preferred classes 59) through 62) with preferred class 27) and 28);
66) the combination of any one of preferred classes 59) through 62) with preferred class 24), 30), and 31);
67) the combination of any one of preferred classes 59) through 62) with preferred class 26), 30), and 31);
68) the combination of any one of preferred classes 59) through 62) with preferred class 27), 30), and 31);
69) the combination of any one of preferred classes 59) through 62) with preferred class 24), 30), and 32);
70) the combination of any one of preferred classes 59) through 62) with preferred class 26), 30), and 32);
71) the combination of any one of preferred classes 59) through 62) with preferred class 27), 30), and 32);
72) the combination of any one of preferred classes 59) through 62) with preferred class 24), 30), and 34);
71) the combination of any one of preferred classes 59) through 62) with preferred class 26), 30), and 34);
72) the combination of any one of preferred classes 59) through 62) with preferred class 27), 30), and 34).

In addition to those compounds presented in the examples, the following compounds further illustrate the scope of the present invention:
1) N-[3-(1-methyl-piperidin-4-yloxy)-phenyl]-2-furancarboxamide;
2) N-[3-(1-methyl-piperidin-4-yloxy)-pyridinyl]-2-furancarboxamide;

3) N-[3-(1-methyl-piperidin-4-yloxy)-pyridinyl]-3-furancarboxamide;
4) N-[3-(piperidin-4-yloxy)-phenyl]-3-chloro-2-furancarboxamide;
5) N-[3-(1-methyl-piperidin-4-yloxy)-phenyl]-2-pyrrolecarboxamide;
6) N-[3-(1-ethyl-piperidin-4-yloxy)-pyridinyl]-2-pyrrolecarboxamide;
7) N-[3-(1-methyl-piperidin-4-yloxy)-phenyl]-4-fluoro-2-pyrrolecarboxamide;
8) N-[3-(piperidin-4-yloxy)-phenyl]-3-pyrrolecarboxamide;
9) 2,4,6-Trifluoro-N-[4-methyl-3-(1-methyl-piperidin-4-yloxy)-phenyl]-benzamide
10) N-[3-(1-Ethyl-piperidin-4-yloxy)-4-methyl-phenyl]-2,4,6-trifluoro-benzamide
11) 2-Chloro-4-fluoro-N-methyl-N-[6-(1-methyl-piperidin-4-yloxy)-pyridin-2-yl]-benzamide
12) 2-Chloro-6-fluoro-N-methyl-N-[6-(1-methyl-piperidin-4-yloxy)-pyridin-2-yl]-benzamide
13) 2-Chloro-N-[6-(1-ethyl-piperidin-4-yloxy)-pyridin-2-yl]-4-fluoro-N-methyl-benzamide
14) 2-Chloro-N-[6-(1-ethyl-piperidin-4-yloxy)-pyridin-2-yl]-4-fluoro-benzamide
15) 2-Chloro-N-[6-(1-ethyl-piperidin-4-yloxy)-pyridin-2-yl]-6-fluoro-benzamide
16) 2-Chloro-4-fluoro-N-[6-(1-propyl-piperidin-4-yloxy)-pyridin-2-yl]-benzamide
17) N-[6-(1-Cyclopropylmethyl-piperidin-4-yloxy)-pyridin-2-yl]-2,4,6-trifluoro-benzamide
18) N-[6-(1-Cyclopropylmethyl-piperidin-4-yloxy)-pyridin-2-yl]-2,6-difluoro-benzamide
19) 2,4,6-Trifluoro-N-[3-(1,2,3-trimethyl-piperidin-4-yloxy)-phenyl]-benzamide
20) 2,4,6-Trifluoro-N-[6-(1,2,3-trimethyl-piperidin-4-yloxy)-pyridin-2-yl]-benzamide
21) 2,4,6-Trifluoro-N-[3-(1,2,3-trimethyl-piperidin-4-ylsulfanyl)-phenyl]-benzamide
22) 2,4,6-Trifluoro-N-[6-(1,2,3-trimethyl-piperidin-4-ylsulfanyl)-pyridin-2-yl]-benzamide
23) 2-Chloro-4-fluoro-N-[2-fluoro-3-(1-methyl-piperidin-4-ylsulfanyl)-phenyl]-benzamide
24) 2-Chloro-4-fluoro-N-[2-fluoro-3-(1-methyl-piperidin-4-yloxy)-phenyl]-benzamide
25) 2-Chloro-4-fluoro-N-[3-(1-methyl-piperidin-4-yloxy)-2-trifluoromethyl-phenyl]-benzamide
26) 2-Chloro-4-fluoro-N-[3-(1-methyl-piperidin-4-ylsulfanyl)-2-trifluoromethyl-phenyl]-benzamide
27) 2-Chloro-N-[3-(1,4-dimethyl-piperidin-4-yloxy)-phenyl]-4-fluoro-benzamide
28) 2-Chloro-N-[6-(1,4-dimethyl-piperidin-4-yloxy)-pyridin-2-yl]-4-fluoro-benzamide
29) 2,4,6-Trifluoro-N-[3-(1,2,3-trimethyl-piperidin-4-ylsulfanyl)-phenyl]-benzamide
30) N-[3-(1,2-Dimethyl-piperidin-4-ylsulfanyl)-phenyl]-2,4,6-trifluoro-benzamide
31) N-[3-(1,3-Dimethyl-piperidin-4-ylsulfanyl)-phenyl]-2,4,6-trifluoro-benzamide
32) 2-Chloro-N-[2,5-difluoro-3-(1-methyl-piperidin-4-yloxy)-phenyl]-benzamide
33) 2-Chloro-N-[2,5-difluoro-3-(1-methyl-piperidin-4-ylsulfanyl)-phenyl]-benzamide
34) 2-Chloro-N-[3-(1,4-dimethyl-piperidin-4-ylsulfanyl)-phenyl]-benzamide
35) 2-Chloro-N-[3-(2-ethyl-1-methyl-piperidin-4-yloxy)-phenyl]-benzamide
36) N-[6-(1,3-Dimethyl-piperidin-4-ylsulfanyl)-pyridin-2-yl]-2,4,6-trifluoro-benzamide
37) N-[6-(1,3-Dimethyl-piperidin-4-ylsulfanyl)-pyridin-2-yl]-4-fluoro-benzamide
38) N-[6-(1,2-Dimethyl-piperidin-4-ylsulfanyl)-pyridin-2-yl]-2,4,6-trifluoro-benzamide
39) 2-Chloro-N-[6-(1,2-dimethyl-piperidin-4-ylsulfanyl)-pyridin-2-yl]-6-fluoro-benzamide
40) 2-Chloro-6-fluoro-N-[3-(2-methyl-piperidin-4-ylsulfanyl)-phenyl]-benzamide
41) 2,4,6-Trifluoro-N-[6-(2-methyl-piperidin-4-ylsulfanyl)-pyridin-2-yl]-benzamide
42) N-[6-(2,3-Dimethyl-piperidin-4-ylsulfanyl)-pyridin-2-yl]-2,4,6-trifluoro-benzamide The compounds of the present invention may be synthesized through a condensation of the desired 1,3-dihalobenzene or 2,6-dihalopyridine with the appropriate N-protected or N-substituted 4-hydroxypiperidine or piperidine-4-thiol, followed by amine substitution of the remaining phenyl or pyridinyl halogen and amide formation with an appropriate $R^1$-acylchloride (see Schemes 1-4). Suitable reaction conditions for the steps of these schemes are well known in the art and appropriate substitutions of solvents and co-reagents are within the skill of the art. Likewise, it will be appreciated by those skilled in the art that synthetic intermediates may by isolated and/or purified by various well known techniques as needed or desired, and that frequently, it will be possible to use various intermediates directly in subsequent synthetic steps with little or no purification. All substituents, unless otherwise indicated, are as previously defined, and all reagents are well known and appreciated in the art. (Piperidinyloxy)phenyl compounds of the present invention can be synthesized according to Scheme 1:

Scheme 1:

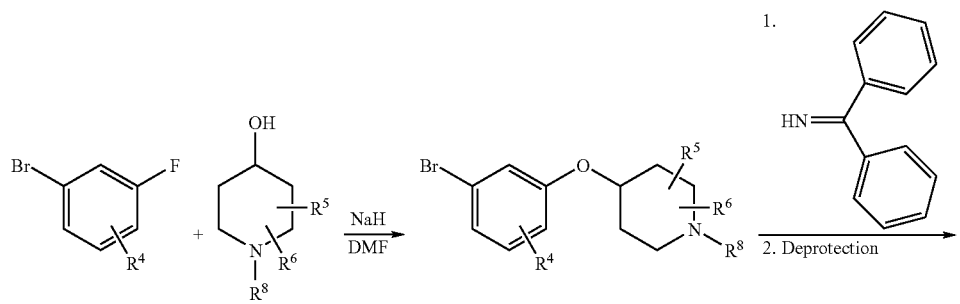

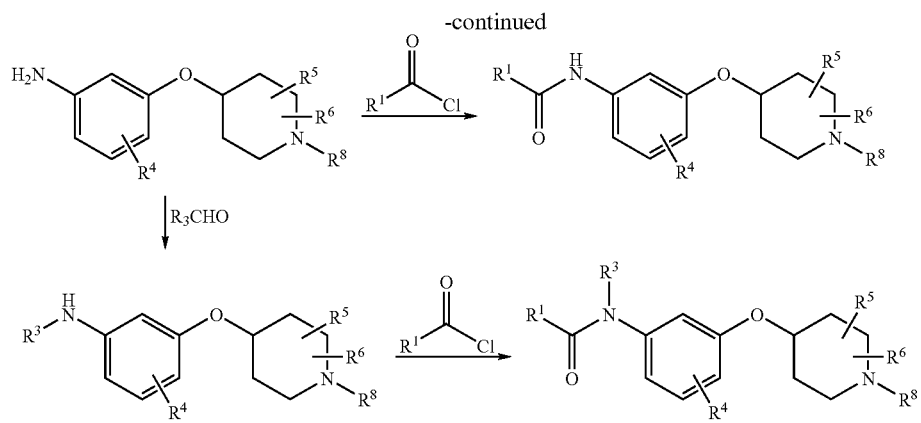

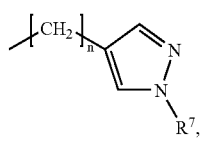

where $R^{1-7}$ are as defined above; and $R^8$ is $C_1$-$C_3$ alkyl optionally substituted with one to three fluoro, $C_3$-$C_6$ cycloalkyl-$C_1$-$C_3$ alkyl, or a group of formula II $$\text{II}$$

or an amino protecting group.

Typically the appropriate N-substituted or N-protected piperidin-4-ol in a suitable solvent, such as DMF, DMSO, NMP, and the like, is added to a suspension of sodium hydride, and heated, as for example, between about ambient temperature to about 100° C., preferably at about 50° C., typically for about 30-90 minutes, say about 45 minutes. 1-bromo-3-fluorobenzene is then added and allowed to react for several hours to overnight at about ambient to 100° C., preferably at about 65° C. The reaction is quenched, as for example by the addition of water or other suitable means. The 3-bromophenoxy-4-piperidine intermediate may be worked up by common procedures, as for example, solvent removal, extraction procedures, and/or further purification by chromatography, etc.

Next, the bromophenoxypiperidine intermediate is aminated at the benzo 3-position, as for example, by reacting the intermediate with (±)BINAP, $Pd_2(dba)_3$, benzhydrylideneamine, and sodium tertbutoxide in a suitable solvent, such as toluene or the like, under an inert atmosphere for about 1 to about 3 hrs., say about 2 hours, at about 50° C. to 100° C., say about 80° C. The resulting 3-(piperidin-4-yloxy)-phenylamine intermediate may then be isolated and purified by common procedures such as, but not limited to, solvent removal, extraction, and/or chromatography, etc.

Compounds wherein $R^3$ is hydrogen can then be synthesized by condensation with the desired $R^1$-acylchloride. Typically, an appropriate 3-(piperidin-4-yloxy)-phenylamine intermediate is reacted with an appropriate $R^1$-acylchloride, in an appropriate solvent, such as dioxane, pyridine, DMF, or the like, at between about ambient temperature and about 100° C., preferably between about 50° C. and about 100° C., until the reaction is complete, as for example, between about 1 hr. and about 4 hrs., say about 2 hrs. The reaction is then quenched by addition of an acid and the final product purified by normal work-up procedures.

Alternatively, the $R^1$ moiety may be added by amide bond formation by reacting the 3-(piperidin-4-yloxy)-phenylamine intermediate with the appropriate $R^1$-carboxylic acid. Typically, the desired amine intermediate is reacted with the appropriate $R^1$-carboxylic acid, with HATU and collidine, in an appropriate solvent, such as dioxane, pyridine, DMF, or the like, at between about ambient temperature and about 100° C., preferably at about room temperature, until the reaction is complete, as for example, between about 1 and about 4 hrs., preferably about 2 hrs. The reaction is then quenched by addition of an acid, as for example, acetic acid in methanol, and the final product purified by normal work-up procedures.

(Piperidinylsulfanyl)phenyl compounds of the present invention may be synthesized in the analogous manner to the methods for synthesizing (piperidinyloxy)phenyl compounds described above by substituting the appropriate piperidinethiol intermediate for the piperidinol intermediate.

(Piperidinyloxy)pyridine compounds of the present invention may be prepared via Scheme 2, utilizing either 2,6-dichloropyridine or 2,6-dibromopyridine.

Scheme 2:

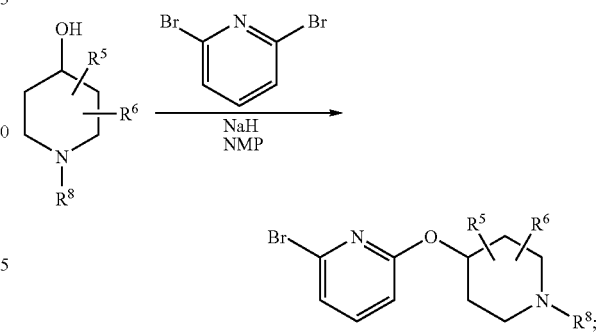

where the substituents are as defined above.

The appropriate isomer/racemate of the piperidinol intermediate is reacted with NaH in a suitable solvent, as for example, NMP or the like, at from about ambient temperature to about 100° C. for about 2-3 hours, or until the release of hydrogen gas is no longer observable. 2,6-Dibromopyridine is added and the mixture reacted at about ambient temperature to about 100° C. for about 1-5 hr. The reaction mixture is then cooled to about ambient temperature and quenched with saturated aqueous NaCl aq. The product can be worked up with well known procedures, such as solvent removal, extraction, silica gel purification, chromatography, etc.

The 2-bromo-6-(piperidin-4-yloxy)pyridine can be aminated by various known methods, including reaction with an excess of 7 M $NH_3$, with an appropriate catalyst, such as copper (I) oxide, or the like, in a suitable solvent, such as ethyleneglycol, NMP, and the like, preferably under pressure, as for example in an autoclave. The 2-amino-6-(piperidin-4-yloxy)pyridine intermediate may then be isolated and purified by known methods, as for example, solvent removal, extraction, and/or chromatography, etc.

These two initial steps can alternatively be run substituting 2,6-dichloropyridine for 2,6-dibromopyridine.

The final condensation step with an appropriate $R^1$ acylchloride or $R^1$ carboxylic acid is as for the 3-aminophenoxypiperidine analogs described above.

(Piperidinylsulfanyl)pyridinyl compounds of the present invention can be made by the analogous procedures, utilizing the corresponding piperidinethiol intermediate in place of the piperidinol intermediate.

(Piperidinylsulfanyl)phenyl compounds of the present invention may also be synthesized according to Scheme 3:

If, in any of the above syntheses, the piperidinyl nitrogen is protected by an amino protecting group, this group is removed after the condensation reaction with the $R^1$-acylchloride or $R^1$-carboxylic acid. The piperidinyl nitrogen can then remain as a secondary amine for compounds of the present invention wherein $R^2$ is hydrogen, or it may be further alkylated by known procedures to provide compounds of the present invention wherein $R^2$ is $C_1$-$C_3$ alkyl, $C_3$-$C_6$ cycloalkyl-$C_1$-$C_3$ alkyl, or a group of formula II

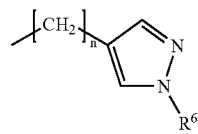

II

A typical alkylation reaction would react the secondary amine with an appropriate aldehyde, glacial acetic acid or trifluoroacetic acid, and sodium cyanoborohydride, in an appropriate solvent, such as methanol, wherein an appropriate aldehyde is one which will react with the secondary amine to provide the desired $R^2$ substituent, as by way of illustration, Scheme 3:

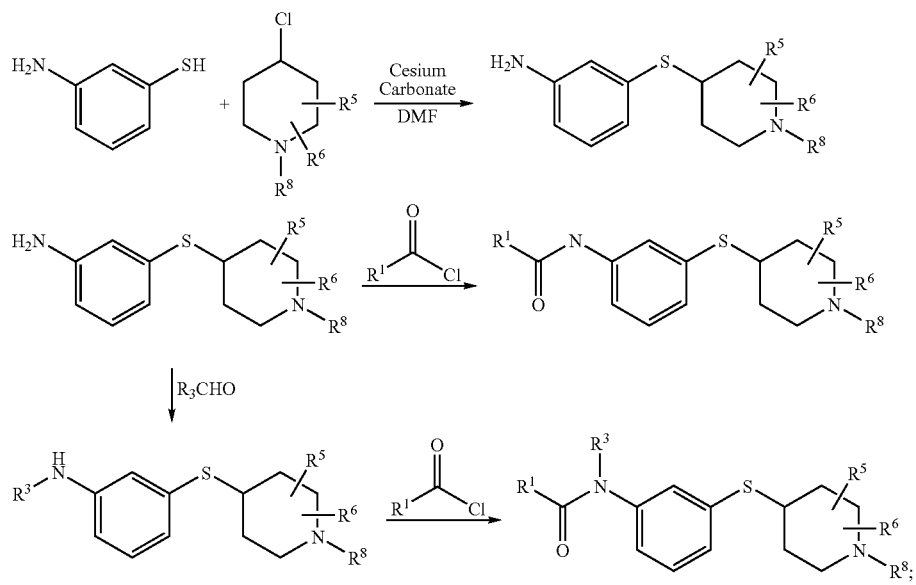

where the substituents are as defined above.

Typically, 3-amino-benzenethiol is reacted with an appropriate N-substituted or N-protected-4-chloropiperidine intermediate and cesium carbonate in a suitable solvent, such as DMF, DMSO, or the like, at between about ambient to about 100° C., say about 80° C., for several hours, as for example, about 12 to about 24 hrs., say about 18 hrs. The 3-(piperidin-4-ylsulfanyl)phenylamine intermediate may then be isolated and purified by well known procedures such as filtration, extraction, solvent removal, chromatography, etc.

The 3-(piperidin-4-ylsulfanyl)phenylamine intermediate may then be used in a condensation reaction with an appropriate $R^1$-acylchloride or $R^1$-carboxylic acid as with the corresponding 3-(piperidin-4-yloxy)phenylamine intermediates described above.

N-methylpyrazol-4-ylethanal for compounds having N-methylpyrazol-4-ylethyl as the $R^2$ substituent.

(Piperidinyloxy)phenyl compounds of the present invention wherein $R^3$ is $C_1$-$C_3$ alkyl can be synthesized by reacting the 3-(piperidin-4-yloxy/thio)phenylamine or 3-(piperidin-4-yloxy/thio)pyridinylamine intermediate with the appropriate aldehyde or ketone, (i.e. formaldehyde, acetaldehyde, propanal, or propan-2-one, for compounds wherein $R^3$ is methyl, ethyl, propyl, or isopropyl, respectively, in an appropriate solvent, as for example, methanol, for about 2 to about 4 hrs., say 3 hrs. Sodium borohydride is then added and the mixture reacted for several hours to overnight. The reaction is then quenched with acid and the resulting N-alkyl-3-(piperidin-4-yloxy/thio)phenylamine or N-alkyl-3-(piperidin-4-yloxy/ thio)pyridinylamine intermediate may be isolated and purified by common methods, as for example, solvent removal, filtration, extraction, chromatography, etc.

The N-alkyl-3-(piperidin-4-yloxy/thio)phenylamine or N-alkyl-3-(piperidin-4-yloxy/thio)pyridinylamine intermediate is then used in a condensation reaction with an appropriate $R^1$-acylchloride, as described above, to provide the product compound.

This amine intermediate is then used in a condensation reaction with an appropriate $R^1$-acylchloride, as described above, to provide the product compound.

Compounds of the present invention wherein $R^5$ and $R^6$ are other than hydrogen can be synthesized by the above schemes utilizing the corresponding substituted piperidinyl starting reagents, which can be synthesized according to Scheme 4 as follows:

Scheme 4:

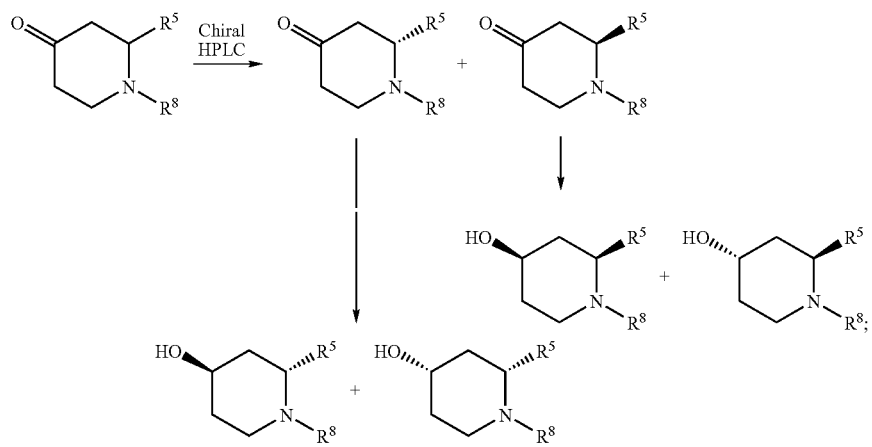

(Piperidinyloxy)pyridinyl compounds where $R^3$ is other than hydrogen can be made by running the amination step as described above, with the 3-bromo-(piperidin-4-yloxy)pyridinyl intermediate and an excess of the appropriate alkyl amine, rather than ammonia (e.g. methylamine, ethylamine, propylamine, or isopropylamine to produce compounds having an $R^3$ substituent of methyl, ethyl, n-propyl, and isopropyl respectively). The 2-alkylamino-6-(piperidin-4-yloxy)pyridine intermediate may then be used in the final condensation step with an appropriate $R^1$ acylchloride as described above.

Compounds wherein $R^{4a}$, $R^{4b}$, and/or $R^{4c}$ if present, is other than hydrogen can be synthesized utilizing the corresponding $R^{4a}$, $R^{4b}$, and/or $R^{4c}$-substituted 1-bromo-3-fluorobenzene or 2,6-dibromo/chloropyridine in the initial condensation reaction with the 4-piperidinol intermediate as described above.

Alternatively, compounds wherein $R^{4a}$, $R^{4b}$, or $R^{4c}$ if present, is other than hydrogen can also be synthesized utilizing the corresponding $R^{4a}$, $R^{4b}$, or $R^{4c}$ substituted 1-fluoro-3-nitrobenzene or 2-fluoro-6-nitropyridine in the respective initial condensation reactions with the 4-piperidinol intermediate. The resulting $R^4$-substituted-1-(piperidin-4yloxy/thio)-3-nitrobenzene or $R^4$-substituted-1-(piperidin-4yloxy/thio)-6-nitropyridine intermediate is then reduced to the desired $R^4$-substituted-3-(piperidin-4yloxy/thio)-3-phenylamine or $R^4$-substituted-1-(piperidin-4yloxy/thio)-6-nitropyridine intermediate, as for example, by refluxing the nitro intermediate with iron dust and hydrochloric acid in a suitable solvent, such as methanol or the like, for about 24-36 hr. The resulting amine intermediate may then be isolated and purified by common methods, as for example, solvent removal, filtration, extraction, chromatography, etc.

where the substituents are as defined above.

Typically, a racemic N—$R^8$-2-$R^5$-piperidin-4-one may be resolved into its enantiomers by chiral HPLC, as for example on a Chiralcel OD® or Chiralcel OJ® column (Daicel Chemical Industries, Ltd., Osaka Japan), followed by reduction of the ketone to provide the trans and cis diasteriomers of the selected 4-piperidinone enantiomer. The diasteriomers may then be further resolved by well known work-up procedures as desired, and as is well appreciated in the art. The analogous reactions can be run using the N—$R^8$-3-$R^5$ substituted-piperidin-4-one starting reagents to produce N—$R^8$-3-$R^5$-piperidin-4-ol intermediates.

Various methods for reduction of the ketone to a hydroxy group are well known in the art and the ordinarily skilled chemist will appreciate the advantages and limitation of the various methods with regard to selection of $R^2$ or the N-protecting group desired. Typical reduction reactions include treatment with sodium borohydride, $H_2$ with a Pd/C catalyst, or with lithium aluminum hydride, in an appropriate solvent, such as absolute ethanol, tetrahydrofuran, and the like, will reduce the ketone into trans- and cis-hydroxy isomers.

Alternatively, a degree of stereoselectivity may be achieved in the reduction reaction by treatment with chirally selective reducing agents such as lithium tri-tert-butoxyaluminum hydride, lithium tri-sec-butylborohydride (e.g. L-Selectride™, Sigma Chemical Corp.), diisobutylaluminum hydride, and the like. The stereoisomer enriched products can then be further purified by other known methods.

Various methods may be used to resolve stereochemically enriched/pure intermediates including chromatographic separation on chiral separation media and stereoselective crystallization.

Compounds wherein $R^6$ is other than hydrogen can be made from the appropriately substituted piperidin-4-ol intermediate in the analogous manner, as for example reduction of 2,2,($R^2$/N-protected)- or 2,3,($R^2$/N-protected)-trisubstituted-piperidin-4-one to the corresponding racemic 4-hydroxypiperidine intermediates.

The following Preparations and Examples are provided to better elucidate the practice of the present invention and should not be interpreted in any way so as to limit the scope thereof. Note that when the "isomer 1" and "isomer 2" nomenclature is used, the absolute stereochemistry is not known. In those situations, the stereochemistry shown in the structure is to accurately indicate the resolution of one cis or one trans configurations, but not the accurate "R" or "S" absolute stereochemistry of the chiral centers for that resolved isomer; the absolute configurations may be the opposite of that shown. Hence, one resolved isomer is arbitrarily designated "isomer 1", leaving the opposite isomer to be designated "isomer 2". Where the absolute stereochemistry is known, the appropriate R/S nomenclature is used.

Preparation 1.
2-Methyl-4-oxo-piperidine-1-carboxylic acid tert-butyl ester isomers 1 and 2

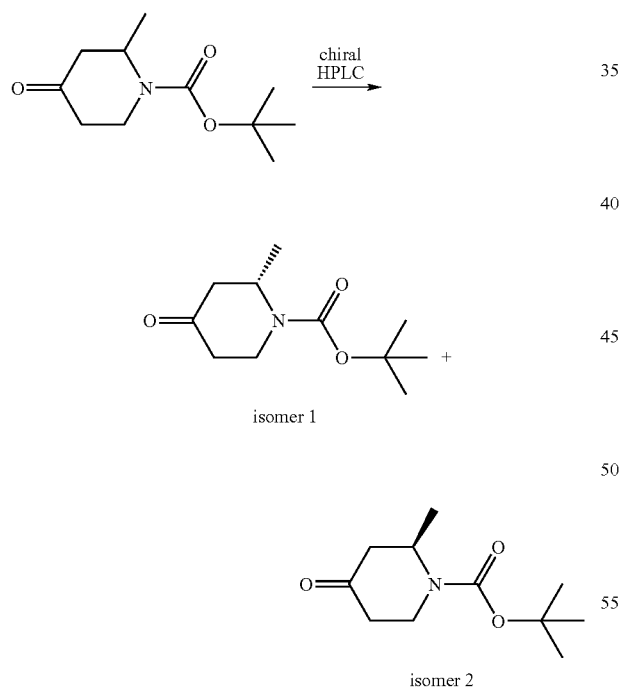

(Absolute stereoconfiguration is depicted arbitrarily.)

Resolve racemic 2-methyl-4-oxo-piperidine-1-carboxylic acid tert-butyl ester (15.0 g) using a chiralpak AD™ (4.6×250 nm) column, eluting with absolute ethanol at a flow rate of 1.0 mL/minute (UV=220 nm) to obtain isomer 1 (5.28 g, 35%) and isomer 2 (5.01 g, 33%). $^1$H NMR (CDCl$_3$): 4.7 (m, 1H), 4.2 (m, 1H), 3.3 (m, 1H), 2.7 (m, 1H), 2.5 (m, 1H), 2.3 (m, 1H), 2.2 (m, 1H), 1.5 (s, 9H), 1.2 (d, 3H); identical for both isomers.

Preparation 2.
4-Hydroxy-2-methyl-piperidine-1-carboxylic acid tert-butyl ester trans isomer 1 and cis isomer 1

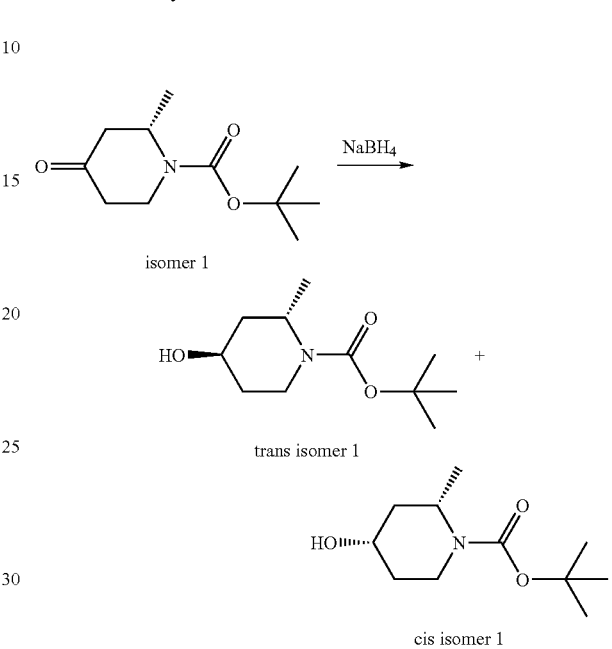

Combine 2-methyl-4-oxo-piperidine-1-carboxylic acid tert-butyl ester isomer 1 (10.0 g, 46.89 mmol), absolute ethanol (200 mL), and sodium borohydride (2.66 g, 70.33 mmol) with stirring. After 2 hr., concentrate the reaction mixture and then partition the residue between water (100 mL) and 1:1 hexane:ethyl acetate (100 mL). Separate the aqueous layer and wash with 1:1 hexane:ethyl acetate (4×100 mL), combine the organic layers, wash with aqueous NaCl solution, dry over sodium sulfate, filter and concentrate. Purify the residue by silica gel flash chromatography eluting with 7:3 hexane:ethyl acetate to obtain the resolved trans isomer 1 (3.03 g, 30%) and cis isomer 1 (5.2 g, 52%). Trans isomer 1: $^1$H NMR (CDCl$_3$): 4.5 (m, 1H), 4.05 (m, 1H), 3.95 (m, 1H), 2.9 (m, 1H), 1.9 (m, 1H), 1.8 (m, 1H), 1.5 (m, 1H), 1.45 (s, 9H), 1.4 (m, 1H), 1.35 (m, 1H), 1.1 (d, 3H). Cis isomer 1: $^1$H NMR (CDCl$_3$): 4.25 (m, 1H), 4.15 (m, 1H), 3.8 (m, 1H), 3.25 (m, 1H), 1.8 (m, 1H), 1.65 (m, 3H), 1.4 (s, 9H), 1.3 (d, 3H).

Preparation 3.
4-Hydroxy-2-methyl-piperidine-1-carboxylic acid tert-butyl ester trans isomer 2 and cis isomer 2

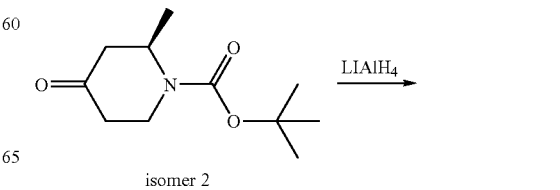

-continued

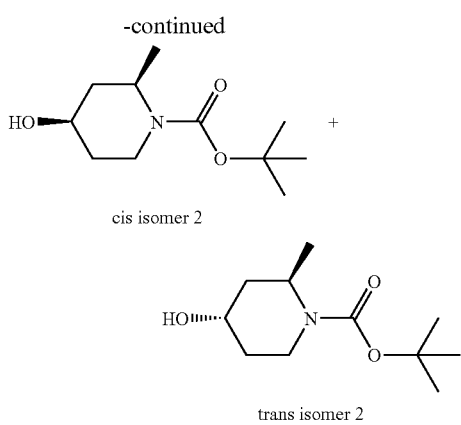

cis isomer 2 trans isomer 2

Combine 2-methyl-4-oxo-piperidine-1-carboxylic acid tert-butyl ester isomer 2 (5.01 g, 23.49 mmol) and ethanol (100 mL). Add Lithium Aluminum Hydride (0.89 g, 23.49 mmol) and stir at ambient temperature. After 2 hr., quench the reaction with saturated potassium sodium tartrate solution (50 mL), extract with ethyl acetate 2×50 mL), wash combined organic layers with aqueous NaCl solution, dry over sodium sulfate, filter and concentrate. Purify the residue by silica gel flash chromatography eluting with 7:3 hexanes:ethyl acetate to obtain trans isomer 2 (1.04 g, 20%) and cis isomer 2 (1.24 g, 25%). Trains isomer 2: $^1$H NMR (CDCl$_3$): 4.5 (m, 1H), 4.05 (m, 1H), 3.95 (m, 1H), 2.9 (m, 1H), 1.9 (m, 1H), 1.8 (m, 1H), 1.5 (m, 1H), 1.45 (s, 9H), 1.4 (m, 1H), 1.35 (m, 1H), 1.1 (d, 3H).

Cis isomer 2: $^1$H NMR (CDCl$_3$): 4.25 (m, 1H), 4.15 (m, 1H), 3.8 (m, 1H), 3.25 (m, 1H), 1.8 (m, 1H), 1.65 (m, 3H), 1.4 (s, 9H), 1.3 (d, 3H).

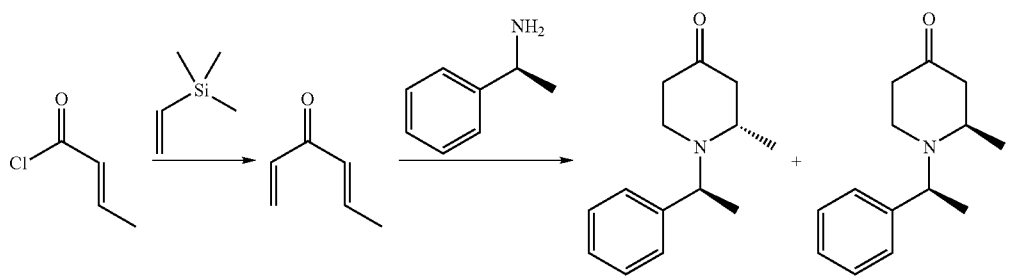

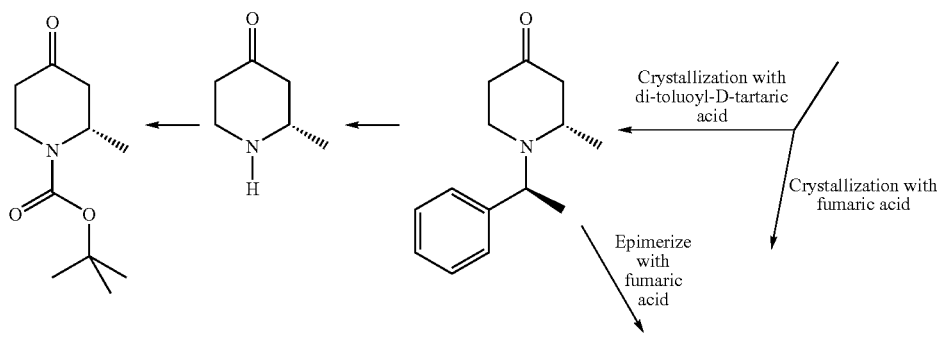

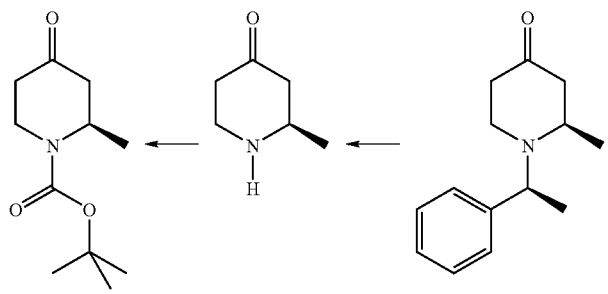

Preparation 4A. N-(1-(S)-phenylethyl)-2-methylpiperidin-4-one diastereomeric mixture Dissolve aluminium chloride (2360 g, 17.7 mole, 1.02 eq.) in cold methylene dichloride (11.1 L) at −35° C. under nitrogen. Add a solution of 2-trans-crotonyl chloride (90% pure, 2000 g, 17.2 mole) in methylene dichloride (4.3 L) maintaining the temperature between −35° C. and −30° C. Stir the reaction mixture for 15 minutes. Add a solution of vinyltrimethylsilane (1780 g, 17.76 mole, 1.03 eq.) in methylene dichloride (4.3 L) over 45 minutes, maintaining the temperature at between −35° C. and −30° C. Stir the reaction mixture for 30 minutes at −30° C. and then cool to below −50° C. to facilitate the hydrolysis step. Add the cold reaction mixture to a cold solution of potassium carbonate (12 Kg) in water (33.3 L) at −12° C. Warm the resulting mixture to room temperature and stir vigorously for 15 minutes. Separate the layers and extract the water layer three times with tert-butyl methyl ether (10 L, 5 L, 11 L). Pool the organic layers and wash with water (8 L). Dry the organic layer over $MgSO_4$ (350 g), filter and concentrate to yield the divinylketone intermediate (1860 g, 112.5%) as a brown residue.

Dissolve S-(−)-α-methylbenzylamine (1870 g, 15.56 mole, 0.91 eq.) in acetonitrile (12 L) and add to a solution of aqueous $NaHCO_3$ (6 L, 1100 g, 13.09 mole, 0.76 eq.). Cool the resulting white suspension to 16° C. Slowly add a solution of the crude divinylketone (1.645 kg, 17.11 moles) in acetonitrile (6 L) over 40 minutes. Stir the reaction mixture for 1 hour at reflux. Evaporate the acetonitrile, add Cyclohexane (26 L) to the resulting residue, and stir for 20 minutes. Separate the layers and wash the organic layer successively with water (3 L), 10% aqueous acetic acid (2.2 L), and water (3 L). Dry the organic layer over $MgSO_4$ (500 g) and filter. Further purify by plug-filtration through silicagel (1000 g), washing with cyclohexane (3 L). Concentrate the cyclohexane filtrate under vacuum, to yield the title intermediate (typical 55:45) (2290 g, 10.53 mole, 61%) as a yellow/red oil.

Preparation 4B. N-(1-(S)-phenylethyl)-2(S)-methylpiperidin-4-one

Dissolve di-p-toluoyl-D-tartaric acid (1176 g, 8.23 mole) in acetone (5 L). Slowly add a solution of N-(1-S-phenylethyl)-2-(R/S)-methylpiperidin-4-one (96%, 1863 g, 8.23 mole) in acetone (5 L), maintaining the temperature between 18° C. and 22° C. Heat the reaction mixture under reflux for 1 hr. Cool the stirred suspension to 20° C. over 2.5 hours. Filter off the solid, wash with acetone (5 L), and dry at 50° C. under vacuum to obtain the title compound as the di-p-toluoyl-D-tartrate salt (3.7 kg, 74.5%, ratio (S,2S)/(S,2R)=95/5).

Combine the filtrates, concentrate to 4.7 kg, and reflux for 1.5 hr. Cool the mixture to 20° C. and stir overnight at 20° C. Filter off the solid, wash with acetone (3 L), and dry at 50° C. under vacuum, to yield additional title compound as the di-p-toluoyl-D-tartrate salt (460 g, 9.3%, ratio (S,2S)/(S,2R)=95/5)(Overall recovery 78.8%).

Suspend the N—(S)-1-phenylethyl-2(S)-methyl-4-piperidinone di-p-toluoyl-D-tartrate (1200 g, 1.99 mole) in a mixture of methyl-tert-butylether (3 L) and water (2.25 L) and cool to 13° C. Add a solution of NaOH (175 g, 4.38 mole, 2.2 eq.) in water (1050 ml) drop-wise to the suspension. Stir the solution 5 min. and then separate the aqueous layer. Wash the organic layer with water (1.5 L) followed by aqueous acetic acid (9%, 250 ml). Dry the organic layer over $MgSO_4$ (120 g), filter and concentrated under vacuum to provide the title compound as the free base (339 g, 77%).

Preparations 4C. N-(1-(S)-phenylethyl)-2(R)-methylpiperidin-4-one

N-(1-(S)-phenylethyl)-2(S)-methylpiperidin-4-one is epimerized to N-(1-(S)-phenylethyl)-2(R)-methylpiperidin-4-one by crystallization directed induced resolution of the diastereomers as follows:

Add a solution of 1-(1-S-phenylethyl)-2(S)-methylpiperidin-4-one (900 g, 4.14 mole) in acetone (1 L) to a suspension of fumaric acid (432 g, 3.72 mole) in acetone (6.2 L) at 22° C. Heat the reaction mixture at 46° C. to gradually transform the mixture to a suspension. Distill off part of the solvent (3.6 L) and stir until the diastereoisomeric ratio (S,2R)/(S,2S) is 66/34 by PMR. The suspension is then stirred for 16 hr. at 20° C. during which time the ratio (S,2R)/(S,2S) increases further to 74/26. Cool the mixture to 5° C. and stir for 2 hr. Filter off the solid, wash with cold acetone (1 L, 5° C.), and dry under vacuum to obtain the title compound (910 g, 66% yield, 91/9 diastereoisomeric ratio, 44/56 diastereoisomeric ratio in the mother liquors).

Preparation 4D. 2-S-methyl-4-piperidinone hydrochloride

Dissolve N—(S)-1-phenylethyl-2-S-methyl-4-piperidinone (280 g, 1.2885 mole) in acetic acid (1400 ml) under nitrogen in a hydrogenation flask. Add Pd/C 10% (14 g), place the reaction mixture on a Parr apparatus, and hydrogenate under $H_2$ (50 psi, 345 kPa) for 3 hr. Filter off the catalyst and wash with acetic acid (100 ml). Concentrate the filtrates under vacuum to yield the title acetate salt as a brown residue (329.5 g, 150%).

Dissolve 2-Methyl-4-piperidinone acetate (329.5 g, estimated 1.2855 mole free base content) in isopropanol (1 L). Add 12N HCl (aqueous solution, 110 ml) and concentrate the resulting mixture under vacuum. Dissolve the residue in a mixture of toluene (2 L) and isopropanol (2 L) and concentrate again to obtain the hydrochloride salt as a very hygroscopic solid (204.5 g, 106%).

Preparation 4E. N-tert-butyloxycarbonyl-2-S-methyl-4-piperidinone

Dissolve 2-Methyl-4-piperidinone hydrochloride (200 g, estimated 1.2855 mole free base content) in water (500 ml). Add the solution to a mixture of methylene dichloride (1 L) and aqueous $NaHCO_3$ (180 g in 1.2 L water) at room temperature. Add a solution of di-tert-butyl dicarbonate (280 g, 1.28 mole) in methylene dichloride (500 ml) and stir the reaction mixture overnight at 20° C. Separate the water layer and extract twice with methylene dichloride (500 ml). Combine the organic layers, wash with water (500 ml), dry over $MgSO_4$ (60 g), filter and concentrate under vacuum (276.5 g as red oil). Dissolve the oil in cyclohexane (1 L) and plug-filter through silicagel (300 g). Elute the silicagel with cyclohexane (2 L) and 50/50 cyclohexane/ethyl acetate (1 L). Concentrate the filtrates under vacuum to obtain the title compound as a yellow residue (261 g, 95).

Alternatively, N-tert-butyloxycarbonyl-2-S-methyl-4-piperidinone is prepared in a one-pot synthesis from N—(S)-1-phenylethyl-2-S-methyl-4-piperidinone as follows: Dissolve N—(S)-1-phenylethyl-2-S-methyl-4-piperidinone (200 g, 0.9208 mole) in THF (200 ml), Add a solution of di-tert-butyl dicarbonate (214.7 g, 0.9838 mole) in THF (200 ml). Place the reaction mixture under a nitrogen flow and add Pd/C (10% content, dry catalyst, 10 g). Pressurize the reactor three times with $N_2$, followed by three times with $H_2$. Heat the reaction mixture to 50° C. and hydrogenate overnight with stirring (3 bar $H_2$, ≅43.5 psi, ≅300 kPa, 300 rpm). Determine the end of the reaction by TLC analysis (silica plate, cyclohexane/ethylacetate 50/50, complete disappearance of the starting product). Cool the reaction mixture to room temperature and purge the reactor by pressurizing three times with $N_2$. Filter off the catalyst using a celite pad and wash with THF (200 ml). Remove the solvent by evaporation (40° C., vacuum) to obtain the crude product as a yellow oil (183.5 gram, 93%).

Dissolve the crude product in n-hexane (200 mL) and stir overnight at 20° C. Filter off the solid, wash with n-hexane (50 mL), and dry under vacuum at 20° C. to obtain the title compound (78 g, 39%). Concentrate the mother liquors under vacuum to 140 g residual. Cool the solution and stir overnight at 20° C. Cool the resulting suspension to 5° C. and stir for 15 minutes. Filter off the solid, wash with n-hexane (20 ml) and dry under vacuum at 20° C. to obtain additional title compound (30.6 g, 15%).

Preparation 5. 1-Benzyl-3-methyl-piperidin-4-ol (all 4 isomers)

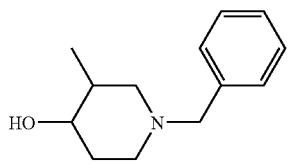

Suspend lithium aluminum hydride (0.76 g, 20.0 mmol) in dry tetrahydrofuran (10 mL) and cool to 0° C. Add, dropwise with stirring, 1-benzyl-3-methyl-piperidin-4-one (4.06 g, 20.0 mmol) in tetrahydrofuran (20 mL). After 1 hr., quench with saturated potassium sodium tartrate solution. After 20 min., extract with ethyl acetate (2×100 mL), wash the combined organic layers with aqueous NaCl solution (100 mL), dry over sodium sulfate, filter, and concentrate to obtain the title compound (4.15 g, >100%). Mass spectrum (electrospray): m/z=206.1 (M+1).

Preparation 6. 1-Benzyl-cis-3-methyl-piperidin-4-ol

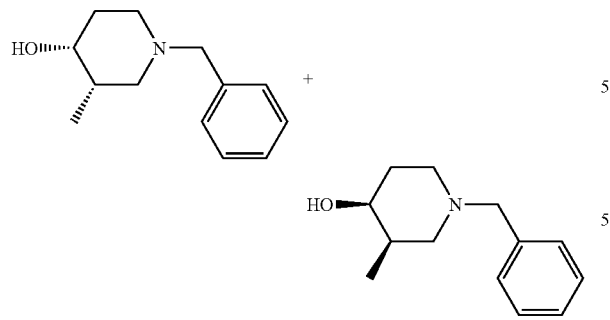

Dissolve 1-benzyl-3-methyl-piperidin-4-one (5.0 g, 24.6 mmol) in dry tetrahydrofuran (100 mL) and cool the resulting solution to 0° C. Add 1 mL-lithium tri-sec-butylborohydride (L-Selectride®) solution in tetrahydrofuran (29.6 mL, 29.6 mmol) dropwise over 30 min. After stirring at 0° C. for 1 hr., quench with water (50 mL), extract with ethyl acetate (2×100 mL), wash the combined organic layers with aqueous NaCl solution (100 mL), separate the organic layer, dry over sodium sulfate, filter and concentrate. Purify the residue by silica gel flash chromatography eluting with 5% (2M $NH_3$/methanol)/methylene dichloride to obtain of the title compound as a mixture of enantiomers (3.84 g, 76%). $^1$H NMR (CDCl$_3$): 7.25 (m, 5H), 3.8 (m, 1H), 3.5 (s, 2H), 2.4 (m, 3H), 2.2 (m, 1H), 1.9 (m, 1H), 1.8 (m, 2H), 0.95 (d, 3H).

Preparation 7. Racemic 1-benzyl-3-trans-methyl-piperidin-4-ol

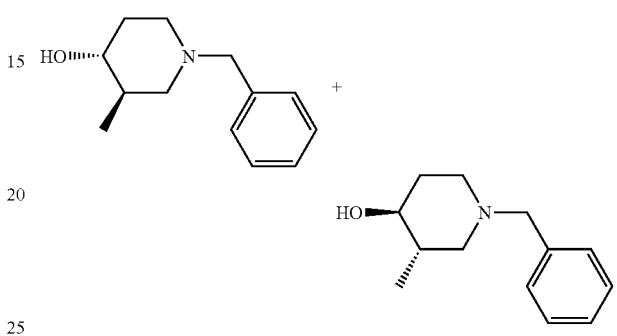

Add phosphoric acid (85%, 8.17 g) to a suspension of 1-benzyl-3-methyl-piperidin-4-one (14.4 g) in water (100 mL) and methanol (43 mL) and cool the mixture to −10° C. Add sodium borohydride (5.36 g) portion wise over 1 hr. and warm the reaction mixture to room temperature overnight. Basify the reaction mixture with 20 mL of 5 N NaOH and partition between ethyl acetate and saturated aqueous NaCl, dry over anhydrous sodium sulfate, evaporate and purify on a silica gel column (110 g, solvent: dichloromethane-2M $NH_3$ in methanol, gradient) to give the title compound as a colorless oil (14.504 g). Mass spectrum (electrospray) m/z=206 (M+1); $^1$H NMR (CDCl$_3$): 7.31 (m, 4H), 7.26 (m, 1H), 3.48 (s, 2H), 3.14 (m, 1H), 2.86 (m, 1H), 2.79 (m, 1H), 2.02 (m, 1H), 1.90 (m, 1H), 1.62 (m, 3H), 0.95 (d, J=6.3 Hz, 3H).

Preparation 8. N—(S)-Phenethyl-2-(R)-Methyl-piperidin-4-(R)-ol

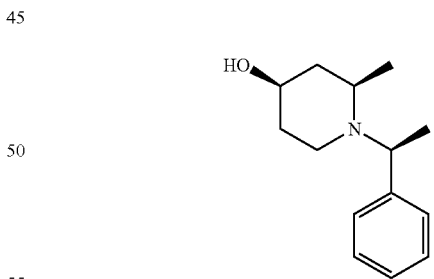

Add LiAlH(t-butoxy)$_3$ (80.73 mL of 1M in THF, 80.73 mmol) to a solution of N—(S)-phenethyl-2-(R)-methyl-piperidin-4-one (14.6 g, 80.73 mmol) in THF (146 mL) at −70° C. Stir for 18 hr. Add saturated aqueous NH$_4$Cl (50 mL) and stir at room temperature for 15 min. Filter the heterogeneous mixture on celite. Add MTBE (100 mL) and saturated NH$_4$Cl (50 mL), extract off the organic layer, and wash the aqueous phase with MTBE (50 mL). Combine the organic fractions, dry over MgSO$_4$, filter and concentrate under reduce pressure to give the title compound (14.6 g, 98% yield, 92% diastereoisomeric excess). $^1$H NMR (CDCl$_3$, 400 MHz): 7.40-7.20

(m, 5H), 4.30 (q, J=7.1 Hz, 1H), 3.50-3.35 (m, 1H), 3.15-3.00 (m, 1H), 2.30-2.15 (m, 1H), 2.00-1.80 (m, 3H), 1.60-1.40 (m, 5H), 1.38-1.20 (m, 4H).

Preparation 9. 1-Benzyl-2,2-dimethyl-piperidin-4-ol

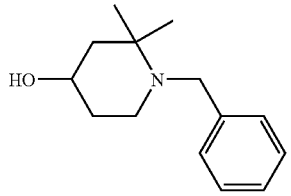

Combine 1-benzyl-2,2-dimethyl-piperidin-4-one (1.0 g, 4.6 mmol) and tetrahydrofuran (20 mL) and cool to 0° C. Add lithium aluminum hydride (0.175 g, 4.6 mmol) with stirring. After 30 min., warm to ambient temperature. After 30 min., quench the reaction mixture with water (50 mL). Extract with ethyl acetate (2×75 mL), combine the organic layers and wash with aqueous NaCl solution (50 mL), dry over sodium sulfate, filter and concentrate to obtain the title compound (1.0 g, 100%). Mass spectrum (electrospray): m/z=220.1 (M+1); $^1$H NMR (CDCl$_3$): 7.3 (m, 5H), 4.0 (m, 1H), 3.8 (m, 1H), 3.0 (m, 1H), 2.6 (m, 1H), 2.3 (m, 1H), 1.8 (m, 2H), 1.4 (m, 3H), 1.25 (s, 3), 1.1 (s, 3H).

Preparation 10. 1-Allyl-2-methyl-piperidin-4-ol

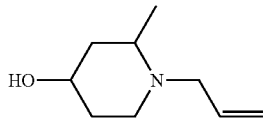

Using the method of example 9, using 1-allyl-2-methyl-piperidin-4-one, prepare the title compound and isolate as the free base (71%). $^1$H NMR (CDCl$_3$): 5.9 (m, 1H), 5.2 (m, 2H), 3.6 (m, 1H), 3.4 (m, 1H), 3.1 (m, 1H), 2.9 (m, 2H), 2.6 (m, 1H), 2.4 (m, 1H), 2.3 (m, 1H), 2.1 (m, 1H), 1.95 (m, 1H), 1.6 (m, 1H), 1.2 (m, 3H).

Preparation 11. 1-Cyclopropylmethyl-piperidin-4-ol

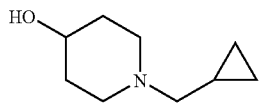

Add bromomethylcyclopropane (2.025 g, 15 mmol) to a solution of 4-hydroxypiperidine (3.035 g, 30 mmol) in THF (10 mL) and stir the mixture overnight. Dilute the mixture with ethylacetate, wash with saturated NaHCO$_3$ solution, dry over Na$_2$SO$_4$, filter and concentrate to give a residue. Chromatography (silica gel, eluting with 8% 2M NH$_3$-methanol in CH$_2$Cl$_2$) provides 1.087 g (47%) of the title compound: mass spectrum (ion spray): m/z=156.2 (M+1); $^1$H NMR (CDCl$_3$, ppm): 3.60 (m, 1H), 2.81 (m, 2H), 2.16 (d, 1H), 2.10 (m, 3H), 1.84 (m, 2H), 1.53 (m, 3H), 0.79 (m, 1H), 0.44 (m, 2H), 0.00 (m, 2H).

Preparation 12.
4-(3-Bromo-phenoxy)-1-methyl-piperidine

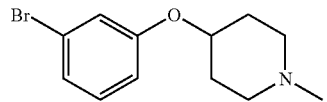

Dissolve 1-methyl-piperidin-4-ol (10.06 g, 87.34 mmol) in DMF (30 mL) and add to a stirred suspension of sodium hydride (5.24 g, 131.01 mmol) in DMF (155 mL). After the addition is complete, heat at 50° C. After 45 min., add a solution of 1-bromo-3-fluoro-benzene (12.2 mL, 109.18 mmol) in DMF (15 mL) and stir and heat at 65° C. After 18 hr., cool to ambient temperature, quench with water (5 mL), remove the DMF under reduced pressure, wash with water (50 mL) and extract with ethyl acetate/hexanes (2/1 mixture, 2×35 mL). Combine the organic layers, dry over magnesium sulfate, filter under reduced vacuum and concentrate to dryness. Purify by flash chromatography using dichloromethane/ammonia (2.0M in methanol) 20/1 as the eluent to give of the title compound (15.4 g, 65%). Mass spectrum (ion spray): m/z=270.0 (M+1); $^1$H NMR (CDCl$_3$): 7.12 (t, J=8.3 Hz, 1H), 7.07-7.04 (m, 2H), 6.83 (bd, J=8.3 Hz, 1H), 4.35-4.26 (bm, 1H), 2.73-2.64 (bm, 2H), 2.37-2.28 (bm, 5H), 2.05-1.96 (bm, 2H), 1.89-1.79 (bm, 2H).

Preparation 13.
4-(3-Bromo-phenoxy)-1-ethyl-piperidine

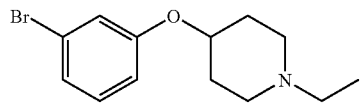

Using a method similar to preparation 12, using 1-ethyl-piperidin-4-ol (850 mg, 6.58 mmol) gives the title compound as a pale yellow oil (797 mg, 43%). Mass spectrum (ion spray): m/z=284.1 (M+1); $^1$H NMR (CDCl$_3$): 7.12 (t, J=8.2 Hz, 1H), 7.07-7.04 (m, 2H), 6.83 (dd, J=2.1 Hz, 8.2 Hz, 1H), 4.36-4.29 (bm, 1H), 2.79-2.71 (bm, 2H), 2.47 (q, J=7.0 Hz, 2H), 2.40-2.30 (bm, 2H), 2.09-1.99 (bm, 2H), 1.89-1.80 (bm, 2H), 1.12 (t, J=7.0 Hz, 3H).

Preparation 14.
4-(3-Bromo-phenoxy)-piperidine-1-carboxylic acid tert-butyl ester

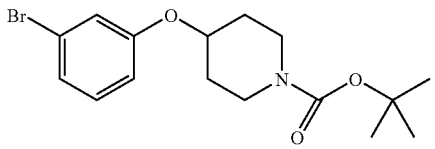

Using a method similar to preparation 12, using 4-hydroxy-piperidine-1-carboxylic acid tert-butyl ester (10 g, 49.7 mmol) gives the title compound as a colorless oil (15.3 g, 87%). Mass spectrum (ion spray): m/z=356.0 (M+1); $^1$H NMR (CDCl$_3$): 7.13 (t, J=7.9 Hz, 1H), 7.09-7.05 (m, 2H), 6.84 (dd, J=1.1 Hz, 2.4 Hz, 1H), 6.82 (t, J=1.8 Hz, 1H), 4.44 (septet, J=3.6 Hz, 1H), 3.67 (ddd, J=3.9 Hz, 7.7 Hz, 13.5 Hz, 2H), 3.34 (ddd, J=3.9 Hz, 7.7 Hz, 13.5 Hz, 2H), 1.94-1.86 (m, 2H), 1.78-1.69 (m, 2H), 1.47 (s, 9H).

Preparation 15.
4-(5-Bromo-2-chloro-phenoxy)-1-methyl-piperidine

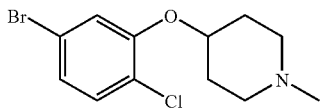

Using a method similar to preparation 12, using 4-bromo-1-chloro-2-fluoro-benzene (2.0 g, 9.55 mmol) gives the title compound as a pale yellow oil (2.01 g, 83%). Mass spectrum (ion spray): m/z=304.0 (M+1); $^1$H NMR (CDCl$_3$): 7.21 (d, J=8.4 Hz, 1H), 7.06 (d, J=2.1 Hz, 1H), 7.02 (dd, J=2.1 Hz, 8.4 Hz, 1H), 4.44-4.35 (bm, 1H), 2.74-2.63 (bm, 2H), 2.45-2.36 (bm, 2H), 2.33 (s, 3H), 2.06-1.98 (bm, 2H), 1.96-1.88 (bm, 2H).

Preparation 16.
4-(3-Bromo-5-fluoro-phenoxy)-1-methyl-piperidine

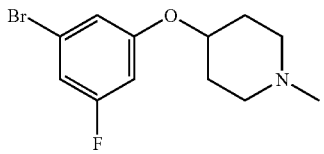

Combine 1-methyl-piperidin-4-ol (5.97 g, 51.81 mmol) and N,N-dimethylformamide (100 mL) and treat, in portions, the resulting solution with 95% sodium hydride (1.31 g, 51.81 mmol) and stir. After 1 hr., add 1-bromo-3,5-difluoro-benzene (10.0 g, 51.81 mmol), stir and heat to 80° C. After 2 hr., cool to ambient temperature, partition between water (100 mL) and ethyl acetate (100 mL), separate and wash the water layer with ethyl acetate (100 mL). Combine the ethyl acetate layers and wash with water (5×75 mL). Wash the organic layer with aqueous NaCl solution (75 mL), dry over sodium sulfate, filter and concentrate to an oil. Purify the residue by silica gel flash chromatography eluting with 10% (2M NH$_3$/methanol)/methylene dichloride to obtain of the title compound (10.61 g, 71%). Mass spectrum (electrospray): m/z=288 (M+1–1), 290 (M+1+1); $^1$H NMR (CDCl$_3$): 6.85 (s, 1H), 6.8 (m, 1H), 6.55 (m, 1H), 4.3 (m, 1H), 2.6 (m, 2H), 2.3 (m, 5H), 2.0 (m, 2H), 1.8 (m, 2H).

Preparation 17.
4-(2-Fluoro-phenoxy)-1-methyl-piperidine

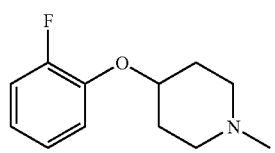

Dissolve 1-methyl-piperidin-4-ol (4.61 g) in DMF (25 mL) and add slowly to a suspension of sodium hydride (95%) (1.11 g) in DMF (25 mL) at room temperature. Heat the mixture in an oil bath at 65° C. After 30 min., add 1,2-difluorobenzene (4.56 g) and stir at 65° C. After 2 hr., partition between water and ether, dry over anhydrous sodium sulfate, evaporate to give a yellow oil (5.88 g, 70% yield). Mass spectrum (electric spray) m/z=210 (M+1); $^1$H NMR (CDCl$_3$): 7.05 (m, 3H), 6.92 (m, 1H), 4.29 (m, 1H), 2.71 (m, 2H), 2.30 (s, 3H), 2.27 (m, 2H), 1.99 (m, 2H), 1.89 (m, 2H).

Preparation 18.
4-(3-Bromo-2-fluoro-phenoxy)-1-methyl-piperidine

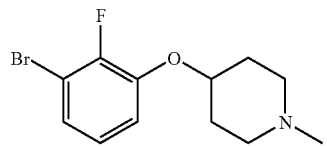

Add n-butyl lithium (1.6 M in hexane, 7.4 mL) to a solution of 2,2,6,6-tetramethyl-piperidine (1.67 g) in THF (30 mL) at –78° C. and stir. After 15 min., add dropwise a solution of 4-(2-fluoro-phenoxy)-1-methyl-piperidine preparation 17, 1.65 g) in THF (20 mL) and stir. After 1 hr., add dropwise 1,2-dibromo-1,1,2,2-tetrachloro-ethane (2.57 g) in THF (15 mL) and stir. After 30 min. at –78° C. and 1 hr. at room temperature, partition between ethyl acetate and saturated aqueous NaCl, dry over anhydrous sodium sulfate, evaporate and purify on a silica gel column (110 g, solvent: dichloromethane-2M NH$_3$ in methanol, gradient) to give the title compound (1.25 g). Mass spectrum (electric spray) m/z=288 (M+1), 290 (M+2+1); $^1$H NMR (CDCl$_3$): 7.12 (m, 1H), 6.92 (m, 2H), 4.30 (m, 1H), 2.69 (m, 2H), 2.30 (s, 3H), 2.28 (m, 2H), 1.97 (m, 2H), 1.89 (m, 2H).

Preparation 19.
4-(3-Bromo-2-fluoro-phenoxy)-1-methyl-piperidine

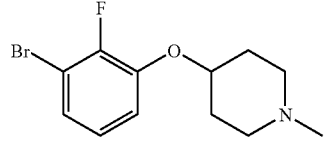

Add slowly a solution of 1-methyl-piperidin-4-ol (2.98 g) in DMF (20 mL) into a suspension of sodium hydride (95%) (0.72 g) in DMF (25 mL) at room temperature. Heat the mixture in an oil bath at 65° C. After 30 min., add 1-bromo-2,3-difluoro-benzene (5.0 g) and stir at 65° C. After 2 hr., partition the reaction mixture between water and ether, dry over anhydrous sodium sulfate, and evaporate to give a yellow oil. Separate on a silica gel column (110 g, solvent: ether, ether-2M NH$_3$ in methanol 19:1, 9:1) to obtain 4-(2-bromo-6-fluoro-phenoxy)-1-methyl-piperidine (4.06 g, 54% yield) and the title compound (1.60 g, 21% yield). Mass spectrum (electric spray) m/z=288 (M+1), 290 (M+2+1); $^1$H NMR (CDCl$_3$): 7.12 (m, 1H), 6.92 (m, 2H), 4.30 (m, 1H), 2.69 (m, 2H), 2.30 (s, 3H), 2.28 (m, 2H), 1.97 (m, 2H), 1.89 (m, 2H).

Preparation 20.
4-(5-Bromo-2-methyl-phenoxy)-1-methyl-piperidine

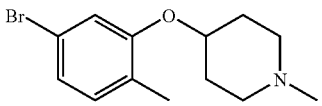

Add sodium hydride (60% dispersion in oil, 880 mg, 22 mmol) to a solution of 4-hydroxy-1-methyl-piperidine (2.304 g, 20 mmol) in DMF (12 mL), stir. After 30 min., add 4-bromo-2-fluorotoluene (4.159 g, 22 mmol) and beat at 70° C. After 21 hr., quench the reaction with saturated NaHCO$_3$ solution, extract with ether three times, combine the organic layers, wash with saturated NaCl solution, dry over Na$_2$SO$_4$, filter and concentrate to give a residue. Purify by chromatography (silica gel, eluting with 6% 2M NH$_3$-methanol in CH$_2$Cl$_2$) provides of the title compound as a slightly yellow oil (3.90 g, 69%). Mass spectrum (ion spray): m/z=284.0 (M+1); $^1$H NMR (CDCl$_3$, ppm): 7.01 (m, 3H), 4.35 (m, 1H), 2.66 (m, 2H), 2.36 (m, 2H), 2.34 (s, 3H), 2.19 (s, 3H), 2.03 (m, 2H), 1.85 (m, 2H).

Preparation 21.
4-(3-Fluoro-5-nitro-phenoxy)-1-methyl-piperidine

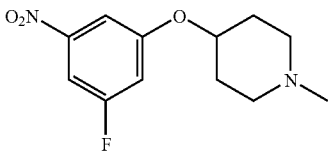

Dissolve 1-methyl-piperidin-4-ol (3.62 g, 31.43 mmol) in N,N-dimethylformamide (20 mL) and add 95% sodium hydride (0.83 g, 33.0 mmol) at ambient temperature. After 40 min., add 1,3-difluoro-5-nitro-benzene (5.0 g, 31.43 mmol), stir and heat at 65° C. After 2 hr., cool to ambient temperature and pour slowly into water (100 mL). Extract the reaction mixture with ethyl acetate (3×150 mL), wash the combined organic layers with aqueous NaCl solution (100 mL), dry over sodium sulfate, filter and concentrate. Purify the residue by silica gel flash chromatography eluting with 10% (2M NH$_3$/methanol)/methylene dichloride to obtain of the title compound (2.76 g, 35%). $^1$H NMR (CDCl$_3$): 7.6 (s, 1H), 7.5 (d, 1H), 7.0 (d, 1H), 4.4 (m, 1H), 2.7 (m, 2H), 2.4 (m, 5H), 2.0 (m, 2H), 1.9 (m, 2H).

Preparation 22. 4-(3-Bromo-phenoxy)-cis-2-methyl-piperidine-1-carboxylic acid tert-butyl ester isomer 1

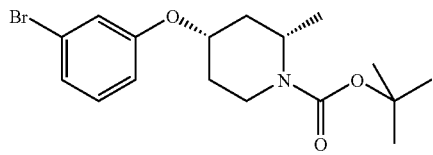

Dissolve 4-hydroxy-cis-2-methyl-piperidine-1-carboxylic acid tert-butyl ester isomer 1 (preparation 2, 2.53 g, 11.75 mmol) in 1-methyl-2-pyrrolidinone (50 mL) and treat with 95% sodium hydride (0.33 g, 12.93 mmol), stir and heat at 70° C. After 1 hr., add 1-bromo-3-fluoro-benzene (1.44 mL, 12.93 mmol), stir and heat at 100° C. After 16 hr., cool to ambient temperature and quench with water (100 mL). Extract with 4:1 hexane:ethyl acetate (2×100 mL). Combine the organic layers and wash with aqueous NaCl solution (75 mL), dry over sodium sulfate, filter and concentrate. Purify residue by silica gel flash chromatography eluting with 4:1 hexanes: ethyl acetate to obtain the title compound (2.47 g, 57%). $^1$H NMR (CDCl$_3$): 7.15 (m, 1H), 7.05 (m, 2H), 6.8 (dd, 1H), 4.6 (m, 1H), 4.35 (m, 1H), 3.9 (m, 1H), 3.25 (m, 1H), 1.9 (m, 3H), 1.75 (m, 1H), 1.5 (s, 9H), 1.3 (d, 3H).

Preparation 23. 4-(3-Bromo-phenoxy)-cis-2-methyl-piperidine-1-carboxylic acid tert-butyl ester isomer 2

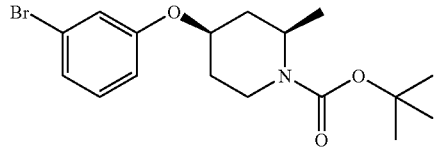

Combine 4-hydroxy-cis-2-methyl-piperidine-1-carboxylic acid tert-butyl ester isomer 2 (preparation 3, 0.986 g) in DMF (10 mL) and add to a suspension of sodium hydride (95%, 0.127 g) in DMF (10 mL) and heat in an oil bath at 65° C. After 30 min., add 1-bromo-3-fluoro-benzene (0.96 g) and heat at 65° C. After 18 hr., partition between ethyl acetate-hexane (1:4) and saturated aqueous NaCl, dry over anhydrous sodium sulfate, evaporate and purify on a 35 g silica gel column eluting with ethyl acetate-hexane (1:9) to give the title compound as a colorless oil (0.759 g). $^1$H NMR (CDCl$_3$): 7.13 (dd, 1H), 7.05 (ddd, 1H), 7.04 (m, 1H), 6.81 (ddd, 1H), 4.63 (m, 1H), 4.35 (m, 1H), 3.88 (m, 1H), 3.23 (m, 1H), 1.90 (m, 3H), 1.73 (m, 1H), 1.46 (s, 9H), 1.27 (d, J=7.0 Hz, 3H).

Preparation 24. (3-Bromo-phenoxy)-trans-2-methyl-piperidine-1-carboxylic acid tert-butyl ester isomer 2

Using a method similar to preparation 23, using 4-hydroxy-trans-2-methyl-piperidine-1-carboxylic acid tert-butyl ester isomer 2, (preparation 3) gives the title compound. Mass spectrum (electrospray) m/z 272 and 270 (M-BOC); $^1$H NMR (CDCl$_3$): 7.11 (dd, 1H), 7.06 (ddd, 1H), 7.03 (m, 1H), 6.81 (ddd, 1H), 4.54 (m, 1H), 4.47 (m, 1H), 4.09 (m, 1H), 2.94 (m, 1H), 2.07 (m, 1H), 1.95 (m, 1H), 1.72 (m, 1H), 1.48 (m, 1H), 1.46 (s, 9H), 1.21 (d, J=7.0 Hz, 3H).

Preparation 25. 4-(3-Bromo-phenoxy)-trans 2-methyl-piperidine-1-carboxylic acid tert-butyl ester isomer 1

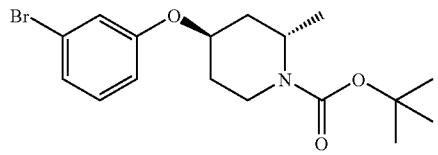

Dissolve 4-hydroxy-trans-2-methyl-piperidine-1-carboxylic acid tert-butyl ester isomer 1 (preparation 2, 3.03 g, 14.07 mmol) in 1-methyl-2-pyrrolidinone (50 mL), treat with 95% sodium hydride (0.33 g, 12.93 mmol), stir and beat at 70° C. After 1 hr., add 1-bromo-3-fluoro-benzene (1.73 mL, 15.5 mmol), stir, and heat at 100° C. After 16 hr., cool to ambient temperature and quench with water (100 mL). Extract with 4:1 hexane:ethyl acetate (2×100 mL), combine the organic layers and wash with aqueous NaCl solution (75 mL), dry over sodium sulfate, filter and concentrate. Purify the residue by silica gel flash chromatography eluting with 4:1 hexanes: ethyl acetate to obtain of the title compound (2.42 g, 46%). $^1$H NMR (CDCl$_3$): 7.1 (m, 3H), 6.8 (m, 1H), 4.55 (m, 1H), 4.5 (m, 1H), 4.1 (m, 1H), 2.95 (m, 1H), 2.1 (m, 1H), 1.95 (m, 1H), 1.7 (m, 1H), 1.5 (m, 1H), 1.45 (s, 9H), 1.2 (d, 3H).

Preparation 26. 1-Benzyl-4-(3-bromo-phenoxy)-cis-3-methyl-piperidine

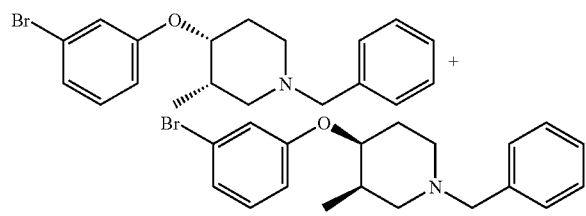

Dissolve 1-benzyl-cis-3-methyl-piperidin-4-ol (preparation 6, 3.84 g, 18.73 mmol) in dry N,N-dimethylformamide (100 mL), treat with 60% sodium hydride (1.05 g, 26.22 mmol), heat and stir at 80° C. After 1 hr., add-1-bromo-3-fluoro-benzene (2.51 mL, 22.45 mmol), stir and heat at 110° C. After 16 hr., cool to ambient temperature. Partition between water (100 mL) and ethyl acetate (100 mL), wash the aqueous layer with ethyl acetate (2×100 mL), combine the organic layers, wash with water (5×100 mL) and aqueous NaCl solution (100 mL). Dry the organic layer over sodium sulfate, filter and concentrate. Purify the residue by silica gel flash chromatography eluting with 2% (2M NH$_3$/methanol)/methylene dichloride to obtain the title compound as a mixture of enantiomers (1.69 g, 24%). $^1$H NMR (CDCl$_3$): 7.3 (m, 5H), 7.1 (m, 3H), 6.8 (m, 1H), 4.3 (m, 1H), 3.5 (d, 2H), 2.5 (m, 2H), 2.4 (m, 2H), 2.0 (m, 2H), 1.8 (m, 1H), 1.0 (d, 3H).

Preparation 27. Racemic 1-benzyl-4-(3-bromo-phenoxy)-3-trans-methyl-piperidine

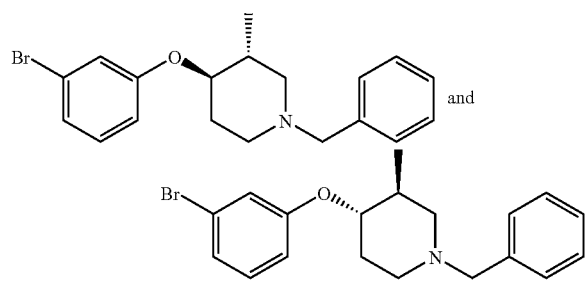

Add sodium hydride (95%, 0.35 g) into a solution of 1-benzyl-3-trans-methyl-piperidin-4-ol (preparation 7, 2.37 g) in 1-methyl-2-pyrrolidinone (50 mL) and heat in an oil bath at 65° C. After 30 min., add 1-bromo-3-fluoro-benzene (2.22 g) and heat at 100° C. After 4 hr., partition between ethyl acetate-hexane (1:4) and saturated aqueous NaCl, dry over anhydrous sodium sulfate, evaporate and purify on a 110 g silica gel column eluting with ethyl acetate-hexane (1:9) to give the title compound (2.515 g). mass spectrum (electrospray) m/z=360 (M+1), 362 (M+2+1); $^1$H NMR (CDCl$_3$): 7.32 (m, 4H), 7.27 (m, 1H), 7.11 (m, 1H), 7.05 (m, 2H), 6.82 (m, 1H), 3.76 (m, 1H), 3.52 (s, 2H), 2.86 (m, 2H), 2.09 (m, 2H), 2.00 (m, 1H), 1.85 (m, 1H), 1.65 (m, 1H), 0.97 (d, J=6.7 Hz, 3H).

Preparation 28. 3-(1-Methyl-piperidin-4-yloxy)-phenylamine

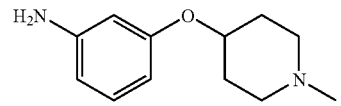

Combine under nitrogen 4-(3-bromo-phenoxy)-1-methyl-piperidine (preparation 12, 5 g, 18.5 mmol), (±)BINAP (576 mg, 0.925 mmol), Pd$_2$(dba)$_3$ (424 mg, 0.463 mmol), benzhydrylideneamine (3.73 mL, 22.2 mmol), sodium tert-butoxide (2.49 g, 25.9 mmol) and toluene (37 mL), stir, and heat at 80° C. After 2 hr., cool to ambient temperature, dilute with ethyl acetate/hexanes (2/1 mixture, 40 mL), wash with water (2×60 mL), dry over magnesium sulfate, filter under reduced vacuum and concentrate to dryness to give 6.8 g. Dissolve the residue in THF (60 mL) and stir. Add hydrochloric acid (aq. 1N, 60 mL) and stir for 30 min. Dilute with ethyl acetate (25 mL) and wash with water (2×60 mL). Separate the aqueous layer and basify it with sodium hydroxide (aq. 2N, to obtain pH 9, 20 mL). Extract the aqueous layer with dichloromethane (3×100 mL). Dry over magnesium sulfate, filter under reduced vacuum, and concentrate to dryness. Load onto SCX columns (divided in three 10 g SCX columns) and elute with ammonia (2.0 M in methanol) to give of the title compound as an off-white solid (2.52 g, 66%, 2 steps). Mass spectrum (ion spray): m/z=207.1 (M+1); $^1$H NMR (CDCl$_3$): 7.03 (t, J=8.1 Hz, 1H), 6.34-6.24 (m, 3H), 4.30-4.22 (bm, 1H), 3.63 (bs, 2H), 2.73-2.65 (bm, 2H), 2.30 (s, 3H), 2.29-2.23 (bm, 2H), 2.03-1.95 (bm, 2H), 1.87-1.79 (bm, 2H).

Preparation 29. 3-(1-Ethyl-piperidin-4-yloxy)-phenylamine

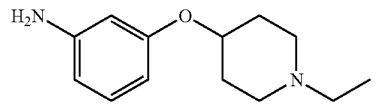

Using a method similar to preparation 28, using 4-(3-bromo-phenoxy)-1-ethyl-piperidine (preparation 13, 792 mg, 2.78 mmol) gives the title compound (425 mg, 69%, 2 steps): Mass spectrum (ion spray): m/z=221.1 (M+1); $^1$H NMR (CDCl$_3$): 7.04 (t, J=8.0 Hz, 1H), 6.32 (dd, J=2.2 Hz, 8.0 Hz, 1H), 6.28 (dd, J=2.0 Hz, 8.0 Hz, 1H), 6.25 (t, J=2.2 Hz, 1H), 4.34-4.25 (bm, 1H), 3.63 (bs, 2H), 2.81-2.72 (bm, 2H), 2.48 (q, J=7.1 Hz, 2H), 2.41-2.31 (bm, 2H), 2.09-2.00 (bm, 2H), 1.90-1.80 (bm, 2H), 1.13 (t, J=7.3 Hz, 3H).

Preparation 30. 4-(3-Amino-phenoxy)-piperidine-1-carboxylic acid tert-butyl ester

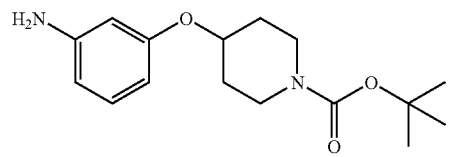

Using a method similar to preparation 28, using 4-(3-bromo-phenoxy)-piperidine-1-carboxylic acid tert-butyl ester (preparation 14, 5.01 g, 14.07 mmol) gives 6.42 g of the corresponding 4-[3-(benzhydrylidene-amino)-phenoxy]-piperidine-1-carboxylic acid tert-butyl ester. Add sequentially sodium acetate (anhydrous, 2.77 g, 33.78 mmol) and hydroxylamine hydrochloride (1.76 g, 25.33 mmol) to a stirred solution of 4-[3-(benzhydrylidene-amino)-phenoxy]-piperidine-1-carboxylic acid tert-butyl ester (6.42 g, 14.07 mmol) in methanol (anhydrous, 140 mL) and stir at ambient room temperature. After 1 hr., dilute with dichloromethane (40 mL) and wash with sodium hydroxide (aq. 0.1 N, 60 mL), extract with dichloromethane (2×60 mL), dry over magnesium sulfate, filter under reduced vacuum and concentrate to dryness. Purify by flash chromatography (20-60% ethyl acetate/hexanes) to give the title compound as a pale yellow solid (3.85 g, 93%, 2 steps). Mass spectrum (ion spray): m/z=237.1 (M+1); $^1$H NMR (CDCl$_3$): 7.04 (t, J=8.0 Hz, 1H), 6.34-6.26 (m, 3H), 4.41 (septet, J=3.5 Hz, 1H), 3.72-3.64 (m, 2H), 3.32 (ddd, J=3.9 Hz, 7.7 Hz, 13.2 Hz, 2H), 1.93-1.84 (m, 2H), 1.77-1.68 (m, 2H), 1.46 (s, 9H).

Preparation 31. 4-Chloro-3-(1-methyl-piperidin-4-yloxy)-phenylamine

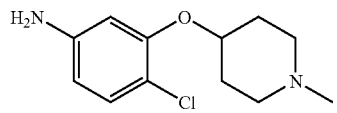

Using a method similar to preparation 28, using 4-(5-bromo-2-chloro-phenoxy)-1-methyl-piperidine (preparation 15, 2.01 g, 6.58 mmol) gives the title compound (1.41 g, 89%, 2 steps). Mass spectrum (ion spray): m/z=241.2 (M+1); $^1$H NMR (CDCl$_3$): 7.09 (d, J=8.5 Hz, 1H), 6.29 (d, J=2.5 Hz, 1H), 6.23 (dd, J=2.5 Hz, 8.5 Hz, 1H), 4.33-4.26 (bm, 1H), 3.64 (bs, 2H), 2.73-2.64 (bm, 2H), 2.36-2.31 (bm, 2H), 2.30 (s, 3H), 2.01-1.86 (bm, 4H).

Preparation 32. 3-Fluoro-5-(1-methyl-piperidin-4-yloxy)-phenylamine

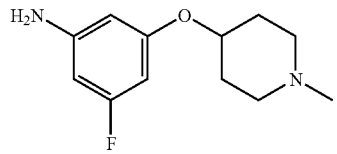

Combine 4-(3-fluoro-5-nitro-phenoxy)-1-methyl-piperidine (preparation 16, 2.75 g, 10.82 mmol), iron dust (2.0 g, 35.69 mmol), methanol (150 mL) and 1M aqueous hydrochloric acid solution (3.25 mL, 3.25 mmol), stir and heat at reflux. After 32 hr., cool to ambient temperature, filter through celite and concentrate to an oil. Partition between ethyl acetate (100 mL) and 1M aqueous sodium hydroxide solution (50 mL), separate the organic layer, dry over sodium sulfate, filter and concentrate. Purify residue by silica gel flash chromatography eluting with 10% (2M NH$_3$/methanol)/methylene dichloride to give the title compound (1.35 g, 56%). $^1$H NMR (CDCl$_3$): 6.0 (m, 3H), 4.2 (m, 1H), 3.7 (bs, 2H), 2.7 (m, 2H), 2.3 (m, 5H), 2.0 (m, 2H), 1.8 (m, 2H).

Preparation 33. 2-Fluoro-3-(1-methyl-piperidin-4-yloxy)-phenylamine

Heat a mixture of 4-(3-bromo-2-fluoro-phenoxy)-1-methyl-piperidine (preparation 18 or 19, 1.60 g), benzhydrylideneamine (1.21 g), tris(dibenzylidineacetone)-dipalladium(0) (0.11 g), racemic-2,2'-bis(diphenylphosphino)-1,1'binaphthyl (0.138 g) and sodium t-butoxide (0.75 g) in toluene (100 mL) and reflux. After 3 hr., cool to room temperature, load on a SCX column (10 g), wash with methanol, elute the product with 2 M NH$_3$ in methanol. Evaporate the NH$_3$-methanol solution and purify on a 35 g silica gel column eluting with dichloromethane-2M NH$_3$ in methanol, gradient to give benzhydrylidene-[2-fluoro-3-(1-methyl-piperidin-4-yloxy)-phenyl]-amine. Dissolve the amine in THF and add 1N HCl. After 10 min., basify with NH$_4$OH and partition between ethyl acetate and saturated aqueous NaCl, dry over sodium sulfate, evaporate and purify on a 35 g silica gel column eluting with: dichloromethane-2M NH$_3$ in methanol, gradient) to give the title compound (1.19 g): mass spectrum (electric spray) m/z=225 (M+1); $^1$H NMR (CDCl$_3$): 6.78 (m, 1H), 6.38 (m, 2H), 4.25 (m, 1H), 3.73 (br s, 2H), 2.69 (m, 2H), 2.27 (s, 3H), 2.26 (m, 2H), 1.97 (m, 2H), 1.87 (m, 2H).

Preparation 34. 4-Methyl-3-(1-methyl-piperidin-4-yloxy)-phenylamine

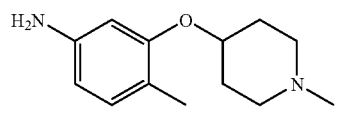

Combine 4-(5-bromo-2-methyl-phenoxy)-1-methyl-piperidine (preparation 20, 3.90 g, 13.7 mmol), benzophenone imine (2.98 g, 16.44 mmol), Pd$_2$(dba)$_3$ (251 mg, 0.27 mmol), BINAP (512 mg, 0.82 mmol), sodium f-butoxide (1.843 g, 19.18 mmol) and toluene (40 mL) and heat at 85° C. After 9 hr., quench the reaction with saturated NaHCO$_3$ solution, extract with ethylacetate three times, combine the organic layers, dry over Na$_2$SO$_4$, filter and concentrate to give a residue. Dissolve the residue in THF (55 mL) and add 5N HCl (5.5 mL) and stir. After 1 hr., dilute the mixture with 0.1N HCl, extract with ethylacetate/hexanes (1:2) twice, keep aqueous layer, adjust pH>11 with 5N NaOH, extract with methylene dichloride three time. Combine methylene dichloride layers, dry over Na$_2$SO$_4$, filter and concentrate to give a residue. Purify by silica gel chromatography, eluting with 6.5% 2M NH$_3$-methanol in methylene dichloride to give the title compound as a yellow oil (2.80 g, 93%). Mass spectrum (ion spray): m/z=221.1 (M+1); $^1$H NMR (CDCl$_3$, ppm): 6.79 (d, 1H), 6.09 (m, 2H), 4.16 (m, 1H), 3.41 (s, br, 1H), 2.53 (m, 2H), 2.24 (m, 2H), 2.19 (s, 3H), 2.00 (s, 3H), 1.93-1.68 (m, 4H).

Preparation 35. 4-(3-Amino-phenoxy)-cis-2-methyl-piperidine-1-carboxylic acid tert-butyl ester isomer 1

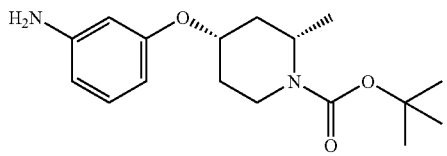

Combine 4-(3-bromo-phenoxy)-cis 2-methyl-piperidine-1-carboxylic acid tert-butyl ester isomer 1 (preparation 22, 2.47 g, 6.67 mmol), benzhydrylideneamine (1.45 g, 8.0 mmol), toluene (100 mL), sodium-t-butoxide (0.9 g, 9.34 mmol) and 2,2'-bis(diphenylphosphino)-1,1'-binaphthyl (0.17 g, 0.27 mmol), stir and heat at 100° C. After 10 min., add tris(dibenzylideneacetone)-dipalladium(0) (0.12 g, 0.13 mmol), stir and heat at 100° C. After 4 hr., cool to ambient temperature and partition between water (200 mL) and 4:1 hexane:ethyl acetate (200 mL). Separate organic layer, wash with water (100 mL) and aqueous NaCl solution (100 mL). Dry organic layer over sodium sulfate, filter and concentrate to an oil. Dissolve residue in methanol (80 mL) and treat with sodium acetate (1.31 g, 16.01 mmol) followed by hydroxylamine monohydrogen chloride (0.83 g, 12.0 mmol) with stirring. After 1 hr., partition between 4:1 hexane:ethyl acetate (200 mL) and 0.5 M aqueous sodium hydroxide solution (200 mL). Separate organic layer, wash with aqueous NaCl solution (100 mL), dry over sodium sulfate, filter and concentrate. Purify residue by silica gel flash chromatography eluting with 4:1 hexanes:ethyl acetate to obtain the title compound (1.17 g, 59%). $^1$H NMR (CDCl$_3$): 7.05 (m, 1H), 6.3 (m, 2H), 6.25 (m, 1H), 4.6 (m, 1H), 4.35 (m, 1H), 3.85 (m, 1H), 3.7 (bs, 2H), 3.25 (m, 1H), 1.95 (m, 2H), 1.8 (m, 1H), 1.7 (m, 1H), 1.45 (s, 9H), 1.3 (d, 3H).

Preparation 36. 4-(3-Amino-phenoxy)-2-methyl-piperidine-1-carboxylic acid tert-butyl ester trans isomer 1

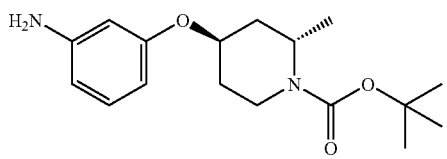

Using a method similar to preparation 31, using 4-(3-bromo-phenoxy)-trans-2-methyl-piperidine-1-carboxylic acid tert-butyl ester trans isomer 1 (preparation 25, the title compound is prepared and isolated (23% yield). $^1$H NMR (CDCl$_3$): 7.1 (m, 1H), 6.3 (m, 2H), 6.2 (m, 1H), 4.55 (m, 1H), 4.45 (m, 1H), 4.1 (m, 1H), 3.65 (bs, 2H), 2.95 (m, 1H), 2.1 (m, 1H), 2.0 (m, 1H), 1.7 (m, 1H), 1.55 (m, 1H), 1.5 (s, 9H), 1.2 (d, 3H).

Preparation 37. 4-[3-(Benzhydrylidene-amino)-phenoxy]-cis-2-methyl-piperidine-1-carboxylic acid tert-butyl ester isomer 2

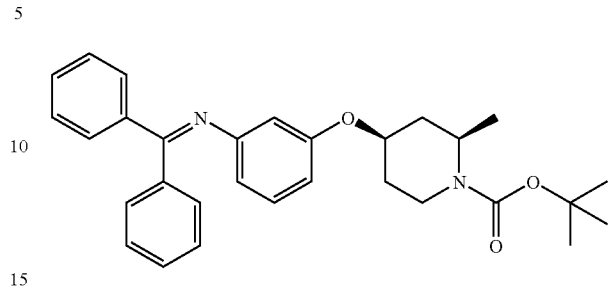

Heat a mixture of 4-(3-bromo-phenoxy)-cis-2-methyl-piperidine-1-carboxylic acid tert-butyl ester isomer 2 (preparation 23, 0.759 g), benzhydrylideneamine (0.446 g), racemic-2,2'-bis(diphenylphosphino)-1,1' binaphthyl (50 mg) and sodium t-butoxide (0.269 g) in toluene (20 mL) at 100° C. After 10 min., add tris(dibenzylidineacetone)-dipalladium(0) (37 mg) and heat at 100° C. After 2.5 hr., partition between ethyl acetate-hexane (1:4) and saturated aqueous NaCl, dry over anhydrous sodium sulfate, evaporate and purify on a 35 g silica gel column eluting with dichloromethane-2M NH$_3$ in methanol gradient to give the crude title compound (0.74 g). Mass spectrum (electrospray) m/z 471 (M+1).

Preparation 38. 4-[3-(Benzhydrylidene-amino)-phenoxy]-trans-2-methyl-piperidine-1-carboxylic acid tert-butyl ester isomer 2

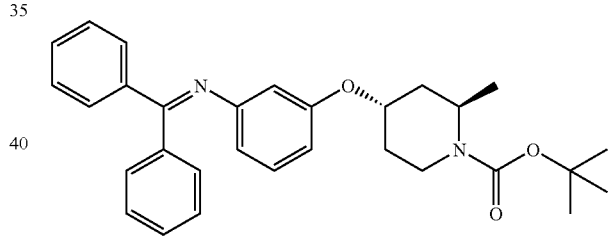

Using a method similar to preparation 37, using 4-(3-bromo-phenoxy)-trans-2-methyl-piperidine-1-carboxylic acid tert-butyl ester isomer 2 (preparation 20B) gives the title compound. Mass spectrum (electrospray) m/z=471 (M+1).

Preparation 39. 4-(3-Amino-phenoxy)-cis-2-methyl-piperidine-1-carboxylic acid tert-butyl ester isomer 2

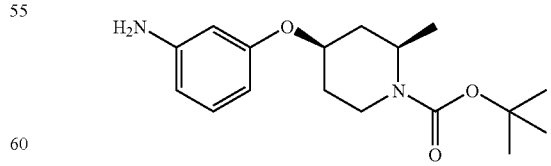

Add sodium acetate (0.309 g) and hydroxyamine hydrochloride (0.197 g) to 4-[3-(benzhydrylidene-amino)-phenoxy]-cis-2-methyl-piperidine-1-carboxylic acid tert-butyl ester isomer 2 (preparation 37) and stir at room temperature. After 1 hr., partition between ethyl acetate and saturated aqueous NaCl, dry over anhydrous sodium sulfate and evaporate. Purify on a silica gel column (35 g, solvent: dichloromethane-2M NH₃ in methanol, gradient) to give the title compound (0.290 g). Mass spectrum (electrospray) m/z=251 (M-57+1), 207 (M-BOC+1); ¹H NMR (CDCl₃): 7.04 (t, 1H), 6.37 (d, 1H), 6.35 (d, 1H), 6.32 (t, 1H), 4.61 (m, 1H), 4.33 (m, 3H), 3.86 (m, 1H), 3.25 (m, 1H), 1.93 (m, 2H), 1.86 (m, 1H), 1.70 (m, 1H), 1.46 (s, 9H), 1.29 (d, J=7.1 Hz, 3H).

Preparation 40. 4-(3-Amino-phenoxy)-trans-2-methyl-piperidine-1-carboxylic acid tert-butyl ester isomer 2

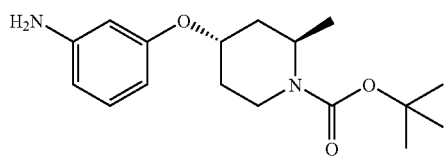

Using a method similar to preparation 39, using 4-[3-(benzhydrylidene-amino)-phenoxy]-trans-2-methyl-piperidine-1-carboxylic acid tert-butyl ester isomer 2 (preparation 34B) gives the title compound. Mass spectrum (electrospray) m/z=307 (M+1). ¹H NMR (CDCl₃): 7.04 (t, 1H), 6.31 (m, 2H), 6.24 (m, 1H), 4.53 (m, 1H), 4.46 (m, 1H), 4.07 (m, 1H), 3.87 (br, 2H), 2.94 (m, 1H), 2.09 (m, 1H), 1.97 (m, 1H), 1.66 (m, 1H), 1.51 (m, 1H), 1.46 (s, 9H), 1.20 (d, J=7.1 Hz, 3H).

Preparation 41. Racemic 3-(1-Benzyl-3-methyl-piperidin-4-yloxy)-phenylamine

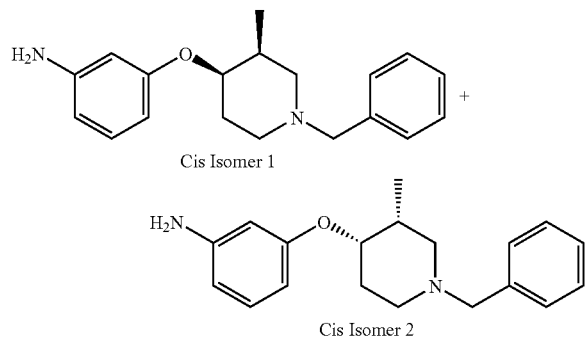

Combine 1-benzyl-4-(3-bromo-phenoxy)-cis-3-methyl-piperidine (preparation 26, 1.29 g, 3.58 mmol), dry toluene (50 mL), benzhydrylideneamine (0.84 mL, 5.01 mmol), sodium-t-butoxide (0.55 g, 5.73 mmol) and 2,2'-bis(diphenylphosphino)-1,1'-binaphthyl (0.09 g, 0.14 mmol), stir and heat at 100° C. After 10 min., add tris(dibenzylideneacetone)-dipalladium(0) (0.066 g, 0.07 mmol), stir and heat at 100° C. After 2 hr., cool to ambient temperature, partition between water (50 mL) and ethyl acetate (100 mL), separate and wash the organic layer with aqueous NaCl solution, dry over sodium sulfate, filter and concentrate.

Dissolve the residue in tetrahydrofuran (100 mL) and treat with 1M aqueous hydrochloric acid (30 mL). After 30 min., basify with 1M aqueous sodium hydroxide (40 mL). Extract with ethyl acetate (2×100 mL), wash combined organic layers with aqueous NaCl solution (50 mL), dry over sodium sulfate, filter and concentrate. Purify by SCX column (10 g) using methanol wash, elute with 2M ammonia/methanol and concentrate eluent. Purify residue by silica gel flash chromatography eluting with 5% (2M NH₃/methanol)/methylene dichloride to obtain the title compound (0.81 g, 76%). Mass spectrum (electrospray): m/z=297.2 (M+1); ¹H NMR (CDCl₃): 7.3 (m, 5H), 7.0 (t, 1H), 6.3 (m, 1H), 6.2 (m, 2H), 4.3 (m, 1H), 3.6 (bs, 2H), 3.5 (d, 2H), 2.4 (m, 4H), 2.0 (m, 2H), 1.7 (m, 1H), 1.0 (d, 3H).

Preparation 42. 3-(1-Benzyl-3-methyl-piperidin-4-yloxy)-phenylamine cis isomer 1

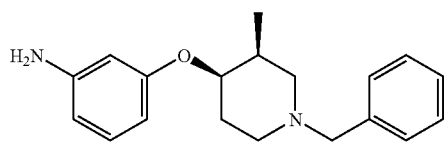

Resolve racemic cis 3-(1-benzyl-3-methyl-piperidin-4-yloxy)-phenylamine (preparation 41, 15.65 g) using a Chiralcel OD™ 4.6×250 mm column eluting with 20/80 IPA/Heptane w/0.2% DMEA at a flow rate of 1.0 mL/min to obtain of the title compound in 94.1% EE (5.98 g, 38%). Mass spectrum (electrospray): m/z=297.2 (M+1); ¹H NMR (CDCl₃): 7.3 (m, 5H), 7.0 (t, 1H), 6.35 (dd, 1H), 6.25 (m, 2H), 4.3 (m, 1H), 3.6 (bs, 2H), 3.5 (m, 2H), 2.4 (m, 4H), 2.0 (m, 2H), 1.75 (m, 1H).

Preparation 43. 3-(1-Benzyl-3-methyl-piperidin-4-yloxy)-phenylamine cis isomer 2

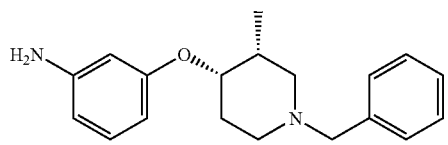

Resolve racemic cis 3-(1-benzyl-3-methyl-piperidin-4-yloxy)-phenylamine (preparation 41, 15.65 g) using a Chiralcel OD™ 4.6×250 mm column eluting with 20/80 IPA/Heptane w/0.2% DMEA at a flow rate of 1.0 mL/min to obtain of the title compound in 99.2% EE (5.72 g, 37%). Mass spectrum (electrospray): m/z=297.2 (M+1); ¹H NMR (CDCl₃): 7.3 (m, 5H), 7.0 (t, 1H), 6.35 (dd, 1H), 6.25 (m, 2H), 4.3 (m, 1H), 3.6 (bs, 2H), 3.5 (m, 2H), 2.4 (m, 4H), 2.0 (m, 2H), 1.75 (m, 1H).

Preparation 44. Racemic 3-(1-Benzyl-3-trans-methyl-piperidin-4-yloxy)-phenylamine

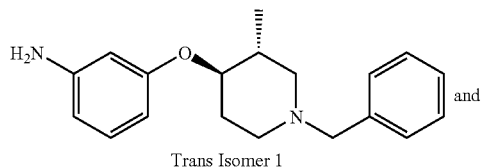

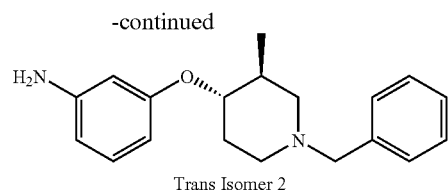

Trans Isomer 2

Heat a mixture of 1-benzyl-3-trans-methyl-4-(3-bromophenoxy)piperidine (preparation 27, 2.50 g), benzhydrylideneamine (1.509 g), 2,2'-bis(diphenylphosphino)-1,1'binaphthyl (0.173 g) and sodium t-butoxide (0.934 g) in toluene (100 mL) at 100° C. After 10 min., add tris(dibenzylidineacetone)-dipalladium(0) (127 mg) and heat at 100° C. After 4 hr., add concentrated hydrochloric acid (4 mL) to the resulting benzhydrylidene-[3-(1-benzyl-3-methyl-piperidin-4-yloxy)-phenyl]-amine mixture and heat for 20 min. at 100° C. Partition between ethyl acetate and saturated aqueous NaCl aqueous NaCl. Basify the aqueous phase with 5N NaOH, extract with dichloromethane, dry over anhydrous sodium sulfate, evaporate and purify on a 35 g silica gel column eluting with dichloromethane-2M $NH_3$ in methanol, gradient to give the crude title compound (1.602 g). Mass spectrum (electrospray) m/z=297 (M+1); $^1$H NMR (CDCl$_3$): 7.32 (m, 4H), 7.26 (m, 1H), 7.03 (m, 1H), 6.33 (m, 1H), 6.28 (m, 1H), 6.25 (m, 1H), 3.73 (m, 1H), 3.62 (br s, 2H), 3.51 (s, 2H), 2.85 (m, 2H), 2.09 (m, 2H), 1.97 (m, 1H), 1.83 (m, 1H), 1.65 (m, 1H), 0.97 (d, J=6.3 Hz, 3H).

Preparation 45. 3-(1-Benzyl-3-trans-methyl-piperidin-4-yloxy)-phenylamine isomer 1 and 2

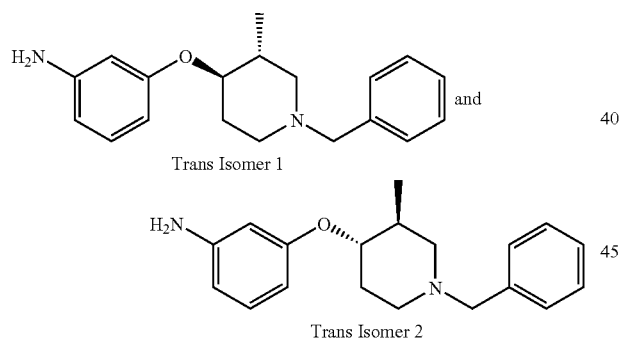

Trans Isomer 1

Trans Isomer 2

Resolve the racemic 3-(1-benzyl-3-trans-methyl-piperidin-4-yloxy)-phenylamine (preparation 44) using Chiralpak AD™/100% acetonitrile into isomer 1 (574 mg) and 2 (672 mg).

Preparation 46.
2-Chloro-6-(1-methyl-piperidin-4-yloxy)-pyridine

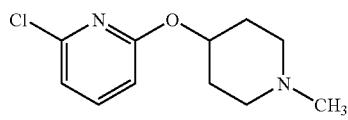

Add sodium hydride (60% dispersion in mineral oil, 5.4 g, 135.1 mmol) to DMF (100 mL) and cool to 0° C. Add 4-hydroxy-1-methylpiperidine (15.6 g, 135.1 mmol) in DMF (100 mL). Warm the reaction to room temperature over 1 hr., add, in portions, 2,6-dichloropyridine (20.0 g, 135.1 mmol) as a solid. Stir the reaction and heat at 120° C. for 12 hr. Cool the reaction to room temperature and partition between diethyl ether and water. Extract 3 times with diethyl ether, combine organics and wash with saturated aqueous NaCl, dry over MgSO$_4$, and concentrate. Chromatograph (silica gel, eluting with ethylacetate, then 5% 2 M NH$_3$-methanol/ethylacetate), to provide the title compound as a pale yellow liquid (25.5 g, 83% yield). Mass spectrum (ion spray): m/z=227.1 (M+1); $^1$H NMR: δ (CDCl$_3$, ppm) 7.46 (t, J=7.2 Hz, 15.6 Hz, 1H), 6.82 (d, J=6.3 Hz, 1H), 6.59 (d, J=8.0 Hz, 1H), 5.03 (m, 1H), 2.66 (bs, 2H), 2.28 (bs, 5H), 2.00 (m, 2H), 1.80 (m, 2H); Anal calcd for $C_{11}H_{15}ClN_2O \cdot 0.8H_2O$: Theory: C, 54.80; H, 6.94; N, 11.62. Found: C, 54.51; H, 6.20; N, 11.60.

Preparation 47. 2-(1-Allyl-2-methyl-piperidin-4-yloxy)-6-chloro-pyridine

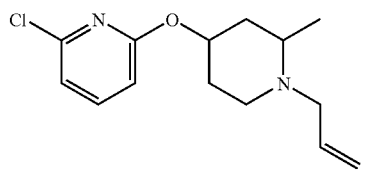

Using a method similar to preparation 46, using N-allyl-2-methyl-4-hydroxypiperidine (preparation 10), gives the title compound as the free base (61% yield). $^1$H NMR (CDCl$_3$): 7.5 (dd, 1H), 6.8 (d, 1H), 6.6 (d, 1H), 5.9 (m, 1H), 5.2 (m, 2H), 5.0 (m, 1H), 3.5 (m, 1H), 3.0 (m, 2H), 2.45 (m, 1H), 2.3 (m, 1H), 2.2 (m, 2H), 1.7 (m, 1H), 1.5 (m, 1H), 1.2 (d, 3H).

Preparation 48. 4-(6-Chloro-pyridin-2-yloxy)-cis-2-methyl-piperidine-1-carboxylic acid tert-butyl ester isomer 2

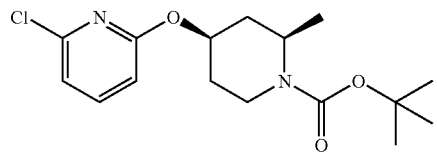

Add sodium hydride (95%, 0.318 g) to a solution of 4-hydroxy-cis-2-methyl-piperidine-1-carboxylic acid tert-butyl ester isomer 2 (preparation 3, 2.465 g) in DMSO (100 mL) and heat in an oil bath at 65° C. After 30 min., add 2,6-dichloropyridine (1.864 g) and beat at 100° C. After 4 hr., partition between ethyl acetate-hexane (1:4) and saturated aqueous NaCl aqueous NaCl, dry over anhydrous sodium sulfate, evaporate and purify on a 35 g silica gel column eluting with ethyl acetate-hexane (1:39) to give the title compound (3.26 g). $^1$H NMR (CDCl$_3$): 7.50 (t, 1H), 6.87 (d, 1H), 6.61 (d, 1H), 5.38 (m, 1H), 4.35 (m, 1H), 3.89 (m, 1H), 3.22 (m, 1H), 1.93 (m, 3H), 1.75 (m, 1H), 1.46 (s, 9H), 1.26 (d, 3H).

Preparation 49. 4-(6-Chloro-pyridin-2-yloxy)-2-methyl-piperidine-1-carboxylic acid tert-butyl ester cis isomer 1

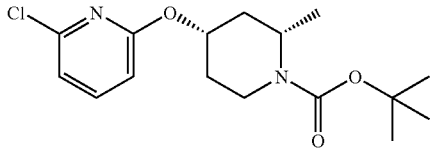

Using a method similar to preparation 48, using 4-hydroxy-2-methyl-piperidine-1-carboxylic acid tert-butyl ester cis 1 (preparation 2), gives the title compound (88% yield). $^1$H NMR (CDCl$_3$): 7.5 (dd, 1H), 6.9 (d, 1H), 6.6 (d, 1H), 5.4 (m, 1H), 4.4 (m, 1H), 3.9 (m, 1H), 3.2 (m, 1H), 1.9 (m, 3H), 1.75 (m, 1H), 1.45 (s, 9H), 1.25 (d, 3H).

Preparation 50. 4-(6-Chloro-pyridin-2-yloxy)-2-methyl-piperidine-1-carboxylic acid tert-butyl ester trans isomer 1

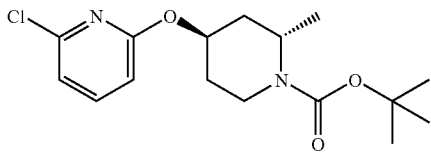

Using a method similar to preparation 48, using 4-hydroxy-2-methyl-piperidine-1-carboxylic acid tert-butyl ester trans isomer 1 (preparation 2) gives the title compound (41% yield). $^1$H NMR (CDCl$_3$): 7.5 (dd, 1H), 6.85 (d, 1H), 6.6 (d, 1H), 5.3 (m, 1H), 4.6 (m, 1H), 4.1 (m, 1H), 3.0 (m, 1H), 2.2 (m, 1H), 2.0 (m, 1H), 1.7 (m, 1H), 1.5 (m, 1H), 1.45 (s, 9H), 1.25 (d, 3H).

Preparation 51. 2-(1-Benzyl-3-methyl-piperidin-4-yloxy)-6-chloro-pyridine (4 isomers)

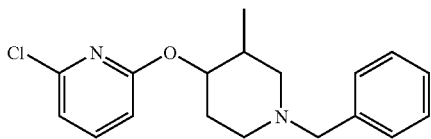

Using a method similar to preparation 48, using racemic 1-benzyl-4-hydroxy-3-methyl-piperidine (preparation 5) gives the title compound. $^1$H NMR (CDCl$_3$): 7.48 (dd, 1H), 7.30 (m, 5H), 6.84 (d, 1H), 6.62 (d, 1H), 4.66 (m, 1H), 3.54 (s, 2H), 2.88 (m, 2H), 2.21 (m, 2H), 1.92 (m, 2H), 1.63 (q, 1H), 0.92 (d, 3H).

Preparation 52. 6-(1-Benzyl-3-methyl-piperidin-4-yloxy)-pyridin-2-ylamine (cis isomers)

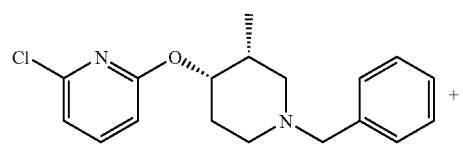

-continued

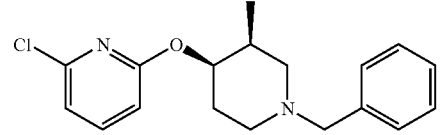

Using a method similar to preparation 48, using racemic 1-benzyl-cis-3-methyl-piperidin-4-ol (preparation 6) gives the title compounds (84% yield). Mass spectrum (electrospray): m/z=317.2 (M+1); $^1$H NMR (CDCl$_3$): 7.48 (dd, 1H), 7.26 (m, 5H), 6.84 (d, 1H), 6.64 (d, 1H), 5.20 (m, 1H), 3.52 (s, 2H), 2.55 (m, 2H), 2.31 (m, 2H), 2.06 (m, 2H), 1.83 (m, 1H), 0.95 (d, 3H).

Preparation 53. Racemic 2-(1-benzyl-3-trans-methyl-piperidin-4-yloxy)-6-chloro-pyridine

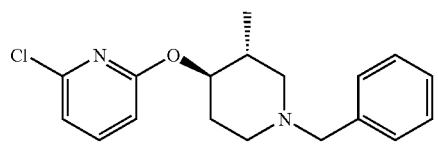

Combine racemic 1-benzyl-3-trans-methyl-piperidin-4-ol (preparation 713.356 g) and 1-methyl-2-pyrrolidinone (50 mL) and add sodium hydride (95%, 1.81 g) and beat in an oil bath at 100° C. After 30 min., add 2,6-dichloropyridine (11.55 g) and beat at 100° C. After 18 hr., partition between ethyl acetate-hexane (1:4) and saturated aqueous NaCl, dry over anhydrous sodium sulfate, evaporate and purify on two silica gel columns eluting with: ethyl acetate-hexane (1:9) to give of the title compound (17.25 g). Mass spectrum (electrospray) m/z=317 (M+1), 319 (M+2+1); $^1$H NMR (CDCl$_3$): 7.48 (t, 1H), 7.32 (m, 4H), 7.26 (m, 1H), 6.84 (dd, 1H), 6.61 (dd, 1H), 4.68 (m, 1H), 3.52 (s, 2H), 2.87 (m, 2H), 2.12 (m, 2H), 1.98 (m, 1H), 1.88 (m, 1H), 1.62 (m, 1H), 0.91 (d, J=6.7 Hz, 3H). (file: mn4-a01246-184)

Preparation 54. 2-(1-Benzyl-2,2-dimethyl-piperidin-4-yloxy)-6-chloro-pyridine

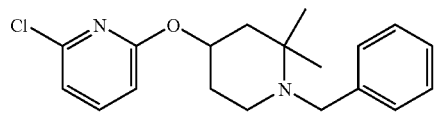

Combine 1-benzyl-2,2-dimethyl-piperidin-4-ol (preparation 9) 1.08 g, 4.92 mmol), N,N-dimethylformamide (20 mL) and 95% sodium hydride (0.12 g, 4.92 mmol) and stir. After 30 min., add 2,6-dichloropyridine (0.67 g, 4.52 mmol), stir and heat at 120° C. After 18 hr., cool to ambient temperature and partition between water (100 mL) and ethyl acetate (100 mL). Separate the organic layer and wash the aqueous layer with ethyl acetate (2×100 mL). Combine the organic layers, wash with water (5×100 mL), wash with aqueous NaCl solution, dry over sodium sulfate, filter and concentrate. Purify the residue by silica gel flash chromatography eluting with 9:1 hexane:ethyl acetate to obtain of the title compound (0.57 g, 38%). Mass spectrum (electrospray): m/z=331.1 (M+1); $^1$H NMR (CDCl₃): 7.5 (dd, 1H), 7.3 (m, 5H), 6.8 (d, 1H), 6.6 (d, 1H), 5.2 (m, 1H), 3.9 (d, 1H), 3.2 (d, 1H), 2.65 (m, 1H), 2.4 (m, 1H), 2.0 (m, 2H), 1.7 (m, 1H), 1.6 (m, 1H), 1.3 (s, 3H), 1.2 (s, 3H).

Preparation 55: 2-bromo-6-(1-(S)-phenylethyl-2-cis-(R)-methyl-piperidin-4-yloxy)pyridine

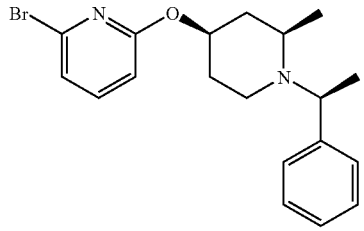

Add N—(S)-Phenethyl-2-(R)-Methyl-piperidin-4-(R)-ol (preparation 8, 14.6 g, 66.6 mmol) to a solution of 60% NaH (4 g, 99.9 mmol) in NMP (116 mL) at room temperature. After 15 min., warm the reaction mixture to 50° C. for 2 hr. or until the end of the H₂ release. Quickly add 2,6-dibromopyridine (16 g, 67.93 mmol) at 50° C., then heat the reaction mixture at 100° C. for 2.5 hr. Cool the reaction mixture to room temperature and add aqueous NaCl (200 mL) and water (100 mL). Extract the aqueous layer with MTBE (3×200 mL). Combine the organic fractions and dry over MgSO₄, filter, and concentrate under reduce pressure. Further purify the crude product on silica gel, to obtain the title compound (87%).

Preparation 56. 2-Chloro-6-(1-cyclopropylmethyl-piperidin-4-yloxy)-pyridine

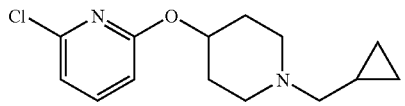

Add NaH (60% dispersion in oil, 130 mg, 3.25 mmol) to a solution of 1-cyclopropylmethyl-piperidin-4-ol (preparation 11, 458 mg, 2.95 mmol) in DMF (8 mL) and stir for 20 min. Then add 2,6-dichloropyridine to the mixture and heat at 120° C. overnight. Quench the reaction with saturated NaHCO₃, extract with methylene dichloride three times. Combine the organic layers, wash with saturated NaCl solution, dry over Na₂SO₄, filter and concentrate to give a residue. Chromatography (silica gel) eluting with 4% 2M NH₃-methanol in methylene dichloride provides 480 mg (61%) of the title compound: mass spectrum (ion spray): m/z=267.2 (M+1); ¹H NMR (CDCl₃, ppm): 7.39 (t, 1H), 6.75 (d, 1H), 6.52 (d, 1H), 4.96 (m, 1H), 2.75 (m, 2H), 2.30 (m, 2H), 2.19 (d, 2H), 1.97 (m, 2H), 1.75 (m, 2H), 0.76 (m, 1H), 0.43 (m, 2H), 0.00 (m, 2H).

Preparation 57. 4-(6-Chloro-pyridin-2-yloxy)-piperidine-1-carboxylic acid tert-butyl ester

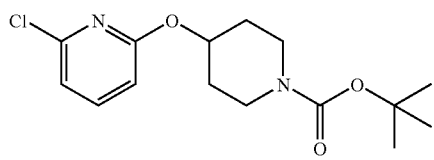

Add NaH (60% dispersion in oil, 420 mg, 10.5 mmol) to a solution of N-1-Boc-4-hydroxypiperidine (2.013 g, 10 mmol) in DMSO (20 mL) and stir for 20 min. Then add 2,6-dichloropyridine (1.479 g, 10 mmol) to the above mixture and heat at 110° C. for 12 hr. Quench the reaction with 0.1N NaOH, extract with ether/ethyl acetate (4:1) three times. Combine the organic layers, wash with saturated NaCl solution, dry over Na₂SO₄, filter and concentrate to give a residue. Chromatography (silica gel) eluting with 8% ethyl acetate in hexanes provides 2.256 g (72%) of the title compound: mass spectrum (ion spray): m/z=335.0 (M+Na); ¹H NMR (CDCl₃, ppm): 7.52 (t, 1H), 6.89 (d, 1H), 6.64 (d, 1H), 5.24 (m, 1H), 3.77 (m, 2H), 3.32 (m, 2H), 2.00 (m, 2H), 1.76 (m, 2H), 1.49 (s, 9H).

Preparation 58.
2-Chloro-6-(1-methyl-piperidin-4-yloxy)-pyridine

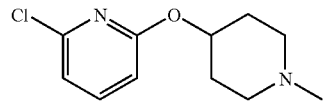

Using a similar method to preparation 56, using 4-hydroxy-1-methylpiperidine (2.303 g, 20 mmol) and DMSO (40 mL) as the solvent, provides 3.484 g (77%) of the title compound: mass spectrum (ion spray): m/z=228.0 (M+1); ¹H NMR (CDCl₃, ppm): 7.52 (t, 1H), 6.88 (d, 1H), 6.64 (d, 1H), 5.09 (m, 1H), 2.72 (m, 2H), 2.33 (m, 5H), 2.05 (m, 2H), 1.86 (m, 2H).

Preparation 59: 2-amino-6-(1-(S)-phenylethyl-2-cis-(R)-methyl-piperidin-4-yloxy)pyridine

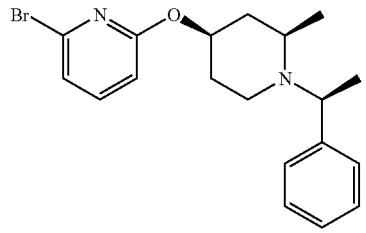

Add 7 M NH₃ in ethyleneglycol (58.28 mL, 408 mmol) and copper (I) oxide (58.38 mg, 0.408 mmol) to a solution of 2-bromo-6-(1-(S)-phenylethyl-2-cis-(R)-methyl-piperidin-4-yloxy)pyridine (preparation 55, 15.3 g, 40.8 mmol) in NMP (20 ml) in an autoclave. Sealing the autoclave and warm the mixture to 85° C. for 20 hr. Cooling the reaction mixture to room temperature and add water (80 mL) and 10 M NaOH (16 mL). Extract the aqueous layer with cyclohexane (3×200 mL). Combine the organic layers, dry over MgSO₄, filter and concentrate under reduce pressure to obtain the crude title compound (13.5 g). Filter on silicagel to provide the title compound (10 g, 95% purity, 85% corrected yield).

Preparation 60.
6-(1-Methyl-piperidin-4-yloxy)-pyridin-2-ylamine

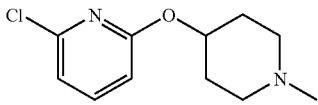

Combine 2-chloro-6-(1-methyl-piperidin-4-yloxy)-pyridine (preparation 46, 7.0 g, 31.0 mmol), Pd$_2$(dba)$_3$ (1.41 g, 1.5 mmol), (±)-BINAP (1.92 g, 3.0 mmol), sodium tert-butoxide (4.15 g, 43.0 mmol), and benzophenone imine (6.9 mL, 37.0 mmol), heat at 80° C. in 200 mL of toluene. After 18 hr., cool the reaction to room temperature, and partition between ethylacetate and water. Extract with ethylacetate (1×), and methylene dichloride (2×), combine organics and dry over MgSO$_4$, and concentrate. Dissolve residue in of 1:1 1 N aqueous HCl/THF (200 mL), stir at room temperature. After 2 hr., adjust aqueous layer to pH>10 with 5 N NaOH. Partition between ethylacetate and water, extract aqueous layer with ethylacetate (1×) and methylene dichloride three times. Combine organics, dry over MgSO$_4$, concentrate, and further purify by chromatography (silica gel, eluting with 0-20% 2 M NH$_3$ in methanol/ethylacetate), to obtain the title compound (6.3 g, 99% yield). Mass spectrum (ion spray): m/z=208.1 (M+1); Anal calcd for C$_{11}$H$_{17}$N$_3$O.HCl.0.85H$_2$O: Theory: C, 51.00; H, 7.67; N, 16.22. Found: C, 50.72; H, 7.27; N, 16.22.

Preparation 61. 4-[6-(Benzhydrylidene-amino)-pyridin-2-yloxy]-2-methyl-piperidine-1-carboxylic acid tert-butyl ester cis isomer 1

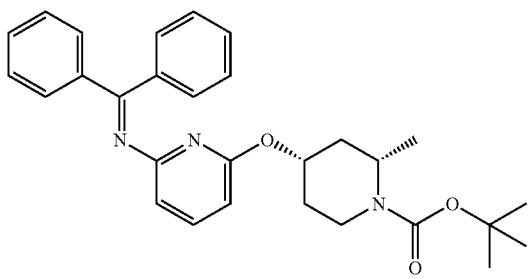

Combine 4-(6-chloro-pyridin-2-yloxy)-2-methyl-piperidine-1-carboxylic acid tert-butyl ester cis isomer 1 (preparation 49, 4.50 g, 13.77 mmol), toluene (150 mL), benzhydrylideneamine (3.0 g, 16.52 mmol), sodium-t-butoxide (1.85 g, 19.28 mmol), and 2,2'-bis(diphenylphosphino)-1,1'-binaphthyl (0.343 g, 0.55 mmol), stir and heat at 100° C. After 10 min., add tris(dibenzylideneacetone)-dipalladium(0) (0.252 g, 0.275 mmol), stir and heat at 100° C. After 3 hr., cool to ambient temperature. Partition between water (200 mL) and 4:1 hexane:ethyl acetate (200 mL). Separate the aqueous fraction and wash again with 4:1 hexane:ethyl acetate (200 mL). Dry the combined organic layers over sodium sulfate, filter and concentrate. Purify the residue by silica gel flash chromatography eluting with 9:1:0.2 hexane:ethyl acetate: 2M ammonia/methanol to obtain the title compound (6.08 g, 94%). $^1$H NMR (CDCl$_3$): 7.8 (d, 2H), 7.45 (m, 4H), 7.3 (m, 3H), 7.2 (m, 2H), 6.3 (dd, 2H), 5.1 (m, 1H), 4.2 (m, 1H), 3.8 (m, 1H), 3.2 (m, 1H), 1.6 (m, 4H), 1.5 (s, 9H), 1.2 (d, 3H).

Preparation 62. 4-[6-(Benzhydrylidene-amino)-pyridin-2-yloxy]-cis-2-methyl-piperidine-1-carboxylic acid tert-butyl ester isomer 2

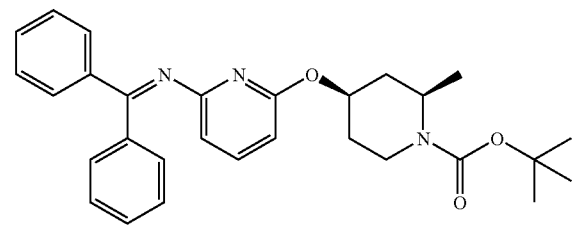

Combine 4-(6-chloro-pyridin-2-yloxy)-cis-2-methyl-piperidine-1-carboxylic acid tert-butyl ester isomer 2 (preparation 48, 0.725 g), benzhydrylideneamine (0.482 g), racemic-2,2'-bis(diphenylphosphino)-1,1'binaphthyl (55 mg) and sodium t-butoxide (0.299 g) in toluene (20 mL) and heat at 100° C. After 10 min., add tris(dibenzylidineacetone)-dipalladium(0) (41 mg) and heat at 100° C. After 2.5 hr., partition between ethyl acetate-hexane (1:4) and saturated aqueous NaCl, dry over anhydrous sodium sulfate, evaporate and purify on a 10 g silica gel column eluting with dichloromethane-2M NH$_3$ in methanol, gradient) to give the crude title compound (1.19 g). Mass spectrum (electrospray): m/z=472 (M+1).

Preparation 63. 4-(6-Amino-pyridin-2-yloxy)-2-methyl-piperidine-1-carboxylic acid tert-butyl ester cis isomer 1

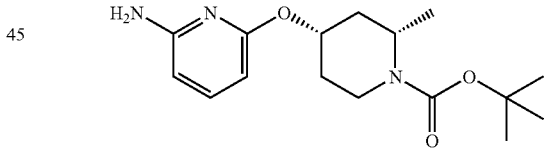

Combine 4-[6-(benzhydrylidene-amino)-pyridin-2-yloxy]-2-methyl-piperidine-1-carboxylic acid tert-butyl ester cis isomer 1 (preparation 61), methanol (150 mL), sodium acetate (2.54 g, 30.94 mmol), and hydroxylamine monohydrogen chloride (1.61 g, 23.2 mmol) and stir. After 30 min., partition between 0.25 M sodium hydroxide solution (100 mL) and 1:1 hexane:ethyl acetate (300 mL). Combine organic layers, wash with aqueous NaCl solution, dry over sodium sulfate, filter and concentrate. Purify the residue by silica gel flash chromatography eluting with 9:1:0.2 hexane: ethyl acetate:2M ammonia/methanol to obtain the title compound (2.81 g, 70%). $^1$H NMR (CDCl$_3$): 7.3 (dd, 1H), 6.05 (m, 2H), 5.3 (m, 1H), 4.3 (m, 1H), 4.25 (bs, 2H), 3.85 (m, 1H), 3.25 (m, 1H), 1.9 (m, 3H), 1.7 (m, 1H), 1.5 (s, 9H), 1.3 (d, 3H).

Preparation 64. 4-(6-Amino-pyridin-2-yloxy)-cis-2-methyl-piperidine-1-carboxylic acid tert-butyl ester isomer 2

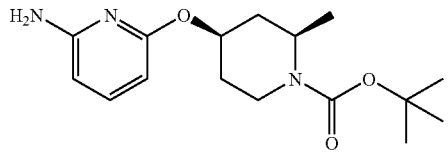

Combine 4-[6-(benzhydrylidene-amino)-pyridin-2-yloxy]-cis-2-methyl-piperidine-1-carboxylic acid tert-butyl ester isomer 2 (preparation 62, 1.19 g) in methanol (30 mL), add sodium acetate (0.497 g), and hydroxyamine hydrochloride (0.316 g) and stir at room temperature. After 1 hr., partition between dichloromethane and saturated aqueous NaCl, dry over anhydrous sodium sulfate, evaporate and purify on a silica gel column, eluting with dichloromethane-2M $NH_3$ in methanol, gradient) to give the title compound (0.687 g). $^1$H NMR (CDCl$_3$): 7.33 (t, 1H), 6.03 (m, 21), 5.25 (m, 1H), 4.33 (m, 3H), 3.87 (m, 1H), 3.25 (m, 1H), 1.91 (m, 3H), 1.73 (m, 1H), 1.46 (s, 9H), 1.27 (d, 3H).

Preparation 65. Racemic 6-(1-benzyl-3-trans-methyl-piperidin-4-yloxy)-pyridin-2-ylamine

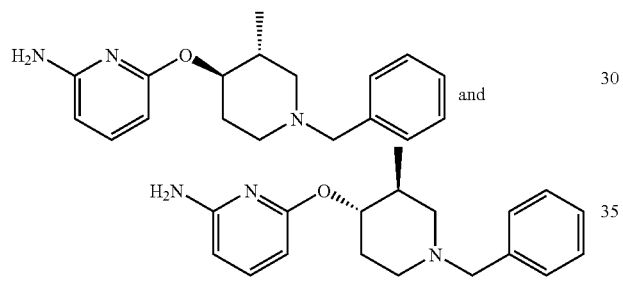

Combine racemic 2-(1-benzyl-3-trans-methyl-piperidin-4-yloxy)-6-chloro-pyridine (preparation 53, 10.32 g), benzhydrylideneamine (7.08 g), racemic-2,2'-bis(diphenylphosphino)-1,1'binaphthyl (0.811 g) and sodium t-butoxide (4.38 g) in toluene (200 mL) and heat at 100° C. After 15 min., add tris(dibenzylidineacetone)-dipalladium(0) (0.596 g) and heat at 100° C. After 4 hr., add concentrated hydrochloric acid (10 mL) to the resulting benzhydrylidene-[6-(1-benzyl-3-trans-methyl-piperidin-4-yloxy)-pyridin-2-yl]-anine and heat at 100° C. After for 30 min., partition between ethyl acetate and saturated aqueous NaCl. Basify the aqueous phase with 5N NaOH and extract with ethyl acetate and dry over anhydrous sodium sulfate, evaporate and purify on a silica gel column eluting with dichloromethane-2M NH$_3$ in methanol, gradient to give the title compound (7.6 g, 78% yield). Mass spectrum (electrospray) m/z=298 (M+1); $^1$H NMR (CDCl$_3$): 7.33 (m, 5H), 7.26 (m, 1H), 6.06 (d, 1H), 6.02 (d, 1H), 4.51 (m, 1H), 4.22 (br s, 2H), 3.52 (s, 2H), 2.85 (m, 2H), 2.15 (m, 2H), 1.97 (m, 1H), 1.85 (m, 1H), 1.63 (m, 1H), 0.92 (d, J=6.7 Hz, 3H).

Preparation 66. 6-(1-Benzyl-2,2-dimethyl-piperidin-4-yloxy)-pyridin-2-ylamine

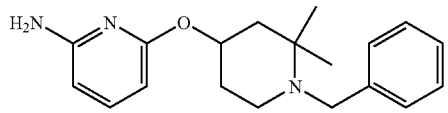

Combine 2-(1-benzyl-2,2-dimethyl-piperidin-4-yloxy)-6-chloro-pyridine (preparation 54, 0.57 g, 1.72 mmol), benzhydrylideneamine (0.31 g, 1.72 mmol) and toluene (20 mL), add sodium-t-butoxide (0.22 g, 2.24 mmol), 2,2'-bis(diphenylphosphino)-1,1'-binaphthyl (0.043 g, 0.69 mmol), stir and heat at 80° C. After 10 min., add tris(dibenzylideneacetone)-dipalladium(0) (0.032 g, 0.345 mmol), stir and heat at 80° C. After 16 hr., add tris(dibenzylideneacetone)-dipalladium(0) (0.032 g, 0.345 mmol) and continue heating. After additional 24 hr., cool to ambient temperature. Partition between water (50 mL) and ethyl acetate (50 mL). Separate the organic layer, wash with aqueous NaCl solution (50 mL), dry over sodium sulfate, filter and concentrate. Dissolve residue in tetrahydrofuran (80 mL) and treat with 1M aqueous hydrochloric acid (30 mL) with stirring. After 1 hr., make the reaction mixture basic by adding 2M aqueous sodium hydroxide solution; extract with ethyl acetate. Separate the organic layer, dry over sodium sulfate, filter and concentrate. Purify residue by silica gel flash chromatography eluting with 5% (2M ammonia/methanol)/dichloromethane to of impure title compound (0.50 g). Mass spectrum (electrospray): m/z=312.2 (M+1).

Preparation 67. 6-(1-Allyl-2-methyl-piperidin-4-yloxy)-pyridin-2-ylamine

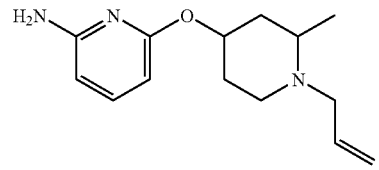

Using a method similar to preparation 66, using 2-chloro-6-(1-Allyl-2-methyl-piperidin-4-yloxy)pyridine (preparation 47) gives the title compound (41%). Use this product as is in subsequent steps without characterization to obtain compounds of the present invention.

Preparation 68. 6-(1-Benzyl-3-methyl-piperidin-4-yloxy)-pyridin-2-ylamine (4 isomers)

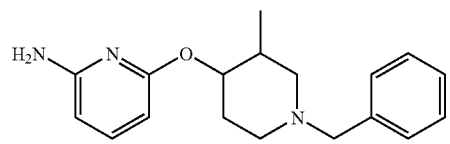

Using a method similar to preparation 66, using 2-chloro-6-(1-benzyl-3-methyl-piperidin-4-yloxy)pyridine (preparation 51, gives the title compound (39%). $^1$H NMR (CDCl$_3$): 7.35 (m, 6H), 6.08 (d, 1H), 6.02 (d, 1H), 4.51 (m, 1H), 4.23 (s, 2H), 3.54 (bs, 2H), 2.89 (m, 2H), 2.14 (m, 2H), 1.93 (m, 2H), 1.63 (m, 1H), 0.94 (d, 3H).

Preparation 69. 6-(1-Benzyl-3-methyl-piperidin-4-yloxy)-pyridin-2-ylamine cis isomers 1 and 2

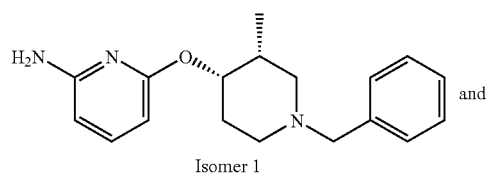
Isomer 1

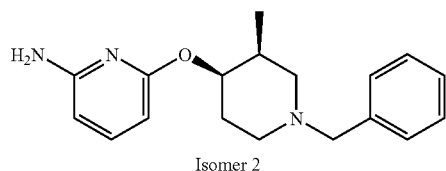
Isomer 2

Using a method similar to preparation 66, using racemic 2-chloro-6-(1-benzyl-cis-3-methyl-piperidin-4-yloxy)pyridine (preparation 52), and resolving on a Chiralcel OJ™ 4.6×250 mm column eluting with 20/5/75 IPA/methanol/Heptane w/0.2% DMEA at a flow rate of 1.0 mL/min. to obtain the two cis enantiomers: Mass spectrum (electrospray): m/z=298.2 (M+1).

Preparation 70. 6-(1-cyclopropylmethyl-piperidin-4-yloxy)-pyridin-2-ylamine

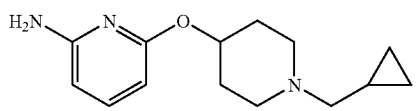

Combine 2-chloro-6-(1-cyclopropylmethyl-piperidin-4-yloxy)-pyridine (preparation 56, 480 mg, 1.80 mmol), benzophenone imine (391 mg, 2.16 mmol), BINAP (67 mg, 0.11 mmol), pd$_2$(dba)$_3$ (33 mg, 0.036 mmol), sodium t-butoxide (242 mg, 2.52 mmol) and toluene (8 mL) and heat at 100° C. for 14 hr. Quench the reaction with saturated NaHCO$_3$ solution, extract with ethyl acetate three times. Combine the organic layers, dry over Na$_2$SO$_4$, filter and concentrate under reduced pressure to give a residue. Dissolve the residue in THF (10 mL), add 5N HCl (1.0 mL) and stir for 30 min. Dilute the mixture with 0.1N HCl solution, extract twice with ethyl acetate-hexanes (1:2). Keep the aqueous layer and adjust pH>11 with 5N NaOH solution, extract with methylene dichloride three times. Combine the organic layers, dry over Na$_2$SO$_4$, filter and concentrate to give a residue. Chromatography (silica gel) eluting with 7% 2M NH$_3$-methanol in methylene dichloride provides 310 mg (70%) of the title compound as a white solid: mass spectrum (ion spray): m/z=248.1 (M+1); $^1$H NMR (CDCl$_3$, ppm): 7.23 (t, 1H), 5.95 (pseudo-t, 2H), 4.81 (m, 1H), 4.14 (s, br, 2H), 2.76 (m, 2H), 2.26 (m, 2H), 2.18 (d, 2H), 1.92 (m, 2H), 1.71 (m, 2H), 0.80 (m, 1H), 0.44 (m, 2H), 0.00 (m, 2H).

Preparation 71. 4-(6-Amino-pyridin-2-yloxy)-piperidine-1-carboxylic acid tert-butyl ester

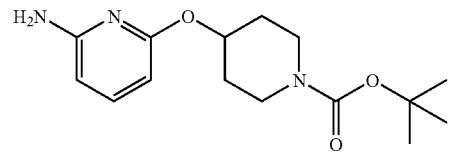

Combine 4-(6-chloro-pyridin-2-yloxy)-piperidine-1-carboxylic acid tert-butyl ester (preparation 57, 2.256 g, 7.2 mmol), benzophenone imine (1.568 g, 8.6 mmol), BINAP (269 mg, 0.43 mmol), Pd$_2$(dba)$_3$ (132 mg, 0.144 mmol), sodium t-butoxide (969 mg, 10.08 mmol) and toluene (50 mL) and heat at 95° C. for 12 hr. Quench the reaction with saturated NaHCO$_3$ solution, extract with ethyl acetate three times. Combine the organic layers, dry over Na$_2$SO$_4$, filter and concentrate to give a residue. Dissolve the residue in methanol (70 mL), add sodium acetate (1.42 g, 17.3 mmol) and hydroxylamine hydrochloride (900 mg, 13 mmol), stir at room temperature for 30 min. Partition between 1N NaOH and CH$_2$Cl$_2$, extract the aqueous layer twice with CH$_2$Cl$_2$. Combine the organic layers and wash with saturated NaCl solution, dry over Na$_2$SO$_4$, filter and concentrate to give a residue. Chromatography (silica gel, eluting with 12-25% ethyl acetate in hexanes) provides 2.06 g (98%) of the title compound as a yellow solid: mass spectrum (ion spray): 294.1 (M+1); $^1$H NMR (CDCl$_3$, ppm): 7.35 (t, 1H), 6.08 (d, 1H), 6.06 (d, 1H), 5.09 (m, 1H), 4.32 (s, br, 2H), 3.75 (m, 2H), 3.29 (m, 2H), 1.94 (m, 2H), 1.73 (m, 2H), 1.49 (s, 9H).

Preparation 72. 6-(1-Methyl-piperidin-4-yloxy)-pyridin-2-ylamine

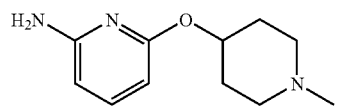

Using a method similar to preparation 70, using 2-chloro-6-(1-methyl-piperidin-4-yloxy)-pyridine (preparation 58, 1.525 g, 6.73 mmol) provides 1.097 g (79%) of the title compound: mass spectrum (ion spray): m/z=208.0 (M+1); $^1$H NMR (CDCl$_3$, ppm): 7.34 (t, 1H), 6.06 (m 2H), 4.92 (m, 1H), 4.26 (s, br, 2H), 2.72 (m, 2H), 2.32 (m, 5H), 2.05 (m, 2H), 1.82 (m, 2H).

Preparation 73. N-[6-(1-Methyl-piperidin-4-yloxy)-pyridin-2-yl]-acetamide

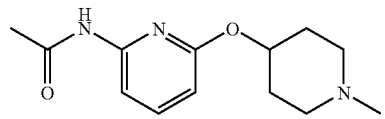

Add acetyl chloride (118 mg, 0.11 mL, 1.50 mmol) slowly to a solution of 6-(1-methyl-piperidin-4-yloxy)-pyridin-2-ylamine (preparation 72, 260 mg, 1.25 mmol) in triethylamine (190 mg, 0.26 mL, 1.88 mmol) and THF (10 mL), heat at 40° C. overnight. Quench the reaction with 0.1N NaOH, extract with methylene dichloride three times. Combine the organic layers, dry over $Na_2SO_4$, filter and concentrate to give a residue. Chromatography (silica gel) eluting with 4.5% 2M $NH_3$-methanol in methylene dichloride provides 238 mg (76%) of the title compound as an oil: mass spectrum (ion spray): m/z=250.0 (M+1); $^1$H NMR ($CDCl_3$, ppm): 7.70 (m, 2H), 7.56 (t, 1H), 6.44 (d, 1H), 4.91 (m, 1H), 2.68 (m, 2H), 2.34 (m, 5H), 2.20 (s, 3H), 2.00 (m, 2H), 1.81 (m, 2H).

Preparation 74. Ethyl-[6-(1-methyl-piperidin-4-yloxy)-pyridin-2-yl]-amine

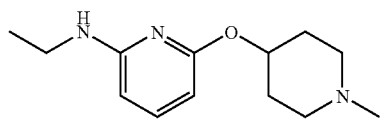

Add $LiAlH_4$ (108 mg, 2.85 mmol) to a solution of N-[6-(1-methyl-piperidin-4-yloxy)-pyridin-2-yl]-acetamide (preparation 73, 238 mg, 0.95 mmol) in THF (10 mL) and heat at reflux for 3 days. Quench the reaction with water, add 1N NaOH and water, stir for 30 min. Extract with methylene dichloride three times, combine the organic layers, dry over $Na_2SO_4$, filter and concentrate to give a residue. Chromatography (silica gel) eluting with 4% 2M $NH_3$-methanol in methylene dichloride provides 110 mg (49%) of the title compound as a colorless oil: mass spectrum (ion spray): m/z=236.0 (M+1); $^1$H NMR ($CDCl_3$, ppm): 7.34 (t, 1H), 6.00 (d, 1H), 5.90 (d, 1H), 4.95 (m, 1H), 4.30 (m, 1H), 3.26 (m, 2H), 2.73 (m, 2H), 2.31 (s, 3H), 2.29 (m, 2H), 2.02 (m, 2H), 1.84 (m, 2H), 1.25 (t, 3H).

Preparation 75. 4-(3-Fluoro-5-nitro-phenylsulfanyl)-1-methyl-piperidine

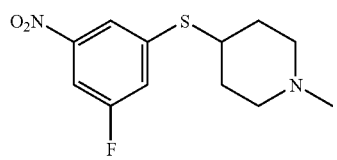

Combine 1-methyl-piperidine-4-thiol (1.4 g, 10.67 mmol) and N,N-dimethylformamide (10 mL) and cool to 0° C. Add 95% sodium hydride (0.28 g, 11.20 mmol), warm to ambient temperature and stir. After 40 min., add 1,3-difluoro-5-nitro-benzene (1.21 mL, 10.67 mmol), stir and heat at 65° C. After 3 hr., cool to ambient temperature and add water (50 mL). Extract with ethyl acetate (3×50 mL), wash combined organic layers with water (3×50 mL), aqueous NaCl solution (50 mL), dry organic layer over sodium sulfate, filter and concentrate. Purify residue by silica gel flash chromatography eluting with 10% (2M $NH_3$/methanol)/methylene dichloride to obtain the title compound (0.31 g, 11%). Mass spectrum (electrospray): m/z=271.1 (M+1).

Preparation 76.
3-(1-Methyl-piperidin-4-ylsulfanyl)-phenyl amine

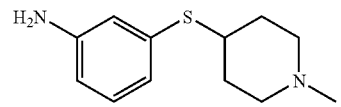

Combine 3-amino-benzenethiol (1.87 mL, 17.83 mmol), 4-chloro-1-methyl-piperidine hydrochloride (2.0 g, 11.76 mmol), cesium carbonate (8.42 g, 25.87 mmol), and dimethylformamide (60 mL), stir and heat at 80° C. After 18 hr., cool to ambient temperature and filter. Wash the filtrate with water (3×20 mL) and extract with diethyl ether (2×30 mL). Combine the organic layers, dry over magnesium sulfate, filter and concentrate. Purify through a plug of silica gel using dichloromethane/2.0 M ammonia in methanol (20:1 mixture ratio) to give the title compound as a pale orange oil (1.52 g, 58%): Mass spectrum (ion spray): m/z=223.1 (M+1), $^1$H NMR (free base, $CDCl_3$): 7.10 (t, J=7.8 Hz, 1H), 6.84-6.80 (m, 1H), 6.77 (t, J=2.0 Hz, 1H), 6.58 (ddd, J=0.8, 2.2, 8.0 Hz, 1H), 3.69 (bs, 2H), 3.09 (bs, 1H), 2.85 (m, 2H), 2.31 (s, 3H), 2.16-1.99 (m, 4H), 1.79-1.64 (m, 2H). $^{13}$C NMR (free base, $CDCl_3$): 146.7, 135.2, 129.4, 122.0, 118.4, 113.7, 55.1, 46.1, 43.6, 32.5.

Example 1

N-[3-(1-Methyl-piperidin-4-yloxy)-phenyl]-benzamide hydrochloride

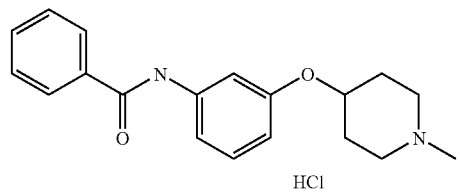

Add benzoyl chloride (0.062 mL, 0.534 mmol) to a solution of 3-(1-methyl-piperidin-4-yloxy)-phenylamine (preparation 28, 102 mg, 0.494 mmol) in dioxane (3.5 mL) in a sealed tube and heat at 110° C. for 2 hr. Purification by SCX column, eluting with ammonia (2.0 N in methanol) gives the title compound as the free base (137 mg, 91%). Dissolve the residue in diethyl ether and treat with ethereal hydrogen chloride (1.0 M). Triturate the resulting gum with ether to give the title compound as the hydrochloride salt (139 mg, off-white solid). Mass spectrum (free base, ion spray): m/z=311.2 (M+1), $^1$H NMR (free base, $CDCl_3$): 7.97 (bs, N—H), 7.85-7.82 (m, 2H), 7.52 (tt, J=1.3 Hz, 7.3 Hz, 1H), 7.49-7.42 (m, 3H), 7.22 (t, J=8.1 Hz, 1H), 7.05 (d, J=8.1 Hz, 1H), 6.69 (dd, J=2.1 Hz, 8.3 Hz, 1H), 4.38-4.30 (bm, 1H), 2.72-2.62 (bm, 2H), 2.35-2.23 (bm, 5H), 2.04-1.96 (bm, 2H), 1.89-1.79 (bm,

Example 2

2-Chloro-N-[3-(1-methyl-piperidin-4-yloxy)-phenyl]-benzamide hydrochloride

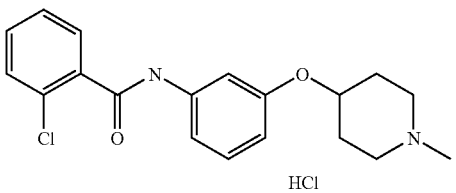

Combine 3-(1-methyl-piperidin-4-yloxy)-phenylamine (preparation 28, 185 mg, 0.90 mmol) in dichloromethane (9 mL), add pyridine (0.145 mL, 1.79 mmol) and stir at 0° C. for 5 min. Add 2-chloro-benzoyl chloride (0.142 mL, 1.12 mmol) and allow to warm to ambient temperature and stir. After 18 hr., dilute with dichloromethane (10 mL) and wash with sodium hydroxide (1N, 3×10 mL). Combine the organic layers, dry over sodium sulfate and concentrate under reduced pressure. Purify by flash chromatography, eluting with dichloromethane/ammonia (2.0 N in methanol) [20/1] to give the title compound as free base (112 mg, 36%). Dissolve the residue in diethyl ether and treat with ethereal hydrogen chloride (1.0 M). Triturate the resulting gum with ether to give the title compound as a white solid (115 mg). Mass spectrum (ion spray): m/z=345.1 (M+1); $^1$H NMR (free base, CDCl$_3$): 7.88 (bs, N—H), 7.76 (dd, J=1.5 Hz, 7.3 Hz, 1H), 7.52 (bs, 1H), 7.47-7.36 (m, 3H), 7.28-7.24 (m, 2H), 7.03 (d, J=8.0 Hz, 1H), 6.72 (dd, J=8.2 Hz, 2.4 Hz, 1H), 4.48 (bs, 1H), 2.88-2.80 (bm, 2H), 2.66-2.56 (bm, 2H), 2.45 (s, 3H), 2.22-2.13 (bm, 2H), 2.01-1.92 (bm, 2H).

Example 3

4-Fluoro-N-[3-(1-methyl-piperidin-4-yloxy)-phenyl]-benzamide hydrochloride

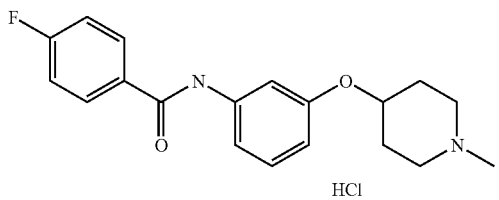

Using a method similar to Example 2, using 4-fluoro-benzoyl chloride (0.154 mL, 1.30 mmol), gives the title compound as free base (250 mg, 73%). Following a method similar to Example 2 gives the title compound as the hydrochloride salt (259 mg, yellow solid). Mass spectrum (free base, ion spray): m/z=329.2 (M+1), $^1$H NMR (free base, CDCl$_3$): 7.90-7.86 (m, 2H), 7.80 (bs, N—H), 7.46 (t, J=2.0 Hz, 1H), 7.24 (t, J=8.2 Hz, 2H), 7.16 (t, J=8.5 Hz, 2H), 7.03 (d, J=8.3 Hz, 1H), 6.71 (dd, J=2.1 Hz, 8.3 Hz, 1H), 4.43-4.36 (bm, 1H), 2.78-2.69 (bm, 2H), 2.34-2.44 (bm, 2H), 2.35 (s, 3H), 2.11-2.03 (bm, 2H), 1.94-1.85 (bm, 2H). Analysis calculated for C$_{19}$H$_{23}$ClN$_2$O$_2$.0.6H$_2$O: C, 63.80; H, 6.82; N, 7.83. Found C, 63.67; H, 6.62; N, 7.83.

Example 4

2-Bromo-N-[3-(1-methyl-piperidin-4-yloxy)-phenyl]-benzamide hydrochloride

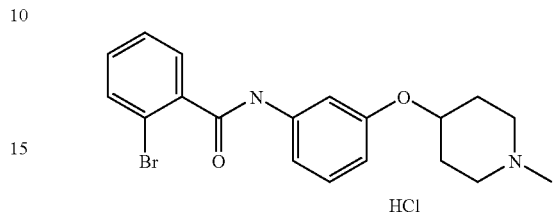

Using a method similar to Example 1, using 2-bromo-benzoyl chloride (0.070 ml, 0.534 mmol), gives the title compound as the free base (186 mg, 98%). Following a method similar to Example 1 gives the title compound as the hydrochloride salt (180 mg, off-white solid): Mp: 269° C. (dec.); mass spectrum (free base, ion spray): m/z=389.0 (M+1), $^1$H NMR (free base, CDCl$_3$): 7.67-7.62 (m, 3H), 7.49 (bs, N—H), 7.42 (td, J=1.2 Hz, 7.6 Hz, 1H), 7.33 (td, J=1.8 Hz, 7.8 Hz, 1H), 7.26 (t, J=8.2 Hz, 1H), 7.03 (d, J=8.2 Hz, 1H), 6.72 (dd, J=2.4 Hz, 8.4 Hz, 1H), 4.46-4.37 (bm, 1H), 2.82-2.68 (bm, 2H), 2.51-2.27 (bm, 5H), 2.17-2.04 (bm, 2H), 1.97-1.85 (bm, 2H). Analysis calculated for C$_{19}$H$_{22}$BrClN$_2$O$_2$.0.5H$_2$O: C, 52.49; H, 5.33; N, 6.44. Found C, 52.56; H, 5.26; N, 6.35.

Example 5

2,6-Difluoro-N-[3-(1-methyl-piperidin-4-yloxy)-phenyl]-benzamide hydrochloride

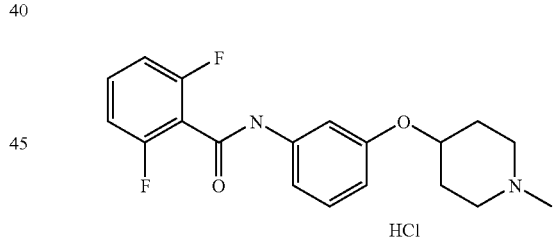

Using a method similar to Example 1, add 2,6-difluoro-benzoyl chloride (0.68 ml, 0.544 mmol) to a solution of 3-(1-methyl-piperidin-4-yloxy)-phenylamine (preparation 24, 102 mg, 0.494 mmol) in dioxane (3.5 mL) in a sealed tube and heat at 110° C. for 2 hr. Purification by SCX column, eluting with ammonia (2.0 N in methanol) gives the title compound as the free base (154 mg, 90%). Following a method similar to Example 1 gives the title compound as the hydrochloride salt (147 mg, white solid). Mp: 136-8° C.; mass spectrum (free base, ion spray): m/z=347.1 (M+1); $^1$H NMR (free base, CDCl$_3$): 7.62 (bs, N—H), 7.47 (s, 1H), 7.42 (t, J=2.0 Hz, 7.4 Hz, 1H), 7.24 (t, J=8.1 Hz, 1H), 7.04-6.97 (m, 3H), 6.73 (dd, J=2.0 Hz, 8.1 Hz, 1H), 4.43-4.35 (bm, 1H), 2.75-2.67 (bm, 2H), 2.39-2.33 (bm, 2H), 2.32 (s, 3H), 2.09-2.00 (bm, 2H), 1.92-1.82 (bm, 2H). Analysis calculated for C$_{19}$H$_{21}$ClF$_2$N$_2$O$_2$.0.5H$_2$O: C, 58.24; H, 5.66; N, 7.15. Found C, 58.56; H, 5.50; N, 7.12.

Example 6

3,4-Difluoro-N-[3-(1-methyl-piperidin-4-yloxy)-phenyl]-benzamide hydrochloride

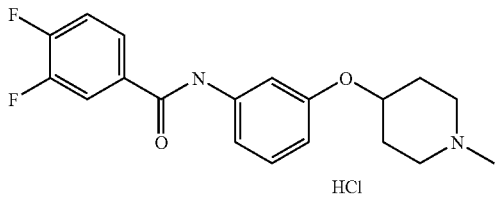

Using a method similar to Example 5, using 3,4-difluorobenzoyl chloride (0.012 mL), gives the title compound as the free base (33 mg, 100%). Following a method similar to Example 2 gives the title compound as the hydrochloride salt (10 mg, yellow solid). Mass spectrum (free base, ion spray): m/z=347.1 (M+1); $^1$H NMR (free base, CDCl$_3$): 8.00 (bs, N—H), 7.75-7.68 (m, 1H), 7.63-7.58 (m, 1H), 7.23 (dd, J=8.3 Hz, 16.4 Hz, 1H), 7.04 (d, J=7.8 Hz, 1H), 6.70 (dd, J=1.8 Hz, 8.3 Hz, 1H), 4.36-4.29 (bm, 1H), 2.72-2.63 (bm, 2H), 2.35-2.25 (bm, 5H), 2.05-1.96 (bm, 2H), 1.89-1.79 (bm, 2H); Analysis calculated for C$_{19}$H$_{21}$ClF$_2$N$_2$O$_2$.0.25H$_2$O: C, 58.92; H, 5.60; N, 7.23. Found C, 58.78; H, 5.56; N, 6.98.

Example 7

2,4-Difluoro-N-[3-(1-methyl-piperidin-4-yloxy)-phenyl]-benzamide hydrochloride

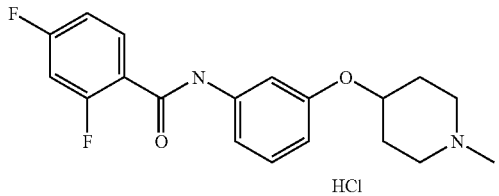

Using a method similar to Example 5, using 2,4-difluorobenzoyl chloride (0.060 mL, 0.485 mmol) gives the title compound as the free base (145 mg, 86%). Following a method similar to Example 2 gives the title compound as the hydrochloride salt (143 mg, tan solid). Mass spectrum (free base, ion spray): m/z=347.1 (M+1); $^1$H NMR (free base, CDCl$_3$): 8.32 (bd, J=15.3 Hz, N—H), 8.24-8.17 (m, 1H), 7.49 (s, 1H), 7.28-7.24 (m, 1H), 7.09-7.02 (m, 2H), 6.97-6.91 (m, 1H), 6.72 (dd, J=2.3 Hz, 8.3 Hz, 1H), 4.48-4.40 (bm, 1H), 2.83-2.73 (bm, 2H), 2.56-2.43 (bm, 2H), 2.40 (s, 3H), 2.19-2.07 (bm, 2H), 1.99-1.87 (bm, 2H).

Example 8

2,6-Dichloro-N-[3-(1-methyl-piperidin-4-yloxy)-phenyl]-benzamide hydrochloride

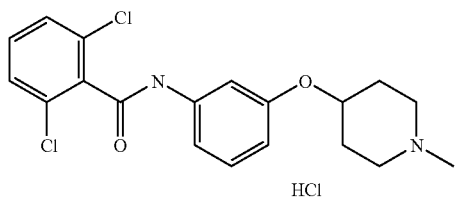

Using a method similar to Example 5, using 2,6-dichloro-benzoyl chloride (0.076 mL, 0.533 mmol) gives the title compound as the free base (170 mg, 92%). Following a method similar to Example 2 gives the title compound as the hydrochloride salt (163 mg, off-white solid). Mp: 170-1° C.; mass spectrum (free base, ion spray): m/z=379.1 (M+1); $^1$H NMR (free base, CDCl$_3$): 7.46-7.43 (bm, 2H), 7.38-7.23 (m, 4H), 7.04 (d, J=8.2 Hz, 1H), 6.74 (dd, J=2.2 Hz, 8.2 Hz, 1H), 4.43-4.37 (bm, 1H), 2.77-2.68 (bm, 2H), 2.43-2.34 (bm, 2H), 2.34 (s, 3H), 2.11-2.02 (bm, 2H), 1.94-1.84 (bm, 2H). Analysis calculated for C$_{19}$H$_{21}$Cl$_3$N$_2$O$_2$.0.5H$_2$O: C, 53.73; H, 5.22; N, 6.60. Found C, 53.42; H, 5.06; N, 6.58.

Example 9

2,4-Dichloro-N-[3-(1-methyl-piperidin-4-yloxy)-phenyl]-benzamide hydrochloride

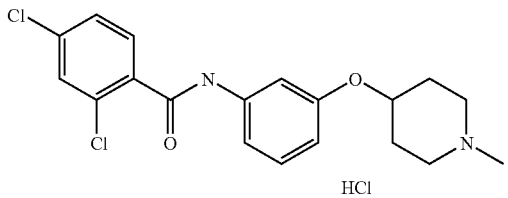

Using a method similar to Example 5, using 2,6-dichloro-benzoyl chloride (0.075 ml, 0.534 mmol) gives the title compound as the free base (156 mg, 85%). Following a method similar to Example 2 gives the title compound as the hydrochloride salt (157 mg, white solid). Mp: 131-3° C.; mass spectrum (free base, ion spray): m/z=379.0 (M+1); $^1$H NMR (free base, CDCl$_3$): 7.86 (bs, N—H), 7.73 (d, J=8.4 Hz, 1H), 7.48 (d, J=2.0 Hz, 1H), 7.46 (bs, 1H), 7.37 (dd, J=2.0 Hz, 8.4 Hz, 1H), 7.25 (t, J=8.2 Hz, 1H), 7.03 (d, J=8.2 Hz, 1H), 6.73 (dd, J=2.2 Hz, 8.4 Hz, 1H), 4.45-4.36 (bm, 1H), 2.80-2.69 (bm, 2H), 2.49-2.36 (bm, 2H), 2.37 (s, 3H), 2.14-2.04 (bm, 2H), 1.95-1.86 (bm, 2H); Analysis calculated for C$_{19}$H$_{21}$Cl$_3$N$_2$O$_2$.0.5H$_2$O: C, 53.73; H, 5.22; N, 6.60. Found C, 53.56; H, 4.87; N, 6.50.

Example 10

2-Chloro-6-fluoro-N-[3-(1-methyl-piperidin-4-yloxy)-phenyl]-benzamide hydrochloride

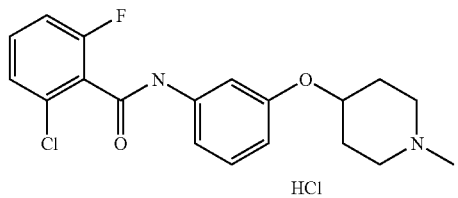

Using a method similar to Example 5, using 2-chloro-6-fluoro-benzoyl chloride (106 mg, 0.549 mmol) gives the title compound as the free base (159 mg, 90%). Following a method similar to Example 2 gives the title compound as the hydrochloride salt (173 mg, off-white solid). Mp: 153-4° C.; mass spectrum (free base, ion spray): m/z=363.1 (M+1); $^1$H NMR (free base, CDCl$_3$): 7.49 (bs, N—H), 7.46 (bs, 1H), 7.39-7.33 (m, 1H), 7.28-7.23 (m, 2H), 7.09 (t, J=8.4 Hz, 1H), 7.03 (d, J=8.2 Hz, 1H), 6.73 (dd, J=2.1 Hz, 8.1 Hz, 1H), 4.43-4.37 (bm, 1H), 2.76-2.68 (bm, 2H), 2.43-2.34 (bm, 2H), 2.34 (s, 3H), 2.10-2.02 (bm, 2H), 1.93-1.84 (bm, 2H); Analysis calculated for C$_{19}$H$_{21}$Cl$_2$FN$_2$O$_2$.0.25H$_2$O: C, 56.52; H, 5.37; N, 6.94. Found C, 56.68; H, 5.28; N, 7.02.

Example 11

2-Chloro-4-fluoro-N-[3-(1-methyl-piperidin-4-yloxy)-phenyl]-benzamide hydrochloride

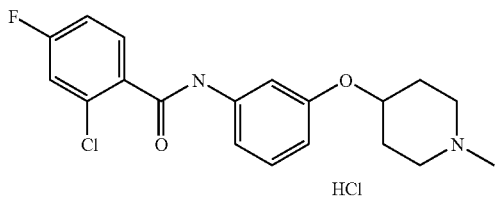

Using a method similar to Example 5, using 2-chloro-4-fluoro-benzoyl chloride (0.138 mL, 1.06 mmol) gives the title compound as the free base (152 mg, 86%). Following a method similar to Example 2 gives the title compound as the hydrochloride salt (156 mg, off-white solid). Mp: 213° C.; mass spectrum (free base, ion spray): m/z=363.1 (M+1H); $^1$H NMR (free base, CDCl$_3$): 8.68 (bs, 1H), 7.43-7.32 (m, 2H), 7.13-6.87 (m, 4H), 6.64 (bs, 1H), 4.22 (bs, 1H), 2.56 (bs, 2H), 2.19 (bs, 5H), 1.88 (bs, 2H), 1.75 (bs, 2H).

Example 12

2-Chloro-N-[3-(1-ethyl-piperidin-4-yloxy)-phenyl]-4-fluoro-benzamide hydrochloride

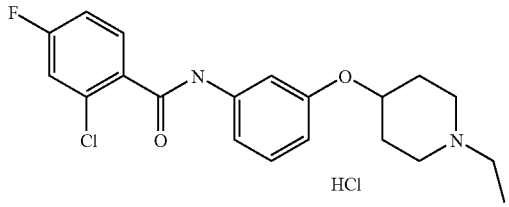

Using a method similar to Example 5, using 2-chloro-4-fluoro-benzoyl chloride (0.054 mL, 0.420 mmol) and 3-(1-ethyl-piperidin-4-yloxy)-phenylamine (preparation 29) gives the title compound as the free base (131 mg, 91%). Following a method similar to Example 2 gives the title compound as the hydrochloride salt (130 mg, white solid). Mp: 91° C.; mass spectrum (free base, ion spray): m/z=377.2 (M+1); $^1$H NMR (free base, CDCl$_3$): 8.14 (bs, N—H), 7.68 (dd, J=6.1 Hz, 8.7 Hz, 1H), 7.40 (bs, 1H), 7.21 (t, J=8.1 Hz, 1H), 7.14 (dd, J=2.5 Hz, 8.3 Hz, 1H), 7.06-7.01 (m, 2H), 6.70 (dd, J=2.4 Hz, 8.3 Hz, 1H), 4.38-4.31 (m, 1H), 2.75-2.67 (bm, 2H), 2.41 (q, J=7.1 Hz, 2H), 2.33-2.24 (bm, 2H), 2.04-1.97 (bm, 2H), 1.87-1.78 (bm, 2H), 1.08 (t, J=7.4 Hz, 3H); Analysis calculated for C$_{20}$H$_{23}$Cl$_2$FN$_2$O$_2$.0.25H$_2$O: C, 57.49; H, 5.67; N, 6.70. Found C, 57.45; H, 5.31; N, 6.59.

Example 13

2-Chloro-N-[3-(1-ethyl-piperidin-4-yloxy)-phenyl]-6-fluoro-benzamide hydrochloride

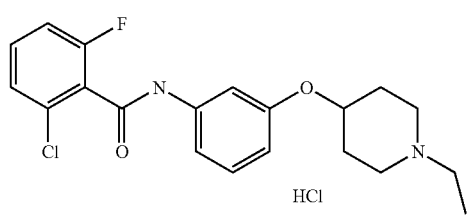

Using a method similar to Example 12, using 2,6-difluoro-benzoyl chloride (0.054 mL, 0.420 mmol) gives the title compound as the free base (100 mg, 69%). Following a method similar to Example 2 gives the title compound as the hydrochloride salt (103 mg, white solid). Mp: 262° C. (dec.); mass spectrum (free base, ion spray): m/z=377.2 (M+1); $^1$H NMR (free base, CDCl$_3$): 8.02 (bs, N—H), 7.40 (s, 1H), 7.29 (dd, J-=7.2 Hz, 15.3 Hz, 1H), 7.23-7.16 (m, 2H), 7.05-6.98 (m, 2H), 6.69 (dd, J=1.9 Hz, 8.1 Hz, 1H), 4.35-4.29 (bm, 1H), 2.73-2.66 (bm, 2H), 2.40 (q, J=7.4 Hz, 2H), 2.29-2.22 (bm, 2H), 2.03-1.95 (bm, 2H), 1.85-1.76 (bm, 2H), 1.07 (t, J=7.1 Hz, 3H); Analysis calculated for C$_{20}$H$_{23}$Cl$_2$FN$_2$O$_2$.0.25H$_2$O: C, 57.49; H, 5.67; N, 6.70. Found C, 57.14; H, 5.81; N, 6.52.

Example 14

2,4,6-Trifluoro-N-[3-(1-methyl-piperidin-4-yloxy)-phenyl]-benzamide hydrochloride

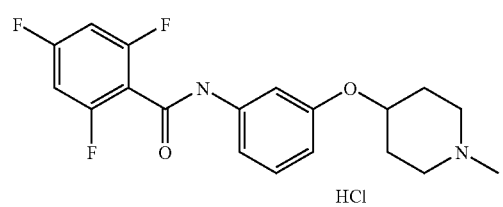

Using a method similar to Example 5, using 2,4,6-trifluoro-benzoyl chloride (106 mg, 0.545 mmol) gives the title compound as the free base (144 mg, 81%). Following a method similar to Example 2 gives the title compound as the hydrochloride salt (147 mg, off-white solid). Mp: 136° C. (dec.); mass spectrum (free base, ion spray): m/z=365.1 (M+1), $^1$H NMR (free base, CDCl$_3$): 7.60 (bs, 1H), 7.44 (bs, 1H), 7.27-7.22 (m, 1H), 7.01 (d, J=8.1 Hz, 1H), 6.80-6.71 (m, 3H), 4.42-4.35 (bm, 1H), 2.75-2.67 (bm, 2H), 2.41-2.34 (bm, 2H), 2.34 (s, 3H), 2.10-2.02 (bm, 2H), 1.92-1.83 (bm, 2H); Analysis calculated for C$_{19}$H$_{20}$ClF$_3$N$_2$O$_2$.0.5H$_2$O: C, 55.68; H, 5.16; N, 6.84. Found C, 55.59; H, 5.20; N, 6.86.

Example 15

2,3,4-Trifluoro-N-[3-(1-methyl-piperidin-4-yloxy)-phenyl]-benzamide hydrochloride

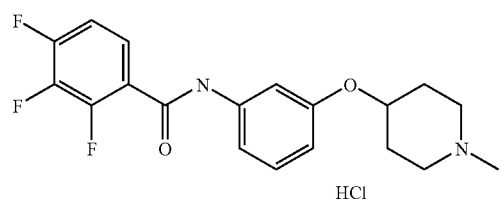

Using a method similar to Example 5, using 2,3,4-trifluoro-benzoyl chloride (0.016 mL) gives the title compound as the free base (36 mg, 99%). Following a method similar to Example 2 gives the title compound as the hydrochloride salt (10 mg, off-white solid). Mass spectrum (free base, ion spray): m/z=365.1 (M+1); $^1$H NMR (free base, CDCl$_3$): 8.21 (bd, J=12.9 Hz, N—H), 7.93-7.86 (m, 1H), 7.42 (bs, 1H), 7.26 (t, J=8.2 Hz, 1H), 7.16-7.09 (m, 1H), 7.05 (d, J=8.2 Hz, 1H), 6.73 (dd, J=2.3 Hz, 8.2 Hz, 1H), 4.40-4.33 (bm, 1H), 2.73-2.65 (bm, 2H), 2.37-2.27 (bm, 5H), 2.07-2.98 (bm, 2H), 1.91-1.81 (bm, 2H).

Example 16

N-[3-(1-Methyl-piperidin-4-yloxy)-phenyl]-2-trifluoromethoxy-benzamide hydrochloride

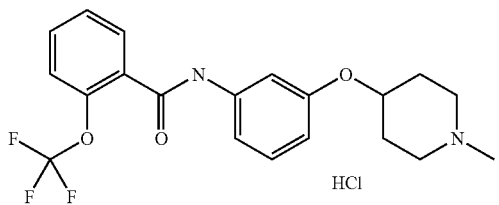

Using a method similar to Example 5, using 2-trifluoromethoxy-benzoyl chloride (122 mg, 0.544 mmol) gives the title compound as the free base (133 mg, 70%). Following a method similar to Example 2 gives the title compound as the hydrochloride salt (145 mg, white solid): Mp: 119-21° C.; mass spectrum (free base, ion spray): m/z=395.1 (M+1); $^1$H NMR (free base, CDCl$_3$): 8.27 (bs, N—H), 8.09 (dd, J=1.8 Hz, 7.8 Hz, 1H), 7.57 (td, J=1.8 Hz, 7.8 Hz, 1H), 7.49-7.44 (m, 2H), 7.35 (dt, J=1.2 Hz, 8.3 Hz, 1H), 7.25 (t, J=8.2 Hz, 1H), 7.02 (dd, J=1.4 Hz, 8.0 Hz, 1H), 6.73 (dd, J=2.4 Hz, 8.3 Hz, 1H), 4.43-4.36 (bm, 1H), 2.77-2.68 (bm, 2H), 2.43-2.34 (bm, 2H), 2.34 (s, 3H), 2.11-2.02 (bm, 2H), 2.94-2.85 (bm, 2H); Analysis calculated for C$_{20}$H$_{22}$ClF$_3$N$_2$O$_3$: C, 55.75; H, 5.15; N, 6.50. Found C, 55.49; H, 5.21; N, 6.67.

Example 17

N-[3-(1-Methyl-piperidin-4-yloxy)-phenyl]-2-trifluoromethyl-benzamide hydrochloride

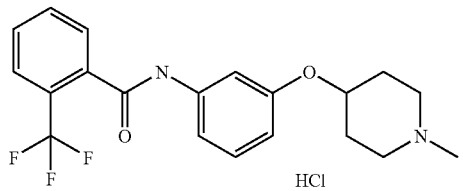

Using a method similar to Example 5, using 2-trifluoromethyl-benzoyl chloride (0.079 ml, 0.533 mmol) gives the title compound as the free base (149 mg, 81%). Following a method similar to Example 2 gives the title compound as the hydrochloride salt (146 mg, white solid). Mp: 135-6° C.; mass spectrum (free base, ion spray): m/z=379.1 (M+1); $^1$H NMR (free base, CDCl$_3$): 7.76 (bd, J=7.6 Hz, 1H), 7.65 (d, J=4.6 Hz, 2H), 7.63-7.57 (m, 1H), 7.43 (bs, 1H), 7.41 (bt, J=2.2 Hz, 1H), 7.25 (t, J=8.2 Hz, 1H), 7.00 (dd, J=1.4 Hz, 8.1 Hz, 1H), 6.73 (dd, J=2.2 Hz, 8.3 Hz, 1H), 4.44-4.35 (bm, 1H), 2.77-2.68 (bm, 2H), 2.44-2.34 (bm, 2H), 2.34 (s, 3H), 2.11-2.02 (bm, 2H), 1.93-1.84 (bm, 2H); Analysis calculated for C$_{20}$H$_{22}$ClF$_3$N$_2$O$_2$.0.25H$_2$O: C, 57.28; H, 5.41; N, 6.68. Found C, 57.13; H, 5.42; N, 6.82.

Example 18

4-Fluoro-N-[3-(1-methyl-piperidin-4-yloxy)-phenyl]-2-trifluoromethyl-benzamide hydrochloride

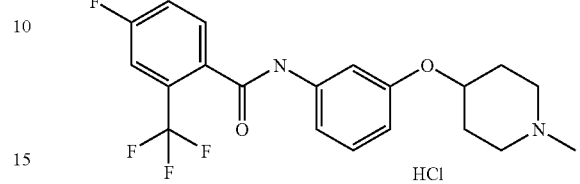

Using a method similar to Example 5, using 4-fluoro-2-trifluoromethyl-benzoyl chloride (0.018 ml) gives the title compound as the free base (39 mg, 100%). Following a method similar to Example 2 gives the title compound as the hydrochloride salt (10 mg, off-white solid). Mass spectrum (free base, ion spray): m/z=397.1 (M+1); $^1$H NMR (free base, CDCl$_3$): 7.66-7.60 (m, 2H), 7.42 (dd, J=2.4 Hz, 8.8 Hz, 1H), 7.35 (t, J=2.0 Hz, 1H), 7.30 (td, j=2.4 Hz, 8.1 Hz, 1H), 7.23 (t, J=8.1 Hz, 1H), 6.99 (dd, J=1.4 Hz, 8.0 Hz, 1H), 6.72 (dd, J=2.0 Hz, 8.3 Hz, 1H), 4.38-4.31 (bm, 1H), 2.72-2.64 (bm, 2H), 2.36-2.25 (bm, 5H), 2.06-1.97 (bm, 2H), 1.89-1.80 (bm, 2H); Analysis calculated for C$_{20}$H$_{21}$ClF$_4$N$_2$O$_2$.0.25H$_2$O: C, 54.93; H, 4.96; N, 6.41. Found C, 54.96; H, 4.94; N, 6.13.

Example 19

6-Fluoro-N-[3-(1-methyl-piperidin-4-yloxy)-phenyl]-2-trifluoromethyl-benzamide hydrochloride

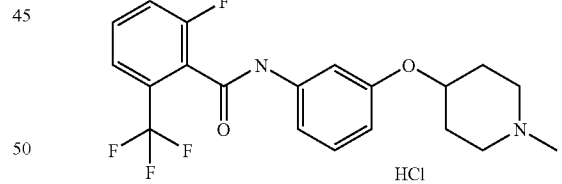

Using a method similar to Example 5, using 2-fluoro-6-trifluoromethyl-benzoyl chloride (0.015 mL) gives the title compound as the free base (39 mg, 98%). Following a method similar to Example 2 gives the title compound as the hydrochloride salt (12 mg, off-white solid). Mass spectrum (free base, ion spray): m/z=397.1 (M+1); $^1$H NMR (free base, CDCl$_3$): 7.75 (bs, N—H), 7.57-7.50 (m, 2H), 7.37-7.32 (m, 2H), 7.23 (t, J=8.2 Hz, 1H), 7.01 (dd, J=1.7 Hz, 8.0 Hz, 1H), 6.72 (dd, J=2.2 Hz, 8.3 Hz, 1H), 4.38-4.31 (bm, 1H), 2.72-2.63 (bm, 2H), 2.36-2.26 (bm, 5H), 2.05-1.97 (bm, 2H), 1.89-1.79 (bm, 2H).

Preparation 77. 4-[3-(2-Chloro-4-fluoro-benzoylamino)-phenoxy]-piperidine-1-carboxylic acid tert-butyl ester

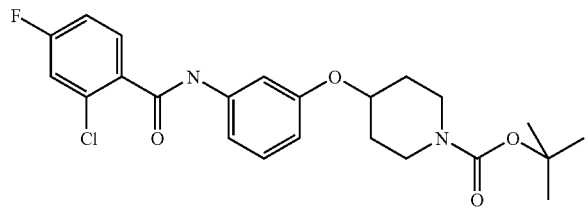

Add pyridine (0.66 mL, 8.21 mmol) to a solution of 4-(3-amino-phenoxy)-piperidine-1-carboxylic acid tert-butyl ester (preparation 30, 2.0 g, 6.84 mmol) in dichloromethane (35 mL) at 0° C. Stir and add 2-chloro-4-fluorobenzoyl chloride dropwise (1.45 g, 7.52 mmol). Stir at 0° C. for 30 min and 1 hr. at room temperature. Dilute with dichloromethane (30 mL) and wash with sodium hydroxide (1N, 2×25 mL). Combine the organic layers, dry over sodium sulfate and concentrate under reduced pressure. Purification by flash chromatography, eluting with ethyl acetate/hexanes [20-40%] to give the title compound (3.0 g, 98%). Mass spectrum (ion spray): m/z=449.0 (M+1); $^1$H NMR (CDCl$_3$): 7.87 (bs, N—H), 7.80 (dd, J=6.1 Hz, 8.6 Hz, 1H), 7.48 (s, 1H), 7.28-7.24 (m, 1H), 7.21 (dd, J=2.5 Hz, 8.4 Hz, 1H), 7.11 (td, J=2.2 Hz, 8.4 Hz, 1H), 7.03 (d, J=8.4 Hz, 1H), 6.73 (dd, J=2.2 Hz, 8.4 Hz, 1H), 4.52 (septet, J=3.6 Hz, 1H), 3.69 (ddd, J=3.7 Hz, 7.7 Hz, 13.6 Hz, 2H), 3.35 (ddd, J=3.9 Hz, 7.7 Hz, 13.6 Hz, 2H), 1.97-1.89 (m, 2H), 1.81-1.72 (m, 2H), 1.46 (s, 9H).

Example 20

2-Chloro-4-fluoro-N-[3-(piperidin-4-yloxy)-phenyl]-benzamide hydrochloride

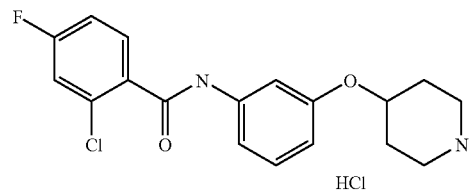

Combine 4-[3-(2-chloro-4-fluoro-benzoylamino)-phenoxy]-piperidine-1-carboxylic acid tert-butyl ester (preparation 77, 2.99 g, 6.67 mmol), dioxane (30 mL) and a solution of hydrogen chloride in dioxane (4M, 15 mL) and stir at room temperature. After 2 hr., concentrate at reduced pressure to remove the solvent, dry under vacuum to give the title compound as a white solid (2.56 g, 100%): Mass spectrum (ion spray): m/z=349.0 (M+1); Analysis calculated for C$_{18}$H$_{19}$Cl$_2$FN$_2$O$_2$.0.25H$_2$O: C, 55.47; H, 5.04; N, 7.19. Found C, 55.26; H, 5.09; N, 6.80.

Example 21

2-Chloro-6-fluoro-N-[3-(piperidin-4-yloxy)-phenyl]-benzamide hydrochloride

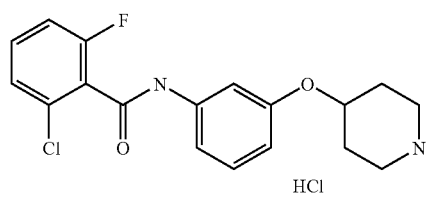

Combine 4-(3-amino-phenoxy)-piperidine-1-carboxylic acid tert-butyl ester (preparation 30, 100 mg, 0.342 mmol), dioxane (2 mL) and polymer bound morpholine resin (205 mg, 0.513 mmol) and add 2-chloro-6-fluoro-benzoyl chloride (0.048 mL, 0.376 mmol), shake (in a J-KEM® block) and heat at 106° C. After 2 hr., dilute with methanol (5 mL) and add tris-amine resin (100 mg), shake in a rotary evaporator overnight, filter, concentrate and use directly in the next step. Combine methanol (5 mL) and acetyl chloride (2.5 mL) and stir at 0° C. After 1 hr., add a solution of 4-[3-(2-chloro-6-fluoro-benzoylamino)-phenoxy]-piperidine-1-carboxylic acid tert-butyl ester in methanol (2 mL) and stir at room temperature. After 30 min., concentrate under reduced pressure, dissolve the residue in ethyl acetate (10 mL), wash with NaHCO$_3$ (sat. aq., 10 mL), dry the organic layers over magnesium sulfate, filter and concentrate under reduced pressure to give 100 mg (84%, 2 steps) of the titled compound as the free base. Following a method similar to Example 2 gives the title compound as the hydrochloride salt (130 mg, off-white solid). Mp: 139-42° C.; mass spectrum (free base, ion spray): m/z=311.2 (M+1); $^1$H NMR (free base, CDCl$_3$): 8.19 (bs, N—H), 7.41 (t, J=2.1 Hz, 1H), 7.35-7.29 (m, 1H), 7.26-7.20 (m, 2H), 7.07-7.02 (m, 2H), 6.70 (dd, J=2.3 Hz, 8.4 Hz, 1H), 4.43-4.36 (m, 1H), 3.11-3.04 (m, 2H), 2.74-2.67 (m, 2H), 2.50 (bs, N—H), 2.04-1.95 (m, 2H), 1.72-1.62 (m, 2H).

Example 22

2,4,6-Trifluoro-N-[3-piperidin-4-yloxy)-phenyl]-benzamide hydrochloride

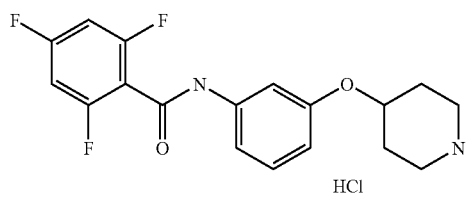

Using a method similar to Example 21 using 2,4,6-trifluoro-benzoyl chloride (0.049 mL, 0.376 mmol) gives the title compound as the free base (80 mg, 67%, 2 steps). Following a method similar to Example 21 gives the title compound as the hydrochloride salt (87 mg, off-white solid). Mp: 185-7° C.; mass spectrum (free base, ion spray): m/z=311.2 (M+1); $^1$H NMR (free base, CDCl$_3$): 7.62 (bs, N—H), 7.43 (t, J=2.1 Hz, 1H), 7.28-7.23 (m, 1H), 7.04 (dd, J=1.5 Hz, 8.2 Hz, 1H), 6.81-6.71 (m, 3H), 4.51-4.45 (bm, 1H), 3.22-3.14 (bm, 2H), 2.90-2.81 (bm, 2H), 2.12-1.74 (bm, 5H).

Example 23

N-[3-(1-Methyl-piperidin-4-yloxy)-phenyl]-nicotinamide dihydrochloride

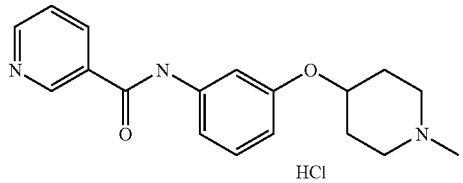

Using a method similar to Example 2, using nicotinoyl chloride (161 mg, 0.903 mmol) gives the title compound as free base (109 mg, 48%). Following a method similar to Example 2 gives the title compound as hydrochloride (125 mg, white solid). Mp: 73-4° C.; mass spectrum (free base, ion spray): m/z=312.1 (M+1); $^1$H NMR (free base, CDCl3): 9.09 (d, J=2.0 Hz, 1H), 8.78 (dd, J=1.7 Hz, 4.9 Hz, 1H), 8.21 (dt, J=2.0 Hz, 8.0 Hz, 1H), 7.88 (bs, N—H), 7.49-7.43 (m, 2H), 7.27 (t, J=8.0 Hz, 1H), 7.07 (d, J=8.0 Hz, 1H), 6.74 (dd, J=2.0 Hz, 8.0 Hz, 1H), 4.45-4.39 (bm, 1H), 2.81-2.72 (bm, 2H), 2.51-2.42 (bm, 2H), 2.38 (s, 3H), 2.16-2.06 (bm, 2H), 1.96-1.87 (bm, 2H); Analysis calculated for $C_{18}H_{23}Cl_2N_3O_2 \cdot 0.25H_2O$: C, 55.60; H, 6.09; N, 10.81. Found C, 55.91; H, 6.31; N, 10.54.

Example 24

N-[3-(1-Methyl-piperidin-4-yloxy)phenyl]-isonicotinamide dihydrochloride

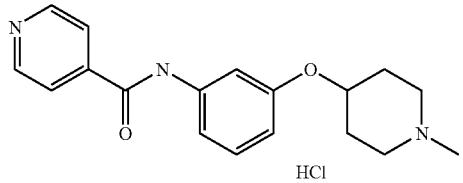

Using a method similar to Example 5, using isonicotinoyl chloride (95 mg, 0.533 mmol) gives the title compound as the free base (114 mg, 75%). Following a method similar to Example 2 gives the title compound as the hydrochloride salt (135 mg, tan solid). Mp: 172-5° C.; mass spectrum (free base, ion spray): m/z=312.2 (M+1); $^1$H NMR (free base, CDCl$_3$): 9.09 (bs, 1H), 8.78 (d, J=4.4 Hz, 1H), 8.20 (d, J=8.0 Hz, 1H), 7.92 (bs, N—H), 7.48-7.42 (m, 2H), 7.26 (t, J=8.0 Hz, 1H), 7.07 (d, J=8.0 Hz, 1H), 6.73 (dd, J=2.0 Hz, 8.3 Hz, 1H), 4.42-4.35 (bm, 1H), 2.77-2.67 (bm, 2H), 2.41-2.34 (bm, 2H), 2.33 (s, 3H), 2.10-2.01 (bm, 2H), 1.93-1.83 (bm, 2H).

Example 25

3-Chloro-thiophene-2-carboxylic acid [3-(1-methyl-piperidin-4-yloxy)-phenyl]-amide hydrochloride

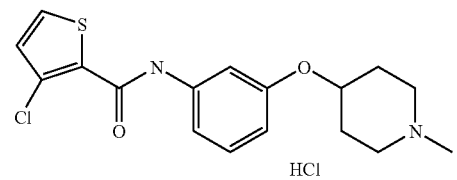

Using a method similar to Example 5, using 3-chloro-thiophene-2-carbonyl chloride (0.018 ml) gives the title compound as the free base (35 mg, 100%). Following a method similar to Example 2 gives the title compound as the hydrochloride salt (10 mg, off-white solid). Mass spectrum (free base, ion spray): m/z=351.0 (M+1); $^1$H NMR (free base, CDCl$_3$): 8.74 (bs, N—H), 7.53 (bd, J=5.3 Hz, 1H), 7.47 (bs, 1H), 7.23 (t, J=8.2 Hz, 1H), 7.05-7.01 (m, 2H), 6.71 (dd, J=1.8 Hz, 8.2 Hz, 1H), 4.42-4.34 (bm, 1H), 2.73-2.63 (bm, 2H), 2.39-2.38 (bm, 5H), 2.07-1.98 (bm, 2H), 1.91-1.81 (bm, 2H); Analysis calculated for $C_{17}H_{20}Cl_2N_2O_2S$: C, 52.72; H, 5.20; N, 7.23. Found C, 52.39; H, 5.06; N, 6.88.

Example 26

Cyclobutanecarboxylic acid [3-(1-methyl-piperidin-4-yloxy)-phenyl]-amide hydrochloride

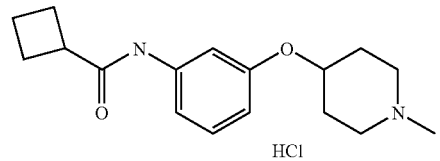

Using a method similar to Example 5, using cyclobutanecarbonyl chloride (0.011 mL) gives the title compound as the free base (39 mg, 100%). Following a method similar to Example 2 gives the title compound as the hydrochloride salt (10 mg, yellow solid). Mass spectrum (free base, ion spray): m/z=289.1 (M+1); $^1$H NMR (free base, CDCl$_3$): 7.41 (bs, N—H), 7.19-7.12 (m, 2H), 6.89 (bd, J=7.6 Hz, 1H), 6.63 (bd, J=7.6 Hz, 1H), 4.37-4.29 (bm, 1H), 3.19-3.08 (bm, 1H), 2.72-2.63 (bm, 2H), 2.41-2.28 (bm, 6H), 2.25-2.16 (bm, 2H), 2.05-1.78 (bm, 6H); Analysis calculated for $C_{17}H_{25}ClN_2O_2 \cdot 0.5H_2O$: C, 61.16; H, 7.85; N, 8.39. Found C, 61.21; H, 7.77; N, 8.16.

Example 27

3-Methyl-N-[3-(1-methyl-piperidin-4-yloxy)-phenyl]-butyramide hydrochloride

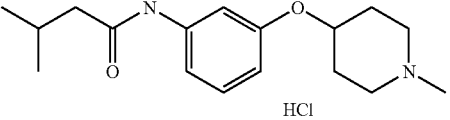

Using a method similar to Example 5, using 3-methyl-butyryl chloride (0.012 mL) gives the title compound as free base (26 mg, 90%). Following a method similar to Example 2 gives the title compound as hydrochloride (11 mg, tan solid). Mass spectrum (free base, ion spray): m/z=291.2 (M+1); $^1$H NMR (free base, CDCl$_3$): 7.37 (bs, N—H), 7.24 (bs, 1H), 7.17 (t, J=8.2 Hz, 1H), 6.91 (d, J=8.0 Hz, 1H), 6.64 (d, J=8.0 Hz, 1H), 4.37-4.29 (bm, 1H), 2.72-2.63 (bm, 2H), 2.34-2.26 (bm, 5H), 2.20 (s, 3H), 2.04-1.96 (bm, 2H), 1.88-1.79 (bm, 2H), 1.00 (d, J=5.6 Hz, 6H).

Example 28

N-[3-(1-Methyl-piperidin-4-yloxy)-phenyl]-3-phenyl-propionamide hydrochloride

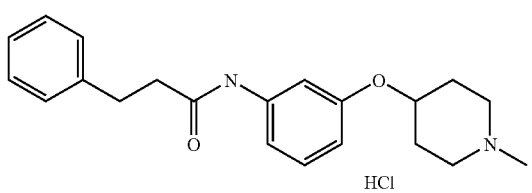

Using a method similar to Example 5, using 3-phenyl-propionyl chloride (0.015 mL) gives the title compound as the free base (30.5 mg, 90%). Following a method similar to Example 2 gives the title compound as the hydrochloride salt (10 mg, yellow solid). Mass spectrum (free base, ion spray): m/z=339.2 (M+1), $^1$H NMR (free base, CDCl$_3$): 7.33-7.12 (m, 8H), 6.83 (d, J=8.0 Hz, 1H), 6.63 (d, J=8.0 Hz, 1H), 4.35-4.27 (bm, 1H), 3.03 (t, J=7.2 Hz, 2H), 2.72-2.65 (bm, 2H), 2.64 (t, J=7.2 Hz, 2H), 2.34-2.29 (bm, 5H), 2.04-1.96 (bm, 2H), 1.88-1.78 (bm, 2H).

Example 29

Cyclopropanecarboxylic acid [3-(1-methyl-piperidin-4-yloxy)-phenyl]-amide hydrochloride

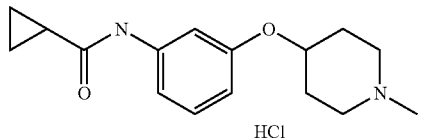

Using a method similar to Example 5, using cyclopropanecarbonyl chloride (0.009 mL) gives the title compound as the free base (27 mg, 99%). Following a method similar to Example 2 gives the title compound as the hydrochloride salt (11 mg, yellow solid). Mass spectrum (free base, ion spray): m/2=275.1 (M+1); $^1$H NMR (free base, CDCl$_3$): 7.51 (bs, N—H), 7.39 (s, 1H), 7.17 (t, J=8.2 Hz, 1H), 6.89 (d, J=7.9 Hz, 1H), 6.63 (d, J=7.9 Hz, 1H), 4.38-4.29 (bm, 1H), 2.73-2.63 (bm, 2H), 2.38-2.29 (bm, 5H), 2.05-1.97 (bm, 2H), 1.89-1.80 (bm, 2H), 1.54-1.49 (bm, 1H), 1.10-1.04 (m, 2H), 0.87-0.80 (m, 2H).

Example 30

Cyclohexanecarboxylic acid [3-(1-methyl-piperidin-4-yloxy)-phenyl]-amide hydrochloride

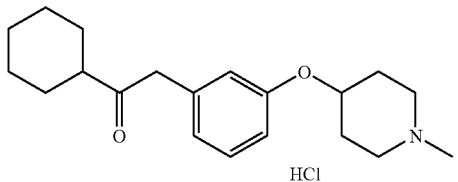

Using a method similar to Example 5, using cyclohexanecarbonyl chloride (0.023 mL, 0.175 mmol) gives the title compound as the free base (44 mg, 96%). Following a method similar to Example 2 gives the title compound as the hydrochloride salt (48 mg, tan solid). Mp: 141-2° C.; mass spectrum (free base, ion spray): m/z=317.2 (M+1); $^1$H NMR (free base, CDCl$_3$): 7.41 (bs, 1H), 7.23 (bs, 1H), 7.17 (t, J=8.1 Hz, 1H), 6.89 (d, J=8.1 Hz, 1H), 6.64 (dd, J=2.0 Hz, 8.1 Hz, 1H), 4.36-4.29 (bm, 1H), 2.71-2.62 (bm, 2H), 2.35-2.26 (bm, 5H), 2.20 (tt, J=3.3 Hz, 11.8 Hz, 1H), 2.03-1.90 (m, 4H), 1.88-1.78 (m, 4H), 1.72-1.66 (bm, 1H), 1.58-1.47 (m, 2H), 1.36-1.24 (m, 2H), 1.20 (t, J=7.2 Hz, 1H).

Example 31

N-[3-(1-methyl-piperidin-4-yloxy)-phenyl]-cyclopentanecarboxamide hydrochloride

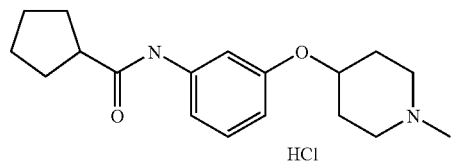

Using a method similar to Example 5, using cyclopentanecarbonyl chloride (0.021 mL, 0.175 mmol) gives the title compound as the free base (40 mg, 91%). Following a method similar to Example 2 gives the title compound as the hydrochloride salt (44 mg, pale yellow solid). Mass spectrum (free base, ion spray): m/z=303.2 (M+1), $^1$H NMR (free base, CDCl$_3$): 7.40 (bs, 2H), 7.15 (t, J=8.2 Hz, 1H), 6.90 (d, J=8.2 Hz, 1H), 6.62 (dd, J=2.0 Hz, 8.2 Hz, 1H), 4.34-4.27 (bm, 1H), 2.69-2.59 (m, 3H), 2.33-2.21 (bm, 5H), 2.01-1.71 (m, 10H), 1.64-1.54 (m, 2H); Analysis calculated for C$_{18}$H$_{27}$ClN$_2$O$_2$.0.5H$_2$O: C, 62.15; H, 8.11; N, 8.05. Found C, 61.95; H, 7.84; N, 7.85.

Example 32

N-[3-(1-Methyl-piperidin-4-yloxy)-phenyl]-isobutyramide hydrochloride

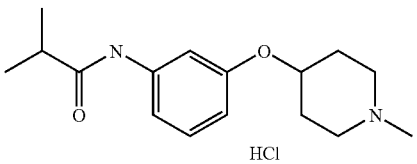

Using a method similar to Example 5, using isobutyryl chloride (0.018 mL, 0.175 mmol) gives the title compound as the free base (37 mg, 93%). Following a method similar to Example 2 gives the title compound as the hydrochloride salt (41 mg, yellow solid). Mp: 104-5° C.; mass spectrum (free base, ion spray): m/z=277.1 (M+1); $^1$H NMR (free base, CDCl$_3$): 7.41 (bs, 1H), 7.32 (bs, 1H), 7.20-7.13 (m, 1H), 6.94-6.88 (bm, 1H), 6.67-6.61 (bm, 1H), 4.36-4.28 (bm, 1H), 2.70-2.60 (bm, 2H), 2.54-2.44 (m, 1H), 2.34-2.22 (bm, 5H), 2.03-1.93 (bm, 2H), 1.88-1.77 (bm, 2H), 1.26-1.21 (m, 6H).

Example 33

N-[4-Chloro-3-(1-methyl-piperidin-4-yloxy)-phenyl]-2-trifluoromethoxy-benzamide hydrochloride

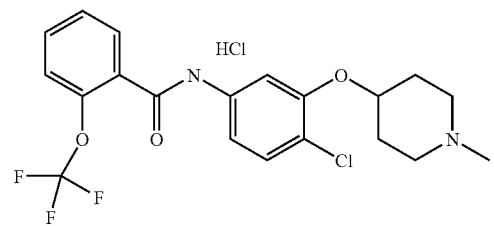

Using a method similar to Example 5, using 2-trifluoromethoxy-benzoyl chloride (0.066 ml, 0.439 mmol) and 4-chloro-3-(1-methyl-piperidin-4-yloxy)-phenylamine (preparation 31) gives the title compound as the free base (132 mg, 77%). Following a method similar to Example 2 gives the title compound as the hydrochloride salt (141 mg, pale yellow solid). Mp: 95-7° C.; mass spectrum (free base, ion spray): m/z=429.2 (M+1), $^1$H NMR (free base, CDCl$_3$): 8.43 (bs, N—H), 7.98 (dd, J=1.7 Hz, 7.9 Hz, 1H), 7.65 (d, J=2.4 Hz, 1H), 7.53 (td, J=1.7 Hz, 7.9 Hz, 1H), 7.41 (t, J=7.6 Hz, 1H), 7.33-7.25 (m, 2H), 6.87 (dd, J=2.4 Hz, 8.6 Hz, 1H), 4.46-4.38 (bm, 1H), 2.69-2.61 (bm, 2H), 2.37-2.29 (bm, 2H), 2.28 (s, 3H), 2.03-1.86 (bm, 4H). Analysis calculated for $C_{20}H_{21}Cl_2F_3N_2O_3$: C, 51.63; H, 4.55; N, 6.02. Found C, 51.33; H, 4.58; N, 5.88.

Example 34

2-Chloro-N-[4-chloro-3-(1-methyl-piperidin-4-yloxy)-phenyl]-benzamide hydrochloride

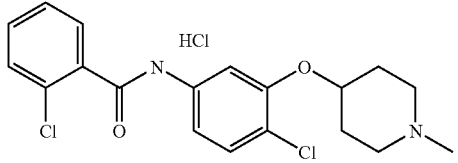

Using a method similar to Example 33, using 2-chlorobenzoyl chloride (0.057 mL, 0.448 mmol) gives the title compound as the free base (142 mg, 92%). Following a method similar to Example 2 gives the title compound as the hydrochloride salt (156 mg, off-white solid). Mp: 259° C. (dec.); mass spectrum (free base, ion spray): m/z=379.1 (M+1); $^1$H NMR (free base, CDCl$_3$): 8.19 (bs, N—H), 7.67-7.64 (m, 2H), 7.43-7.26 (m, 4H), 6.91 (dd, J=2.3 Hz, 8.4 Hz, 1H), 4.46-4.38 (bm, 1H), 2.69-2.60 (bm, 2H), 2.37-2.27 (bm, 2H), 2.27 (s, 3H), 2.03-1.86 (bm, 4H).

Example 35

2-Bromo-N-[4-chloro-3-(1-methyl-piperidin-4-yloxy)-phenyl]-benzamide hydrochloride

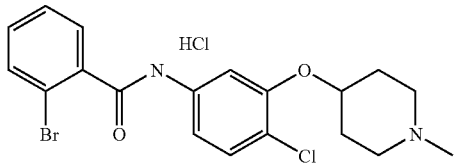

Using a method similar to Example 33, using 2-bromobenzoyl chloride (0.059 mL, 0.452 mmol) gives the title compound as the free base (150 mg, 86%). Following a method similar to Example 2 gives the title compound as the hydrochloride salt (151 mg, white solid). Mp: 146-8° C.; mass spectrum (free base, ion spray): m/z=423.1 (M+1); $^1$H NMR (free base, CDCl$_3$): 8.15 (bs, N—H), 7.62 (d, J=2.1 Hz, 1H), 7.59 (d, J=8.0 Hz, 1H), 7.54 (dd, J=1.8 Hz, 7.6 Hz, 1H), 7.35 (t, J=7.6 Hz, 1H), 7.31-7.25 (m, 2H), 6.92 (dd, J=2.4 Hz, 8.6 Hz, 1H), 4.44-4.36 (bm, 1H), 2.68-2.59 (bm, 2H), 2.36-2.27 (bm, 2H), 2.26 (s, 3H), 2.01-1.85 (bm, 4H).

Example 36

N-[4-Chloro-3-(1-methyl-piperidin-4-yloxy)-phenyl]-2,6-difluoro-benzamide hydrochloride

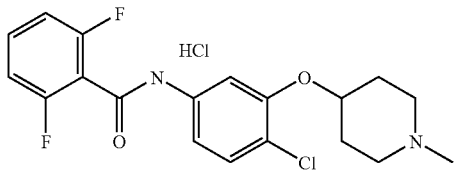

Using a method similar to Example 33, using 2,6-difluorobenzoyl chloride (0.056 mL, 0.443 mmol) gives the title compound as the free base (128 mg, 84%). Following a method similar to Example 2 gives the title compound as the hydrochloride salt (81 mg, off-white solid). Mp: 261° C. (dec.); mass spectrum (free base, ion spray): m/z=381.1 (M+1); $^1$H NMR (free base, CDCl$_3$): 8.50 (bs, N—H), 7.61 (d, J=2.1 Hz, 1H), 7.40-7.32 (m, 1H), 7.26 (d, J=8.6 Hz, 1H), 6.95-6.88 (m, 3H), 4.42-4.33 (bm, 1H), 2.66-2.57 (bm, 2H), 2.53-2.44 (bm, 2H), 2.32-2.25 (bm, 2H), 2.24 (s, 3H), 1.99-1.82 (bm, 4H).

Example 37

N-[4-Chloro-3-(1-methyl-piperidin-4-yloxy)-phenyl]-2,4-difluoro-benzamide hydrochloride

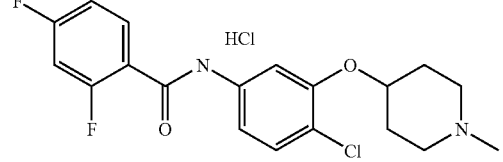

Using a method similar to Example 33, using 2,4-difluorobenzoyl chloride (0.057 mL, 0.462 mmol) gives the title compound as the free base (141 mg, 88%). Following a method similar to Example 2 gives the title compound as the hydrochloride salt (151 mg, white solid). Mp: 257° C. (dec.); mass spectrum (free base, ion spray): m/z=381.1 (M+1), $^1$H NMR (free base, CDCl$_3$): 8.39 (bd, J=14.8 Hz, N—H), 8.12 (dd, J=7.4 Hz, 18.2 Hz, 1H), 7.64 (d, J=2.3 Hz, 1H), 7.28 (d, J=8.5 Hz, 1H), 7.02 (td, J=2.3 Hz, 8.2 Hz, 1H), 6.93-6.87 (m, 2H), 4.46-4.40 (bm, 1H), 2.69-2.61 (bm, 2H), 2.38-2.30 (bm, 2H), 2.28 (s, 3H), 2.04-1.87 (bm, 4H). Analysis calculated for $C_{19}H_{20}ClF_2N_2O_2 \cdot 0.25H_2O$: C, 54.11; H, 4.90; N, 6.64. Found C, 54.14; H, 4.71; N, 6.58.

Example 38

2-Chloro-N-[4-chloro-3-(1-methyl-piperidin-4-yloxy)-phenyl]-4-fluoro-benzamide hydrochloride

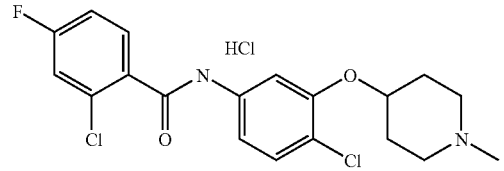

Using a method similar to Example 33, using 2-chloro-4-fluoro-benzoyl chloride (0.064 mL, 0.498 mmol) gives the title compound as the free base (158 mg, 88%). Following a method similar to Example 2 gives the title compound as the hydrochloride salt (159 mg, off-white solid). Mass spectrum (free base, ion spray): m/z=397.1 (M+1); $^1$H NMR (free base, CDCl$_3$): 8.29 (bs, N—H), 7.68 (dd, J=6.0 Hz, 8.5 Hz, 1H), 7.62 (d, J=2.1 Hz, 1H), 7.28 (d, J=8.5 Hz, 1H), 7.15 (dd, J=2.4 Hz, 8.5 Hz, 1H), 7.04 (td, J=2.4 Hz, 8.5 Hz, 1H), 6.91 (dd, J=2.3 Hz, 8.5 Hz, 1H), 4.44-4.37 (bm, 1H), 2.69-2.59 (bm, 2H), 2.37-2.29 (bm, 2H), 2.27 (s, 3H), 2.01-1.85 (bm, 4H); Analysis calculated for $C_{19}H_{20}Cl_3FN_2O_2 \cdot 0.75H_2O$: C, 51.02; H, 4.85; N, 6.26. Found C, 50.81; H, 4.52; N, 6.27.

Example 39

2-Chloro-N-[4-chloro-3-(1-methyl-piperidin-4-yloxy)-phenyl]-6-fluoro-benzamide hydrochloride

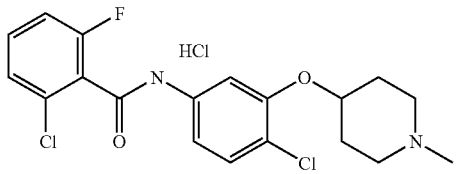

Using a method similar to Example 33, using 2-chloro-6-fluoro-benzoyl chloride (0.062 mL, 0.480 mmol) gives the title compound as the free base (149 mg, 86%). Following a method similar to Example 2 gives the title compound as the hydrochloride salt (149 mg, white solid). Mp: 259-60° C.; mass spectrum (free base, ion spray): m/z=397.1 (M+1), $^1$H NMR (free base, CDCl$_3$): 8.29 (bs, N—H), 7.60 (d, J=2.4 Hz, 1H), 7.35-7.26 (m, 2H), 7.21 (bd, J=8.1 Hz, 1H), 4.44-4.37 (bm, 1H), 2.68-2.60 (bm, 2H), 2.36-2.27 (bm, 2H), 2.26 (s, 3H), 2.01-1.84 (bm, 4H); Analysis calculated for C$_{19}$H$_{20}$Cl$_3$FN$_2$O$_2$.0.5H$_2$O: C, 51.54; H, 4.78; N, 6.33. Found C, 51.82; H, 4.49; N, 6.20.

Example 40

N-[4-Chloro-3-(1-methyl-piperidin-4-yloxy)-phenyl]-2,4,6-trifluoro-benzamide hydrochloride

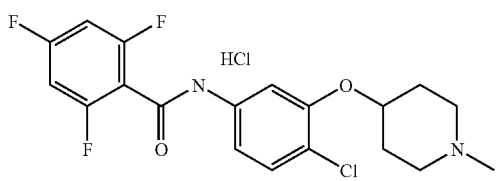

Using a method similar to Example 33, using 2,4,6-trifluoro-benzoyl chloride (0.061 mL, 0.471 mmol) gives the title compound as the free base (145 mg, 85%). Following a method similar to Example 2 gives the title compound as the hydrochloride salt (143 mg, white solid). Mp: >270° C.; mass spectrum (free base, ion spray): m/z=399.1 (M+1); $^1$H NMR (free base, CDCl$_3$): 8.52 (bs, N—H), 7.58 (d, J=2.1 Hz, 1H), 7.27 (d, J=8.2 Hz, 1H), 6.91 (dd, J=2.5 Hz, 8.2 Hz, 1H), 6.70 (t, J=8.2 Hz, 2H), 4.40-4.33 (bm, 1H), 2.66-2.59 (bm, 2H), 2.34-2.26 (bm, 2H), 2.24 (s, 3H), 1.99-1.83 (bm, 4H); Analysis calculated for C$_{19}$H$_{19}$Cl$_2$F$_3$N$_2$O$_2$.0.5H$_2$O: C, 51.37; H, 4.54; N, 6.31. Found C, 51.11; H, 4.24; N, 6.21.

Example 41

2-Chloro-4-fluoro-N-methyl-N-[3-(1-methyl-piperidin-4-yloxy)-phenyl]-benzamide hydrochloride

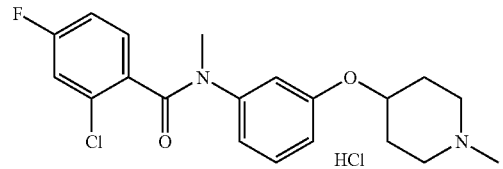

Combine 3-(1-methyl-piperidin-4-yloxy)-phenylamine (preparation 28, 1.43 g, 6.93 mmol), formaldehyde (37% aq., 0.73 mL) and methanol (43 mL), and stir the resulting solution. After 3 hr., add sodium borohydride in small portions (983 mg) and stir. After 18 hr., quench the reaction with HCl (aq. 1N, 0.3 mL). Remove the solvent till ⅓ of the original volume. Wash with NaOH (aq., 1M, 20 mL), extract with dichloromethane (2×25 mL), dry the organic layers over magnesium sulfate, filter and concentrate under reduced pressure. Load the residue onto an SCX column to provide methyl-[3-(1-methyl-piperidin-4-yloxy)-phenyl]-amine (211 mg, 15%). Using a method similar to Example 5, using 2-chloro-4-fluoro-benzoyl chloride (0.33 mL, 0.260 mmol) gives the title compound as the hydrochloride salt (77 mg, 87%). Mass spectrum (ion spray): m/z=377.1 (M+1); 3H NMR (free base, CDCl$_3$): 7.26-7.08 (m, 2H), 6.98 (bd, J=6.6 Hz, 1H), 6.84-6.78 (m, 1H), 6.72-6.64 (m, 2H), 4.13 (bs, 1H), 3.49 (s, 3H), 2.66 (bm, 2H), 2.31 (s, 3H), 2.23 (bm, 2H), 1.83-1.69 (bm, 4H).

Example 42

2-Chloro-6-fluoro-N-methyl-N-[3-(1-methyl-piperidin-4-yloxy)-phenyl]-benzamide hydrochloride

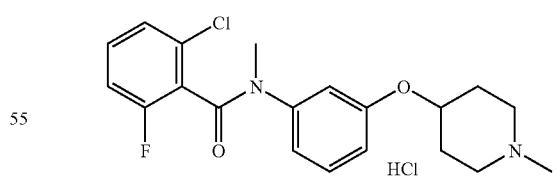

Using a method similar to Example 41, using 2-chloro-6-fluoro-benzoyl chloride (0.33 mL, 0.260 mmol) gives the title compound as the hydrochloride salt (88 mg, 99%). Mass spectrum (ion spray): m/z=377.1 (M+1); $^1$H NMR (DMSO-d$_6$): 7.32-7.09 (m, 4H), 6.94-6.83 (m, 3H), 4.64 (bs, 1H), 3.48-3.24 (m, 2H), 3.38 (s, 3H), 3.06 (bm, 2H), 2.75 (bs, 3H), 2.07-2.04 (bm, 2H), 1.87-1.83 (bm, 2H).

Example 43

2,4,6-Trifluoro-N-methyl-N-[3-(1-methyl-piperidin-4-yloxy)-phenyl]-benzamide hydrochloride

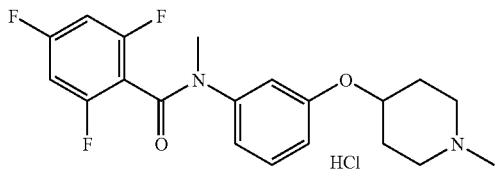

Using a method similar to Example 41, using 2,4,6-trifluoro-benzoyl chloride (0.34 mL, 0.260 mmol) gives the title compound as the hydrochloride salt (80 mg, 90%). Mass spectrum (ion spray): m/z=379.1 (M+1), $^1$H NMR (DMSO-$d_6$): 7.26-7.11 (m, 3H), 6.95-6.87 (m, 2H), 6.77 (t, J=7.2 Hz, 1H), 4.67 (bs, 1H), 3.48-3.23 (m, 2H), 3.37 (s, 3H), 3.13-3.02 (m, 2H), 2.75 (bs, 3H), 2.05-1.77 (m, 4H).

Example 44

4-Fluoro-N-[4-methyl-3-(1-methyl-piperidin-4-yloxy)-phenyl]-benzamide

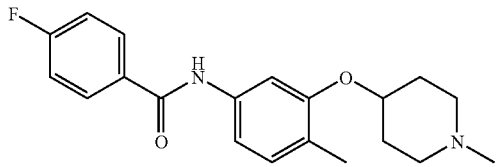

Add 4-fluorobenzoyl chloride (222 mg, 1.4 mmol) to a solution of 4-Methyl-3-(1-methyl-piperidin-4-yloxy)-phenylamine (preparation 34, 280 mg, 1.27 mmol) in pyridine (10 mL), beat at 55° C. for 20 hr. Remove volatiles in vacuo, dissolve the residue in $CH_2Cl_2$, wash with 0.1N NaOH and saturated NaCl solution sequentially, dry over $Na_2SO_4$, filter and concentrate to give a residue. Chromatography on a silica gel column eluting with 6% 2M $NH_3$-methanol in $CH_2Cl_2$) provides the title compound as a colorless oil (375 mg, 86%). Mass spectrum (ion spray): m/z=343.3 (M+1); $^1$H NMR ($CDCl_3$, ppm): 7.94 (s, br, 1H), 7.88 (m, 2H), 7.85 (s, br, 1H), 7.12 (m, 3H), 6.87 (dd, 1H), 4.39 (m, 1H), 2.62 (m, 2H), 2.33 (m, 2H), 2.31 (s, 3H), 2.22 (s, 3H), 2.06-1.83 (m, 4H); Anal calcd for $C_{20}H_{23}FN_2O_2 \cdot HCl \cdot H_2O$: C, 60.53; H, 6.60; N, 7.06. Found: C, 60.77; H, 6.20; N, 7.10.

Example 45

2-Chloro-4-fluoro-N-[4-methyl-3-(1-methyl-piperidin-4-yloxy)-phenyl]-benzamide

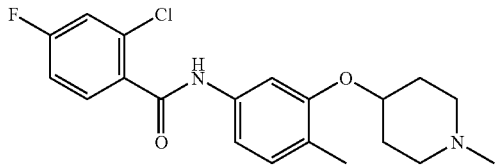

Using a method similar to example 44, using 2-chloro-4-fluoro-benzoyl chloride provides the title compound as a slightly yellow oil (80%). Mass spectrum (ion spray): m/z=377.2 (M+1); $^1$H NMR ($CDCl_3$, ppm): 7.97 (s, br, 1H), 7.77 (dd, 1H), 7.51 (d, 1H), 7.20 (dd, 1H), 7.13 (m, 2H), 6.88 (dd, 1H), 4.42 (1H), 2.62 (m, 2H), 2.35 (m, 2H), 2.32 (s, 3H), 2.23 (s, 3H), 2.09-1.84 (m, 4H); Anal calcd for $C_{20}H_{22}ClFN_2O_2 \cdot HCl \cdot 0.5H_2O$: C, 56.88; H, 5.73; N, 6.63. Found: C, 56.66; H, 5.52; N, 6.49.

Example 46

2-Chloro-6-fluoro-N-[4-methyl-3-(1-methyl-piperidin-4-yloxy)-phenyl]-benzamide

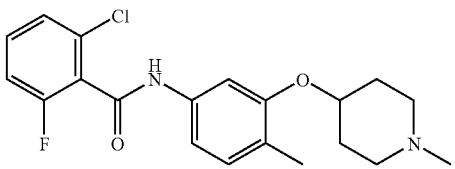

Using a method similar to example 44, using 2-chloro-6-fluorobenzoyl chloride provides the title compound as a slightly yellow oil (96%). Mass spectrum (ion spray): m/z=377.0 (M+1); $^1$H NMR ($CDCl_3$): 7.81 (s, br, 1H), 7.48 (d, 1H), 7.31 (m, 2H), 7.09 (m, 2H), 6.87 (dd, 1H), 4.40 (m, 1H), 2.63 (m, 2H), 2.34 (m, 2H), 2.30 (s, 3H), 2.23 (s, 3H), 2.06-1.82 (m, 4H). Hydrochloride salt: Anal calcd for $C_{20}H_{22}ClFN_2O_2 \cdot HCl \cdot 0.25H_2O$: C, 57.49; H, 5.67; N, 6.70. Found: C, 57.18; H, 5.41; N, 6.87.

Example 47

4-Fluoro-N-[3-fluoro-5-(1-methyl-piperidin-4-yloxy)-phenyl]-benzamide mono hydrochloric acid salt

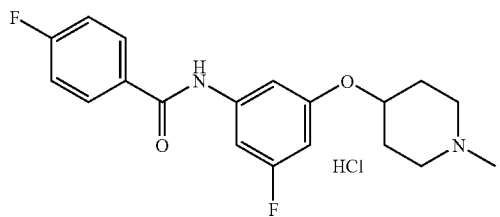

Combine 3-fluoro-5-(1-methyl-piperidin-4-yloxy)-phenylamine (preparation 32, 0.23 g, 1.03 mmol), 4-fluoro-benzoyl chloride (0.195 g, 1.23 mmol), and 1,4-dioxane (5 mL), stir and heat at reflux. After 3 hr., cool to ambient temperature. Load on an SCX column (10 g), wash with methanol, elute with 2M ammonia/methanol. Concentrate eluent to obtain free base compound (0.35 g, 92%) as an oil. Dissolve this material in dichloromethane (5 mL) and treat with 1M hydrochloric acid in ether (1.1 mL). Concentrate and dry under vacuum to obtain the title compound. mp 150° C.; mass spectrum: obs. m/z 347.1566; calc. m/z 347.1571; $^1$H NMR ($CDCl_3$) for free base: 7.8 (m, 2H), 7.1 (m, 2H), 7.05 (s, 1H), 7.0 (m, 1H), 6.4 (m, 1H), 4.3 (m, 1H), 2.7 (m, 2H), 2.3 (m, 5H), 2.0 (m, 2H), 1.8 (m, 2H).

Using methods similar to example 47, substituting the appropriately substituted benzoylchloride reagent, prepare, isolate and convert the analogous compounds to mono hydrochloride acid salts, as indicated below:

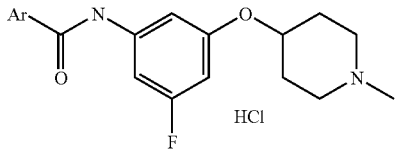

| No. | Ar | Data |
|---|---|---|
| 48 | 2-chloro-4-fluoro-phenyl | mass spectrum; Obs. m/z 381.1150; Calc. m/z 381.1181; Analysis calculated for $C_{19}H_{20}C_{12}F_2N_2O_2$ 0.8$H_2O$: C,52.86; H, 5.04; N, 6.49. Found: C, 52.42; H, 4.94; N, 6.49; $^1$H NMR (CDCl$_3$) for free base: 8.0 (bs, 1H), 7.7 (m, 1H), 7.2 (m, 1H), 7.0 (m, 3H), 6.4 (m, 1H), 4.4 (m, 1H), 2.7 (m, 2H), 2.3 (m, 5H), 2.1 (m, 2H), 1.9 (m, 2H). |
| 49 | 2,4-difluoro-phenyl | Mass spectrum: Obs. m/z 365.1467; Calc. m/z 365.1477; Analysis calculated for $C_{19}H_{20}C_{11}F_3N_2O_2$ 0.8 $H_2O$: C, 54.96; H, 5.24; N, 6.75. Found: C, 55.07; H, 5.09; N, 6.91; $^1$H NMR (DMSO-D$_6$): 10.8 (bs, 1H), 10.6 (s, 1H), 7.8 (m, 1H), 7.4 (m, 1H), 7.2 (m, 3H), 7.7 (m, 1H), 4.6 (m, 1H), 3.4 (m, 2H), 3.1 (m, 2H), 2.5 (s, 3H), 2.1 (m, 4H). |
| 50 | 2-chloro-phenyl | mp = 140° C.; Mass spectrum: Obs. m/z 363.1284; Calc. m/z 363.1275; $^1$H NMR (CDCl$_3$) for free base: 8.1 (s, 1H), 7.6 (m, 1H), 7.4 (m, 3H), 7.05 (s, 1H), 7.0 (m, 1H), 6.4 (m, 1H), 4.3 (m, 1H), 2.6 (m, 2H), 2.3 (m, 5H), 2.0 (m, 2H), 1.8 (m, 2H). |
| 51 | 2,4,6-trifluoro-phenyl | mp = 186–190° C.; Mass spectrum: Obs. m/z 383.1390; calc. m/z 383.1382; Analysis calculated for $C_{19}H_{19}C_{11}F_4N_2O$ 20.5 $H_2O$: C, 53.34; H, 4.71; N, 6.55. Found: C, 53.41; H, 4.58; N, 6.41. |

Example 52

2-Chloro-N-[2-fluoro-3-(1-methyl-piperidin-4-yloxy)-phenyl]-benzamide

Heat a mixture of 2-fluoro-3-(1-methyl-piperidin-4-yloxy)-phenylamine (preparation 33, 0.26 g) and 2-chlorobenzoyl chloride (0.233 g) in 1,4-dioxane (10 mL) for 2 hrs. Evaporate and purify on a silica gel column (10 g, solvent: dichloromethane-2M NH$_3$ in methanol, gradient) to give the title compound (0.453 g). Mass spectrum (electric spray) m/z=363 (M+1); $^1$H NMR (CDCl$_3$): 8.27 (br s, 1H), 8.07 (m, 1H), 7.80 (dd, 1H), 7.42 (m, 3H), 7.07 (ddd, 1H), 6.79 (ddd, 1H), 4.31 (m, 1H), 2.70 (m, 2H), 2.30 (s, 3H), 2.28 (m, 2H), 2.00 (m, 2H), 1.89 (m, 2H).

Dissolve the benzamide in dichloromethane and add 1.25 mL of 1N HCl in ether, evaporate and dry in vacuum to give its hydrochloric acid salt.

Using methods similar to Example 52, substituting the appropriately substituted benzoylchloride reagent, prepare, isolate, and convert the analogous compounds as indicated below to mono hydrochloric acid salts as indicated below:

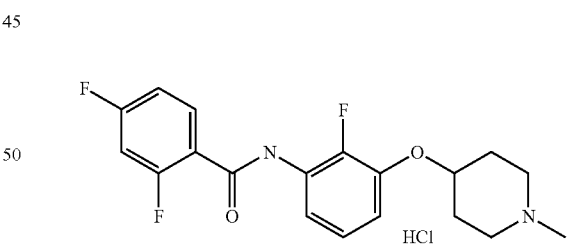

| Ex. | Ar | Data |
|---|---|---|
| 53 | 4-fluorophenyl | mass spectrum (electric spray) m/z = 347 (M + 1); $^1$H NMR (CDCl$_3$)(free base): 8.02 (ddd, 1H), 7.93 (br d, 1H), 7.90 (m, 2H), 7.19 (m, 2H), 7.07 (ddd, 1H), 6.79 (ddd, 1H), 4.33 (m, 1H), 2.72 (m, 2H), 2.33 (s, 3H), 2.33 (m, 2H), 2.03 (m, 2H), 1.92 (m, 2H). |
| 54 | 2-chloro-4-fluorophenyl | mass spectrum (electric spray) m/z = 381 (M + 1); $^1$H NMR (CDCl$_3$)(free base): 8.28 (br s, 1H), 8.04 (m, 1H), 7.86 (dd, 1H), 7.23 (dd, 1H), 7.10 (m, 2H), 6.80 (ddd, 1H), 4.33 (m, 1H), 2.71 (m, 2H), 2.32 (s, 3H), 2.32 (m, 2H, 2.00 (m, 2H), 1.89 (m, 2H). |

Example 55

2,4-Difluoro-N-[2-fluoro-3-(1-methyl-piperidin-4-yloxy)phenyl]-benzamide hydrochloride Heat a mixture of 2-fluoro-3-(1-methyl-piperidin-4-yloxy)-phenylamine (preparation 33, 0.126 g) and 2,4-difluorobenzoyl chloride (0.119 g) in 1,4-dioxane (5 mL) for 2.5 hrs. Cool to room temperature, collect the white crystals and wash with ether to give the free base of title compound (0.164 g). The free base is converted to the mono hydrochloric acid salt using a method similar to Example 52 to provide the title compound. Mass spectrum (electric spray) m/z=365 (M+1); $^1$H NMR (CD3OD-CDCl3): 8.04 (m, 1H), 7.85 (m, 1H), 7.05 (m, 3H), 6.88 (m, 1H), 4.69 (m, 1H), 3.37 (m, 2H), 3.31 (s, 2H), 2.84 (s, 3H), 2.34 (m, 2H), 2.20 (m, 2H).

Example 56

2-Bromo-N-[2-fluoro-3-(1-methyl-piperidin-4-yloxy)-phenyl]-benzamide hydrochloride

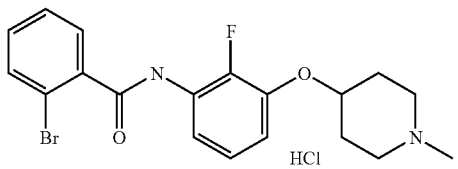

Using the method of example 55 using 2-bromobenzoyl chloride gives the free base of the title compound. The free base is converted to the mono hydrochloric acid salt using a method similar to Example 52 to provide the title compound. Mass spectrum (electric spray) m/z=407 (M+1), 409 (M+2+1); $^1$H NMR (CDCl$_3$-CD$_3$OD): 7.66 (m 1H), 7.50 (dd, 1H), 7.43 (dd, 1H), 7.28 (ddd, 1H), 7.20 (ddd, 1H), 6.97 (ddd, 1H), 6.73 (ddd, 1H), 4.54 (m, 1H), 3.22 (m, 2H), 3.12 (m, 2H), 2.68 (s, 3H), 2.21 (m, 2H), 2.05 (m, 2H).

Preparation 78. 4-[3-(2-Chloro-4-fluoro-benzoylamino)-phenoxy]-2-methyl-piperidine-1-carboxylic acid tert-butyl ester cis isomer 1

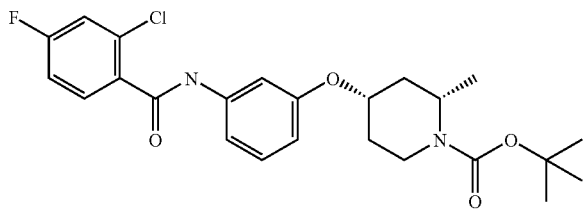

Combine 4-(3-amino-phenoxy)-2-methyl-piperidine-1-carboxylic acid tert-butyl ester cis isomer 1 (preparation 35, 0.40 g, 1.31 mmol), 1,4-dioxane (20 mL), triethylamine (0.22 mL, 1.57 mmol) and 2-chloro-4-fluoro-benzoyl chloride (0.30 g, 1.57 mmol) with stirring. After 4 hr., partition between 4:1 hexane:ethyl acetate (100 mL) and 0.5M aqueous sodium hydroxide solution (100 mL). Separate the organic layer, dry over sodium sulfate, filter and concentrate to obtain of the title compound (0.60 g, 100%): $^1$H NMR (CDCl$_3$): 7.9 (bs, 1H), 7.8 (dd, 1H), 7.45 (m, 1H), 7.25 (m, 1H), 7.2 (dd, 1H), 7.1 (m, 1H), 7.0 (dd, 1H), 6.7 (dd, 1H), 4.7 (m, 1H), 4.35 (m, 1H), 3.9 (m, 1H), 3.25 (m, 1H), 2.0 (m, 2H), 1.9 (m, 1H), 1.7 (m, 1H), 1.45 (s, 9H), 1.3 (d, 3H).

Preparation 79. 4-[3-(2-Chloro-4-fluoro-benzoylamino)-phenoxy]-2-methyl-piperidine-1-carboxylic acid tert-butyl ester trans isomer 1

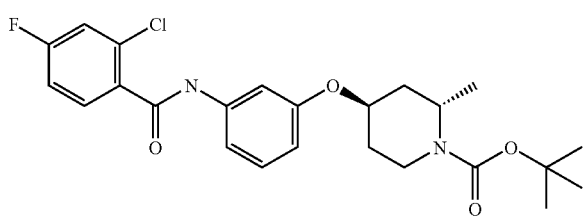

Using a method similar to preparation 78, using 4-(3-amino-phenoxy)-2-methyl-piperidine-1-carboxylic acid tert- butyl ester trans isomer 1 (preparation 36, 0.40 g, 1.31 mmol) (0.40 g, 1.31 mmol) prepare the title compound (100% yield). $^1$H NMR (CDCl$_3$): 7.9 (bs, 1H), 7.8 (dd, 1H), 7.5 (m, 1H), 7.25 (m, 2H), 7.1 (m, 1H), 7.05 (m, 1H), 6.8 (m, 1H), 4.6 (m, 2H), 4.1 (m, 1H), 3.0 (m, 1H), 2.15 (m, 1H), 2.0 (m, 1H), 1.7 (m, 1H), 1.6 (m, 1H), 1.4 (s, 9H), 1.25 (d, 3H).

Example 57

2-Chloro-4-fluoro-N-[3-(2-methyl-piperidin-4-yloxy)-phenyl]-benzamide cis isomer 1

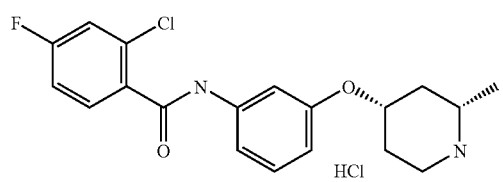

Combine 4-[3-(2-chloro-4-fluoro-benzoylamino)-phenoxy]-2-methyl-piperidine-1-carboxylic acid tert-butyl ester cis isomer 1 (Preparation 78, 0.60 g, 1.31 mmol), toluene (20 mL), and p-toluenesulfonic acid monohydrate (2.5 g, 13.1 mmol), stir, and heat at 100° C. After 1 hr., cool to ambient temperature. Concentrate the reaction mixture. Partition the residue between ethyl acetate (100 mL) and 1M aqueous sodium hydroxide solution (50 mL). Separate the organic layer, wash with 1M aqueous sodium hydroxide solution (2×50 mL), wash with aqueous NaCl solution (50 mL), dry over sodium sulfate, filter and concentrate. Purify residue by silica gel flash chromatography eluting with 10% (2M ammonia/methanol) in dichloromethane to obtain the title compound (0.26 g, 55%). Mass spectrum: Obs. m/z 363.1289; Calc. m/z 363.1275; Analysis calculated for C$_{19}$H$_{21}$C$_{12}$FN$_2$O$_2$·0.9H$_2$O: C, 54.92; H, 5.53; N, 6.74. Found: C, 54.90; H, 5.36; N, 6.55. $^1$H NMR (CDCl$_3$) of free base: 7.9 (bs, 1H), 7.8 (m, 1H), 7.4 (s, 1H), 7.2 (m, 3H), 7.1 (m, 2H), 6.7 (dd, 1H), 4.3 (m, 1H), 3.2 (m, 1H), 2.75 (m, 2H), 2.15 (m, 2H), 1.45 (m, 2H), 1.1 (d, 3H).

Example 58

2-Chloro-4-fluoro-N-[3-(trans-2-methyl-piperidin-4-yloxy)-phenyl]-benzamide isomer 1

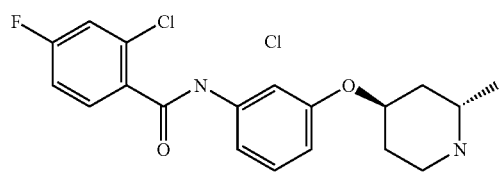

Using a method similar to example 57, using 4-[3-(2-Chloro-4-fluoro-benzoylamino)-phenoxy]-2-methyl-piperidine-1-carboxylic acid tert-butyl ester trans isomer 1 (preparation 79), the title compound is prepared, isolated and converted to the mono hydrogen chloride salt to obtain the title compound (64%). Mass spectrum: Obs. m/z 363.1284; Calc. m/z 363.1275; $^1$H NMR (DMSO-d$_6$): 10.5 (bs, 1H), 9.1 (bs, 1H), 7.6 (m, 2H), 7.5 (s, 1H), 7.3 (m, 3H), 6.8 (m, 1H), 4.8 (m, 1H), 3.4 (m, 2H), 3.15 (m, 2H), 2.0 (m, 2H), 1.8 (m, 1H), 1.3 (d, 3H).

Example 59

2-Chloro-4-fluoro-N-[3-(cis-1,2-dimethyl-piperidin-4-yloxy)-phenyl]benzamide isomer 1

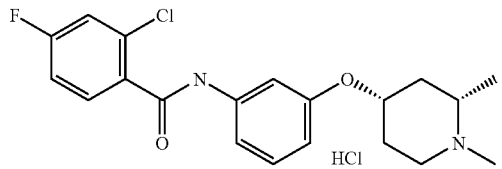

Combine 2-chloro-4-fluoro-N-[3-(2-methyl-piperidin-4-yloxy)-phenyl]-benzamide cis isomer 1 (example 57, 0.26 g, 0.72 mmol), dichloromethane (20 mL), and 37% aqueous formaldehyde (0.58 mL, 7.2 mmol) with stirring. After 10 min., add glacial acetic acid (0.08 mL, 1.44 mmol) followed by sodium triacetoxyborohydride (0.23 g, 1.08 mmol). After 3 hr., partition between 1M aqueous sodium hydroxide solution (50 mL) and dichloromethane (50 mL). Separate the organic layer, wash with aqueous NaCl solution, dry over sodium sulfate, filter and concentrate. Purify residue by silica gel flash chromatography eluting with 10% (2M ammonia/methanol) in dichloromethane to obtain of the title compound (0.46 g, 85%). Mass spectrum: Obs. m/z 377.1443; Calc. m/z 377.1432; mp: 152° C.

Example 60

2-Chloro-N-[3-(1,2-dimethyl-piperidin-4-yloxy)-phenyl]4-fluoro-benzamide trans isomer 1, mono-hydrogen chloride salt

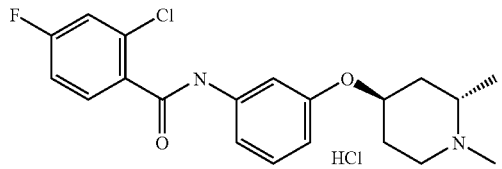

Using a method similar to example 59, using N-[3-(2-methyl-piperidin-4-yloxy)-phenyl]-2-chloro-4-fluoro-benzamide trans isomer 1, (example 58), prepare the title compound, purify and convert to the mono hydrogen chloride salt to obtain the title compound (39%). M.p.: 145 C; Mass spectrum: Obs. m/z 377.1446; Calc. m/z 377.1432; $^1$H NMR (CDCl$_3$) of free base: 7.9 (bs, 1H), 7.8 (dd, 1H), 7.4 (s, 1H), 7.2 (m, 2H), 7.1 (m, 1H), 7.0 (m, 1H), 6.7 (dd, 1H), 4.6 (m, 1H), 2.65 (m, 1H), 2.55 (m, 1H), 2.45 (m, 1H), 2.35 (s, 3H), 2.0 (m, 3H), 1.6 (m, 1H), 1.1 (d, 3H).

Example 61

N-[4-tert-Butyl-3-(1,2-dimethyl-piperidin-4-yloxy)-phenyl]-2-chloro-4-fluoro-benzamide trans isomer 1

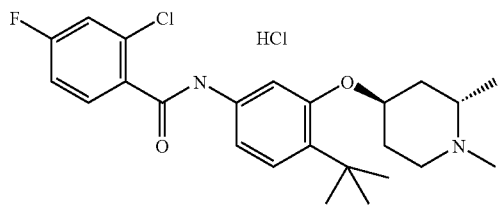

Using a series of methods similar to preparation 79, example 58, and example 60, using 4-(3-amino-6-t-butyl-phenoxy)-2-methyl-piperidine-1-carboxylic acid 1-butyl ester trans isomer 1, which is produced as a minor by-product in preparation 36, prepare, isolate and convert the title compound into the mono hydrogen chloride salt to obtain the title compound (11% yield). Mp: 260° C.; Mass spectrum: Obs. m/z 433.2070; Calc. m/z 433.2058; $^1$H NMR (CDCl$_3$) of free base: 7.8 (m, 2H), 7.55 (s, 1H), 7.25 (m, 1H), 7.2 (dd, 1H), 7.1 (m, 1H), 6.8 (dd, 1H), 4.75 (m, 1H), 2.75 (m, 1H), 2.6 (m, 1H), 2.5 (m, 1H), 2.4 (s, 3H), 2.1 (m, 3H), 1.7 (m, 1H), 1.4 (s, 9H), 1.1 (d, 3H).

Preparation 80. N-[3-(1-Benzyl-3-methyl-piperidin-4-yloxy)-phenyl]-2-chloro-4-fluoro-benzamide cis isomer 1

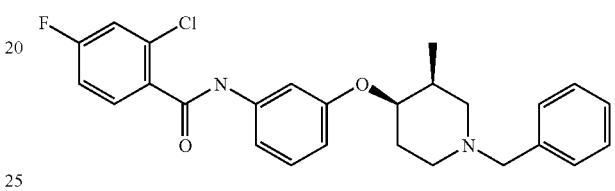

Combine racemic 3-(1-benzyl-cis-3-methyl-piperidin-4-yloxy)-phenylamine (preparation 41, 0.80 g, 2.7 mmol), 1,4-dioxane (20 mL), and 2-chloro-4-fluoro-benzoyl chloride (0.625 g, 3.24 mmol), stir and heat at reflux. After 2 hr., cool to ambient temperature. Dilute with methanol and load the resulting solution on 210 g SCX columns. Wash each with methanol (2×50 mL). Elute product from each column with 2M ammonia/methanol (2×50 mL). Combine and concentrate the eluents. Purify residue by silica gel flash chromatography eluting with 5% (2M NH$_3$/methanol)/methylene dichloride to obtain the title compound as a racemic mixture (1.07 g, 87.7%). Resolve using a Chiralpak AD™ 4.6×250 mm column eluting at 1.0 mL/min. with 10% absolute ethanol/90% Heptane with 0.2% DMEA to obtain of the title compound (0.524 g, 49.0%). Mass spectrum (electrospray): m/z=453.2 (M+1); $^1$H NMR (CDCl$_3$): 7.85 (bs, 1H), 7.8 (dd, 1H), 7.45 (s, 1H), 7.3 (m, 7H), 7.1 (m, 1H), 7.0 (m, 1H), 6.75 (dd, 1H), 4.4 (m, 1H), 3.5 (m, 2H), 2.5 (m, 2H), 2.4 (m, 2H), 2.1 (m, 2H), 1.8 (m, 1H), 1.0 (d, 3H).

Preparation 81. N-[3-(1-Benzyl-3-methyl-piperidin-4-yloxy)-phenyl]-2-chloro-4-fluoro-benzamide cis isomer 2

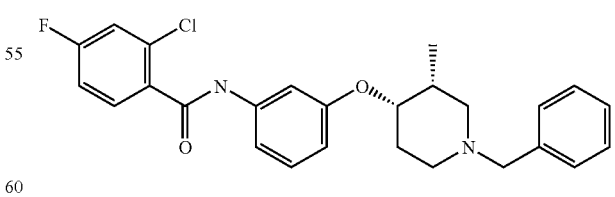

Resolve mixture from preparation 80 using a Chiralpak AD™ 4.6×250 mm column eluting at 1.0 mL/min with 10% absolute ethanol/90% Heptane with 0.2% DMEA to obtain the title compound (0.492 g, 46.0%). Mass spectrum (electrospray): m/z=453.2 (M+1); $^1$H NMR (CDCl$_3$): 7.85 (bs, 1H), 7.8 (dd, 1H), 7.45 (s, 1H), 7.3 (m, 7H), 7.1 (m, 1H), 7.0

(m, 1H), 6.75 (dd, 1H), 4.4 (m, 1H), 3.5 (m, 2H), 2.5 (m, 2H), 2.4 (m, 2H), 2.1 (m, 2H), 1.8 (m, 1H), 1.0 (d, 3H).

Example 62

2-chloro-4-fluoro-N-[3-(3-methyl-piperidin-4-yloxy)-phenyl]-benzamide monohydrogen chloride salt cis isomer 1

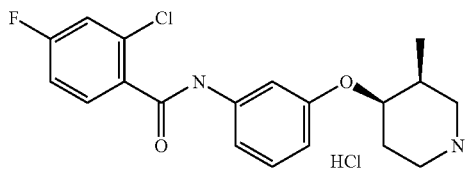

Combine N-[3-(1-benzyl-3-methyl-piperidin-4-yloxy)-phenyl]-2-chloro-4-fluoro-benzamide cis isomer 1 (preparation 80, 0.52 g, 1.15 mmol), 1,2-dichloroethane (20 mL) and 1-chloroethyl chloroformate (1.24 mL, 11.5 mmol), stir and heat at reflux. After 2 hr., cool to ambient temperature and concentrate. Dissolve the residue in methanol (20 mL), stir and heat at reflux. After 1.5 hr., cool to ambient temperature. Load reaction mixture on an SCX column (10 g), wash with methanol, elute with 2M ammonia/methanol. Concentrate eluent. Purify residue by silica gel flash chromatography eluting with 10% (2M $NH_3$/methanol)/methylene dichloride and converted to the mono hydrogen chloride salt to obtain the title compound (0.139 g, 33%). Mass spectrum: obs. m/z 363.1292; calc. m/z 363.1275; Analysis calculated for $C_{19}H_{21}Cl_2FN_2O_2 \cdot 0.35H_2O$: C, 56.39; H, 5.38; N, 6.92. Found: C, 56.43; H, 5.48; N, 6.73.

Example 63

2-chloro-4-fluoro-N-[3-(3-methyl-piperidin-4-yloxy)-phenyl]-benzamide monohydrogen chloride salt cis isomer 2

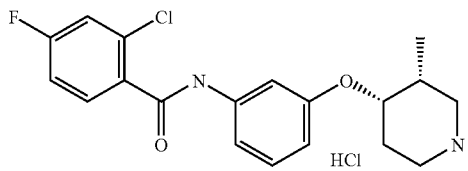

Dissolve N-[3-(1-benzyl-3-methyl-piperidin-4-yloxy)-phenyl]-2-chloro-4-fluoro-benzamide cis isomer 2 (preparation 81, 0.49 g, 1.09 mmol) in 1,2-dichloroethane (20 mL) and treat with 1-chloroethyl chloroformate (1.18 mL, 10.9 mmol), heat and stir at reflux. After 2 hr., cool to ambient temperature and concentrate to an oil. Dissolve residue in methanol (20 mL), heat and stir at reflux. After 1.5 hr., cool to ambient temperature. Load reaction mixture on an SCX column (10 g), wash with methanol, elute with 2M ammonia/methanol. Concentrate eluent. Purify residue by silica gel flash chromatography eluting with 10% (2M $NH_3$/methanol)/methylene dichloride and converted to the mono hydrogen chloride salt to obtain the title compound (0.156 g, 39%). Mass spectrum: Obs. m/z 363.1281; Calc. m/z 363.1275; Analysis calculated for $C_{19}H_{21}Cl_2FN_2O_2 \cdot 0.9H_2O$: C, 54.92; H, 5.53; N, 6.74. Found: C, 54.89; H, 5.33; N, 6.63.

Example 64

2-Chloro-N-[3-(1,3-dimethyl-piperidin-4-yloxy)-phenyl]-4-fluoro-benzamide monohydrogen chloride salt cis isomer 1

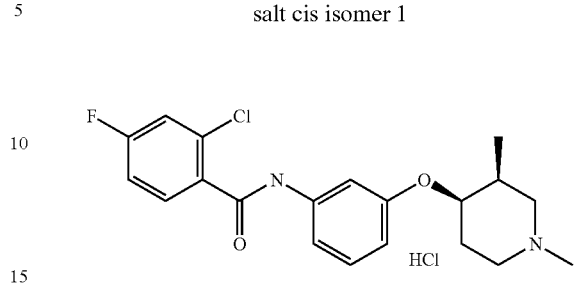

Combine 2-chloro-4-fluoro-N-[3-(3-methyl-piperidin-4-yloxy)-phenyl]-benzamide cis isomer 1 (free base of example 62, 0.10 g, 0.28 mmol), dichloromethane (10 mL), and 37% formaldehyde (0.23 mL, 2.8 mmol), stir at ambient temperature. After 10 minutes, add glacial acetic acid (0.024 mL, 0.42 mmol) and sodium-triacetoxyborohydride (0.09 g, 0.42 mmol). After 1.5 hr., concentrate to an oil. Dissolve residue in methanol (10 mL) and load on an SCX column (10 g), wash with methanol, elute with 2M ammonia/methanol. Concentrate eluent to obtain of the free base of the product (0.103 g, 100%). Dissolve this material in 1:1 dichloromethane: diethyl ether and treat with 1M hydrogen chloride in diethyl ether. Concentrate and dry under vacuum to obtain the title compound. Mass spectrum: Obs. m/z 377.1440; Calc. m/z 377.1432; $^1$H NMR ($CDCl_3$) for the free base: 7.9 (bs, 1H), 7.8 (m, 1H), 7.45 (m, 1H), 7.2 (m, 2H), 7.1 (m, 1H), 7.0 (m, 1H), 6.7 (m, 1H), 4.4 (m, 1H), 2.5 (m, 2H), 2.3 (m, 5H), 2.1 (m, 2H), 1.8 (m, 1H), 1.0 (d, 3H).

Example 65

2-Chloro-N-[3-(1,3-dimethyl-piperidin-4-yloxy)-phenyl]-4-fluoro-benzamide monohydrogen chloride salt cis isomer 2

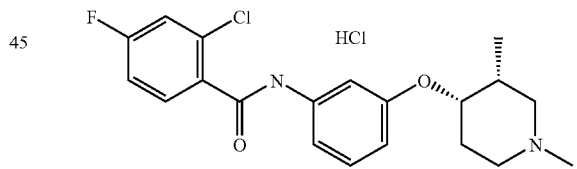

Combine 2-chloro-4-fluoro-N-[3-(3-methyl-piperidin-4-yloxy)-phenyl]-benzamide cis isomer 2 (free base of Example 63, 0.10 g, 0.28 mmol), dichloromethane (10 mL), and 37% formaldehyde (0.23 mL, 2.8 mmol), stir at ambient temperature. After 10 minutes, add glacial acetic acid (0.024 mL, 0.42 mmol) and sodium-triacetoxyborohydride (0.09 g, 0.42 mmol). After 1.5 hr., concentrate to an oil. Dissolve residue in methanol (10 mL) and load on an SCX column (10 g), wash with methanol, elute with 2M ammonia/methanol. Concentrate eluent to obtain the free base of the product (0.103 g, 100%). Dissolve this material in 1:1 dichloromethane:diethyl ether and treat with 1M hydrogen chloride in diethyl ether. Concentrate and dry under vacuum to obtain the title compound. Mass spectrum: Obs. m/z 377.1448; Calc. m/z 377.1432; $^1$H NMR ($CDCl_3$): 10.5 (bs, 1H), 10.4 (bs, 1H), 7.6 (m, 3H), 7.35 (m, 1H), 7.3 (m, 1H), 7.15 (m, 1H), 6.8

(dd, 1H), 4.5 (m, 1H), 3.25 (m, 2H), 3.0 (m, 2H), 2.8 (s, 3H), 2.3 (m, 1H), 2.1 (m, 2H), 1.0 (d, 3H).

Using procedures similar to preparation 80, using the appropriate Ar-acyl chloride, prepare and isolate the analogous compounds as free bases as indicated below:

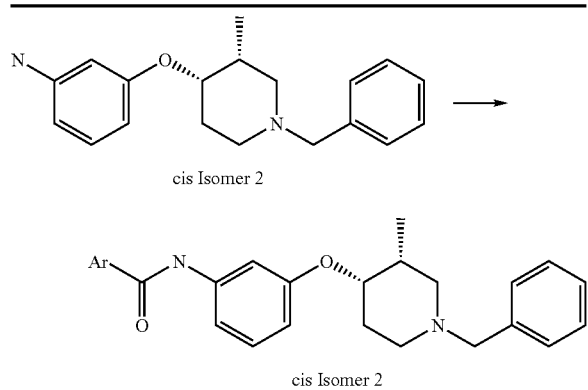

| Prep. | Ar | Data |
|---|---|---|
| 82 | 2,4,6-trifluoro-phenyl | Mass spectrum (electrospray): m/z = 455.3 (M + 1); $^1$H NMR (CDCl$_3$): 8.2 (bs, 1H), 7.4 (m, 1H), 7.3 (m, 6H), 7.0 (dd, 1H), 6.7 (m, 3H), 4.4 (m, 1H), 3.5 (m, 2H), 2.6 (m, 2H), 2.4 (m, 4H), 2.0 (m, 2H), 1.8 (m, 1H), 1.0 (d, 3H). |
| 83 | 2,4-difluoro-phenyl | Mass spectrum (electrospray): m/z = 437.3 (M + 1); $^1$H NMR (CDCl$_3$): 8.3 (d, 1H), 8.2 (m, 1H), 7.5 (m, 1H), 7.35 (m, 4H), 7.25 (m, 2H), 7.05 (m, 2H), 6.95 (dd, 1H), 6.7 (dd, 1H), 4.4 (m, 1H), 3.55 (m, 2H), 2.55 (m, 2H), 2.4 (m, 2H), 2.1 (m, 2H), 1,8 (m, 1H), 1.0 (d, 3H). |
| 84 | 2-chloro-phenyl | Mass spectrum (electrospray): m/z = 435.3 (M + 1); $^1$H NMR (CDCl$_3$): 7.85 (bs, 1H), 7.8 (dd, 1H), 7.35 (m, 10H), 7.0 (dd, 1H), 6.7 (dd, 1H), 4.4 (m, 1H), 3.55 (m, 2H), 2.6 (m, 2H), 2.4 (m, 2H), 2.1 (m, 2H), 1.8 (m, 1H), 1.0 (d, 3H). |
| 85 | 2-chloro-6-fluoro-phenyl | Mass spectrum (electrospray): m/z = 453.2 (M + 1); $^1$H NMR (CDCl$_3$): 7.9 (bs, 1H), 7.4 (m, 1H), 7.3 (m, 5H), 7.25 (m, 3H), 7.0 (m, 2H), 6.7 (dd, 1H), 4.4 (m, 1H), 3.55 (m, 2H), 2.6 (m, 2H), 2.4 (m, 2H), 2.1 (m, 2H), 1.8 (m, 1H), 1.0 (d, 3). |

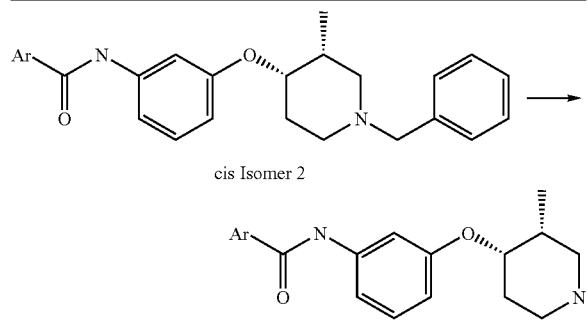

Using procedures similar to example 63, prepare, isolate, and convert the analogous compounds into the monohydrogen chloride salts as indicated below:

| Ex | Ar | Data |
|---|---|---|
| 66 | 2,4,6-trifluoro-phenyl | Mass spectrum (electrospray): m/z = 365.2 (M + 1); $^1$H NMR (CDCl$_3$): 7.7 (bs, 1H), 7.4 (m, 1H), 7.2 (m, 1H), 6.95 (dd, 1H), 6.7 (m, 3H), 4.4 (m, 1H), 2.8 (m, 4H), 2.1 (m, 1H), 2.0 (m, 2H), 1.6 (m, 1H), 0.95 (d, 3H). |
| 67 | 2,4-difluoro-phenyl | Mass spectrum: Obs. m/z 347.1583; Calc. m/z 347.1571; $^1$H NMR (DMSO-d$_6$): 10.4 (bs, 1H), 9.0 (bs, 1H), 7.75 (m, 1H), 7.5 (s, 1H), 7.4 (m, 1H), 7.2 (m, 2H), 6.8 (m, 1H), 4.5 (m, 1H), 3.1 (m, 2H), 2.9 (m, 2H), 2.25 (m, 1H), 2.0 (m, 2H), 1.0 (d, 3H). |
| 68 | 2-chloro-phenyl | Mass spectrum: Obs. m/z 345.1382; Calc. m/z 345.1370; $^1$H NMR (DMSO-d$_6$): 10.5 (bs, 1H), 9.1 (bs, 1H), 7.5 (m, 5H), 7.2 (m, 2H), 6.8 (m, 1H), 4.5 (m, 1H), 3.1 (m, 2H), 2.9 (m, 2H), 2.3 (m, 1H), 2.0 (m, 2H), 1.0 (d, 3H). |
| 69 | 2-chloro-6-fluoro-phenyl | Mass spectrum: Obs. m/z 363.1293; Calc. m/z 363.1275; $^1$H NMR (DMSO-d$_6$): 10.8 (bs, 1H), 9.0 (bs, 1H), 7.5 (m, 2H), 7.4 (m, 2H), 7.3 (m, 1H), 7.15 (m, 1H), 6.8 (dd, 1H), 4.55 (m, 1H), 3.1 (m, 2H), 2.95 (m, 2H), 2.25 (m, 1H), 2.0 (m, 2H), 1.0 (d, 3H). |

Using procedures similar to example 65, prepare, isolate, and convert the analogous compounds into the monohydrogen chloride salts as indicated below:

| Ex. | Ar | Data |
|---|---|---|
| 70 | 2,4,6-trifluoro-phenyl | Mass spectrum: Obs. m/z 379.1629; Calc. m/z 379.1633; $^1$H NMR (DMSO-d$_6$):10.8 (bs, 1H), 10.5 (bs, 1H), 7.55 (s, 1H), 7.4 (m, 2H), 7.3 (m, 1H), 7.1 (m, 1H), 6.8 (m, 1H), 4.5 (m, 1H), 3.3 (m, 2H), 3.0 (m, 2H), 2.8 (s, 3H), 2.3 (m, 1H), 2.1 (m, 2H), 1.0 (d, 3H). |
| 71 | 2,4-difluoro-phenyl | Mass spectrum: Obs. m/z 361.1735; Calc. m/z 361.1728, $^1$H NMR (DMSO-d$_6$): 10.6 (bs, 1H), 10.4 (bs, 1H), 7.75 (m, 1H), 7.6 (s, 1H), 7.4 (m, 1H), 7.2 (m, 3H), 6.8 (m, 1H), 4.5 (m, 1H), 3.25 (m, 2H), 3.0 (m, 2H), 2.8 (s, 3H), 2.35 (m, 1H), 2.1 (m, 2H), 1.0 (d, 3H). |
| 72 | 2-chloro-phenyl | Mass spectrum: Obs. m/z 359.1537; Calc. m/z 359.1526, $^1$H NMR(DMSO-d$_6$): 10.7 (bs, 1H), 10.5 (bs, 1H), 7.5 (m, 5H), 7.2 (m, 2H), 6.8 (m, 1H), 4.5 (m, 1H), 3.25 (m, 2H), 3.0 (m, 2H), 2.8 (s, 3H), 2.35 (m, 1H), 2.1 (m, 2H), 1.0 (d, 3H). |
| 73 | 2-chloro-6-fluoro-phenyl | Mass spectrum: Obs. m/z 377.1443; Calc. m/z 377.1432, $^1$H NMR (DMSO-d$_6$): 10.8 (bs, 1H), 10.6 (bs, 1H), 7.55 (m, 2H), 7.4 (m, 2H), 7.3 (m, 1H), 7.1 (m, 1H), 6.8 (dd, 1H), 4.5 (m, 1H), 3.25 (m, 2H), 3.0 (m, 2H), 2.8 (s, 3H), 2.35 (m, 1H), 2.1 (m, 2H), 1.0 (d, 3H). |

Preparation 86. 4-[3-(2-Chloro-4-fluoro-benzoylamino)-phenoxy]-cis-2-methyl-piperidine-1-carboxylic acid tert-butyl ester isomer 2

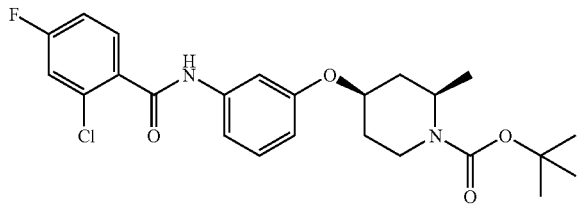

Combine 4-(3-amino-phenoxy)-cis-2-methyl-piperidine-1-carboxylic acid tert-butyl ester isomer 2 (preparation 39, 0.29 g), triethyl amine (95 mg), and 2-chloro-4-fluorobenzoyl chloride (0.201 g) in THF (10 mL) and stir at room temperature. After 18 hr., partition between ethyl acetate and saturated aqueous NaCl, dry over anhydrous sodium sulfate, evaporate and dry in vacuum to give the title compound (0.464 g). Mass spectrum (electrospray) m/z=461 (M−1); $^1$H NMR (CDCl$_3$): 7.87 (br s, 1H), 7.72 (dd, 1H), 7.37 (t, 1H), 7.19 (dd, 1H), 7.13 (dd, 1H), 7.02 (ddd, 1H), 6.97 (dd, 1H), 6.64 (dd, 1H), 4.63 (m, 1H), 4.28 (m, 1H), 3.81 (m, 1H), 3.20 (m, 1H), 1.88 (m, 2H), 1.81 (m, 1H), 1.67 (m, 1H), 1.40 (s, 9H), 1.24 (d, J=7.1 Hz, 3H). (file: mn4-a01246-76).

Preparation 87. Ex. 13 4-[3-(2-Chloro-4-fluoro-benzoylamino)-phenoxy]-trans-2-methyl-piperidine-1-carboxylic acid tert-butyl ester isomer 2

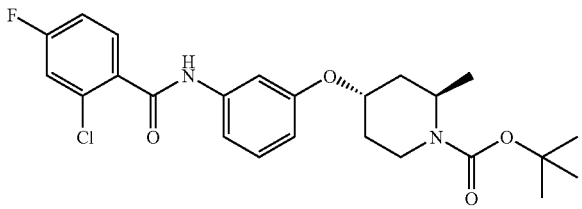

Using a method similar to preparation 86, using 4-(3-amino-phenoxy)-trans-2-methyl-piperidine-1-carboxylic acid tert-butyl ester isomer 2 (preparation 40) gives the title compound. Mass spectrum (electrospray) m/z=463 (M+1); $^1$H NMR (CDCl$_3$): 8.12 (br s, 1H), 7.71 (dd, 1H), 7.45 (t, 1H), 7.23 (dd, 1H), 7.15 (dd, 1H), 7.05 (m, 2H), 6.69 (dd, 1H), 4.54 (m, 2H), 4.07 (m, 1H), 2.94 (m, 1H), 2.12 (m, 1H), 2.03 (m, 1H), 1.68 (m, 1H), 1.53 (m, 1H), 1.44 (s, 9H), 1.21 (d, J=7.1 Hz, 3H). (file: mn4-a1246-83).

Example 74

2-Chloro-4-fluoro-N-[3-(cis-2-methyl-piperidin-4-yloxy)-phenyl]-benzamide isomer 2

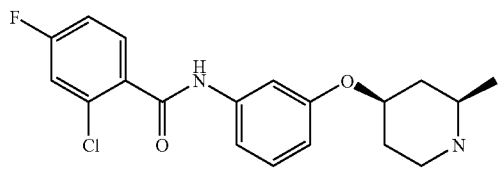

Add 0.7 mL of conc. hydrochloric acid into a solution of 4-[3-(2-chloro-4-fluoro-benzoylamino)-phenoxy]-cis-2-methyl-piperidine-1-carboxylic acid tert-butyl ester isomer 2 (Preparation 86, 0.464 g) in 1,4-dioxane 20 mL and heat at 100° C. for 40 min. Partition between ethyl acetate and saturated aqueous NaCl, dry over anhydrous sodium sulfate, evaporate and purify on a silica gel column (10 g, solvent: dichloromethane-2M NH$_3$ in methanol, gradient) to give the title compound (0.298 g). Mass spectrum (electrospray) m/z=363 (M+1); $^1$H NMR (CDCl$_3$): 7.94 (br s, 1H), 7.77 (dd, 1H), 7.41 (t, 1H), 7.24 (t, 1H), 7.19 (dd, 1H), 7.08 (m, 2H), 6.72 (m, 1H), 4.29 (m, 1H), 3.46 (s, 3H), 3.17 (m, 1H), 2.73 (m, 2H), 2.14 (m, 2H), 1.69 (br, 1H), 1.51 (m, 1H), 1.22 (m, 1H), 1.14 (d, J=6.4 Hz, 3H).

Dissolve the benzamide (0.115 g) in dichloromethane-methanol and add 0.31 mL of 1N HCl in ether, evaporate and dry in vacuum to give the hydrochloric acid salt.

Example 75

2-Chloro-4-fluoro-N-[3-(trans-2-methyl-piperidin-4-yloxy)-phenyl]-benzamide isomer 2 hydrochloride

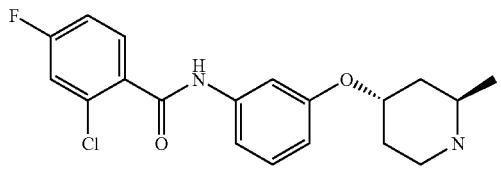

Using a method similar to example 74, using 4-[3-(2-chloro-4-fluoro-benzoylamino)-phenoxy]-trans-2-methyl-piperidine-1-carboxylic acid tert-butyl ester isomer 2 (preparation 87), gives the title compound. Mass spectrum (electrospray) m/z 363 (M+1); $^1$H NMR (CDCl$_3$): 8.07 (br s, 1H), 7.74 (dd, 1H), 7.41 (t, 1H), 7.24 (t, 1H), 7.18 (dd, 1H), 7.06 (m, 2H), 6.71 (dd, 1H), 4.69 (m, 1H), 3.09 (m, 2H), 2.86 (m, 1H), 1.96 (m, 2H), 1.67 (m, 1H), 1.36 (m, 1H), 1.04 (d, J=6.4 Hz, 3H).

Example 76

2-Chloro-N-[3-(1,cis-2-dimethyl-piperidin-4-yloxy)-phenyl]-4-fluoro-benzamide isomer 2

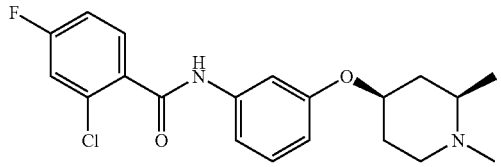

Mix 2-chloro-4-fluoro-N-[3-(2-methyl-piperidin-4-yloxy)-phenyl]-benzamide isomer 2 (example 74, 0.169 g), formaldehyde (37%, 0.2 mL), sodium triacetoxyborohydride (0.138 g) and acetic acid (0.070 g) with dichloromethane (10 mL) and stir for two hours. Dilute with methanol (5 mL) and load on a SCX column (10 g), wash with methanol, elute with 2M NH$_3$-methanol, evaporate to give the title compound (0.166 g, 94%). Mass spectrum (electrospray) m/z=377 (M+1); $^1$H NMR (CDCl$_3$): 7.87 (br s, 1H), 7.79 (dd, 1H), 7.42 (m, 1H), 7.25 (t, 1H), 7.20 (dd, 1H), 7.08 (m, 2H), 6.72 (dd, 1H), 4.27 (m, 1H), 2.99 (m, 1H), 2.33 (s, 3H), 2.25 (m, 1H), 2.13 (m, 3H), 1.80 (m, 1H), 1.53 (m, 1H), 1.17 (d, J=5.9 Hz, 3H).

Dissolve the benzamide (0.166 g) in dichloromethane-methanol and add 0.44 mL of 1N HCl in ether, evaporate and dry in vacuum to give the hydrochloric acid salt.

Example 77

2-Chloro-N-[3-(1,trans-2-dimethyl-piperidin-4-yloxy)-phenyl]-4-fluoro-benzamide isomer 2 hydrochloride

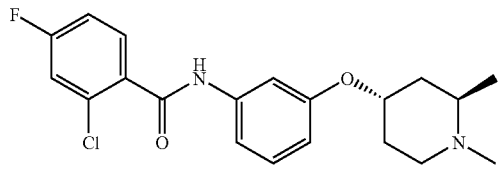

Using a method similar to example 76, using 2-chloro-4-fluoro-N-[3-(trans-2-methyl-piperidin-4-yloxy)-phenyl]-benzamide isomer 2 (example 75) gives the title compound: mass spectrum (electrospray) m/z=377 (M+1); $^1$H NMR (CDCl$_3$): 8.07 (br s, 1H), 7.74 (dd, 1H), 7.41 (t, 1H), 7.24 (t, 1H), 7.18 (dd, 1H), 7.06 (m, 2H), 6.71 (dd, 1H) 4.69 (m, 1H), 3.09 (m, 2H), 2.86 (m, 1H), 1.96 (m, 2H), 1.67 (m, 1H), 1.36 (m, 1H), 1.04 (d, J=6.4 Hz, 3H).

Preparation 88. N-[3-(1-Benzyl-3-trans-methyl-piperidin-4-yloxy)-phenyl]-2-chloro-4-fluoro-benzamide Heat a solution of racemic 3-(1-benzyl-3-trans-methyl-piperidin-4-yloxy)-phenylamine (preparation 44, 0.220 g) and 2-chloro-4-fluorobenzoyl chloride (0.158 g) in 1,4-dioxane (10 mL) at reflux for 2 hours. Load the reaction mixture onto a SCX column (10 g) and wash the column with methanol. Elute the product with 2N NH$_3$-methanol and evaporate to give the title compound (0.324 g): $^1$H NMR (CDCl$_3$): 7.97 (br s, 1H), 7.74 (dd, 1H), 7.41 (t, 1H), 7.33 (m, 4H), 7.26 (m, 1H), 7.23 (m, 1H), 7.17 (dd, 1H), 7.07 (m, 2H), 6.72 (m, 1H), 3.83 (m, 1H), 3.52 (s, 2H), 2.86 (m, 2H), 2.13 (m, 2H), 2.02 (m, 1H), 1.86 (m, 1H), 1.68 (m, 1H), 0.99 (d, J=6.6 Hz, 3H). (file: mn4-a01246-93)

Isolate the product using a chiral column (Chiralpak AD 4.6×250 mm, eluent: 10% IPA, 90% heptane with 0.2% DMEA) to give isomer 1 (58 mg, 99% ee) and isomer 2 (48 mg, 97% ee).

Using a method similar to preparation 88, using racemic 3-(1-benzyl-trans-3-methyl-piperidin-4-yloxy)-phenylamine (preparation 44) and the appropriate Ar-acyl chloride, prepare the analogous free base compounds indicated below:

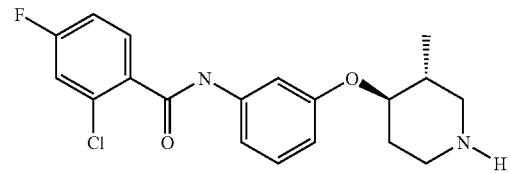

| Prep. | Ar | Data |
|---|---|---|
| 89 | 2,4,6-trichlorophenyl, racemic 6 | mass spectrum (electric spray) m/z = 503 (M + 1); $^1$H NMR (CDCl$_3$): 7.46 (br s, 1H), 7.38 (s, 2H), 7.37 (m, 1H), 7.32 (m, 4H), 7.26 (m, 1H), 7.24 (m, 1H), 7.05 (m, 1H), 6.73 (m, 1H), 3.82 (m, 1H), 3.51 (s, 2H), 2.85 (m, 2H), 2.12 (m, 2H), 2.00 (m, 1H), 1.84 (m, 1H), 1.66 (m, 1H), 0.99 (d, J = 6.4 Hz, 3H). |
| 90 | 2,4,6-trifluorophenyl, racemic | $^1$H NMR (CDCl$_3$): 7.59 (br s, 1H), 7.40 (t, 1H), 7.33 (m, 4H), 7.25 (m, 2H), 7.02 (m, 1H), 6.75 (m, 3H), 3.83 (m, 1H), 3.51 (s, 2H), 2.86 (m, 2H), 2.14 (m, 2H), 2.00 (m, 1H), 1.85 (m, 1H), 1.67 (m, 1H), 0.99 (d, J = 6.4 Hz, 3H). |
| 91 | 2-chloro-6-fluoro-phenyl, racemic | $^1$H NMR (CDCl$_3$): 7.53 (br s, 1H), 7.41 (m, 1H), 7.34 (m, 5H), 7.25 (m, 3H), 7.06 (m, 2H), 6.72 (m, 1H), 3.83 (m, 1H), 3.52 (s, 2H), 2.86 (m, 2H), 2.13 (m, 2H), 2.02 (m, 1H), 1.86 (m, 1H), 1.68 (m, 1H), 0.99 (d, J = 6.4 Hz, 3H). |

Example 78

2-Chloro-4-fluoro-N-[3-(3-trans-methyl-piperidin-4-yloxy)-phenyl]-benzamide isomer 1

Combine N-[3-(1-benzyl-3-trans-methyl-piperidin-4-yloxy)-phenyl]-2-chloro-4-fluoro-benzamide isomer 1 (preparation 88, 58 mg), and 1-chloroethyl chloroformate (183 mg) in 1,2-dichloroethane (10 mL) and reflux. After 1 hr., dilute the reaction mixture with methanol and load onto a SCX column (10 g) and wash the column with methanol. Elute the product with 2N NH$_3$-methanol, evaporate and purify on a silica gel column (10 g, solvent: dichloromethane-2M NH$_3$ in methanol, gradient) to give the title compound (43 mg). Mass spectrum (electrospray) m/z=363 (M+1); $^1$H NMR (CDCl$_3$): 7.90 (br s, 1H), 7.79 (dd, 1H), 7.43 (t, 1H), 7.25 (t, 1H), 7.20 (dd, 1H), 7.10 (m, 1H), 7.05 (m, 1H), 6.73 (m, 1H), 3.92 (m, 1H), 3.12 (m, 2H), 2.71 (m, 1H), 2.40 (m, 1H), 2.17 (m, 1H), 1.90 (m, 1H), 1.50 (m, 1H), 1.01 (d, J=6.6 Hz, 3H).

Dissolve the benzamide (13.2 mg) in dichloromethane-methanol and add 0.04 mL of 1N HCl in ether, evaporate and dry in vacuum to give the hydrochloric acid salt.

Using a method similar to example 78, prepare the analogous compounds and their hydrochloride salts as indicated below:

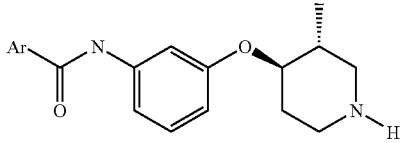

| Ex. | Ar | Data |
| --- | --- | --- |
| 79 | 2-chloro-4-fluorophenyl isomer 2 | mass spectrum (electrospray) m/z = 363 (M + 1); $^1$H NMR (CDCl$_3$)(free base): 7.84 (br s, 1H), 7.82 (dd, 1H), 7.45 (m, 1H), 7.24 (m, 2H), 7.11 (m, 1H), 7.05 (dd, 1H, 6.73 (dd, 1H), 3.95 (m, 1H), 3.18 (m, 2H), 2.77 (m, 1H), 2.45 (m, 1H), 2.21 (m, 1H), 1.90 (m, 1H), 1.52 (m, 1H), 1.05 (d, J = 6.6 Hz, 3H). |
| 80 | 2,4,6-trichlorophenyl isomer 2 | mass spectrum (electric spray) m/z = 413 (M + 1); $^1$H NMR (CDCl$_3$): 8.74 (br s, 1H), 7.36 (t, 1H), 7.30. (s, 2H), 7.21 (t, 1H), 7.06 (m, 1H), 6.70 (m, 1H), 3.82 (m, 1H), 3.00 (m, 2H), 2.58 (m, 1H), 2.25 (m, 1H), 2.11 (m, 1H), 1.71 (m, 1H), 1.41 (m, 1H), 0.95 (d, J = 6.4 Hz, 3H). |
| 81 | 2,4,6-trifluorophenyl isomer 2 | mass spectrum (electric spray) m/z = 365 (M + 1); $^1$H NMR (CDCl$_3$): 7.64 (br s, 1H), 7.43 (t, 1H), 7.24 (m, 1H), 7.02 (m, 1H), 6.76 (m, 3H), 3.91 (m, 1H), 3.13 (m, 2H), 2.70 (m, 1H), 2.39 (m, 1H), 2.17 (m, 1H), 2.03 (br, 1H), 1.83 (m, 1H), 1.51 (m, 1H), 1.01 (d, J = 6.4 Hz, 3H). |
| 82 | 2-chloro-6-fluoro isomer 2 | mass spectrum (electric spray) m/z = 363 (M + 1); $^1$H NMR (CDCl$_3$): 8.57 (br s, 1H), 7.40 (m, 1H), 7.30 (m, 1H), 7.21 (m, 2H), 7.04 (m, 2H), 6.68 (m, 1H), 3.86 (m, 1H), 3.04 (m, 2H), 2.63 (m, 2H), 2.30 (m, 1H), 2.14 (m, 1H), 1.77 (m, 1H), 1.44 (m, 1H), 0.96 (d, J = 6.4 Hz, 3H). |

Example 83

2-Chloro-N-[3-(1,3-dimethyl-piperidin-4-trans-yloxy)-phenyl]-4-fluoro-benzamide isomer 1

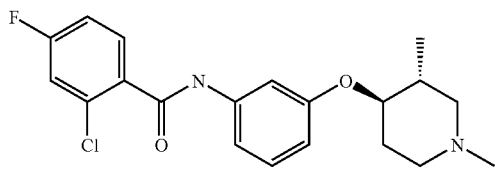

Mix 2-chloro-4-fluoro-N-[3-(3-trans-methyl-piperidin-4-yloxy)-phenyl]-benzamide isomer 1 (example 78, 30 mg), formaldehyde (37%, 25 mg), sodium triacetoxyborohydride (23 mg) and acetic acid (13 mg) with dichloromethane (5 mL) and stir overnight. Dilute with methanol and load on a SCX column (10 g), wash with methanol, elute with 2M NH$_3$-methanol, evaporate to give the title compound (23.2 mg). Mass spectrum (electrospray) m/z=377 (M+1); $^1$H NMR (CDCl$_3$): 7.84 (br s, 1H), 7.80 (dd, 1H), 7.43 (t, 1H), 7.26 (t, 1H), 7.21 (dd, 1H), 7.11 (m, 1H), 7.04 (m, 1H), 6.73 (m, 1H), 3.84 (m, 1H), 2.86 (m, 2H), 2.30 (s, 3H), 2.16 (m, 2H), 2.04 (m, 1H), 1.87 (m, 1H), 1.71 (m, 1H), 1.03 (d, J=6.6 Hz, 3H).

Dissolve the benzamide (23.2 mg) in dichloromethane-methanol and add 0.062 mL of 1N HCl ether, evaporate and dry in vacuum to give the hydrochloric acid salt.

Using a method similar to example 83, prepare the analogous compounds and their mono-hydrochlorides as indicated below:

| Ex. | Ar | Data |
| --- | --- | --- |
| 84 | 2-chloro-4-fluoro isomer 2 (free base) | mass spectrum (electrospray) m/z = 377 (M + 1); $^1$H NMR (CDCl$_3$)(free base): 7.88 (br s, 1H), 7.79 (dd, 1H), 7.43 (m, 1H), 7.25 (m, 1H), 7.20 (m, 1H), 7.10 (m, 1H), 7.04 (m, 1H), 6.72 (m, 1H), 3.83 (m, 1H), 2.85 (m, 2H), 2.29 (s, 3H), 2.13 (m, 2H), 2.05 (m, 1H), 1.86 (m, 1H), 1.70 (m, 1H), 1.03 (d, J = 6.4 Hz, 3H). |
| 85 | 2,4,6-trichloro isomer 2 (free base) LY 675527 | mass spectrum (electrospray) m/z = 427 (M + 1); $^1$H NMR (CDCl$_3$)(free base): 7.98 (br s, 1H), 7.39 (dd, 1H), 7.33 (s, 2H), 7.23 (dd, 1H), 7.06 (m, 1H), 6.72 (m, 1H), 3.80 (m, 1H), 2.83 (m, 2H), 2.28 (s, 3H), 2.13 (m, 2H), 2.02 (m, 1H), 1.85 (m, 1H), 1.70 (m, 1H), 1.00 (d, J = 6.7 Hz, 3H). |
| 86 | 2,4,6-trifluoro isomer 2 (free base) | mass spectrum (electrospray) m/z = 379 (M + 1); $^1$H NMR (CDCl$_3$)(free base): 7.84 (br s, 1H), 7.41 (dd, 1H), 7.22 (m, 1H), 7.02 (m, 1H), 6.73 (m, 3H), 3.80 (m, 1H), 2.81 (m, 2H), 2.26 (s, 3H), 2.10 (m, 2H), 2.00 (m, 1H), 1.80 (m, 1H), 1.65 (m, 1H), 1.00 (d, J = 6.9 Hz, 3H). |
| 87 | 2-chloro-6-fluorophenyl isomer 2 (free base) LY 675529 | mass spectrum (electrospray) m/z = 377 (M + 1); $^1$H NMR (CDCl$_3$)(free base): 7.81 (br s, 1H), 7.42 (m, 1H), 7.33 (m, 1H), 7.23 (m, 2H), 7.06 (m, 2H), 6.75 (m, 1H), 3.80 (m, 1H), 2.81 (m, 2H), 2.26 (s, 3H), 2.12 (m, 2H), 2.01 (m, 1H), 1.81 (m, 1H), 1.65 (m, 1H), 1.21 (d, J = 6.9 Hz, 3H). |

Preparation 92. 4-[6-(2,4,6-Trifluoro-benzoylamino)-pyridin-2-yloxy]-piperidine-1-carboxylic acid tert-butyl ester

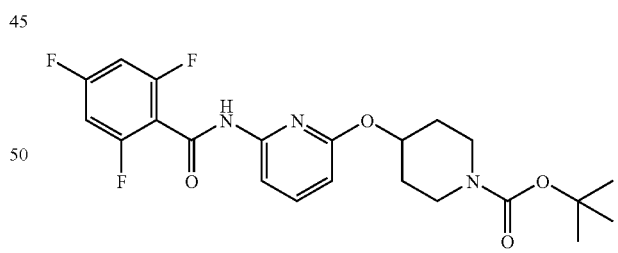

Add 2,4,6-trifluorobenzoyl chloride (1.64 g, 8.42 mmol) to a solution of 4-(6-amino-pyridin-2-yloxy)-piperidine-1-carboxylic acid tert-butyl ester (preparation 71, 2.06 g, 7.02 mmol) in triethylamine (1.066 g, 1.5 mL, 10.53 mmol) and THF (70 mL). Heat at 40° C. overnight. Dilute the mixture with ethyl acetate, wash with 0.1 N HCl, saturated NaHCO$_3$ solution and saturated NaCl solution sequentially. Dry over Na$_2$SO$_4$, filter and concentrate to give a residue. Chromatography (silica gel) eluting with 14% ethyl acetate in hexanes provides 2.482 g (78%) of the title compound: mass spectrum (ion spray): m/z=452.1 (M+1); $^1$H NMR (CDCl$_3$, ppm): 8.01

(s, br, 1H), 7.87 (d, br, 1H), 7.67 (t, 1H), 6.81 (m, 2H), 6.55 (d, 1H), 5.11 (m, 1H), 3.73 (m, 2H), 3.33 (m, 2H), 1.93 (m, 2H), 1.74 (m 2H), 1.49 (s, 9H).

Example 84

2,4,6-Trifluoro-N-[6-(piperidin-4-yloxy)pyridin-2-yl]-benzamide

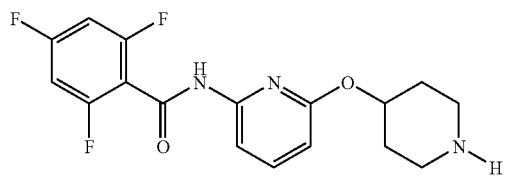

Add trifluoroacetic acid (20 mL) to a solution of 4-[6-(2, 4,6-trifluoro-benzoylamino)-pyridin-2-yloxy]-piperidine-1-carboxylic acid tert-butyl ester (preparation 92, 2.482 g, 5.5 mmol) in methylene dichloride (50 mL) and stir for 30 min. Remove volatiles, dissolve the residue in methylene dichloride, adjust pH>11 with 1N NaOH, extract with methylene dichloride three times. Combine the organic layers, dry over $Na_2SO_4$, filter and concentrate to give a residue. Recrystallization (ethanol-$H_2O$) provides 1.625 g of the title compound as a white solid. Concentrate themother liquor and further purify by chromatography (silica gel, eluting with 5.5% 2M $NH_3$-methanol in $CH_2Cl_2$) to provide another 200 mg (total yield 94%) of the title compound: mass spectrum (ion spray): m/z=352.0 (M+1); $^1$H NMR (CDCl$_3$, ppm): 8.35 (br, 1H), 7.68 (d, br, 1H), 7.46 (t, 1H), 6.60 (m, 2H), 6.34 (d, 1H), 4.84 (m, 1H), 2.93 (m, 2H), 2.59 (m, 2H), 1.85 (m, 2H), 1.46 (m, 3H).

Example 85

2,4,6-Trifluoro-N-[6-(1-propyl-piperidin-4-yloxy)-pyridin-2-yl]-benzamide

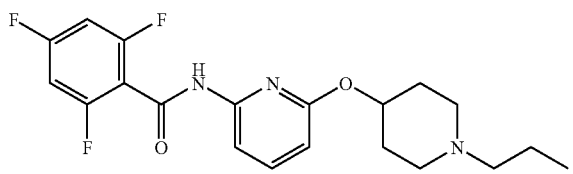

Combine 2,4,6-trifluoro-N-[6-(piperidin-4-yloxy)pyridin-2-yl]-benzamide (example 84, 250 mg, 0.71 mmol), propionaldehyde (124 mg, 2.14 mmol), acetic acid (85 mg, 1.42 mmol), molecular sieve 4 Å (0.4 g) and THF (6 mL), stir for 15 min. Then add NaBH(tri-acetate) portionwise and stir for 3 hr. Quench the reaction with 0.1N NaOH, extract with methylene dichloride three times. Combine the organic layers, dry over $Na_2SO_4$, filter and concentrate to give a residue. Chromatography (silica gel) eluting with 5% 2M $NH_3$-methanol in methylene dichloride provides 192 mg (69%) of the title compound: mass spectrum (ion spray): m/z=394.1 (M+1); $^1$H NMR (CDCl$_3$, ppm): 8.00 (s, br, 1H), 7.84 (d, br, 1H), 7.64 (t, 1H), 6.78 (m, 2H), 6.52 (d, 1H), 4.94 (m, 1H), 2.75 (m, 2H), 2.32 (m, 4H), 2.04 (m, 2H), 1.85 (m, 2H), 1.55 (m, 2H), 0.92 (t, 3H). Mono-hydrochloride salt: Anal calcd for $C_{20}H_{22}F_3N_3O_2$.HCl.0.25$H_2O$: C, 55.30; H, 5.45; N, 9.67. Found: C, 55.13; H, 5.36; N, 9.61.

Example 86

2,4,6-Trifluoro-N-[6-(1-ethyl-piperidin-4-yloxy)-pyridin-2-yl]-benzamide

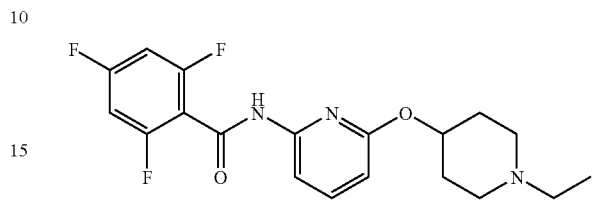

Using a method similar to example 85, using acetaldehyde provides the title compound (36%): mass spectrum (ion spray): m/z=380.1 (M+1); $^1$H NMR (CDCl$_3$, ppm): 8.00 (s, br, 1H), 7.85 (d, br, 1H), 7.65 (t, 1H), 6.79 (m, 2H), 6.54 (d, 1H), 4.96 (m, 1H), 2.75 (m, 2H), 2.46 (q, 2H), 2.33 (m, 2H), 2.03 (m, 2H), 1.84 (m, 2H), 1.12 (t, 3H). Mono-hydrochloride salt: Anal calcd for $C_{19}H_{20}F_3N_3O_2$.HCl: C, 54.88; H, 5.09; N, 10.10. Found: C, 54.58; H, 5.07; N, 10.21.

Example 87

2,4,6-Trifluoro-N-(6-{1-[2-(1-isopropyl-1H-pyrazol-4-yl)-ethyl]-piperidin-4-yloxy}-pyridin-2-yl)-benzamide

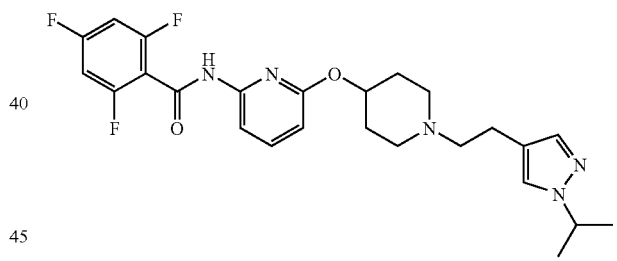

Combine 2,4,6-trifluoro-N-[6-(piperidin-4-yloxy)pyridin-2-yl]-benzamide (example 84, 250 mg, 0.71 mmol), NaHCO$_3$ (96 mg, 1.14 mmol), KI (24 mg, 0.14 mmol) and DMF (5 mL). Add methanesulfonic acid 2-(isopropyl-1H-pyrazol-4-yl)-ethyl ester (214 mg, 0.92 mmol) dropwise to the above mixture and then beat at 80° C. overnight. Quench the reaction with 0.1N NaOH solution, extract with ether/ethylacetate (8:1) three times. Combine the organic layers, dry over $Na_2SO_4$, filter and concentrate to give a residue. Chromatography (silica gel) eluting with 3-4% methanol in methylene dichloride provides 96 mg (28%) of the title compound as a white solid: mass spectrum (ion spray): m/z=488.1 (M+1); $^1$H NMR (CDCl$_3$, ppm): 8.04 (s, br, 1H), 7.86 (d, br, 1H), 7.65 (t, 1H), 7.37 (s, 1H), 7.27 (s, 1H), 6.81 (m, 2H), 6.55 (d, 1H), 4.98 (m, 1H), 4.45 (hept, 1H), 2.81 (m 2H), 2.68 (m, 2H), 2.59 (m, 2H), 2.04 (m, 2H), 2.04 (m, 2H), 1.88 (m, 2H), 1.49 (d, 6H). Hydrochloride salt: Anal calcd for $C_{25}H_{28}F_3N_5O_2$.HCl.0.5$H_2O$: C, 56.34; H, 5.67; N, 13.14. Found: C, 56.35; H, 5.58; N, 12.96.

Preparation 93. N-[6-(1-Benzyl-2,2-dimethyl-piperidin-4-yloxy)-pyridin-2-yl]-2-chloro-4-fluoro-benzamide

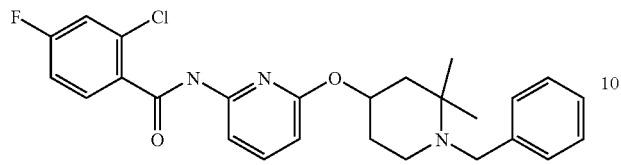

Combine 6-(1-benzyl-2,2-dimethyl-piperidin-4-yloxy)-pyridin-2-ylamine (preparation 66, 0.537 g, 1.72 mmol), 1,4-dioxane (20 mL) and 2-chloro-4-fluoro-benzoyl chloride (0.20 g, 1.04 mmol), stir and heat to reflux. After 1.5 hr., cool to ambient temperature and concentrate. Dissolve the residue in methanol (10 mL) and load on an SCX column (10 g); wash with methanol (2×50 mL); elute product with 2M ammonia/methanol (2×50 mL). Concentrate the eluent. Purify the crude mixture by silica gel flash chromatography eluting with 9:1 hexane:ethyl acetate to obtain the title compound (0.056 g 11.5%). Mass spectrum (electrospray): m/z=468.2 (M+1); $^1$H NMR (CDCl$_3$): 8.3 (bs, 1H), 7.8 (m, 2H), 7.6 (dd, 1H), 7.3 (m, 6H), 7.1 (m, 1H), 6.5 (d, 1H), 5.1 (m, 1H), 3.9 (d, 1H), 3.2 (d, 1H), 2.65 (m, 1H), 2.4 (m, 1H), 2.0 (m, 2H), 1.7 (m, 1H), 1.6 (m, 1H), 1.3 (s, 3H), 1.2 (s, 3H).

Example 88

N-[6-(2,2-dimethyl-piperidin-4-yloxy)-pyridin-2-yl]-4-fluoro-benzamide

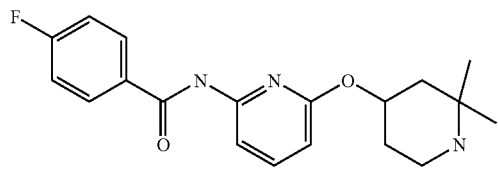

Combine N-[6-(1-benzyl-2,2-dimethyl-piperidin-4-yloxy)-pyridin-2-yl]-2-chloro-4-fluoro-benzamide (preparation 93, 0.056 g, 0.12 mmol), ethanol (5 mL), 10% palladium/carbon (0.01 g) and ammonium formate (0.064 g, 1.2 mmol), stir and heat to 80° C. After 16 hr., cool to ambient temperature. Filter through celite, rinsing with ethanol. Concentrate filtrate. Dissolve the residue in methanol (10 mL) and load on an SCX column (10 g); wash with methanol (2×50 mL); elute product with 2M ammonia/methanol (2×50 mL). Concentrate the eluent to obtain the title compound (0.042 g, 100%): Mass spectrum (electrospray): m/z=344.2 (M+1); $^1$H NMR (CDCl$_3$): 8.2 (bs, 1H), 7.9 (m, 3H), 7.7 (m, 1H), 7.2 (m, 2H), 6.5 (d, 1H), 5.2 (m, 1H), 3.1 (m, 1H), 3.0 (m, 1H), 2.1 (m, 1H), 2.0 (dd, 1H), 1.5 (m, 2H), 1.25 (s, 6H).

Example 89

4-Fluoro-N-[6-(1,2,2-trimethyl-piperidin-4-yloxy)-pyridin-2-yl]-benzamide dihydrogen chloride salt

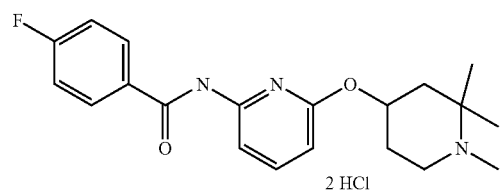

Combine N-[6-(2,2-dimethyl-piperidin-4-yloxy)-pyridin-2-yl]-4-fluoro-benzamide (example 88, 0.042 g, 0.12 mmol), dichloromethane (5 mL) and 37% aqueous formaldehyde (0.10 mL, 1.22 mmol) with stirring. After 5 min., add glacial acetic acid (0.02 mL, 0.30 mmol) followed by sodium-triacetoxyborohydride (0.033 g, 0.16 mmol). After stirring for 3 hr. at ambient temperature, concentrate. Dissolve the residue in methanol (10 mL) and load on an SCX column (10 g); wash with methanol (2×50 mL); elute product with 2M ammonia/methanol (2×50 mL). Concentrate the eluent to an oil. Dissolve the oil in diethyl ether and treat with 1M hydrogen chloride in diethyl ether (0.24 mL, 0.24 mmol). Concentrate and vacuum dry to obtain of the title compound (0.041 g, 79%). Mp.: 145° C.; Mass spectrum: Obs. m/z 358.1915; Calc. m/z 358.1931; $^1$H NMR (CDCl$_3$) for the free base: 8.1 (bs, 1H), 7.8 (m, 3H), 7.6 (m, 1H), 7.2 (m, 2H), 6.4 (d, 5.1 (m, 1H), 2.8 (m, 1H), 2.6 (m, 1H), 2.3 (s, 3H), 2.2 (m, 1H), 1.8 (m, 3H), 1.2 (s, 3H), 1.1 (s, 3H).

Preparation 94. N-[6-(1-Allyl-2-methyl-piperidin-4-yloxy)-pyridin-2-yl]-2-chloro-4-fluoro-benzamide

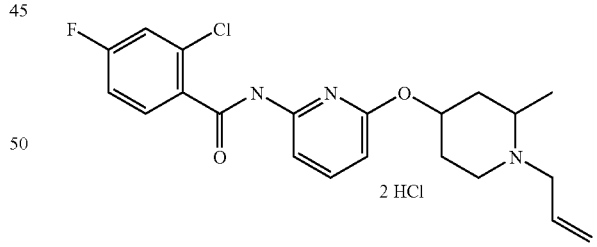

Using a method similar to preparation 93, using 6-(1-allyl-2-methyl-piperidin-4-yloxy)-pyridin-2-ylamine, the product is prepared and isolated. The title compound is obtained by converting the isolated product into the dihydrogen chloride salt using 2M HCl in diethyl ether (69%). Mass spectrum: Obs. m/z 404.1557; Calc. m/z 404.1541; $^1$H NMR (CDCl$_3$) as the free base: 8.2 (bs, 1H), 7.8 (m, 2H), 7.6 (dd, 1H), 7.2 (d, 1H), 7.1 (m, 1H), 6.5 (d, 1H), 6.0 (m, 1H), 5.2 (m, 2H), 4.8 (m, 1H), 3.5 (m, 1H), 3.0 (m, 2H), 2.4 (m, 1H), 2.2 (m, 1H), 2.1 (m, 2H), 2.7 (m, 1H), 1.5 (m, 1H), 1.2 (d, 3H).

Example 90

2-Chloro-4-fluoro-N-[6-(2-methyl-piperidin-4-yloxy)-pyridin-2-yl]-benzamide dihydrogen chloride salt

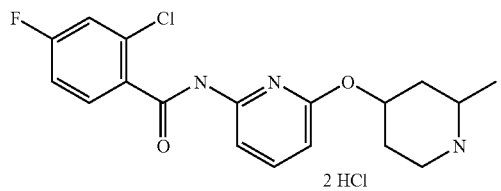

Combine N-[6-(1-allyl-2-methyl-piperidin-4-yloxy)-pyridin-2-yl]-2-chloro-4-fluoro-benzamide (preparation 94, 0.45 g, 1.11 mmol), ethanol (9 mL), water (1 mL) and chlorotris(triphenylphosphine)-rhodium(I) (0.01 g, 0.011 mmol) stir and heat to reflux. Distill off about 5 mL solvent. Add more ethanol (4 mL), water (1 mL) and catalyst (0.005 g) and distill off another 5 mL solvent. Repeat 4 times. Cool reaction mixture to ambient temperature and load on an SCX column (10 g). Wash with methanol (2×50 mL). Elute the product with 2M ammonia/methanol (2×50 mL). Concentrate eluent. Purify the residue by silica gel flash chromatography eluting with 10% (2M ammonia/methanol)/dichloromethane to obtain of the title compound as a free base (0.07 g, 18%). Dissolve the oil in diethyl ether and treat with 1M hydrogen chloride in diethyl. Concentrate and vacuum dry to obtain the title compound. Mass spectrum: Obs. m/z 364.1243; Calc. m/z 364.1228; $^1$H NMR (CDCl$_3$) as the free base: 8.4 (bs, 1H), 7.85 (m, 1H), 7.75 (dd, 1H), 7.6 (dd, 1H), 7.2 (m, 1H), 7.1 (m, 1H), 6.5 (d, 1H), 5.0 (m, 1H), 3.2 (m, 1H), 2.8 (m, 2H), 2.1 (m, 2H), 2.0 (bs, 1H), 1.5 (m, 1H), 1.2 (m, 1H), 1.15 (d, 3H).

Example 91

2-Chloro-4-fluoro-N-[6-(1,2-dimethyl-piperidin-4-yloxy)-pyridin-2-yl]-benzamide dihydrogen chloride salt

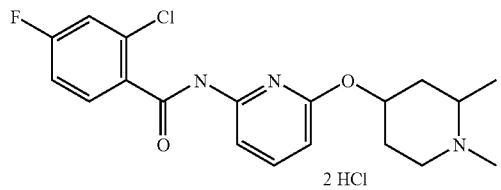

Using a method similar to example 89, the title compound was prepared, isolated and converted into the dihydrogen chloride salt (90%) Mass spectrum: Obs. m/z 378.1400; Calc. m/z 378.1385; $^1$H NMR (CDCl$_3$) as the free base: 8.2 (bs, 1H), 7.8 (m, 2H), 7.6 (m, 1H), 7.2 (m, 1H), 7.1 (m, 1H), 6.5 (d, 1H), 4.9 (m, 1H), 3.0 (m, 1H), 2.4 (s, 3H), 2.2 (m, 2H), 2.1 (m, 2H), 1.8 (m, 1H), 1.5 (m, 1H), 1.2 (d, 3H).

Preparation 95. 4-[6-(2-Chloro-4-fluoro-benzoylamino)-pyridin-2-yloxy]-2-methyl-piperidine-1-carboxylic acid tert-butyl ester cis isomer 1

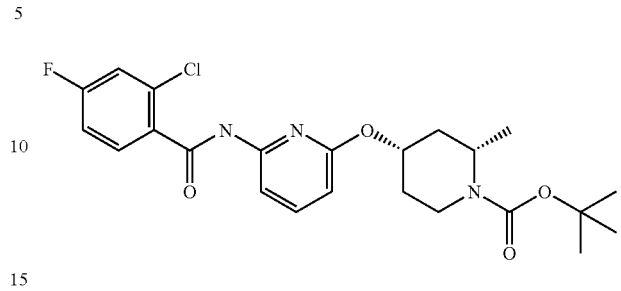

Combine 4-(6-amino-pyridin-2-yloxy)-2-methyl-piperidine-1-carboxylic acid tert-butyl ester cis isomer 1 (preparation 63, 0.025 g, 0.08 mmol), 2-chloro-4-fluoro-benzoyl chloride (0.10 g, 0.52 mmol), triethylamine (0.10 mL, 0.69 mmol) and 1,4-dioxane (10 mL), stir and heat to reflux. After 3 hr., cool to ambient temperature, dilute with methanol (10 mL) and load on an SCX column (10 g). Wash with methanol (2×25 mL). Elute product with 2M ammonia/methanol (2×25 mL). Eluent concentrated to give crude title compound. Mass spectrum (electrospray): m/z=364.1 (M+1-100) loss of t-BOC from parent. Use without further characterization in next step.

Example 92

2-Chloro-4-fluoro-N-[6-(2-methyl-piperidin-4-yloxy)-pyridin-2-yl]-benzamide di hydrogen chloride salt cis isomer 1

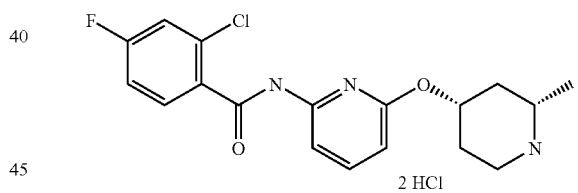

Combine 4-[6-(2-chloro-4-fluoro-benzoylamino)-pyridin-2-yloxy]-2-methyl-piperidine-1-carboxylic acid tert-butyl ester cis isomer 1 (preparation 95, 0.20 g, 0.43 mmol), toluene (20 mL) and p-toluenesulfonic acid monohydrate (1.0 g, 5.26 mmol), stir and heat to reflux. After 2 hr., cool to ambient temperature, dilute with methanol (5 mL) and load on an SCX column (10 g). Wash with methanol (2×25 mL), elute with 2M NH$_3$/methanol (2×25 mL). Concentrate eluent to give crude product. Purify the residue by silica gel flash chromatography eluting with 10% (2M ammonia/methanol)/dichloromethane to obtain the title compound as a free base (0.12 g, 77%). Dissolve in diethyl ether and treat with 1M hydrogen chloride in diethyl ether. Concentrate and vacuum dry to obtain the title compound. Mass spectrum: Obs. m/z 364.1232; Calc. m/z 364.1228; $^1$H NMR (CDCl$_3$): 8.4 (bs, 1H), 7.82 (d, 1H), 7.75 (dd, 1H), 7.64 (dd, 1H), 7.21 (d, 1H), 7.1 (dd, 1H), 6.5 (d, 1H), 4.92 (m, 1H), 3.18 (m, 1H), 2.77 (m, 2H), 2.14 (m, 2H), 1.5 (m, 1H), 1.22 (m, 2H), 1.15 (d, 3H).

Example 93

2-Chloro-N-[6-(1,2-dimethyl-piperidin-4-yloxy)-pyridin-2-yl]-4-fluoro-benzamide dihydrogen chloride salt cis isomer 1

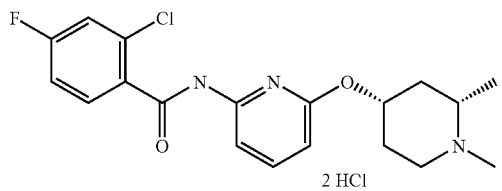

2 HCl

Using a method similar to example 89, using 2-Chloro-4-fluoro-N-[6-(2-methyl-piperidin-4-yloxy)-pyridin-2-yl]-benzamide di hydrogen chloride salt cis isomer 1 (example 92), the title compound was prepared, isolated and converted to the dihydrogen chloride salt (70%). Mass spectrum (electrospray): m/z=378.1 (M+1); $^1$H NMR (CDCl$_3$) of the free base: 8.2 (bs, 1H), 7.8 (m, 2H), 7.75 (m, 1H), 7.6 (m, 1H), 7.2 (m, 1H), 7.12 (m, 1H), 6.5 (d, 1H), 4.84 (m, 1H), 2.94 (m, 1H), 2.3 (s, 3H), 2.2 (m, 4H), 1.75 (m, 1H), 1.45 (m, 1H), 1.17 (d, 3H).

Preparation 96. 4-[6-(2-Chloro-6-fluoro-benzoylamino)-pyridin-2-yloxy]-2-methyl-piperidine-1-carboxylic acid tert-butyl ester cis isomer 1

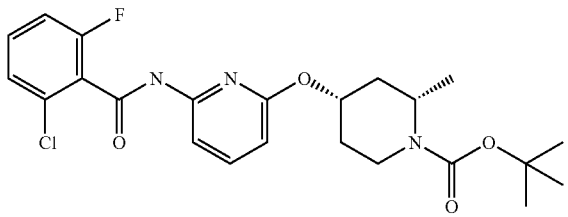

Combine 4-(6-Amino-pyridin-2-yloxy)-2-methyl-piperidine-1-carboxylic acid tert-butyl ester cis isomer 1 (preparation 63, 0.286 g, 0.93 mmol), 1,4-dioxane (10 mL), triethylamine (0.16 mL, 1.12 mmol) and 2-chloro-6-fluorobenzoyl chloride (0.215 g, 1.12 mmol) with stirring at ambient temperature. After 2 hr., partition between water (50 mL) and 4:1 hexane:ethyl acetate (100 mL). Separate aqueous layer and wash with 4:1 hexane:ethyl acetate (50 mL). Combine organic layers, dry over sodium sulfate, filter and concentrate to obtain the title compound (0.53 g>100%). Mass spectrum (electrospray): m/z=462.3 (M−1); $^1$H NMR (CDCl$_3$): 7.9 (m, 2H), 7.65 (dd, 1H), 7.4 (m, 1H), 7.25 (m, 1H), 7.1 (dd, 1H), 6.5 (d, 1H), 5.25 (m, 1H), 4.35 (m, 1H), 3.9 (m, 1H), 3.25 (m, 1H), 1.9 (m, 3H), 1.7 (m, 1H), 1.45 (s, 9H), 1.3 (d, 3H).

Using a method similar to preparation 96, using the appropriate Ar-acylchloride, prepare and isolate the analogous compounds as indicated below:

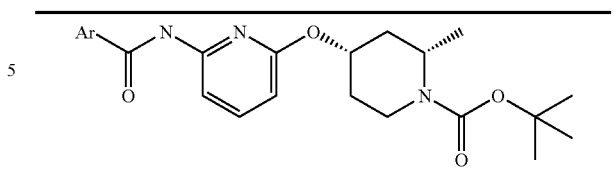

| Prep. | Ar | Data |
|---|---|---|
| 97 | 2,4,6-Trichloro-phenyl | $^1$H NMR (CDCl$_3$): 2.8 (m, 2H), 7.6 (m, 1H), 7.36 (s, 2H), 6.45 (m, 1H), 5.2 (m, 1H), 4.25 (m, 1H), 3.8 (m, 1H), 3.15 (m, 1H), 1.8 (m, 2H), 1.65 (m, 1H), 1.55 (m, 1H), 1.4 (s, 9H), 1.2 (d, 3H). |
| 98 | 2,6-Dichloro-phenyl | Mass spectrum (electrospray): m/z = 478.3 (M − 1); $^1$H NMR (CDCl$_3$): 7.85 (m, 2H), 7.65 (m, 1H), 7.4 (m, 3H), 6.55 (m, 1H), 5.28 (m, 1H), 4.35 (m, 1H), 3.9 (m, 1H), 3.25 (m, 1H), 1.9 (m, 3H), 1.75 (m, 1H), 1.5 (s, 9H), 1.3 (d, 3H). |
| 99 | 2-Bromo-phenyl | Mass spectrum (electrospray): m/z = 488.3 (M − 1 − 1), 490.3 (M + 1 − 1); $^1$H NMR (CDCl$_3$): 8.0 (bs, 1H), 7.85 (m, 1H), 7.6 (m, 2H), 7.4 (m, 2H), 7.35 (m, 1H), 6.5 (d, 1H), 5.25 (m, 1H), 4.35 (m, 1H), 3.9 (m, 1H), 3.25 (m, 1H), 1.9 (m, 3H), 1.7 (m, 1H), 1.45 (s, 9H), 1.3 (d, 3H). |
| 100 | 2,4,6-Trifluoro-phenyl | Mass spectrum (electrospray): m/z = 464.4 (M − 1); $^1$H NMR (CDCl$_3$): 7.95 (bs, 1H), 7.82 (m, 1H), 7.64 (dd, 1H), 6.78 (m, 2H), 6.55 (d, 1H), 5.24 (m, 1H), 4.35 (m, 1H), 3.9 (m, 1H), 3.24 (m, 1H), 1.9 (m, 3H), 1.75 (m, 1H), 1.45 (s, 9H), 1.3 (d, 3H). |
| 101 | 4-fluoro-phenyl | Mass spectrum (electrospray): m/z = 428.3 (M − 1); $^1$H NMR (CDCl$_3$): 8.15 (m, 1H), 7.9 (m, 3H), 7.65 (dd, 1H), 7.2 (m, 2H), 6.5 (d, 1H), 5.3 (m, 1H), 4.35 (m, 1H), 3.9 (m, 1H), 3.28 (m, 1H), 1.9 (m, 3H), 1.8 (m, 1H), 1.44 (s, 9H), 1.27 (d, 3H). |
| 102 | 2,4-Difluoro-phenyl | Mass spectrum (electrospray): m/z = 446.4 (M − 1). |
| 103 | 2,6-Difluoro-phenyl | Mass spectrum (electrospray): m/z = 446.4 (M − 1) |
| 104 | 2-Chloro-phenyl | Mass spectrum (electrospray): m/z = 444.3 (M − 1) |

Using a method similar to example 92, using preparations—97-1-4, prepare, isolate, and convert the analogous compounds into their dihydrogen chloride salts as indicated below:

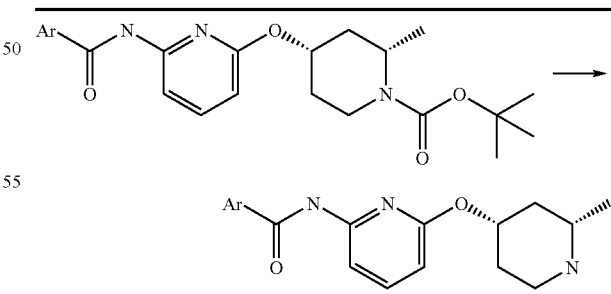

| Ex. | Ar | Data |
|---|---|---|
| 94 | 2,4,6-Trichloro-phenyl | Mass spectrum: Obs. m/z 414.0522; Calc. m/z 414.0543; $^1$H NMR (CDCl$_3$) for free base: 9.41 (bs, 1H), 7.93 (d, 1H), 7.63 (dd, 1H), 7.42 (s, 2H), 6.5 (d, 1H), 4.97 (m, 1H), 3.14 (m, 1H), 2.8 (m, 2H), 2.12 (m, 2H), 1.44 (m,2H), 1.1 (m,1H), 1.08 (d,3H). |

-continued

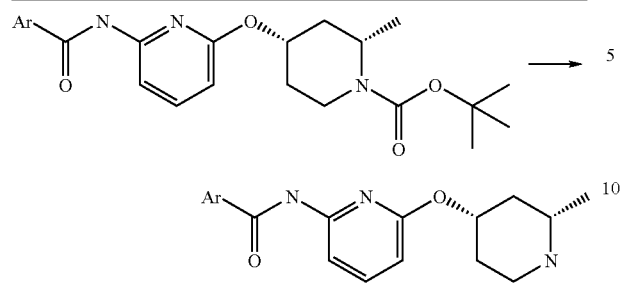 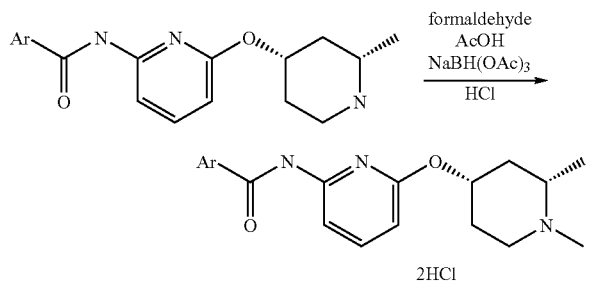

| Ex. | Ar | Data |
|---|---|---|
| 95 | 2,6-Dichloro-phenyl | Mass spectrum: Obs. m/z 380.0931; Calc. m/z 380.0932; ¹H NMR (CDCl₃) for free base: 10.16 (bs, 1H), 8.0 (d, 1H), 7.63 (dd, 1H), 7.35 (m, 3H), 6.44 (d, 1H), 4.98 (m, 1H), 3.1 (m, 1H), 2.8 (m, 2H), 2.15 (m, 1H), 2.05 (m, 1H), 1.37 (m, 1H), 1.01 (m, 4H). |
| 96 | 2-Bromo-phenyl | Mass spectrum: Obs. m/z 390.0820; Calc. m/z 390.0817; ¹H NMR (CDCl₃) for free base: 8.64 (bs, 1H), 7.90 (m, 1H), 7.62 (m, 3H), 7.42 (m, 1H), 7.36 (m, 1H), 6.48 (d, 1H), 4.95 (m, 1H), 3.14 (m, 1H), 2.75 (m, 2H), 2.10 (m, 2H), 1.42 (m, 1H), 1.3 (bs, 1H), 1.12 (m, 1H), 1.08 (d, 3H). |
| 97 | 2,4,6-Trifluoro-phenyl | Mass spectrum: Obs. m/z 366.1429; Calc. m/z 366.1429; ¹H NMR (CDCl₃) for free base: 8.59 (bs, 1H), 7.85 (d, 1H), 7.63 (dd, 1H), 6.8 (dd, 2H), 6.5 (d, 1H), 4.95 (m, 1H), 3.14 (m, 1H), 2.76 (m, 2H), 2.1 (m, 2H), 1.42 (m, 1H), 1.17 (m, 1H), 1.11 (d, 3H). |
| 98 | 4-fluoro-phenyl | Mass spectrum: Obs. m/z 330.1614; Calc. m/z 330.1618; ¹H NMR (CDCl₃) for free base: 8.24 (bs, 1H), 7.88 (dd, 2H), 7.84 (d, 1H), 7.62 (dd, 1H), 7.19 (dd, 2H), 6.48 (d, 1H), 4.93 (m, 1H), 3.18 (m, 1H), 2.77 (m, 2H), 2.1 (m, 2H), 1.44 (m, 1H), 1.4 (bs, 1H), 1.2 (m, 1H), 1.15 (d, 3H). |
| 99 | 2,4-Difluoro-phenyl | Mass spectrum: Obs. m/z 348.1540; Calc. m/z 348.1523; ¹H NMR (CDCl₃) for free base: 8.68 (bd, 1H), 8.19 (m, 1H), 7.88 (d, 1H), 7.63 (dd, 1H), 7.05 (m, 1H), 6.95 (m, 1H), 6.48 (d, 1H), 4.97 (m, 1H), 3.19 (m, 1H), 2.8 (m, 2H), 2.15 (m, 2H), 1.5 (m, 1H), 1.39 (bs, 1H), 1.21 (m, 1H), 1.17 (d, 3H). |
| 100 | 2,6-Difluoro-phenyl | Mass spectrum: Obs. m/z 348.1525; Calc. m/z 348.1523; ¹H NMR (CDCl₃) for free base: 9.08 (bs, 1H), 7.91 (d, 1H), 7.63 (dd, 1H), 7.43 (m, 1H), 7.02 (dd, 2H), 6.49 (d, 1H), 4.95 (m, 1H), 3.1 (m, 1H), 2.78 (m, 2H), 2.1 (m, 2H), 1.4 (m, 1H), 1.1 (m, 1H), 1.05 (d, 3H). |
| 101 | 2-Chloro-phenyl | Mass spectrum: Obs. m/z 346.1325; Calc. m/z 346.1322; ¹H NMR (CDCl₃) for free base: 8.46 (bs, 1H), 7.9 (d, 1H), 7.66 (m, 2H), 7.41 (m, 3H), 6.46 (d, 1H), 4.93 (m, 1H), 3.15 (m, 1H), 2.77 (m, 2H), 2.1 (m, 2H), 1.44 (m, 1H), 1.35 (bs, 1H), 1.15 (m, 1H), 1.1 (d, 3H). |
| 102 | 2-Chloro-6-fluoro-phenyl | Mass spectrum: Obs. m/z 364.1233; Calc. m/z 364.1228; ¹H NMR (CDCl₃) for free base: 10.05 (bs, 1H), 7.98 (d, 1H), 7.61 (dd, 1H), 7.38 (m, 1H), 7.25 (d, 1H), 7.08 (dd, 1H), 6.45 (d, 1H), 4.98 (m, 1H), 3.02 (m, 1H), 2.78 (m, 2H), 2.15 (m, 1H), 2.05 (m, 1H), 1.32 (m, 1H), 0.98 (d, 3H), 0.95 (bs, 1H). |

Using a method similar to example 89, using the compounds of examples—94-102, prepare, isolate, and convert the analogous compounds into their dihydrogen chloride salts as indicated below:

| Ex. | Ar | Data |
|---|---|---|
| 103 | 2,4,6-Trichloro-phenyl | Mass spectrum: Obs. m/z 428.0693; Calc. m/z 428.0699; ¹H NMR (CDCl₃) for free base: 7.88 (bs, 1H), 7.86 (d, 1H), 7.66 (dd, 1H), 7.41 (s, 2H), 6.53 (d, 1H), 4.83 (m, 1H), 2.92 (m, 1H), 2.30 (s, 3H), 2.16 (m, 1H), 2.05 (m, 3H), 1.75 (m, 1H), 1.50 (q, 1H), 1.13 (d, 3H). |
| 104 | 2,6-Dichloro-phenyl | Mass spectrum: Obs. m/z 394.1102; Calc. m/z 394.1089; ¹H NMR (CDCl₃) for free base: 7.89 (d, 1H), 7.82 (bs, 1H), 7.66 (dd, 1H), 7.37 (m, 3H), 6.53 (d, 1H), 4.85 (m, 1H), 2.93 (m, 1H), 2.26 (s, 3H), 2.20 (m, 1H), 2.09 (m, 3H), 1.75 (m, 1H), 1.48 (q, 1H), 1.14 (d, 3H). |
| 105 | 2-Bromo-phenyl | Mass spectrum: Obs. m/z 404.0959; Calc. m/z 404.0974; ¹H NMR (CDCl₃) for free base: 8.03 (bs, 1H), 7.86 (d, 1H), 7.66 (m, 3H), 7.43 (m, 1H), 7.35 (m, 1H), 6.50 (d, 1H), 4.85 (m, 1H), 2.92 (m, 1H), 2.27 (s, 3H), 2.18 (m, 1H), 2.06 (m, 3H), 1.74 (m, 1H), 1.44 (q, 1H), 1.17 (d, 3H). |
| 106 | 2,4,6-Trifluoro-phenyl | Mass spectrum: Obs. m/z 380.1582; Calc. m/z 380.1586; ¹H NMR (CDCl₃) for free base: 7.98 (bs, 1H), 7.83 (d, 1H), 7.61 (dd, 1H), 6.78 (dd, 2H), 6.50 (d, 1H), 4.88 (m, 1H), 2.91 (m, 1H), 2.30 (s, 3H), 2.19 (m, 1H), 2.04 (m, 3H), 1.72 (m, 1H), 1.43 (q, 1H), 1.15 (d, 3H). |
| 107 | 4-fluoro-phenyl | Mass spectrum: Obs. m/z 344.1777; Calc. m/z 344.1774; ¹H NMR (CDCl₃) for free base: 8.15 (bs, 1H), 7.92 (dd, 2H), 7.86 (d, 1H), 7.63 (dd, 1H), 7.19 (dd, 2H), 6.46 (d, 1H), 4.88 (m, 1H), 2.94 (m, 1H), 2.31 (s, 3H), 2.21 (m, 1H), 2.07 (m, 3H), 1.78 (m, 1H), 1.46 (q, 1H), 1.14 (d, 3H). |
| 108 | 2,4-Difluoro-phenyl | Mass spectrum: Obs. m/z 362.1686; Calc. m/z 362.1680; ¹H NMR (CDCl₃) for free base: 8.70 (bd, 1H), 8.19 (m, 1H), 7.85 (d, 1H), 7.62 (dd, 1H), 7.05 (m, 1H), 6.92 (m, 1H), 6.50 (d, 1H), 4.89 (m, 1H), 2.94 (m, 1H), 2.31 (s, 3H), 2.22 (m, 1H), 2.12 (m, 3H), 1.77 (m, 1H), 1.45 (q, 1H), 1.16 (d, 3H). |
| 109 | 2,6-Difluoro-phenyl | Mass spectrum: Obs. m/z 362.1683; Calc. m/z 362.1680; ¹H NMR (CDCl₃) for free base: 7.99 (bs, 1H), 7.86 (d, 1H), 7.63 (dd, 1H), 7.43 (m, 1H), 7.02 (dd, 2H), 6.50 (d, 1H), 4.85 (m, 1H), 2.93 (m, 1H), 2.29 (s, 3H), 2.20 (m, 1H), 2.07 (m, 3H), 1.76 (m, 1H), 1.42 (q, 1H), 1.15 (d, 3H). |
| 110 | 2-Chloro-phenyl | Mass spectrum: Obs. m/z 360.1478; Calc. m/z 360.1479; ¹H NMR (CDCl₃) for free base: 8.18 (bs, 1H), 7.85 (d, 1H), 7.73 (d, 1H), 7.62 (dd, 1H), 7.41 (m, 3H), 6.49 (d, 1H), 4.84 (m, 1H), 2.92 (m, 1H), 2.33 (s, 3H), 2.18 (m, 1H), 2.04 (m, 3H), 1.74 (m, 1H), 1.42 (q, 1H), 1.15 (d, 3H). |
| 111 | 2-Chloro-6-fluoro-phenyl | Mass spectrum: Obs. m/z 378.1385; Calc. m/z 378.1385; ¹H NMR (CDCl₃) for free base: 7.94 (bs, 1H), 7.88 (d, 1H), 7.63 (dd, 1H), 7.37 (m, 1H), 7.28 (m, 1H), 7.09 (dd, 1H), 6.50 (d, 1H), 4.84 (m, 1H), 2.92 (m, 1H), 2.28 (s, 3H), 2.20 (m, 1H), 2.07 (m, 3H), 1.73 (m, 1H), 1.43 (q, 1H), 1.13 (d, 3H). |

Preparation 105. 4-[6-(2-Chloro-6-fluoro-benzoylamino)-pyridin-2-yloxy]-2-cis-methyl-piperidine-1-carboxylic acid tert-butyl ester isomer 2

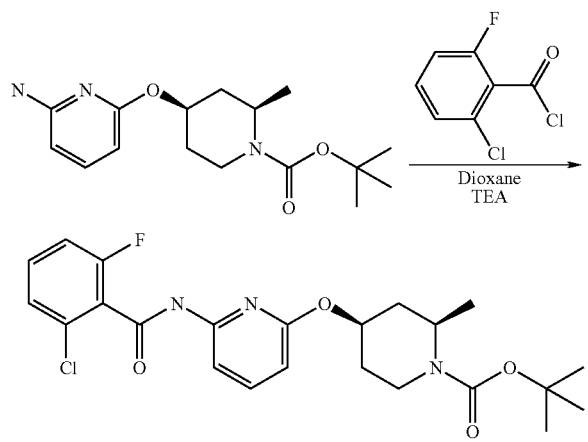

Combine 4-(6-amino-pyridin-2-yloxy)-2-methyl-piperidine-1-carboxylic acid tert-butyl ester cis isomer 2 (preparation 64, 0.35 g, 1.14 mmol), 1,4-dioxane (10 mL), triethyl amine (0.5 mL, 6.8 mmol) and 2-chloro-6-fluorobenzoyl chloride (0.35 g, 1.81 mmol), stir and heat at 80° C. After 2 hr., cool to ambient temperature, partition between water (50 mL) and 4:1 hexane:ethyl acetate (100 mL). Separate aqueous layer and wash with 4:1 hexane:ethyl acetate (50 mL). Combine organic layers, dry over sodium sulfate, filter and concentrate to obtain the title compound (0.53 g, 100%). Mass spectrum (electrospray): m/z=462.0 (M−1).

Example 112

2-Chloro-6-fluoro-N-[6-(2-methyl-piperidin-4-yloxy)-pyridin-2-yl]-benzamide cis isomer 2

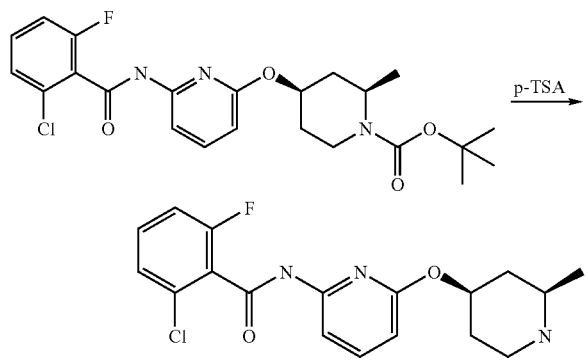

Using a method similar to example 92, using 4-[6-(2-Chloro-6-fluoro-benzoylamino)-pyridin-2-yloxy]-2-methyl-piperidine-1-carboxylic acid tert-butyl ester, preparation 105, the title compound was prepared then used as is in the next step: Mass spectrum (electrospray): m/z=364.1 (M+1).

Example 113

2-Chloro-N-[6-(1,2-dimethyl-piperidin-4-yloxy)-pyridin-2-yl]-6-fluoro-benzamide cis isomer 2 dihydrogen chloride salt

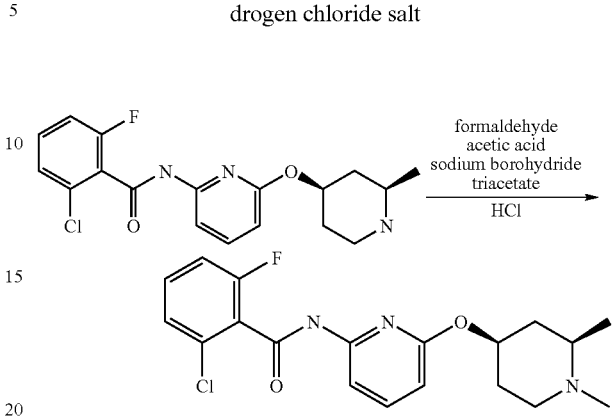

Using a method similar to example 89, using 2-Chloro-6-fluoro-N-[6-(2-methyl-piperidin-4-yloxy)-pyridin-2-yl]-benzamide cis isomer 2 (example 112), the title compound was prepared, isolated and converted into the dihydrogen chloride salt. Mass spectrum: Obs. m/z 378.1376; Calc. m/z 378.1385; $^1$H NMR (CDCl$_3$) for free base: 7.9 (bs, 1H), 7.85 (d, 1H), 7.63 (dd, 1H), 7.37 (m, 1H), 7.26 (d, 1H), 7.09 (dd, 1H), 6.48 (d, 1H), 4.84 (m, 1H), 2.92 (m, 1H), 2.28 (s, 3H), 2.16 (m, 1H), 2.05 (m, 3H), 1.78 (m, 1H), 1.44 (q, 1H), 1.15 (d, 3H).

Example 114

2,6-Dichloro-4-fluoro-N-[6-(1-methyl-piperidin-4-yloxy)-pyridin-2-yl]-benzamide dihydrogen chloride salt

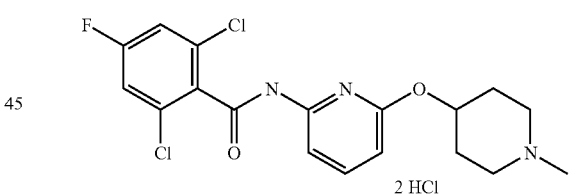

Combine 6-(1-methyl-piperidin-4-yloxy)-pyridin-2-ylamine (preparation 60, 0.15 g, 0.72 mmol), 1,4-dioxane (5 mL) and 2,6-dichloro-4-fluoro-benzoyl chloride (0.18 g, 0.79 mmol), stir and heat at reflux. After 3 hr., cool to ambient temperature, load on an SCX column (10 g). Wash with methanol (2×50 mL), elute with 2M NH$_3$/methanol (2×50 mL). Concentrate eluent to give crude product. Purify the residue by silica gel flash chromatography eluting with 5% (2M ammonia/methanol)/dichloromethane to obtain 0.12 g (42%) of the title compound as a free base. Dissolve in diethyl ether and treat with 1M hydrogen chloride in diethyl ether. Concentrate and vacuum dry to obtain the title compound. Mp=264; Mass spectrum: Obs. m/z 398.0834; Calc. m/z 398.0838; $^1$H NMR (CDCl$_3$) for free base: 7.81 (d, 1H), 7.73 (bs, 1H), 7.59 (dd, 1H), 7.10 (d, 2H), 6.48 (d, 1H), 4.90 (m, 1H), 2.63 (m, 2H), 2.25 (m, 2H), 2.23 (s, 3H), 1.95 (m, 2H), 1.80 (m, 2H).

Preparation 106. N-[6-(1-Benzyl-3-trans-methyl-piperidin-4-yloxy)-pyridin-2-yl]-2-chloro-4-fluoro-benzamide

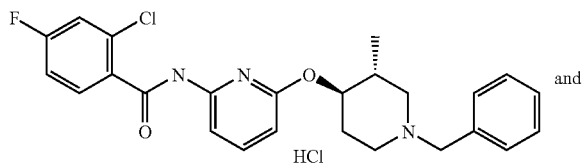
and
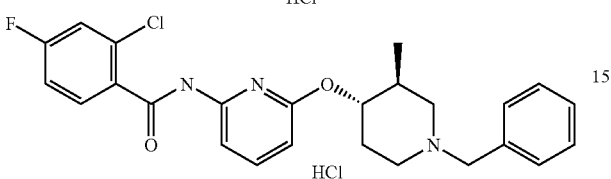

Using a method similar to 54, using 6-(1-benzyl-3-methyl-piperidin-4-yloxy)-pyridin-2-ylamine (Preparation 44) and using lithium aluminum hydride instead of sodium borohydride, the title racemic mixture is prepared, isolated and converted to the monohydrogen chloride salt. Mp=170° C.; Mass spectrum: Obs. m/z 454.1719; Calc. m/z 454.1697; $^1$H NMR (CDCl$_3$) for free base: 8.19 (bs, 1H), 7.83 (d, 1H), 7.77 (dd, 1H), 7.62 (dd, 1H), 7.35 (m, 6H), 7.12 (m, 1H), 6.51 (d, 1H), 4.54 (m, 1H), 3.53 (s, 2H), 2.88 (m, 2H), 2.13 (m, 2H), 2.0 (m, 1H), 1.85 (m, 1H), 1.66 (m, 1H), 0.93 (d, 3H).

Example 115

2-Chloro-4-fluoro-N-[6-(3-methyl-piperidin-4-yloxy)-pyridin-2-yl]-benzamide

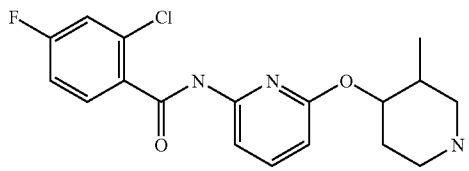

Using a method similar to example 62, using N-[6-(1-Benzyl-3-methyl-piperidin-4-yloxy)-pyridin-2-yl]-2-chloro-4-fluoro-benzamide (preparation 106), the title compound was prepared and used in crude form in the next reaction. Mass spectrum (electrospray): m/z=364.1 (M+1).

Example 116

2-Chloro-N-[6-(1,3-dimethyl-piperidin-4-yloxy)-pyridin-2-yl]-4-fluoro-benzamide

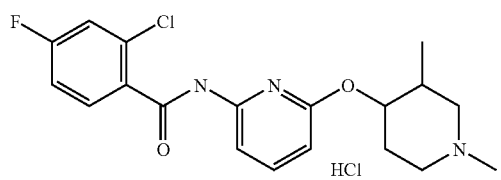

Using a method similar to example 89, using 2-Chloro-4-fluoro-N-[6-(3-methyl-piperidin-4-yloxy)-pyridin-2-yl]-benzamide (example 115), prepare, isolate and convert the title compound into the monohydrogen chloride salt. Mp=155-160° C.; Mass spectrum: Obs. m/z 378.1394; Calc. m/z 378.1385; $^1$H NMR (CDCl$_3$) for free base: 8.20 (bs, 1H), 7.83 (d, 1H), 7.77 (dd, 1H), 7.63 (dd, 1H), 7.23 (m, 1H), 7.11 (m, 1H), 6.52 (d, 1H), 4.53 (m, 1H), 2.88 (m, 2H), 2.30 (s, 3H), 2.12 (m, 3H), 1.87 (m, 1H), 1.75 (m, 1H), 0.96 (d, 3H).

Preparation 107. N-[6-(1-Benzyl-3-methyl-piperidin-4-yloxy)-pyridin-2-yl]-2-chloro-4-fluoro-benzamide cis isomer 1

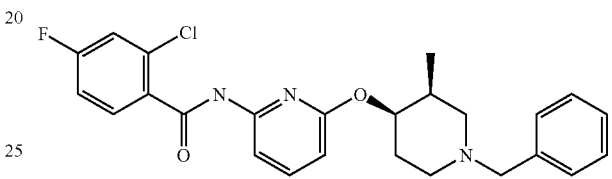

Using a method similar to example 114 and 6-(1-benzyl-3-methyl-piperidin-4-yloxy)-pyridin-2-ylamine cis isomer 1 (preparation 41), prepare and isolate the title compound (89%). Mass spectrum (electrospray): m/z=454.2 (M+1); 8.20 (bs, 1H), 7.81 (d, 1H), 7.72 (dd, 1H), 7.62 (dd, 1H), 7.25 (m, 6H), 7.08 (m, 1H), 6.55 (d, 1H), 5.05 (m, 1H), 3.55 (d, 2H), 2.55 (m, 2H), 2.37 (m, 2H), 2.07 (m, 2H), 1.79 (m, 1H), 0.96 (d, 3H).

Preparation 108. N-[6-(1-Benzyl-3-methyl-piperidin-4-yloxy)-pyridin-2-yl]-2-chloro-4-fluoro-benzamide cis isomer 2

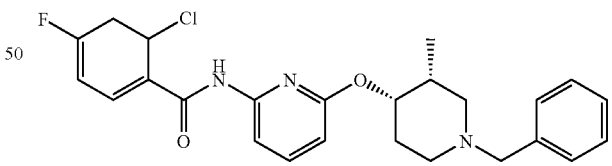

Using a method similar to example 114 and 6-(1-benzyl-3-methyl-piperidin-4-yloxy)-pyridin-2-ylamine cis isomer 2 (preparation 41), prepare and isolate the title compound (98%). Mass spectrum (electrospray): m/z=454.2 (M+1); 8.20 (bs, 1H), 7.81 (d, 1H), 7.72 (dd, 1H), 7.62 (dd, 1H), 7.25 (m, 6H), 7.08 (m, 1H), 6.55 (d, 1H), 5.05 (m, 1H), 3.55 (d, 2H), 2.55 (m, 2H), 2.37 (m, 2H), 2.07 (m, 2H), 1.79 (m, 1H), 0.96 (d, 3H).

Example 117

2-Chloro-4-fluoro-N-[6-(3-methyl-piperidin-4-yloxy)-pyridin-2-yl]-benzamide cis isomer 1

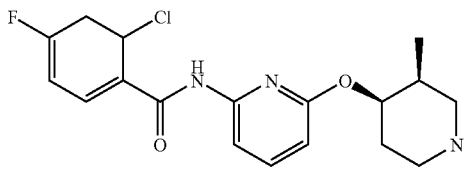

Using a method similar to example 62, using N-[6-(1-Benzyl-3-methyl-piperidin-4-yloxy)-pyridin-2-yl]-2-chloro-4-fluoro-benzamide cis isomer 1 (preparation 107), prepare the title compound and use it in crude form in the next reaction.

Example 118

2-Chloro-4-fluoro-N-[6-(3-methyl-piperidin-4-yloxy)-pyridin-2-yl]-benzamide cis isomer 2

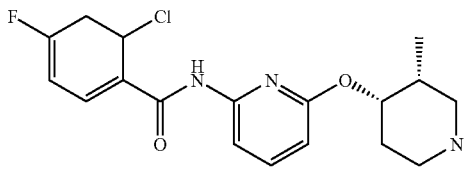

Using a method similar to example 62, using N-[6-(1-Benzyl-3-methyl-piperidin-4-yloxy)-pyridin-2-yl]-2-chloro-4-fluoro-benzamide cis isomer 2 (preparation 108), prepare the title compound and use it in crude form in the next reaction

Example 119

2-Chloro-N-[6-(1,3-dimethyl-piperidin-4-yloxy)-pyridin-2-yl]-4-fluoro-benzamide cis isomer 1 dihydrogen chloride salt

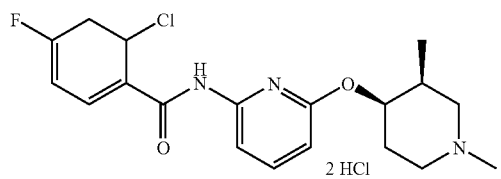

Using the method of example 89, using 2-Chloro-4-fluoro-N-[6-(3-methyl-piperidin-4-yloxy)-pyridin-2-yl]-benzamide cis isomer 2 (example 118), prepare, isolate and convert the title compound into the dihydrogen chloride salt (70%). Mp=238° C.; Mass spectrum: Obs. m/z 378.1387; Calc. m/z 378.1385; $^1$H NMR (CDCl$_3$) for free base: 8.20 (bs, 1H), 7.82 (d, 1H), 7.75 (dd, 1H), 7.62 (dd, 1H), 7.21 (d, 1H), 7.08 (dd, 1H), 6.55 (d, 1H), 5.07 (m, 1H), 2.50 (m, 2H), 2.3 (s, 3H), 2.25 (m, 2H), 2.04 (m, 2H), 1.78 (m, 1H), 0.95 (d, 3H).

Example 120

2-Chloro-N-[6-(1,3-dimethyl-piperidin-4-yloxy)-pyridin-2-yl]-4-fluoro-benzamide cis isomer 2 dihydrogen chloride salt

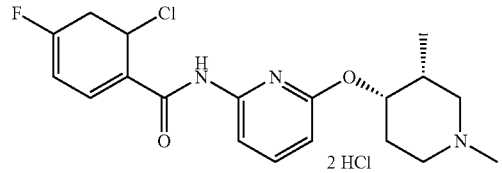

Using the method of example 89, and using 2-Chloro-4-fluoro-N-[6-(3-methyl-piperidin-4-yloxy)-pyridin-2-yl]-benzamide cis isomer 2 (example 118), prepare, isolate and convert the title compound into the dihydrogen chloride salt (73%). Mp=238° C.; Mass spectrum: Obs. m/z 378.1387; Calc. m/z 378.1385; $^1$H NMR (CDCl$_3$) for free base: 8.20 (bs, 1H), 7.82 (d, 1H), 7.75 (dd, 1H), 7.62 (dd, 1H), 7.21 (d, 1H), 7.08 (dd, 1H), 6.55 (d, 1H), 5.07 (m, 1H), 2.50 (m, 2H), 2.3 (s, 3H), 2.25 (m, 2H), 2.04 (m, 2H), 1.78 (m, 1H), 0.95 (d, 3H).

Preparation 109. 4-[6-(2-Chloro-4-fluoro-benzoylamino)-pyridin-2-yloxy]-cis-2-methyl-piperidine-1-carboxylic acid tert-butyl ester isomer 2

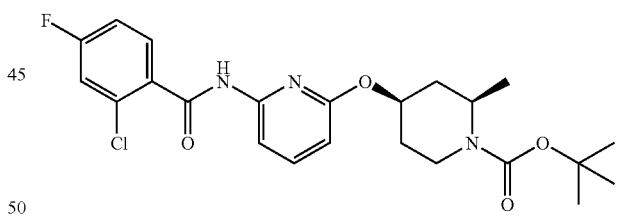

Combine 4-(6-amino-pyridin-2-yloxy)-cis-2-methyl-piperidine-1-carboxylic acid tert-butyl ester isomer 2 (preparation 64, 0.714 g) and 2-chloro-4-fluorobenzoyl chloride (0.493 g) in 1,4-dioxane (20 mL) and heat. After 2.5 hr., partition between ethyl acetate and saturated aqueous NaCl, dry over anhydrous sodium sulfate, evaporate and purify on a silica gel column eluting with dichloromethane-2M NH$_3$ in methanol, gradient to give the title compound (0.678 g). Mass spectrum (electric spray) m/z=464 (M+1); $^1$H NMR (CDCl$_3$): 8.45 (br, 1H), 7.89 (br d, 1H), 7.78 (dd, 1H), 7.68 (ddd, 1H), 7.24 (dd, 1H), 7.12 (ddd, 1H), 6.54 (d, 1H), 5.27 (m, 1H), 4.35 (m, 1H), 3.90 (m, 1H), 3.25 (m, 1H), 1.90 (m, 3H), 1.75 (m, 1H), 1.47 (s, 9H), 1.28 (d, 3H).

Example 121

2-Chloro-4-fluoro-N-[6-(cis-2-methyl-piperidin-4-yloxy)-pyridin-2-yl]-benzamide isomer 2

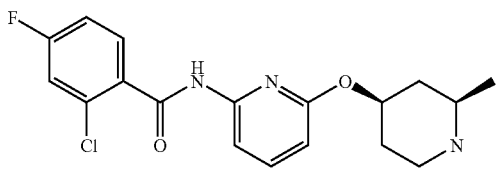

Add 1 mL of conc. hydrochloric acid into a solution of 4-[6-(2-chloro-4-fluoro-benzoylamino)-pyridin-2-yloxy]-cis-2-methyl-piperidine-1-carboxylic acid tert-butyl ester isomer 2 (preparation 109, 0.678 g) in 1,4-dioxane 20 mL and heat at 100° C. After 40 min., partition between ethyl acetate and saturated aqueous NaCl, dry over anhydrous sodium sulfate, evaporate and purify on a silica gel column eluting with dichloromethane-2M $NH_3$ in methanol, gradient to give the title compound (0.53 g). Mass spectrum (electric spray) m/z=364 (M+1); $^1$H NMR (CDCl$_3$): 8.53 (br s, 1H), 7.84 (br d, 1H), 7.73 (dd, 1H), 7.63 (dd, 1H), 7.21 (dd, 1H), 7.10 (ddd, 1H), 6.49 (dd, 1H), 4.93 (m, 1H), 3.14 (m, 1H), 2.78 (m, 2H), 2.12 (m, 2H), 1.75 (br, 1H), 1.48 (m, 1H), 1.19 (m, 1H), 1.12 (d, 3H).

Dissolve the benzamide (0.140 g) in dichloromethane-methanol and add 0.38 mL of 1N HCl in ether, evaporate and dry in vacuum to give the hydrogen chloride salt.

Using a method similar to example 121, using the appropriate 4-[6-(Ar-acylamino)-pyridin-2-yloxy]-cis-2-methyl-piperidine-1-carboxylic acid tert-butyl ester isomer 2, prepare the analogous compounds and their mono-hydrochlorides as indicated below:

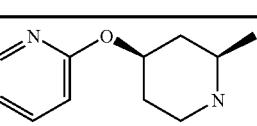

| Ex. | Ar | Data free base |
|---|---|---|
| 122 | 2-Bromophenyl | mass spectrum (electric spray) m/z = 390 (M + 1), 392 (M + 2 + 1); $^1$H NMR (CDCl$_3$) (free base): 7.91 (br d, 1H), 7.60 (m, 2H), 7.50 (dd, 1H), 7.38 (ddd, 1H), 7.30 (ddd, 1H), 6.44 (dd, 1H), 4.95 (m, 1H), 3.03 (m, 1H), 2.73 (m, 2H), 2.06 (m, 2H), 1.32 (m, 1H), 0.98 (m, 1H), 0.97 (d, J=6.7 Hz, 3H). |
| 123 | 2-chlorophenyl | mass spectrum (electric spray) m/z = 346 (M + 1); $^1$H NMR (CDCl$_3$)(free base): 9.25 (br, 1H), 7.88 (br d, 1H), 7.61 (m, 2H), 7.40 (m, 3H), 6.46 (d, 1H), 4.92 (m, 1H), 3.08 (m, 1H), 2.73 (m, 2H), 2.08 (m, 2H), 1.50 (br, 1H), 1.40 (m, 1H), 1.08 (m, 1H), 1.03 (d, J=6.3 Hz, 3H). |
| 124 | 4-fluorophenyl | mass spectrum (electric spray) m/z = 330 (M + 1); $^1$H NMR (CDCl$_3$)(free base): 8.17 (br, 1H), 7.93 (m, 2H), 7.86 (d, 1H), 7.63 (t, 1H), 7.19 (m, 2H), 6.48 (d, 1H), 4.95 (m, 1H), 3.18 (m, 1H), 2.79 (m, 2H), 2.12 (m, 2H), 1.49 (m, 1H), 1.45 (br, 1H), 1.21 (m, 1H), 1.14 (d, J=6.4Hz, 3H). |
| 125 | 2,4-difluorophenyl | mass spectrum (electric spray) m/z = 348 (M + 1); $^1$H NMR (CDCl$_3$)(free base): 8.69 (br d, 1H), 8.18 (m, 1H), 7.86 (d, 1H), 7.62 (t, 1H), 7.05 (m, 1H), 6.95 (m, 1H), 6.49 (d, 1H), 4.97 (m, 1H), 3.17 (m, 1H), 2.77 (m, 2H), 2.13 (m, 2N), 1.49 (m, 1H), 1.40 (br, 1H), 1.21 (m, 1H), 1.14(d, J=6.4Hz, 3N). |
| 126 | 2,6-difluorophenyl | mass spectrum (electric spray) m/z = 348 (M + 1); $^1$H NMR (CDCl$_3$)(free base): 8.98 (br s, 1H), 7.90 (d, 1H), 7.62 (t, 1H), 7.43 (m, 1H), 7.01 (m, 2H), 6.48 (d, 1H), 4.95 (m, 1H), 3.11 (m, 1H), 2.76 (m, 2H), 2.11 (m, 2H), 1.41 (m, 1H), 1.30 (br. 1H), 1.11 (m, 1H), 1.06 (d, J=6.4 Hz, 3H). |
| 127 | 2,4,6-trifluorophenyl | mass spectrum (electric spray) m/z = 366 (M + 1); $^1$H NMR (CDCl$_3$)(free base): 9.22 (br s, 1H), 7.87 (d, 1H), 7.62 (t, 1H), 6.79 (m, 2H), 6.48 (d, 1H), 4.95 (m, 1H), 3.10 (m, 1H), 2.78 (m, 2H), 2.11 (m, 2H), 1.40 (m, 1H), 1.10 (m, 1H), 1.05 (d, J=6.4 Hz, 3H). |
| 128 | 2,6-dichlorophenyl | mass spectrum (electric spray) m/z = 380 (M + 1); $^1$H NMR (CDCl$_3$)(free base): 8.00 (d, 1H), 7.61 (t, 1H), 7.33 (m, 3H), 6.44 (d, 1H), 4.99 (m, 1H), 3.03 (m, 1H), 2.79 (m, 2H), 2.14 (m, 1H), 2.02 (m, 1H), 1.28 (m, 1H), 0.94 (d, J=6.4 Hz, 3H), 0.90 (m, 1H). |
| 129 | 2,4,6-trichlorophenyl | mass spectrum (electric spray) m/z 414 (M$^+$), 416 (M + 2); $^1$H NMR (CDCl$_3$)(free base): 7.94 (d, 1H), 7.63 (t, 1H), 7.40 (s, 2H), 6.49 (d, 1H), 4.97 (m, 1H), 3.09 (m, 1H), 2.79 (m, 2H), 2.15 (m, 1H), 2.07 (m, 1H), 1.40 (m, 1H), 1.25 (m, 1H), 1.03 (d, J=6.4 Hz, 3H). |
| 130 | 2-chloro-6-fluorophenyl | mass spectrum (electric spray) m/z = 364 (M + 1); $^1$H NMR (CDCl$_3$)(free base): 7.93 (d, 1H), 7.63 (t, 1H), 7.37 (m, 1H), 7.27 (m, 1H), 7.10 (m, 1H), 6.48 (d, 1H), 4.96 (m, 1H), 3.08 (m, 1H), 2.77 (m, 2H), 2.13 (m, 1H), 2.05 (m, 1H), 1.38 (m, 1H), 1.05 (m, 1H), 1.03 (d, J=6.4Hz, 3H). |

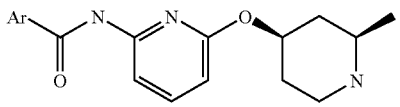

Example 131

2-Chloro-N-[6-(1,cis-2-dimethyl-piperidin-4-yloxy)pyridin-2-yl]-4-fluoro-benzamide isomer 2

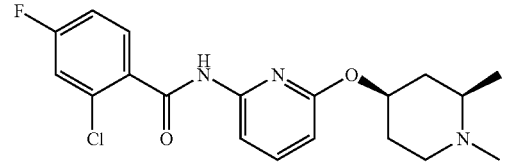

Combine 2-chloro-4-fluoro-N-[6-(cis-2-methyl-piperidin-4-yloxy)-pyridin-2-yl]-benzamide isomer 2 (example 121, 0.150 g), formaldehyde (37%, 0.3 mL), sodium triacetoxyborohydride (0.114 g) and acetic acid (0.062 g) with dichloromethane (10 mL) and stir overnight. Dilute with methanol (5 mL) and load on a SCX column (10 g), wash with methanol, elute the product with 2M $NH_3$-methanol, evaporate to give the title compound (0.156 g, 100%). Mass spectrum (electric spray) m/z=378 (M+1); $^1$H NMR (CDCl$_3$): 8.20 (br s, 1H), 7.84 (br d, 1H), 777 (dd, 1H), 7.63 (t, 1H), 7.22 (dd, 1H), 7.11 (ddd, 1H), 6.50 (d, 1H), 4.86 (m, 1H), 2.96 (m, 1H), 2.31 (s, 3H), 2.23 (m, 1H), 2.10 (m, 3H), 1.79 (br, 1H), 1.51 (q, 1H), 1.15 (d, J=6.1 Hz, 3H).

Dissolve the benzamide (0.156 g) in dichloromethane-methanol and add 0.41 mL of 1N HCl in ether, evaporate and dry in vacuum to give the hydrogen chloride salt.

Using a method similar to example 131, using the appropriate Ar—N-[6-(1,cis-2-dimethyl-piperidin-4-yloxy)-pyridin-2-yl]amide isomer 2, prepare the analogous compounds and their mono-hydrochlorides as indicated below:

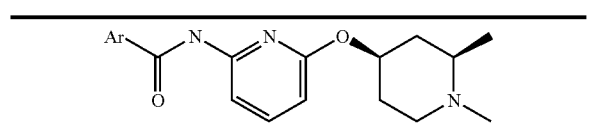

| Ex. | Ar | Data free base |
|---|---|---|
| 132 | 2-Bromophenyl | mass spectrum (electric spray) m/z = 404 (M + 1), 406 (M + 2 + 1); $^1$H NMR (CDCl$_3$) (free base): 8.01 (br s, 1H), 7.86 (br d, 1H), 7.63 (m, 3H), 7.43 (m, 1H), 7.35 (m, 1H), 6.50 (d, 1H), 4.85 (m, 1H), 2.92 (m, 1H), 2.28 (s, 3H), 2.18 (m, 1H), 2.08 (m, 3H), 1.74 (m, 1H), 1.45 (m, 1H), 1.13 (d, J=5.9 Hz, 3H). |
| 133 | 2-chlorophenyl | mass spectrum (electric spray) m/z = 360 (M + 1); $^1$H NMR (CDCl$_3$)(free base): 8.21 (br s, 1H), 7.86 (br d, 1H), 7.71 (dd, 1H), 7.62 (t, 1H), 7.42 (m, 3H), 6.48 (d, 1H), 4.84 (m, 1H), 2.91 (m, 1H), 2.27 (s, 3H), 2.17 (m, 1H), 2.06 (m, 3H), 1.73 (m, 1H), 1.44 (m, 1H), 1.11 (d, J=6.4 Hz, 3H). |
| 134 | 4-fluorophenyl | mass spectrum (electric spray) m/z = 344 (M + 1); $^1$H NMR (CDCl$_3$)(free base): 8.15 (br s, 1H), 7.93 (m, 2H), 7.85 (d, 1H), 7.63 (t, 1H), 7.19 (m, 2H), 6.48 (d, 1H), 4.88 (m, 1H), 2.94 (m, 1H), 2.30 (s, 3H), 2.21 (m, 1H), 2.07 (m, 3H), 1.75 (m, 1H), 1.47 (m, 1H), 1.14 (d, J=6.3 Hz, 3H). |
| 135 | 2,4-difluorophenyl | mass spectrum (electric spray) m/z = 362 (M + 1); $^1$H NMR (CDCl$_3$)(free base): 8.69 (br d, 1H), 8.18 (m, 1H), 7.86 (d, 1H), 7.63 (t, 1H), 7.05 (m, 1H), 6.94 (m, 1H), 6.49 (d, 1H), 4.91 (m, 1H), 2.97 (m, 1H), 2.32 (s, 3H), 2.26 (m, 1H), 2.11 (m, 3H), 1.78 (m, 1H), 1.50 (m, 1H), 1.16 (d, J=5.9Hz, 3H). |
| 136 | 2,6-difluorophenyl | mass spectrum (electric spray) m/z = 362 (M + 1); $^1$H NMR (CDCl$_3$)(free base): 7.80 (br s, 1H), 7.86 (br d, 1H), 7.62 (t, 1H), 7.44 (m, 1H), 7.01 (m, 2H), 6.50 (d, 1H), 4.85 (m, 1H), 2.97 (m, 1H), 2.28 (s, 3H), 2.19 (m, 1H), 2.07 (m, 3H), 1.74 (m, 1H), 1.46 (m, 1H), 1.13 (d, J=6.4 Hz, 3H). |
| 137 | 2,4,6-trifluorophenyl | mass spectrum (electric spray) m/z = 380 (M + 1); $^1$H NMR (CDCl$_3$)(free base): 8.00 (br s, 1H), 7.83 (br d, 1H), 7.63 (t, 1H), 6.79 (m, 2H), 6.51 (d, 1H), 4.85 (m, 1H), 2.94 (m, 1H), 2.29 (s, 3H), 2.21 (m, 1H), 2.08 (m, 3H), 1.77 (m, 1H), 1.49 (m, 1H), 1.14 (d, J=6.4 Hz, 3H). (file: mn4-a01245-163 400). |
| 138 | 2,6-dichlorophenyl | mass spectrum (electric spray) m/z = 394 (M + 1); $^1$H NMR (CDCl$_3$)(free base): 7.89 (d, 1H), 7.79 (br s, 1H), 7.64 (t, 1H), 7.49 (m, 3H), 6.51 (d, 1H), 4.86 (m, 1H), 2.93 (m, 1H), 2.28 (s, 3H), 2.19 (m, 1H), 2.07 (m, 3H), 1.75 (m, 1H), 1.46 (m, 1H), 1.13 (d, J=5.9 Hz, 3H). |
| 139 | 2,4,6-trichlorophenyl | mass spectrum (electric spray) m/z = 428 (M$^+$), 416 (M + 2); $^1$H NMR (CDCl$_3$)(free base): 7.86 (d, 1H), 7.79 (br s, 1H), 7.64 (t, 1H), 7.41 (s, 2H), 6.52 (d, 1H), 4.84 (m, 1H), 2.92 (m, 1H), 2.28 (s, 3H), 2.18 (m, 1H), 2.07 (m, 3H), 1.75 (m, 1H), 1.46(m, 1H), 1.13 (d, J=6.4 Hz, 3H) |
| 140 | 2-chloro-6-fluorophenyl | mass spectrum (electric spray) m/z = 378 (M + 1); $^1$H NMR (CDCl$_3$)(free base): 7.99 (br s, 1H), 7.86 (br d, 1H), 7.62 (t, 1H), 7.35 (m, 1H), 7.25 (m, 1H), 7.08 (m, 1H), 6.49 (d, 1H), 4.83 (m, 1H), 2.90 (m, 1H), 2.25 (s, 3H), 2.16 (m, 1H), 2.05 (m, 3H), 1.72 (m, 1H), 1.46 (m, 1H), 1.10 (d, J=5.9 Hz, 3H). |

Example 141

2-Chloro-4-fluoro-N-[6-(trans-2-methyl-piperidin-4-yloxy)-pyridin-2-yl]-benzamide isomer 2 hydrogen chloride salt

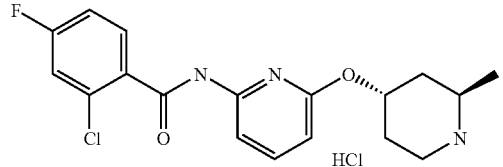

Using a method similar to example 92, using 4-[6-(2-chloro-4-fluoro-benzoylamino)-pyridin-2-yloxy]-2-methyl-piperidine-1-carboxylic acid tert-butyl ester trans isomer 2, the title compound is obtained. Mass spectrum (electric spray) m/z=364 (M+1); $^1$H NMR (CDCl$_3$) (free base): 8.30 (br s, 1H), 7.84 (br d, 1H), 7.74 (dd, 1H), 7.64 (dd, 1H), 7.20 (dd, 1H), 7.09 (ddd, 1H), 6.53 (dd, 1H), 5.25 (m, 1H), 3.08 (m, 2H), 2.90 (m, 1H), 1.93 (m, 3H), 1.69 (m, 1H), 1.36 (m, 1H), 1.05 (d, J=6.2 Hz, 3H).

Example 142

2-Chloro-4-fluoro-N-[6-(1-trans-2-dimethyl-piperidin-4-yloxy)-pyridin-2-yl]benzamide isomer 2 hydrogen chloride salt

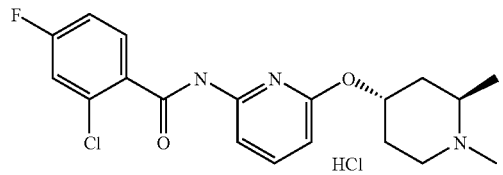

Using a method similar to example 89, using 2-Chloro-4-fluoro-N-[6-(trans-2-methyl-piperidin-4-yloxy)-pyridin-2-yl]benzamide isomer 2, the title compound is obtained. Mass spectrum (electric spray) m/z=378 (M+1); $^1$H NMR (CDCl$_3$) (free base): 8.21 (br s, 1H), 7.85 (br d, 1H), 7.76 (dd, 1H), 7.65 (t, 1H), 7.21 (dd, 1H), 7.10 (ddd, 1H), 6.53 (dd, 1H), 5.19 (m, 1H), 2.65 (m, 1H), 2.43 (m, 2H), 2.29 (s, 3H), 1.88 (m, 3H), 1.56 (m, 1H), 1.05 (d, J=6.5 Hz, 3H).

Example 143

2-Chloro-N-[6-(1-trans-2-dimethyl-piperidin-4-yloxy)-pyridin-2-yl]-4-fluoro-benzamide isomer 1 hydrogen chloride salt

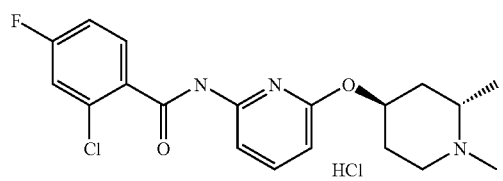

Using a method similar to example 89, using 2-chloro-4-fluoro-N-[6-(trans-2-methyl-piperidin-4-yloxy)-pyridin-2-yl]benzamide isomer 1, the title compound is obtained. Mass spectrum (electric spray) m/z=378 (M+1); $^1$H NMR (CDCl$_3$)

(free base): 7.97 (br s, 1H), 7.89 (d, 1H), 7.65 (t, 1H), 7.36 (ddd, 1H), 7.26 (d, 1H), 7.09 (ddd, 1H), 6.53 (dd, 1H), 5.17 (m, 1H), 2.75 (m, 1H), 2.57 (m, 2H), 2.37 (s, 3H), 1.95 (m, 3H), 1.66 (m, 1H), 1.13 (d, J=6.4 Hz, 3H).

Example 144

N-[6-(1-cis-2-Dimethyl-piperidin-4-yloxy)-pyridin-2-yl]-3-methyl-butyramide isomer 2 hydrogen chloride salt

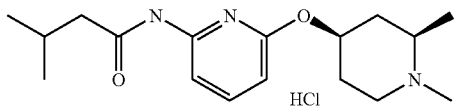

Combine 3-methyl-butyryl chloride (92 mg), 4-(6-amino-pyridin-2-yloxy)-cis-2-methyl-piperidine-1-carboxylic acid tert-butyl ester isomer 2 (preparation 64, 0.196 g) and triethylamine (0.18 mL) and heat at reflux. After 1 hr., add 0.6 mL of conc. HCl and heat at reflux. After 30 min., load the reaction mixture onto a SCX column, wash with methanol, then 2M NH$_3$ in methanol. Evaporate the ammonium methanol solution to give a solid (77 mg). By the method of example 121 and 131 prepare the title compound and its mono-hydrogen chloride salt. Mass spectrum (electric spray) m/z=306 (M+1); $^1$H NMR (CDCl$_3$) (free base): 7.71 (d, 1H), 7.57 (br d, 1H), 7.54 (t, 1H), 6.41 (d, 1H), 4.82 (m, 1H), 2.92 (m, 1H), 2.27 (s, 3H), 2.21 (m, 3H), 2.04 (m, 3H), 1.72 (m, 1H), 1.44 (m, 1H), 1.12 (d, J=5.9 Hz, 3H), 1.00 (d, J=6.4 Hz, 6H).

Preparation 110. Racemic N-[6-(1-benzyl-3-trans-methyl-piperidin-4-yloxy)-pyridin-2-yl]4-fluoro-benzamide

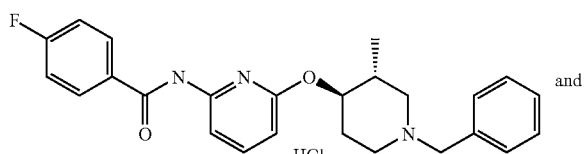

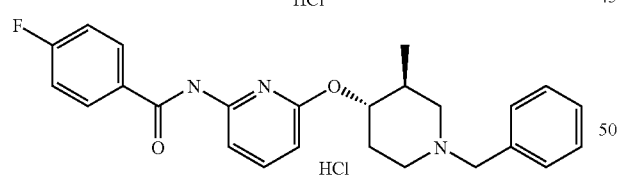

Combine racemic 6-(1-benzyl-3-trans-methyl-piperidin-4-yloxy)-pyridin-2-ylamine (preparation 65, 0.232 g) and 4-fluoro-benzoyl chloride (0.136 g) in 1,4-dioxane (20 mL) and reflux. After 2 hr., add methanol into the reaction mixture and load onto a SCX column (10 g) and wash the column with methanol. Elute the product with 2N NH$_3$-methanol and evaporate to give the title compound (0.307 g). $^1$H NMR (CDCl$_3$): 8.15 (br s, 1H), 7.94 (m, 2H), 7.84 (d, 1H), 7.63 (t, 1H), 7.33 (m, 4H), 7.27 (m, 1H), 7.19 (m, 2H), 6.50 (d, 1H), 4.56 (m, 1H), 3.54 (s, 2H), 2.88 (m, 2H), 2.16 (m, 2H), 2.02 (m, 1H), 1.87 (m, 1H), 1.68 (m, 1H), 0.93 (d, J=6.8 Hz, 3H).

Using a method similar to preparation 110 prepare the analogous compounds and their mono-hydrochlorides as indicated below:

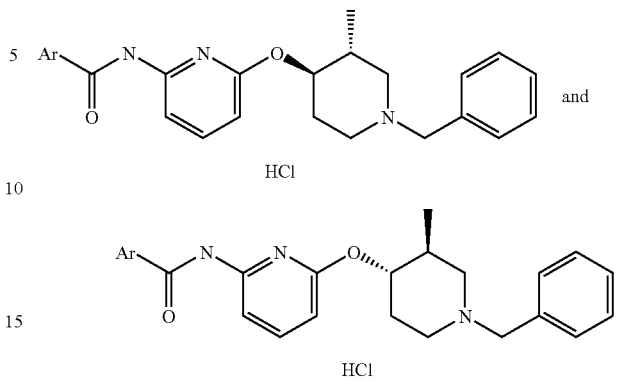

| Prep. | Ar | Data (free base) |
|---|---|---|
| 111 | 2-chloro-4-fluorophenyl | Mass spectrum (electric spray) m/z = 454 (M + 1); $^1$H NMR (CDCl$_3$): 7.89 (br s, 1H), 7.87 (d, 1H), 7.64 (t, 1H), 7.37 (m, 1H), 7.32 (m, 4H), 7.26 (m, 2H), 7.10 (m, 1H), 6.53 (d, 1H), 4.54 (m, 1H), 3.52 (s, 2H), 2.86 (m, 2H), 2.13 (m, 2H), 1.99 (m, 1H), 1.83 (m, 1H), 1.66 (m, 1H), 0.91 (d, J=6.4 Hz, 3H). |
| 112 | 2,4,6-trifluorophenyl | Mass spectrum (electric spray) m/z = 456 (M + 1); $^1$H NMR (CDCl$_3$): 7.99 (br s, 1H), 7.83 (d, 1H), 7.62 (t, 1H), 7.32 (m, 4H), 7.26 (m, 2H), 6.78 (m, 2H), 6.53 (d, 1H), 4.53 (m, 1H), 3.52 (s, 2H), 2.86 (m, 2H), 2.13 (m, 2H), 1.99 (m, 1H), 1.84 (m, 1H), 1.65 (m, 1H), 0.91 (d, J=6.8 Hz, 3H). |
| 113 | 2-chlorophenyl | Mass spectrum (electric spray) m/z = 436 (M + 1); $^1$H NMR (CDCl$_3$): 8.26 (br s, 1H), 7.88 (d, 1H), 7.70 (dd, 1H), 7.64 (t, 1H), 7.53 (m, 2H), 7.40 (m, 6H), 6.50 (d, 1H), 4.62 (m, 1H), 3.52 (s, 2H), 3.20 (m, 2H), 2.69 (m, 1H), 2.53 (m, 1H), 2.32 (m, 2H), 2.18 (m, 1H), 1.00 (d, J=6.4 Hz, 3H). |

Example 144

2-Chloro-4-fluoro-N-[6-(3-trans-methyl-piperidin-4-yloxy)-pyridin-2-yl]-benzamide isomer 1

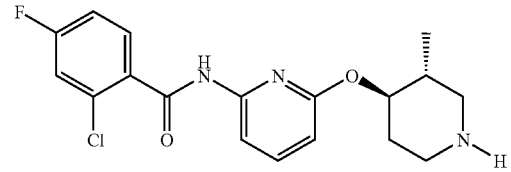

Resolve the racemic N-[6-(1-benzyl-3-trans-methyl-piperidin-4-yloxy)-pyridin-2-yl]-2-chloro-4-fluoro-benzamide (preparation 111) using Chiralpak™ OD, NPA/heptane (5/95) with 0.2% DMEA into isomer 1 (329 mg) and 2 (343 mg). Combine N-[6-(1-benzyl-3-trans-methyl-piperidin-4-yloxy)-pyridin-2-yl]-2-chloro-4-fluoro-benzamide isomer 1 and 1-chloroethyl chloroformate (0.414 g) in 1,2-dichloroethane (20 mL) and reflux. After 1 hr., dilute the reaction mixture with methanol and load onto a SCX column (10 g) and wash the column with methanol. Elute the product with 2N NH$_3$-methanol, evaporate and purify on a silica gel column (35 g, solvent: dichloromethane-2M NH$_3$ in methanol, gradient) to give the title compound (0.208 g). Mass spectrum (electrospray) m/z=364 (M+1); $^1$H NMR (CDCl$_3$): 7.95 (d, 1H), 7.62 (t, 1H), 7.36 (m, 1H), 7.26 (d, 1H), 7.09 (ddd, 1H), 6.48 (d, 1H), 4.74 (m, 1H), 2.94 (m, 2H), 2.75 (m, 1H), 2.48 (m, 1H), 2.14 (m, 1H), 1.63 (m, 1H), 1.45 (br, 2H), 1.29 (m, 1H), 0.90 (d, J=6.6 Hz, 3H).

Dissolve the benzamide (0.118 g) in dichloromethane-methanol and add 0.32 mL of 1N HCl in ether, evaporate and dry in vacuum to give the hydrochloric acid salt.

Using a method similar to example 144, prepare the analogous compounds and their hydrogen chloride salts as indicated below:

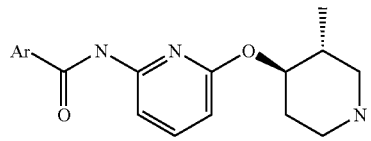

| Ex. | Ar | (Free base) |
|---|---|---|
| 145 | 2-chloro-4-fluorophenyl isomer 2 | mass spectrum (electrospray) m/z = 364 (M + 1); ¹H NMR (CDCl₃): 7.94 (d, 1H), 7.62 (t, 1H, 7.37 (m, 1H), 7.25 (d, 1H), 7.09 (ddd, 1H), 6.48 (d, )H), 4.72 (m, 1H), 2.95 (m, 2H), 2.74 (m, 1H), 2.46 (m, 1H), 2.14 (m, 1H), 1.63 (m, 1H), 1.37 (br, 2H), 1.29 (m, 1H), 0.90 (d, J=6.4 Hz, 3H). |
| 146 | 4-fluorophenyl (racemic) | mass spectrum (electrospray) m/z = 330 (M + 1); ¹H NMR (CDCl₃): 8.34 (br s, 1H), 7.92 (m, 2H), 7.84 (d, 1H), 7.62 (t, 1H), 7.17 (m, 2H), 6.49 (d, 1H), 4.66 (m, 1H), 3.11 (m, 2H), 2.73 (m, 2H), 2.40 (m, 1H), 2.14 (m, 1H), 1.77 (m, 1H), 1.68 (br, 1H), 1.45 (m, 1H), 0.93 (d, J=6.4 Hz, 3H). |
| 147 | 2,4,6-trifluorophenyl (racemic) | mass spectrum (electric spray) m/z = 365 (M + 1); ¹H NMR (CDCl₃—CD₃OD): 7.73 (d, 1H), 7.52 (t, 1H), 6.66 (m, 2H, 6.41 (d, 1H), 4.58 (m, 1H, 3.00 (m, 2H, 2.64 (m, 1H), 2.32 (m, 1H), 2.12 (m, 1H), 1.77 (m, 1H), 1.41 (m, 1H), 0.84 (d, J=6.4 Hz, 3H). |
| 148 | 2-chlorophenyl (racemic) | ¹H NMR (CDCl₃): 7.79 (d, 1H), 7.61 (m, 2H), 7.38 (m, 3H, 6.48 (d, 1H), 4.61 (m, 1H), 4.00 (br s, 2H), 3.03 (m, 2H), 2.63 (m, 1H), 2.31 (m, 1H), 2.14 (m, 1H), 1.77 (m, 1H), 1.42 (m, 1H), 0.89 (d, J=6.9 Hz, 3H). |

Example 149

2-Chloro-N-[6-(1,3-trans-dimethyl-piperidin-4-yloxy)-pyridin-2-yl]4-fluoro-benzamide isomer 1

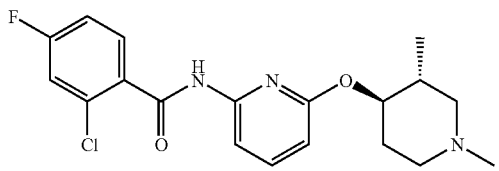

Mix 2-chloro-4-fluoro-N-[6-(3-trans-methyl-piperidin-4-yloxy)-pyridin-2-yl]-benzamide isomer 1 (example 144, 90 mg), formaldehyde (37%, 74 mg), sodium triacetoxyborohydride (68 mg) and acetic acid (37 mg) with dichloromethane (10 mL) and stir for 3 hr. Dilute with methanol and load on a SCX column (10 g), wash with methanol, elute the product with 2M NH₃-methanol, evaporate to give the title compound (94 mg). Mass spectrum (electrospray) m/z=378 (M+1); ¹H NMR (CDCl₃): 7.89 (br s, 1H), 7.88 (d, 1H), 7.64 (t, 1H), 7.38 (m, 1H), 7.26 (m, 1H), 7.11 (m, 1H), 6.53 (d, 1H), 4.52 (m, 1H), 2.83 (m, 2H), 2.27 (s, 3H), 2.13 (m, 2H), 2.02 (m, 1H), 1.81 (m, 1H), 1.66 (m, 1H), 0.93 (d, J=6.6 Hz, 3H).

Dissolve the benzamide (94 mg) in dichloromethane-methanol and add 0.25 mL of 1N HCl in ether, evaporate and dry in vacuum to give the hydrogen chloride salt.

Using a method similar to example 149, using the appropriate N-[6-(3-trans-methyl-piperidin-4-yloxy)-pyridin-2-yl]-Ar-carboxamide isomer 1, prepare the analogous compounds and their mono-hydrochlorides as indicated below:

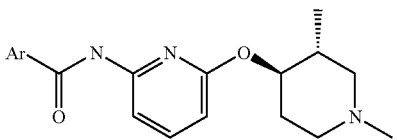

| Ex. | Ar | Data |
|---|---|---|
| 150 | 2-chloro-4-fluorophenyl isomer 2, HCl salt | mass spectrum (electrospray) m/z = 378 (M + 1); ¹H NMR (CDCl₃)(free base): 7.96 (br s, 1H), 7.88 (d, 1H), 7.64 (t, 1H), 7.38 (m, 1H), 7.27 (m, 1H), 7.10(m, 1H), 6.53 (d, 1H), 4.53 (m, 1H), 2.89 (m, 2H), 2.33 (s, 3H), 2.17 (m, 2H), 2.07 (m, 1H), 1.90 (m, 1H), 1.76 (m, 1H), 0.95 (d, J=6.4 Hz, 3H). |
| 151 | 4-fluorophenyl (racemic) (free base) | mass spectrum (electrospray) m/z = 344 (M + 1); ¹H NMR (CDCl₃): 8.18 (br s, 1H), 7.94 (m, 2H), 7.84 (d, 1H), 7.62 (t, 1H), 7.17 (m, 1H), 6.50 (d, 1H), 4.54 (m, 1H), 2.84 (m, 2H), 2.28 (s, 3H), 2.12 (m, 2H), 2.01 (m, 1H), 1.82 (m, 1H), 1.67 (m, 1H), 0.94 (d, J=6.8 Hz, 3H). |
| 152 | 2,4,6-trifluorophenyl (racemic) (free base) | mass spectrum (electrospray) m/z = 380 (M + 1); ¹H NMR (CDCl₃): 8.05 (br s, 1H), 7.82 (d, 1H), 7.62 (t, 1H), 6.77 (m, 2H), 6.52 (d, 1H), 4.51 (m, 1H), 2.84 (m, 2H), 2.27 (s, 3H), 2.11 (m, 2H), 2.00 (m, 1H), 1.80 (m, 1H), 1.66 (m, 1H), 0.92 (d, J=6.8 Hz, 3H). |
| 153 | 2-chlorophenyl (raceinic) (free base) | mass spectrum (electrospray) m/z = 360 (M + 1); ¹H NMR (CDCl₃): 8.19 (br s, 1H), 7.87 (d, 1H), 7.72 (dd, 1H), 7.64 (t, 1H), 7.42 (m, 3H), 6.52 (d, 1H), 4.54 (m, 1H), 2.87 (m, 2H), 2.31 (s, 3H), 2.16 (m, 2H), 2.05 (m, 1H), 1.86 (m, 1H), 1.71 (m, 1H), 0.95 (d, J=6.8 Hz, 3H). |

Example 154

2-Chloro-6-fluoro-N-[6-(1-methyl-piperidin-4-yloxy)-pyridin-2-yl]-benzamide hydrogen chloride salt

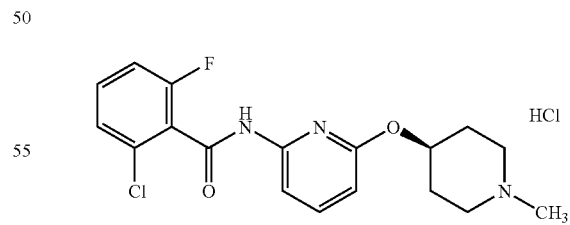

Combine 6-(1-methyl-piperidin-4-yloxy)-pyridin-2-ylamine (preparation 60, 200 mg, 0.96 mmol), and dioxane (15 mL), stir and heat at 50° C. Add 2-chloro-6-fluorobenzoyl chloride (214 □L, 1.1 mmol), and heat at 85° C. for an additional 3 hr. Cool the reaction to room temperature, and load onto a 5 g SCX cartridge. Wash resin with Methanol, then remove product with 2 M NH₃/methanol. Concentrate in vacuo, and silica gel chromatography eluting with 5-20% 2 M NH$_3$ in methanol/methylene dichloride. Dissolve the purified oil (286 mg, 81% isolated yield) in methanol, add NH$_4$Cl (42 mg, 1 eq) as a solid, and sonicate the solution at room temperature for 15 min. Concentration in vacuo provides the title compound: mass spectrum (ion spray): m/z=364.1 (M+1); mp=139.6° C.

Example 155

N-[6-(1-Methyl-piperidin-4-yloxy)-pyridin-2-yl]-2-trifluoromethoxy-benzamide hydrogen chloride salt

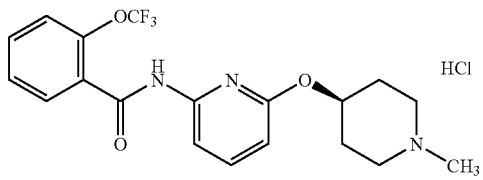

Using a method similar to example 154, using 2-trifluoromethoxybenzoyl chloride, gives the title compound as a white solid. Mass spectrum (ion spray): m/z=396.2 (M+1); mp=88.7° C.

Example 156

2-Bromo-N-[6-(1-methyl-piperidin-4-yloxy)-pyridin-2-yl]-benzamide hydrogen chloride salt

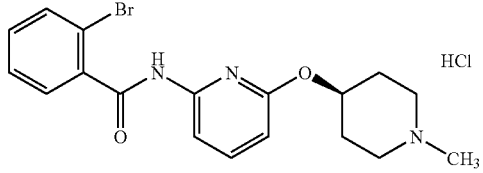

Using a method similar to example 154, using 2-bromobenzoyl chloride, gives the title compound as a white solid. Mass spectrum (ion spray): m/z=390.1 (M+1); mp=104.3° C.

Example 157

2,6-Difluoro-N-[6-(1-methyl-piperidin-4-yloxy)-pyridin-2-yl]-benzamide hydrogen chloride salt

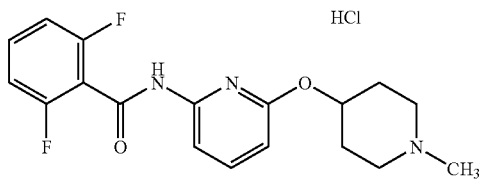

Using a method similar to example 154, using 2,6-difluorobenzoyl chloride, gives the title compound as a white solid. Mass spectrum (ion spray): m/z=348.3 (M+1); mp=261.4° C.

Example 158

Ex. N-[6-(1-Methyl-piperidin-4-yloxy)-pyridin-2-yl]-2,3,4-trifluoro-benzamide hydrogen chloride salt

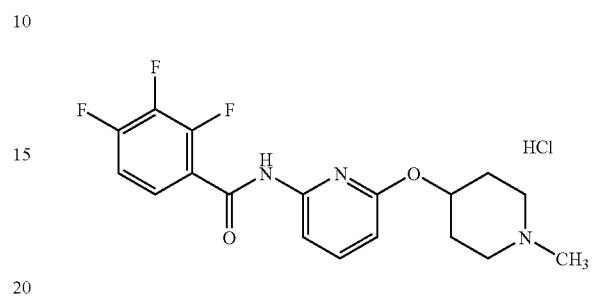

Using a method similar to Example 154, using 2,3,4-trifluorobenzoyl chloride, gives the title compound as a white solid. Mass spectrum (ion spray): m/z=366.4 (M+1); mp=182.4° C. (dec.).

Example 159

N-[6-(1-Methyl-piperidin-4-yloxy)-pyridin-2-yl]-3,4,5-Trifluoro-benzamide hydrogen chloride salt

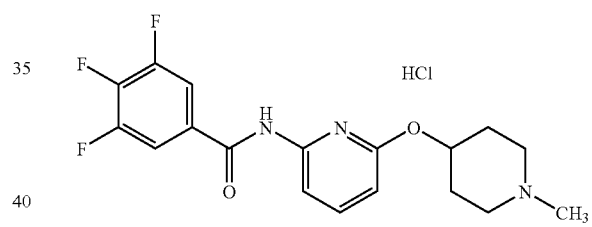

Using a method similar to example 154, using 3,4,5-trifluorobenzoyl chloride, gives the title compound as a white solid: mass spectrum (ion spray). M/Z=366.4 (M+1); mp=171.4° C. (dec.).

Example 160

2-Chloro-4-fluoro-N-[6-(1-methyl-piperidin-4-yloxy)-pyridin-2-yl]-benzamide hydrogen chloride salt

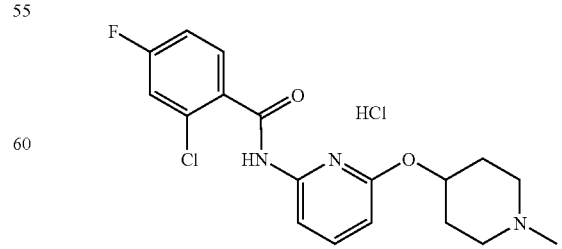

Dissolve 6-(1-methyl-piperidin-4-yloxy)-pyridin-2-ylamine (preparation 60, 150 mg, 0.724 mmol) in pyridine (20 mL). Add 2-chloro-4-fluorobenzoyl chloride (208 mg, 1.08 mmol) and heat at 55° C. After 4 hr., cool to room temperature, concentrate and load residue onto a 5 g SCX cartridge. Wash resin with methanol, then remove product with 2 M NH$_3$/methanol. Concentrate in vacuo, and silica gel chromatography eluting with 2-10% methanol/methylene dichloride to give the free base (280 mg, 97%). Dissolve the purified oil in methanol, add NH$_4$Cl (1 eq) as a solid, and sonicate the solution at room temperature for 15 min. Concentration in vacuo provides the title compound (280 mg, 97%). Mass spectrum (ion spray): m/z 364.0 (M+1); Analysis calculated for $C_{18}H_{19}N_3O_2Cl_2F \cdot 0.5H_2O$. Theory: C, 52.82, H, 5.17, N, 10.27. Found: C, 52.89; H, 5.18; N, 10.37. mp=135-137° C.

Example 161

4-Fluoro-N-[6-(1-methyl-piperidin-4-yloxy)-pyridin-2-yl]-benzamide hydrogen chloride salt

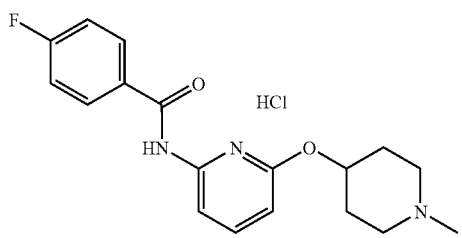

Using a method similar to example 160, starting with 6-(1-methyl-piperidin-4-yloxy)-pyridin-2-ylamine (preparation 60, 150 mg, 0.724 mmol) and 4-fluorobenzoyl chloride (128 μL, 1.08 mmol) yields the title compound (256 mg, 97%). Mass spectrum (ion spray): m/z 330.1 (M+1); Analysis calculated for $C_{18}H_{21}N_3O_2FCl \cdot 0.5H_2O$. The C, 57.68; H, 5.92; N, 11.21. Found: C, 57.76; H, 6.17; N, 11.44. mp=203-205° C.

Example 162

2,4-Difluoro-N-[6-(1-methyl-piperidin-4-yloxy)-pyridin-2-yl]-benzamide hydrogen chloride salt

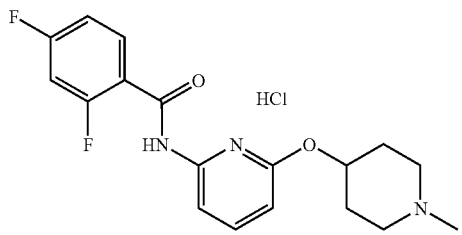

Using a method similar to example 160, using 6-(1-methyl-piperidin-4-yloxy)-pyridin-2-ylamine (preparation 60, 150 mg, 0.724 mmol) and 2,4-difluorobenzoyl chloride (133 μL, 1.08 mmol) yields the title compound (230 mg, 83%). Mass spectrum (ion spray): m/z 348.1 (M+1); Analysis calculated for $C_{18}H_{20}N_3O_2ClF_2 \cdot 0.5H_2O$. Theory: C, 55.03; H, 5.39; N, 10.70. Found: C, 54.88; H, 5.39; N, 10.73. mp=269-271° C.

compound (13.5 g). Filter on silicagel to provide the title compound (10 g, 95% purity, 85% corrected yield).

Example 163

N-[6-(1-Methyl-piperidin-4-yloxy)-pyridin-2-yl]-isonicotinamide hydrogen chloride salt

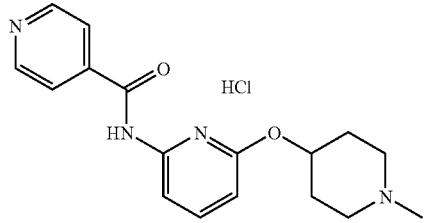

Using a method similar to example 160 using 6-(1-methyl-piperidin-4-yloxy)-pyridin-2-ylamine (preparation 60, 150 mg, 0.724 mmol) and isonicotinoyl chloride hydrochloride (192 mg, 1.08 mmol) yields the title compound (225 mg, 89%). Mass spectrum (ion spray): m/z 313.1 (M+1); Analysis calculated for $C_{17}H_{21}N_4O_2Cl \cdot 0.2H_2O$. Theory: C, 57.93; H, 6.12; N, 15.90. Found: C, 57.78; H, 6.28; N, 15.88. mp=254-256° C.

Example 164

2-Chloro-N-[6-(1-methyl-piperidin-4-yloxy)-pyridin-2-yl]-benzamide hydrogen chloride salt

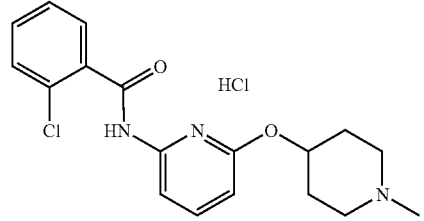

Using a method similar to example 154, using 6-(1-methyl-piperidin-4-yloxy)-pyridin-2-ylamine (preparation 60, 200 mg, 0.965 mmol) and 2-chlorobenzoyl chloride (146 μL, 1.16 mmol) yields the title compound (340 mg, 92%). Mass spectrum (ion spray): m/z 346.0 (M+1); Analysis calculated for $C_{18}H_{20}N_3O_2Cl_2 \cdot 0.5H_2O$. Theory: C, 55.25; H, 5.67; N, 10.74. Found: C, 55.60; H, 5.67; N, 10.74. mp=88-90° C.

Example 165

N-[6-(1-Methyl-piperidin-4-yloxy)-pyridin-2-yl]-2,4,6-trifluoro-benzamide hydrogen chloride salt

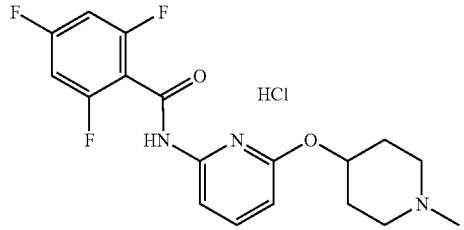

Using a method similar to example 154, using 6-(1-methyl-piperidin-4-yloxy)-pyridin-2-ylamine (preparation 60, 200 mg, 0.965 mmol) and 2,4,6-trifluorobenzoyl chloride (150 μL, 1.16 mmol) yields of the title compound (341 mg, 88%). Mass spectrum (ion spray): m/z 365.8 (M+1); Analysis calculated for $C_{18}H_{19}N_3O_2ClF_3$. Theory: C, 53.81; H, 4.76; N, 10.46. Found: C, 53.74; H, 5.03; N, 10.43. mp=264-6° C.

Example 166

4-Fluoro-N-[6-(piperidin-4-yloxy)-pyridin-2-yl]-benzamide hydrogen chloride salt

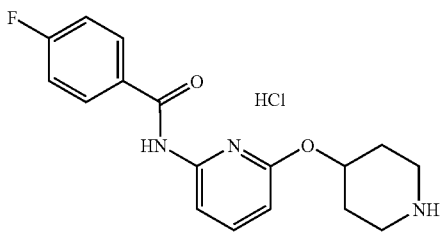

Combine 4-fluoro-N-[6-(1-methyl-piperidin-4-yloxy)-pyridin-2-yl]-benzamide hydrochloride (example 161, 365 mg, 1.11 mmol) and 1,2-dichloroethane (10 mL) and add 1-chloroethyl chloroformate (1.20 mL, 11.1 mmol). Heat the reaction to 80° C. for 18 hr. Add additional 1-chloroethyl chloroformate (600 μL, 5.5 mmol) and continue to heat at 80° C. for 5 hr. Cool reaction to ambient temperature and add methanol. Load solution onto an SCX column and wash with methanol. Flush off product with 2 M ammonia in methanol and concentrate in vacuo. Purify by column chromatography (2%-8% 2 M $NH_3$ in methanol/$CH_2Cl_2$). Make the hydrogen chloride salt by sonication with one equivalent of ammonium chloride dissolved in methanol to yield of the title compound (115 mg, 29%). Mass spectrum (ion spray): m/z 316.3 (M+1); Analysis calculated for $C_{17}H_{19}N_3O_2FCl.0.5H_2O$. Theory: C, 56.59; H, 5.59; N, 11.65. Found: C, 56.83; H, 5.38; N, 11.74. mp=251-3° C.

Example 167

2-Chloro-N-[6-(1-cyclopropylmethyl-piperidin-4-yloxy)-pyridin-2-yl]-4-fluoro-benzamide

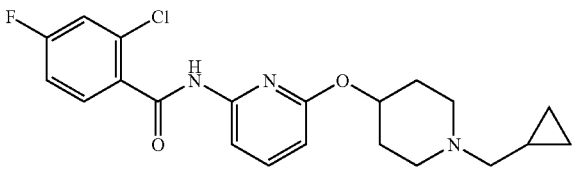

Add 2-chloro-4-fluorobenzoyl chloride (149 mg, 0.58 mmol) to a solution of 6-(1-cyclopropylmethyl-piperidin-4-yloxy)-pyridin-2-ylamine (preparation 70, 130 mg, 0.53 mmol) in pyridine (7 mL) and beat at 55° C. for 15 hr. Remove pyridine in vacuo, dissolve the residue in $CH_2Cl_2$, wash with saturated $NaHCO_3$ solution, dry over $Na_2SO_4$, filter and concentrate to give a residue. Chromatography (silica gel, eluting with 5% 2M $NH_3$-Methanol in $CH_2Cl_2$) provides 170 mg (79%) of the title compound: mass spectrum (ion spray): 404.1 (M+1); $^1H$ NMR ($CDCl_3$, ppm): 8.08 (s, 1H), 7.63 (m, 2H), 7.52 (t, 1H), 7.11 (m, 1H), 6.99 (m, 1H), 6.41 (d, 1H), 4.82 (m, 1H), 2.72 (m, 2H), 2.26 (m, 2H), 2.17 (d, 2H), 1.89 (m, 2H), 1.69 (m, 2H), 0.77 (m, 1H), 0.40 (m, 2H), 0.00 (m, 2H). Hydrochloride salt: Analytical calc. for $C_{21}H_{23}ClFN_3O_2.HCl.0.5H_2O$: C, 56.13; H, 5.61; N, 9.35. Found: C, 56.12; H, 5.30; N, 9.35.

Example 168

2-Chloro-N-[6-(1-cyclopropylmethyl-piperidin-4-yloxy)-pyridin-2-yl]-6-fluoro-benzamide mono-hydrochloride

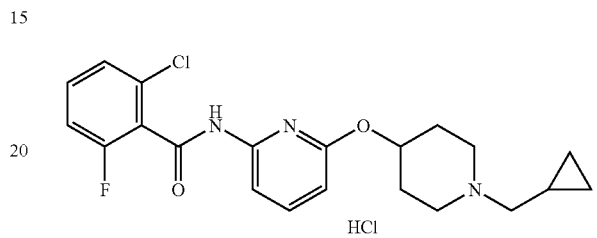

Using a method similar to example 167, using 2-chloro-6-fluorobenzoyl chloride (148 mg, 0.77 mmol) gives 92 mg (30%) of the title compound after reverse phase HPLC purification: mass spectrum (ion spray): 404.1 (M−Cl); $^1H$ NMR (methanol-$d_4$, ppm): 7.80 (m, 2H), 7.49 (m, 1H), 7.37 (m, 1H), 7.23 (m, 1H), 6.62 (dd, 1H), 5.40 (m, 1H), 3.76-3.56 (m, 2H), 3.32 (m, 2H), 3.10 (m, 2H), 2.51-2.31 (m, 2H), 2.18-1.88 (m, 2H), 1.60 (m, 1H), 0.78 (m, 2H), 0.47 (m, 2H).

Example 169

2,4,6-Trifluoro-N-methyl-N-[6-(1-methyl-piperidin-4-yloxy)-pyridin-2-yl]-benzamide

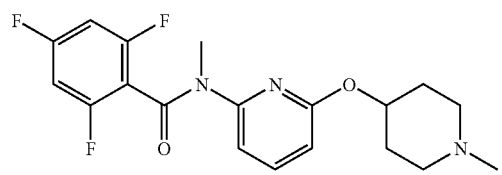

Combine sodium methoxide (290 mg, 5.38 mmol), paraformaldehyde (94 mg, 3.13 mmol), 6-(1-methyl-piperidin-4-yloxy)-pyridin-2-ylamine (preparation 60, 260 mg, 1.25 mmol) and methanol (5 mL), heat at 50° C. for 20 hr. Add $NaBH_4$ (85 mg, 2.25 mmol), beat at reflux for 1.5 hr. Then add 1.0N KOH solution (2 mL), beat at reflux for 2 hr. Partition between water and $CH_2Cl_2$, extract aqueous phase with $CH_2Cl_2$. Combine organic layers, dry over $Na_2SO_4$, filter and concentrate to give a residue. Chromatography (silica gel) eluting with 5% 2M $NH_3$-methanol in methylene dichloride provides 230 mg of methyl-[6-(1-methyl-piperidin-4-yloxy)-pyridin-2-yl]-amine with a small amount (5-10%) of inseparable starting amine.

Dissolve the above amine product in THF (6 mL), add triethylamine (219 mg, 0.29 mL, 2.08 mmol) and 2,4,6-trifluorobenzoyl chloride (303 mg, 1.56 mmol) sequentially, heat at 55° C. overnight. Quench with 0.1N NaOH, extract with methylene dichloride three times. Combine the organic layers, dry over $Na_2SO_4$, filter and concentrate to give a residue. Chromatography (silica gel) eluting with 3.5% 2M NH$_3$-methanol in methylene dichloride provides 204 mg (43% two-step yield) of the title compound as a colorless oil: mass spectrum (ion spray): m/z=380.1 (M+1); $^1$H NMR (CDCl$_3$, ppm): 7.47 (t, 1H), 6.53 (m, 4H), 4.74 (m, 1H), 3.48 (s, 3H), 2.71 (m, 2H), 2.32 (s, 3H), 2.25 (m, 2H), 1.91 (m, 2H), 1.72 (m, 2H). Mono-hydrochloride salt: Anal. calc for C$_{19}$H$_{20}$F$_3$N$_3$O$_2$.HCl.0.5H$_2$O: C, 53.72; H, 5.22; N, 9.89. Found: C, 53.84; H, 5.04; N, 9.73.

Example 170

2,4,6-Trifluoro-N-ethyl-N-[6-(1-methyl-piperidin-4-yloxy)-pyridin-2-yl]-benzamide

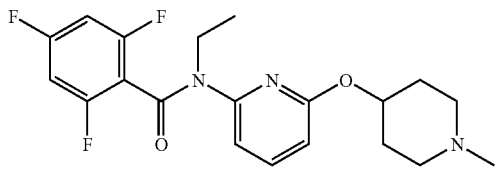

Dissolve ethyl-[6-(1-methyl-piperidin-4-yloxy)-pyridin-2-yl]-amine (preparation 74, 110 mg, 0.47 mmol) in THF (6 mL), add triethylamine (95 mg, 0.94 mmol) and 2,4,6-trifluorobenzoyl chloride (136 mg, 0.70 mmol) sequentially, heat at 55° C. overnight. Quench the reaction with 0.1N NaOH, extract with methylene dichloride three times. Combine the organic layers, dry over Na$_2$SO$_4$, filter and concentrate to give a residue. Chromatography (silica gel) eluting with 3.5% 2M NH$_3$-methanol in methylene dichloride provides 151 mg (82%) of the title compound as an oil: mass spectrum (ion spray): m/z=394.1 (M+1); $^1$H NMR (CDCl$_3$, ppm): 7.43 (t, 1H), 6.52 (m, 4H), 4.82 (m, 1H), 4.03 (q, 2H), 2.73 (m, 2H), 2.33 (s, 3H), 2.26 (m, 2H), 1.95 (m, 2H), 1.75 (m, 2H), 1.31 (t, 3H). Mono-hydrochloride salt: Anal calcd for C$_{20}$H$_{22}$F$_3$N$_3$O$_2$.HCl.H$_2$O: C, 53.63; H, 5.63; N, 9.38. Found: C, 53.66; H, 5.12; N, 9.29.

Example 171

2-Chloro-4-fluoro-N-[3-(1-methyl-piperidin-4-ylsulfanyl)-phenyl]-benzamide hydrogen chloride salt

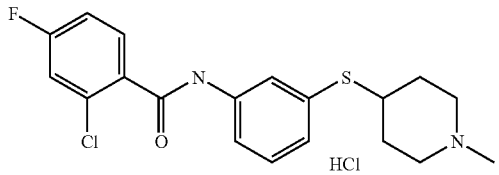

Combine pyridine (0.110 mL, 1.36 mmol), 3-(1-methyl-piperidin-4-ylsulfanyl)-phenylamine (preparation 76,151 mg, 0.679 mmol) in dichloromethane (6.5 mL) at 0° C. Stir and add 2-chloro-4-fluorobenzoyl chloride (0.105 mL, 0.815 mmol). Allow to warm to ambient temperature and stir. After 2 hr., dilute with dichloromethane (10 mL) and wash with sodium hydroxide (1N, 3×10 mL). Combine the organic layers, dry over sodium sulfate and concentrate under reduced pressure. Purification by flash chromatography, eluting with dichloromethane/ammonia (2.0 N in methanol) [20/1] to give the title compound as free base (184 mg, 72%). Dissolve the residue in diethyl ether and treat with ethereal hydrogen chloride (1.0 M). Triturate the resulting gum with ether to give the title compound as the hydrogen chloride salt. $^1$H NMR (free base, CDCl$_3$): 8.37 (bs, 1H), 7.65 (s, 1H), 7.58 (t, J=6.8 Hz, 1H), 7.42 (d, J=7.7 Hz, 1H), 7.21 (t, J=7.8 Hz, 1H), 7.14-7.06 (m, 2H), 6.99-6.93 (m, 1H), 3.05 (bs, 1H), 2.71 (bd, J=11.5 Hz, 2H), 2.19 (s, 3H), 2.03-1.90 (m, 4H), 1.67-1.56 (m, 2H). $^{13}$C NMR (free base, CDCl$_3$): 164.9, 162.2 (d, J$_{C-F}$=167.7 Hz), 137.9, 135.8, 132.0, 131.7 (d, J$_{C-F}$=8.6 Hz), 131.4, 129.3, 128.0, 123.0, 118.6, 117.5 (d, J$_{C-F}$=25.0 Hz), 114.5 (d, J$_{C-F}$=21.3 Hz), 54.9, 46.0, 43.6, 32.4.

Example 172

4-Fluoro-N-[3-(1-methyl-piperidin-4-ylsulfanyl)-phenyl]-benzamide hydrogen chloride salt

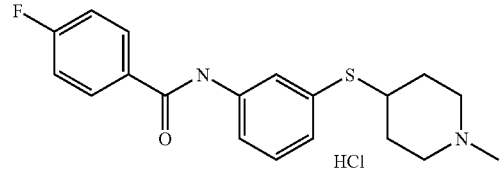

Using a method similar to example 171, using 4-fluorobenzoyl chloride (0.100 mL, 0.836 mmol) gives the title compound as the free base (215 mg, 90%). Following a method similar to example 171 gives the title compound as the hydrogen chloride salt: $^1$H NMR (free base, CDCl$_3$): 8.43 (bs, 1H), 7.78 (dd, J=8.5, 5.3 Hz, 1H), 7.66 (s, 1H), 7.44 (d, J=7.8 Hz, 1H), 7.20-6.97 (m, 4H), 3.02 (bs, 1H), 2.70 (bd, J=11.3 Hz, 2H), 2.18 (s, 3H), 2.00-1.88 (m, 4H), 1.66-1.54 (m, 2H); $^{13}$C NMR (free base, CDCl$_3$): 166.5, 164.0 (d, J$_{C-F}$=138.6 Hz), 138.3, 135.6, 130.8, 129.5 (d, J$_{C-F}$=8.8 Hz), 129.2, 127.9, 123.4, 118.9, 115.6 (d, J$_{C-F}$=21.9 Hz), 54.9, 46.0, 43.6, 32.4.

Example 173

2,6-Difluoro-N-[3-(1-methyl-piperidin-4-ylsulfanyl)-phenyl]-benzamide hydrogen chloride salt

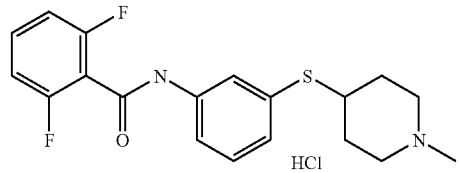

Using a method similar to example 171, using 2,6-difluorobenzoyl chloride (0.263 mL, 2.10 mmol) gives the title compound as the free base (610 mg, 96%). Following a method similar to example 171 gives the title compound as the hydrogen chloride salt. Mass spectrum (free base, ion spray): m/z=363.1 (M+1), $^1$H NMR (free base, CDCl$_3$): 8.11 (bs, 1H), 7.70 (s, 1H), 7.46 (bd, J=7.9 Hz, 1H), 7.43-7.33 (m, 1H), 7.29-7.16 (m, 2H), 6.95 (t, J=8.0 Hz, 2H), 3.11 (bs, 1H), 2.77 (bd, J=11.7 Hz, 2H), 2.23 (s, 3H), 2.08-1.96 (m, 4H), 1.73-1.60 (m, 2H).

Preparation 114. 3-Fluoro-5-(1-methyl-piperidin-4-ylsulfanyl)-phenylamine

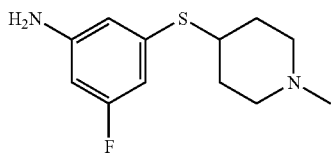

Combine 4-(3-Fluoro-5-nitro-phenylsulfanyl)-1-methyl-piperidine (preparation 75, 0.31 g, 1.15 mmol), iron dust (0.21 g, 3.79 mmol), methanol (10 mL) and aqueous 1M hydrochloric acid (0.35 mL, 0.35 mmol), stir and heat at reflux. After 20 h, cool to ambient temperature and concentrate. Partition residue between ethyl acetate (50 mL) and 1M sodium hydroxide (20 mL). Separate the organic layer, dry over sodium sulfate, filter and concentrate. Purify residue by silica gel flash chromatography eluting with 10% (2M $NH_3$/methanol)/methylene dichloride to obtain 0.11 g (40%) of the title compound: mass spectrum (electrospray): m/z=241.1 (M+1).

Example 174

2-Chloro-4-fluoro-N-[3-fluoro-5-(1-methyl-piperidin-4-ylsulfanyl)-phenyl]-benzamide

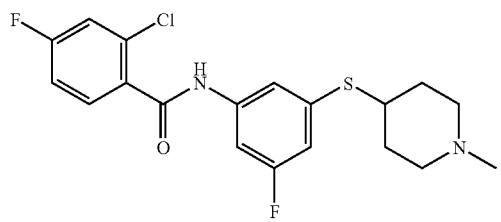

Combine 3-fluoro-5-(1-methyl-piperidin-4-ylsulfanyl)-phenylamine (preparation 114, 0.11 g, 0.46 mmol), 1,4-dioxane (5 mL) and 2-chloro-4-fluoro-benzoyl chloride (0.09 g, 0.46 mmole), stir and heat at reflux. After 3 hr., cool to ambient temperature. Load on an SCX column (10 g), wash with methanol, elute with 2M ammonia/methanol. Concentrate eluent. Purify residue by silica gel flash chromatography eluting with 10% (2M $NH_3$/methanol)/methylene dichloride to obtain the title compound (0.03 g, 17%). Mass spectrum: Obs. m/z 397.0974; calc. m/z 397.0953; $^1$H NMR (CDCl$_3$) free base: 7.9 (bs, 1H), 7.8 (m, 1H), 7.4 (m, 1H), 7.3 (s, 1H), 7.2 (m, 1H), 7.1 (m, 1H), 6.9 (m, 1H), 3.2 (m, 1H), 2.8 (m, 2H), 2.3 (s, 3H), 2.0 (m, 4H), 1.7 (m, 2H).

Examples Using Combinatorial Chemistry

The following examples are synthesized using combinatorial chemistry techniques. The reagents, reaction conditions, and product characterizations are as described below. Recombinant chemistry compounds are characterized by liquid chromatography/mass spectroscopy on a Shimadzu QP8000™. Examples R1-R15, R25-R38, and R55-R65 are run with a Metachem™ C18 column (monochrom 5 micron, 4.6×50 cm) using a 10-80% solvent B gradient in 9 min., where solvent A is 0.1% trifluoroacetic acid in water and solvent B is 0.08% trifluoroacetic acid in acetonitrile. Examples R16-R24 and R39-R54 are run with a Metachem™ C18 column (monochrom 3 micron, 2.5×25 cm) using a 10-90% solvent B gradient in 4.5 min., where solvent A is 0.1% trifluoroacetic acid in water and solvent B is 0.1% trifluoroacetic acid in acetonitrile.

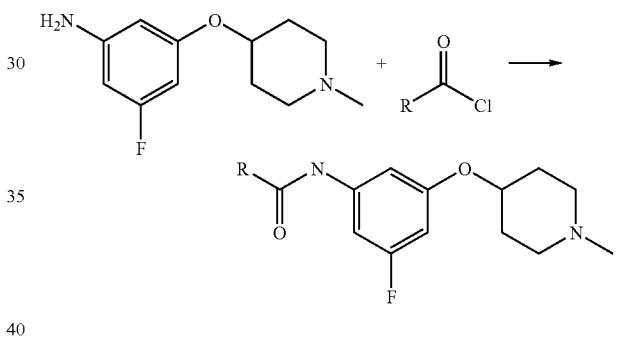

Heat 3-Fluoro-5-(1-methyl-piperidin-4-yloxy)-phenylamine (200 µL of 0.5 M solution in dioxane) and R-acid chloride (0.10 mmol) to 90° C. After 2 hr., dilute the reaction mixture with 10% acetic acid/methanol (0.5 mL). Apply the resulting solution directly to a 2 g SCX column. Thoroughly wash the column with methanol, elute with 1 M ammonia-methanol, concentrate the eluant, and purify by high-throughput mass guided chromatography. The procedure is repeated in parallel for products R1-R9.

| Ex. | Acid Chloride | Product | Product Name | Data |
|---|---|---|---|---|
| R1 | ![acid chloride structure with 2,6-difluoro benzoyl chloride] | ![product structure] | 2,6-Difluoro-N-[3-fluoro-5-(1-methyl-piperidin-4-yloxy)-phenyl]-benzamide | LCMS Rf 3.2 min at 254 nm, m/e 365 (M + 1) |

-continued

| Ex. | Acid Chloride | Product | Product Name | Data |
|---|---|---|---|---|
| R2 | 3-chloro-2-thiophenecarbonyl chloride | | N-[3-fluoro-5-(1-methylpiperidin-4-yloxy)phenyl]-3-chloro-2-thiophenecarboxamide | LCMS Rf 1.75 min at 254 nm, m/e 369 (M + 1). |
| R3 | 2,4,6-trifluorobenzoyl chloride | | 2,4,6-Trifluoro-N-[3-fluoro-5-(1-methyl-piperidin-4-yloxy)-phenyl]-benzamide | LCMS Rf 3.30 min at 254 nm, m/e 383 (M + 1). |
| R4 | cyclobutanecarbonyl chloride | | N-[3-fluoro-5-(1-methyl-piperidin-4-yloxy)-phenyl]-Cyclobutane-carboxamide | LCMS Rf 3.08 min at 254 nm, m/e 307 (M + 1). |
| R5 | 3,4-difluorobenzoyl chloride | | 3,4-Difluoro-N-[3-fluoro-5-(1-methyl-piperidin-4-yloxy)-phenyl]-benzamide | LCMS Rf 3.58 min at 254 nm, m/e 365 (M + 1). |
| R6 | 2-bromobenzoyl chloride | | 2-Bromo-N-[3-fluoro-5-(1-methyl-piperidin-4-yloxy)-phenyl]-benzamide | LCMS Rf 3.39 min at 254 nm, m/e 408 (M + 1). |
| R7 | isonicotinoyl chloride | | N-[3-Fluoro-5-(1-methyl-piperidin-4-yloxy)-phenyl]-isonicotinamide | LCMS Rf 2.55 min at 254 nm, m/e 330 (M + 1). |
| R8 | 2,4-dichlorobenzoyl chloride | | 2,4-Dichloro-N-[3-fluoro-5-(1-methyl-piperidin-4-yloxy)-phenyl]-benzamide | LCMS Rf 3.73 min at 254 nm, m/e 398 (M + 1). |

-continued

| Ex. | Acid Chloride | Product | Product Name | Data |
|---|---|---|---|---|
| R9 | | | 2-Chloro-6-fluoro-N-[3-fluoro-5-(1-methyl-piperidin-4-yloxy)-phenyl]-benzamide | LCMS Rf 3.49 min at 254 nm, m/e 381 (M + 1). |

Examples R10-R14

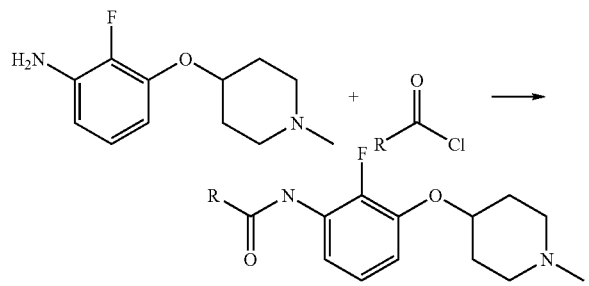

Heat 2-fluoro-3-(1-methyl-piperidin-4-yloxy)-phenylamine (200 μL of 0.5M solution in dioxane) and R-acid chloride (0.10 mmol) to 90° C. After 2 hr., dilute the reaction mixture with 10% acetic acid/methanol (0.5 mL). Directly apply the resulting solution to a 2 g SCX column. Thoroughly wash the column with methanol, elute with 1 M ammonia-methanol, concentrate the eluant, and further purify by high-throughput mass guided chromatography. The procedure is repeated in parallel for products R10-R14

| Ex. | Acid Chloride | Product | Product Name | Data |
|---|---|---|---|---|
| R10 | | | 2,6-Difluoro-N-[2-fluoro-3-(1-methyl-piperidin-4-yloxy)-phenyl]-benzamide | LCMS Rf 2.64 min at 254 nm, m/e 365 (M + 1). |
| R11 | | | 2,4,6-Trifluoro-N-[2-fluoro-3-(1-methyl-piperidin-4-yloxy)-phenyl]-benzamide | LCMS Rf 2.70 min at 254 nm, m/e 383 (M + 1). |
| R12 | | | 3,4-Difluoro-N-[2-fluoro-3-(1-methyl-piperidin-4-yloxy)-phenyl]-benzamide | LCMS Rf 2.81 min at 254 nm, m/e 365 (M + 1). |

-continued

| Ex. | Acid Chloride | Product | Product Name | Data |
|---|---|---|---|---|
| R13 | | | 2,4-Dichloro-N-[2-fluoro-3-(1-methyl-piperidin-4-yloxy)-phenyl]-benzamide | LCMS Rf 3.07 min at 254 nm, m/e 397 (M + 1). |
| R14 | | | 2-Chloro-6-fluoro-N-[2-fluoro-3-(1-methyl-piperidin-4-yloxy)-phenyl]-benzamide | LCMS Rf 2.78 min at 254 nm, m/e 381 (M + 1). |

Example R15

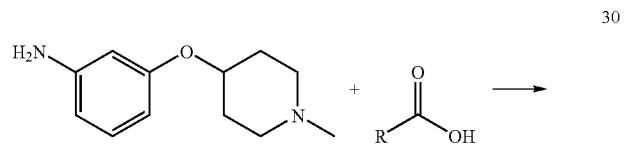

Example R16-R24

Combine R-carboxylic acid (300 μL of 0.5M solution in DMF), HATU (57 mg, 0.15 mmol), collidine (19 μL, 0.15 mmol), 3-(1-methyl-piperidin-4-yloxy)-phenylamine and DMF (1.5 mL), and stir for 48 hr. Dilute the reaction mixture with 10% acetic acid/methanol (0.5 mL) and directly apply the resulting solution to a 2 g SCX column. Thoroughly wash the column with methanol, elute the column with 1 M ammonia-methanol, concentrate the eluant, and further purify by high-throughput mass guided chromatography.

Heat 6-(1-methyl-piperidin-4-yloxy)-pyridin-2-ylamine (200 μL of 0.5M solution in pyridine) to 55° C., add R-acid chloride (0.10 mmol) and heat to 90° C. After 2 hr., concentrate the reaction mixture, dilute with 10% acetic acid/methanol (0.5 mL) and methanol (0.5 mL). Directly apply the resulting solution to a 2 g SCX column. Wash thoroughly with methanol, elute the column with 1 M ammonia-methanol, concentrate the eluant, and further purify by high-throughput mass guided chromatography. The procedure is repeated in parallel for products R16-R24.

| R15 | Acid Chloride | Product | Product Name | Data |
|---|---|---|---|---|
| R15 | |  | N-[3-(1-methyl-piperidin-4-yloxy)-phenyl]-2-thiophenecarboxamide | LCMS Rf 2.69 min at 254 nm, m/e 317 (M + 1). |

| Ex. | Acid Chloride | Product | Product Name | Data |
|---|---|---|---|---|
| R16 | 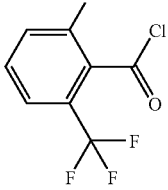 | 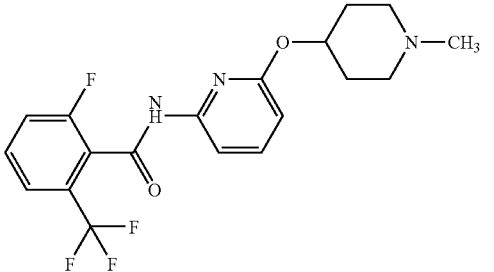 | 2-Fluoro-N-[6-(1-methyl-piperidin-4-yloxy)-pyridin-2-yl]-6-trifluoromethyl-benzamide | LCMS Rf 1.21 min at 254 nm; m/e 398 |
| R17 | 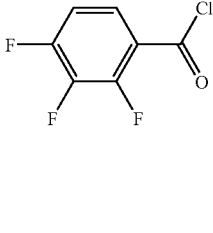 | 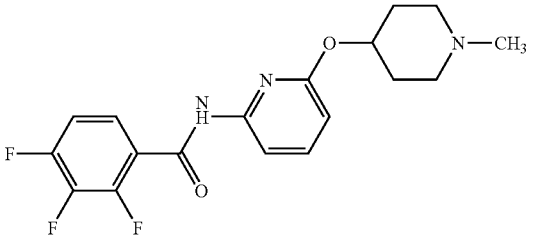 | 2,3,4-Trifluoro-N-[6-(1-methyl-piperidin-4-yloxy)-pyridin-2-yl]-benzamide | LCMS Rf 1.62 min at 254 nm, m/e 398 (M + 1). |
| R18 | 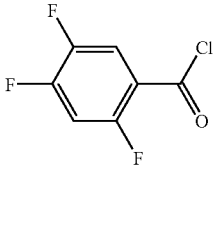 | 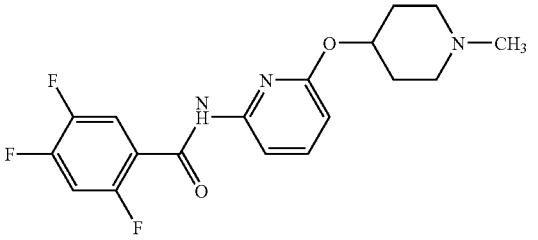 | 2,4,5-Trifluoro-N-[6-(1-methyl-piperidin-4-yloxy)-pyridin-2-yl]-benzamide | LCMS Rf 1.59 min at 254 nm, m/e 366 (M + 1). |
| R19 | 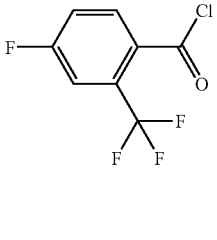 | 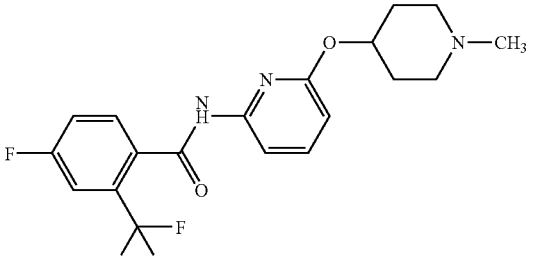 | 4-Fluoro-N-[6-(1-methyl-piperidin-4-yloxy)-pyridin-2-yl]-2-trifluoromethyl-benzamide | LCMS Rf 1.59 min at 254 nm, m/e 398 (M + 1). |
| R20 | 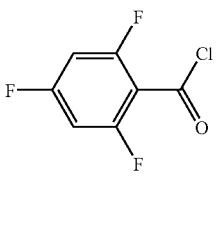 | 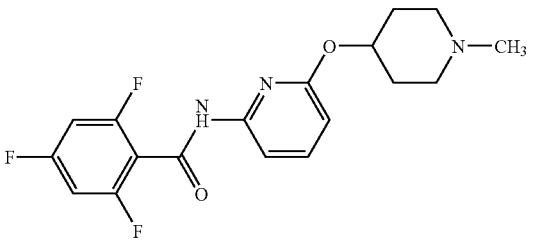 | 2,4,6-Trifluoro-N-[6-(1-methyl-piperidin-4-yloxy)-pyridin-2-yl]-benzamide | LCMS Rf 1.56 min at 254 nm, m/e 366 (M + 1). |
| R21 | 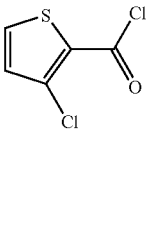 | 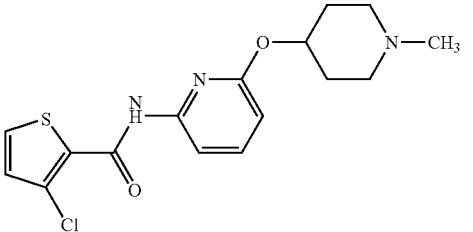 | N-[6-(1-methyl-piperidin-4-yloxy)-pyridin-2-yl]-3-Chloro-2-thiophenecarboxamide | LCMS Rf 1.57 min at 254 nm, m/e 351 (M + 1). |

| Ex. | Acid Chloride | Product | Product Name | Data |
|---|---|---|---|---|
| R22 | | | 2-Chloro-N-[6-(1-methyl-piperidin-4-yloxy)-pyridin-2-yl]-benzamide | LCMS Rf 1.49 min at 254 nm, m/e 346 (M + 1). |
| R23 | | | 2,5-Difluoro-N-[6-(1-methyl-piperidin-4-yloxy)-pyridin-2-yl]-benzamide | LCMS Rf 1.57 min at 254 nm, m/e 348 (M + 1). |
| R24 | | | 2-Fluoro-N-[6-(1-methyl-piperidin-4-yloxy)-pyridin-2-yl]-4-trifluoromethyl-benzamide | LCMS Rf 1.72 min at 254 nm, m/e 398 (M + 1). |

Example R25-R29

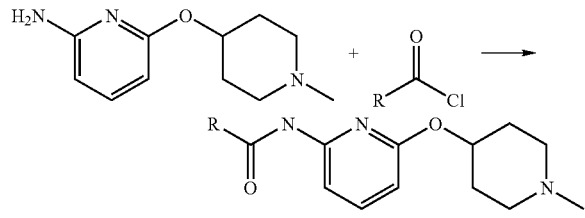

Heat 6-(1-methyl-piperidin-4-yloxy)-pyridin-2-ylamine (200 μL of 0.5M solution in pyridine) to 55° C., add R-acid chloride (0.10 mmol), and heat to 90° C. After 2 hr., concentrate the reaction mixture, dilute with 10% acetic acid/methanol (0.5 mL) and methanol (0.5 mL). Directly apply the resulting solution to a 2 g SCX column. Thoroughly wash the column with methanol, elute with 1 M ammonia-methanol, concentrate the eluant, and further purify by high-throughput mass guided chromatography. The procedure is repeated in parallel for products R25-R29.

| No.: | Acid Chloride | Product | Product Name | Data |
|---|---|---|---|---|
| R25 | | | 2,6-Difluoro-N-[6-(1-methyl-piperidin-4-yloxy)-pyridin-2-yl]-benzamide | LCMS Rf 3.29 min at 254 nm, m/e 348 (M + 1). |

| No.: | Acid Chloride | Product | Product Name | Data |
|---|---|---|---|---|
| R26 | | | N-[6-(1-methyl-piperidin-4-yloxy)-pyridin-2-yl]-cyclopentane-carboxamide | LCMS Rf 2.87 min at 254 nm, m/e 304 (M + 1). |
| R27 | | | 2-Bromo-N-[6-(1-methyl-piperidin-4-yloxy)-pyridin-2-yl]-benzamide | LCMS Rf 3.22 min at 254 nm, m/e 391 (M + 1). |
| R28 | | | N-[6-(1-Methyl-piperidin-4-yloxy)-pyridin-2-yl]-2-trifluoromethoxy-benzamide | LCMS Rf 3.54 min at 254 nm, m/e 396 (M + 1). |
| R29 | | | 2-Chloro-6-fluoro-N-[6-(1-methyl-piperidin-4-yloxy)-pyridin-2-yl]-benzamide | LCMS Rf min at 254 nm, m/e 364 (M + 1). |

Example R30-R38

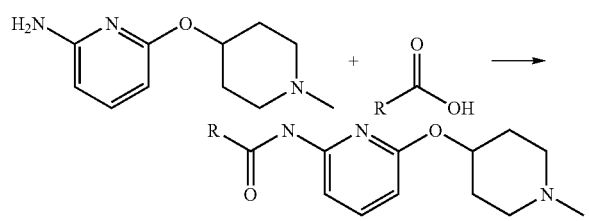

Combine R-acid (300 µL of 0.5M solution in DMF), HATU (57 mg, 0.15 mmol), collidine (19 µL, 0.15 mmol), 6-(1-methyl-piperidin-4-yloxy)-pyridin-2-ylamine and DMF (1.5 mL) and stir. After 48 hr., dilute the reaction mixture with 10% acetic acid/methanol (0.5 mL) and directly apply the resulting solution to a 2 g SCX column. Thoroughly wash the column with methanol, elute with 1 M ammonia-methanol, concentrate the eluant, and further purify by high-throughput mass guided chromatography. The procedure is repeated in parallel for products R30-R38.

| Ex. | Carboxylic Acid | Product | Product Name | Data |
|---|---|---|---|---|
| R30 | | | N-[6-(1-methyl-piperidin-4-yloxy)-pyridin-2-yl]-5-fluoro-2-pyridinecarboxamide | LCMS Rf 2.91 min at 254 nm, m/e 331 (M + 1). |

| Ex. | Carboxylic Acid | Product | Product Name | Data |
|---|---|---|---|---|
| R31 | | | 2-Chloro-4-cyano-N-[6-(1-methyl-piperidin-4-yloxy)-pyridin-2-yl]-benzamide | LCMS Rf 2.98 min at 254 nm, m/e 371 (M + 1). |
| R32 | | | 2-Fluoro-N-[6-(1-methyl-piperidin-4-yloxy)-pyridin-2-yl]-4-nitro-benzamide | LCMS Rf 3.09 min at 254 nm, m/e 374 (M + 1). |
| R33 | | | N-[6-(1-methyl-piperidin-4-yloxy)-pyridin-2-yl]-5-Bromo-2-thiophenecarboxamide | LCMS Rf 3.4 min at 254 nm, m/e 397 (M + 1). |
| R34 | | | N-[6-(1-methyl-piperidin-4-yloxy)-pyridin-2-yl]-5-nitro-2-thiophenecarboxamide | LCMS Rf 3.19 min at 254 nm, m/e 362 (M + 1). |
| R35 | | | 2-Bromo-4-fluoro-N-[6-(1-methyl-piperidin-4-yloxy)-pyridin-2-yl]-benzamide | LCMS Rf 3.04 min at 254 nm, m/e 409 (M + 1). |

| Ex. | Carboxylic Acid | Product | Product Name | Data |
|---|---|---|---|---|
| R36 | thiophene-2-carboxylic acid | N-[6-(1-methyl-piperidin-4-yloxy)-pyridin-2-yl]-thiophene-2-carboxamide structure | N-[6-(1-methyl-piperidin-4-yloxy)-pyridin-2-yl]-2-thiophenecarboxamide | LCMS Rf 2.79 min at 254 nm, m/e 318 (M + 1). |
| R37 | 4-chloro-2-fluorobenzoic acid | 4-Chloro-2-fluoro-N-[6-(1-methyl-piperidin-4-yloxy)-pyridin-2-yl]-benzamide structure | 4-Chloro-2-fluoro-N-[6-(1-methyl-piperidin-4-yloxy)-pyridin-2-yl]-benzamide | LCMS Rf 3.23 min at 254 nm, m/e 364 (M + 1). |
| R38 | 3-bromo-4-fluorobenzoic acid | 3-Bromo-4-fluoro-N-[6-(1-methyl-piperidin-4-yloxy)-pyridin-2-yl]-benzamide structure | 3-Bromo-4-fluoro-N-[6-(1-methyl-piperidin-4-yloxy)-pyridin-2-yl]-benzamide | LCMS Rf 3.39 min at 254 nm, m/e 409 (M + 1). |

Example R39-R54

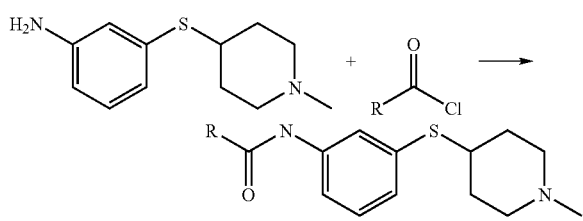

Heat 3-(1-methyl-piperidin-4-ylsulfanyl)-phenylamine (200 µL of 0.5M solution in dioxane) and R-acid chloride (0.10 mmol) to 95° C. After 2 hr., dilute the reaction mixture with 10% acetic acid/methanol (0.5 mL). Directly apply the resulting solution to a 2 g SCX column. Thoroughly wash with methanol, elute the column with 1 M ammonia-methanol, concentrate the eluant, and further purify by high-throughput mass guided chromatography. The procedure is repeated in parallel for products R39-R54.

| Ex. | Acid Chloride | Product | Product Name | Data |
|---|---|---|---|---|
| R39 | 3-chloro-thiophene-2-carbonyl chloride | N-[3-(1-methyl-piperidin-4-ylsulfanyl)-phenyl]-3-chloro-2-thiophenecarboxamide structure | N-[3-(1-methyl-piperidin-4-ylsulfanyl)-phenyl]-3-chloro-2-thiophenecarboxamide | LCMS Rf 1.49 min at 254 nm, m/e 366.1 (M + 1). |

-continued

| Ex. | Acid Chloride | Product | Product Name | Data |
|---|---|---|---|---|
| R40 | | | 2,4-Difluoro-N-[3-(1-methyl-piperidin-4-ylsulfanyl)-phenyl]-benzamide | LCMS Rf 1.53 min at 254 nm, m/e 362.1 (M + 1). |
| R41 | | | 4-Fluoro-N-[3-(1-methyl-piperidin-4-ylsulfanyl)-phenyl]-2-trifluoromethyl-benzamide | LCMS Rf 1.6 min at 254 nm, m/e 412.1 (M + 1). |
| R42 | | | 2,4,6-Trifluoro-N-[3-(1-methyl-piperidin-4-ylsulfanyl)-phenyl]-benzamide | LCMS Rf 1.46 min at 254 nm, m/e 380.1 (M + 1). |
| R43 | | | N-[3-(1-methyl-piperidin-4-ylsulfanyl)-phenyl]-cyclobutane-carboxamide | LCMS Rf 1.34 min at 254 nm, m/e 304.2 (M + 1). |
| R44 | | | 2-Chloro-N-[3-(1-methyl-piperidin-4-ylsulfanyl)-phenyl]-benzamide | LCMS Rf 1.44 min at 254 nm, m/e 360.1 (M + 1). |
| R45 | | | N-[3-(1-methyl-piperidin-4-ylsulfanyl)-phenyl]-cyclopentane-carboxamide | LCMS Rf 1.48 min at 254 nm, m/e 318.2 (M + 1). |
| R46 | | | Cyclohexanecarboxylic acid [3-(1-methyl-piperidin-4-ylsulfanyl)-phenyl]-amide | LCMS Rf 1.47 min at 254 nm, m/e 332.2 (M + 1). |
| R47 | | | 3,4-Difluoro-N-[3-(1-methyl-piperidin-4-ylsulfanyl)-phenyl]-benzamide | LCMS Rf 1.56 min at 254 nm, m/e 362.1 (M + 1). |

-continued

| Ex. | Acid Chloride | Product | Product Name | Data |
|---|---|---|---|---|
| R48 | 2,3,4-trifluorobenzoyl chloride | 2,3,4-trifluoro-N-[3-(1-methyl-piperidin-4-ylsulfanyl)-phenyl]-benzamide | 2,3,4-Trifluoro-N-[3-(1-methyl-piperidin-4-ylsulfanyl)-phenyl]-benzamide | LCMS Rf 1.57 min at 254 nm, m/e 380.1 (M + 1). |
| R49 | 2-bromobenzoyl chloride | 2-bromo-N-[3-(1-methyl-piperidin-4-ylsulfanyl)-phenyl]-benzamide | 2-Bromo-N-[3-(1-methyl-piperidin-4-ylsulfanyl)-phenyl]-benzamide | LCMS Rf 1.45 min at 254 nm, m/e 406.1 (M + 1). |
| R50 | nicotinoyl chloride | N-[3-(1-methyl-piperidin-4-ylsulfanyl)-phenyl]-nicotinamide | N-[3-(1-Methyl-piperidin-4-ylsulfanyl)-phenyl]-nicotinamide | LCMS Rf 1.09 min at 254 nm, m/e 327.1 (M + 1). |
| R51 | isonicotinoyl chloride | N-[3-(1-methyl-piperidin-4-ylsulfanyl)-phenyl]-isonicotinamide | N-[3-(1-Methyl-piperidin-4-ylsulfanyl)-phenyl]-isonicotinamide | LCMS Rf 1.09 min at 254 nm, m/e 327.1 (M + 1). |
| R52 | 2-trifluoromethoxybenzoyl chloride | N-[3-(1-methyl-piperidin-4-ylsulfanyl)-phenyl]-2-trifluoromethoxy-benzamide | N-[3-(1-Methyl-piperidin-4-ylsulfanyl)-phenyl]-2-trifluoromethoxy-benzamide | LCMS Rf 1.58 min at 254 nm, m/e 394.1 (M + 1). |
| R53 | 2-chloro-6-fluorobenzoyl chloride | 2-chloro-6-fluoro-N-[3-(1-methyl-piperidin-4-ylsulfanyl)-phenyl]-benzamide | 2-Chloro-6-fluoro-N-[3-(1-methyl-piperidin-4-ylsulfanyl)-phenyl]-benzamide | LCMS Rf 1.44 min at 254 nm, m/e 378.1 (M + 1). |
| R54 | 2,6-dichlorobenzoyl chloride | 2,6-dichloro-N-[3-(1-methyl-piperidin-4-ylsulfanyl)-phenyl]-benzamide | 2,6-Dichloro-N-[3-(1-methyl-piperidin-4-ylsulfanyl)-phenyl]-benzamide | LCMS Rf 1.54 min at 254 nm, m/e 394.1 (M + 1). |

Example R55-R65

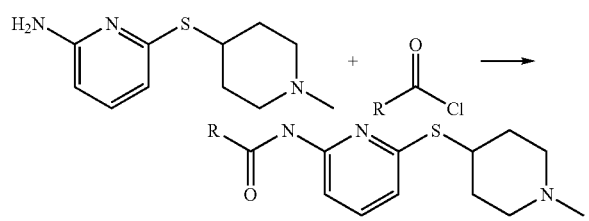

Heat 6-(1-methyl-piperidin-4-ylsulfanyl)-pyridin-2-ylamine (200 μL of 0.5M solution in dioxane) and R-acid chloride (0.10 mmol) to 95° C. After 2 hr. dilute, the reaction mixture with 10% acetic acid/methanol (0.5 mL). Directly apply the resulting solution to a 2 g SCX column. Thoroughly wash the column with methanol, elute with 1 M ammonia-methanol, concentrate the eluant, and further purify by high-throughput mass guided chromatography. The procedure is repeated in parallel for products R55-R65.

| Ex. | Acid Chloride | Product | Product Name | Data |
|---|---|---|---|---|
| R55 | 2,4-Difluorophenyl | | 2,4-Difluoro-N-[2-(1-methyl-piperidin-4-ylsulfanyl)-pyridin-5-yl]-benzamide | LCMS Rf 1.68 min at 254 nm, m/e 363.1 (M + 1). |
| R56 | 4-Fluoro-2-trifluoromethyl-phenyl | | 4-Fluoro-2-trifluoromethyl-N-[2-(1-methyl-piperidin-4-ylsulfanyl)-pyridin-5-yl]-benzamide | LCMS Rf 1.7 min at 254 nm, m/e 413.1 (M + 1). |
| R57 | 2-Chlorophenyl | | 2-Chloro-N-[2-(1-methyl-piperidin-4-ylsulfanyl)-pyridin-5-yl]-benzamide | LCMS Rf 1.68 min at 254 nm, m/e 361.1 (M + 1). |
| R58 | Cyclopentyl | | N-[2-(1-methyl-piperidin-4-ylsulfanyl)-pyridin-5-yl]-cyclopentamide | LCMS Rf 1.63 min at 254 nm, m/e 319.2 (M + 1). |
| R59 | Cyclohexyl | | N-[2-(1-methyl-piperidin-4-ylsulfanyl)-pyridin-5-yl]-cyclohexamide | LCMS Rf 1.63 min at 254 nm, m/e 333.2 (M + 1). |
| R60 | 2-Bromophenyl | | 2-Bromo-N-[2-(1-methyl-piperidin-4-ylsulfanyl)-pyridin-5-yl]-benzamide | LCMS Rf 1.58 min at 254 nm, m/e 407 (M + 1). |
| R61 | 3-Chloro-thiophene-2-yl | | 3-Chloro-N-[2-(1-methyl-piperidin-4-ylsulfanyl)-pyridin-5-yl]-2-thiophene-carboxamide | LCMS Rf 1.70 min at 254 nm, m/e 367.1 (M + 1). |

-continued

| Ex. | Acid Chloride | Product | Product Name | Data |
|---|---|---|---|---|
| R62 | Cyclobutyl | | N-[2-(1-methyl-piperidin-4-ylsulfanyl)-pyridin-5-yl]-cyclobutamide | LCMS Rf 1.45 min at 254 nm, m/e 305.2 (M + 1). |
| R63 | 3,4-Difluorophenyl | | 3,4-Difluoro-N-[2-(1-methyl-piperidin-4-ylsulfanyl)-pyridin-5-yl]-benzamide | LCMS Rf 1.64 min at 254 nm, m/e 363.1 (M + 1). |
| R64 | 2,3,4-Trifluorophenyl | | 2,3,4-Trifluoro-N-[2-(1-methyl-piperidin-4-ylsulfanyl)-pyridin-5-yl]-benzamide | LCMS Rf 1.67 min at 254 nm, m/e 381.1 (M + 1). |
| R65 | 2,4-Dichlorophenyl | | 2,4-Dichloro-N-[2-(1-methyl-piperidin-4-ylsulfanyl)-pyridin-5-yl]-benzamide | LCMS Rf 1.81 min at 254 nm, m/e 395.1 (M + 1). |

The compounds of this invention are useful for increasing activation of the 5-HT$_{1F}$ receptor. An increase in the activation of the 5-HT$_{1F}$ is useful for treating a variety of disorders which have been linked to decreased neurotransmission of serotonin in mammals, e.g., migraine headaches. See U.S. Pat. No. 5,708,008 demonstrating the nexus between activation of the 5-HT$_{1F}$ receptor and migraine. To demonstrate the use of the compounds of the present invention in the treatment of migraine, their ability to bind to the 5-HT$_{1F}$ receptor subtype was determined. The ability of the compounds of this invention to bind to the 5-HT$_{1F}$ receptor subtype was measured essentially as described in N. Adbam, et al., *Proceedings of the National Academy of Sciences (USA)*, 90:408-412, 1993.

Membrane Preparation:

Membranes were prepared from transfected Ltk-cells (transfected with the human 5-HT$_{1F}$ receptor sequence) which were grown to 100% confluency. The cells were washed twice with phosphate-buffered saline, scraped from the culture dishes into 5 mL of ice-cold phosphate-buffered saline, and centrifuged at 200×g for 5 minutes at 4° C. The pellet was resuspended in 2.5 mL of ice-cold Tris buffer (20 mM Tris HCl, pH 7.4 at 23° C., 5 mM EDTA) and homogenized with a Wheaton tissue grinder. The lysate was subsequently centrifuged at 200×g for 5 minutes at 4° C. to pellet large fragments which were discarded. The supernatant was collected and centrifuged at 40,000×g for 20 minutes at 4° C. The resulting pellet was washed once in ice-cold Tris wash buffer and resuspended in a final buffer containing 50 mM Tris HCl and 0.5 mM EDTA, pH 7.4 at 23° C. Membrane preparations were kept on ice and utilized within two hours for the radioligand binding assays. Protein concentrations were determined by the method of Bradford. *Anal. Biochem.*, 72:248-254, 1976.

Radioligand Binding:

[$^3$H] 5-HT binding was performed using slight modifications of the 5-HT$_{1D}$ assay conditions reported by Herrick-Davis and Titeler (*J. Neurochem.*, 50:1624-1631, 1988) with the omission of masking ligands. Radioligand binding studies were achieved at 37° C. in a total volume of 250 μL of buffer (50 mM Tris, 10 mM MgCl$_2$, 0.2 mM EDTA, 10 μM pargyline, 0.1% ascorbate, pH 7.4 at 37° C.) in 96 well microtiter plates. Saturation studies were conducted using [$^3$H] 5-HT at 12 different concentrations ranging from 0.5 nM to 100 nM. Displacement studies were performed using 4.5-5.5 nM [$^3$H] 5-HT. The binding profile of drugs in competition experiments was accomplished using 6-12 concentrations of compound. Incubation times were 30 minutes for both saturation and displacement studies based upon initial investigations which determined equilibrium binding conditions. Nonspecific binding was defined in the presence of 10 μM 5-HT. Binding was initiated by the addition of 50 μL membrane homogenates (10-20 μg). The reaction was terminated by rapid filtration through presoaked (0.5% polyethyleneimine) filters using 48R Brandel Cell Harvester (Gaithersburg, Md.). Subsequently, filters were washed for 5 seconds with ice cold buffer (50 mM Tris HCl, pH=7.4 at 4° C.), dried and placed into vials containing 2.5 mL Readi-Safe (Beckman, Fullerton, Calif.) and radioactivity was measured using a Beckman LS 5000TA liquid scintillation counter. The efficiency of counting of [$^3$H] 5-HT averaged between 45-50%. Binding data was analyzed by computer-assisted nonlinear regression analysis (Accufit and Accucomp, Lunden Software, Chagrin Falls, Ohio). IC$_{50}$ values were converted to K$_i$ values using the Cheng-Prusoff equation. *Biochem. Pharmacol.*, 22:3099-3108 (1973). All experiments were performed in triplicate. Representative compounds of the present invention were found to have high affinity for the 5-$HT_{1F}$ receptor as measured by the procedure described above, as for example $K_i$'s of less than or equal to about 300 nM. Preferred compounds of the present invention have $K_i$'s of less than or equal to about 100 nM. Yet more preferred compounds have a $K_i$ of less than or equal to 50 nM. The exemplified compounds had Ki's of less than or equal 150 nM.

Measurement of cAMP Formation

As was reported by R. L. Weinshank, et al., WO93/14201, the 5-$HT_{1F}$ receptor is functionally coupled to a G-protein as measured by the ability of serotonin and serotonergic drugs to inhibit forskolin stimulated cAMP production in NIH3T3 cells transfected with the 5-$HT_{1F}$ receptor. Adenylate cyclase activity was determined using standard techniques. A maximal effect is achieved by serotonin. An $E_{max}$ is determined by dividing the inhibition of a test compound by the maximal effect and determining a percent inhibition. N. Adham, et al., supra; R. L. Weinshank, et al., *Proceedings of the National Academy of Sciences (USA)*, 89:3630-3634, 1992; and the references cited therein.

Human 5-$HT_{1F}$ receptor transfected NIH3T3 cells (estimated $B_{max}$ from one point competition studies=488 fmol/mg of protein) were incubated in DMEM, 5 mM theophylline, 10 mM HEPES (4-[2-hydroxyethyl]-1-piperazineethanesulfonic acid) and 10 µM pargyline for 20 minutes at 37° C., 5% $CO_2$. Drug dose-effect curves were then conducted by adding 6 different final concentrations of drug, followed immediately by the addition of forskolin (10 µM). Subsequently, the cells were incubated for an additional 10 minutes at 37° C., 5% $CO_2$. The medium was aspirated and the reaction was stopped by the addition of 100 mM HCl. To demonstrate competitive antagonism, a dose-response curve for 5-HT was measured in parallel, using a fixed dose of methiothepin (0.32 µM). The plates were stored at 4° C. for 15 minutes and then centrifuged for 5 minutes at 500×g to pellet cellular debris, and the supernatant was aliquoted and stored at −20° C. before assessment of cAMP formation by radioimmunoassay (cAMP radioimmunoassay kit; Advanced Magnetics, Cambridge, Mass.). Radioactivity was quantified using a Packard COBRA Auto Gamma counter, equipped with data reduction software. Representative compounds of the present invention were tested and found to be agonists of the 5-$HT_{1F}$ receptor in the cAMP assay described above.

Protein Extravasation Assay

The following test was performed to determine the ability of compounds of the present invention to inhibit protein extravasation, which test is also a functional assay for, the neuronal mechanism of migraine.

Harlan Sprague-Dawley rats (225-325 g) or guinea pigs from Charles River Laboratories (225-325 g) were anesthetized with sodium pentobarbital intraperitoneally (65 mg/kg or 45 mg/kg respectively) and placed in a stereotaxic frame (David Kopf Instruments) with the incisor bar set at −3.5 mm for rats or −4.0 mm for guinea pigs. Following a midline sagital scalp incision, two pairs of bilateral holes were drilled through the skull (6 mm posteriorly, 2.0 and 4.0 mm laterally in rats; 4 mm posteriorly and 3.2 and 5.2 mm laterally in guinea pigs, all coordinates referenced to bregma). Pairs of stainless steel stimulating electrodes, insulated except at the ends (Rhodes Medical Systems, Inc.), were lowered through the holes in both hemispheres to a depth of 9 mm (rats) or 10.5 mm (guinea pigs) from dura.

The femoral vein was exposed and a dose of the test compound was injected intravenously (1 mL/kg). Approximately 7 minutes later, a 50 mg/kg dose of Evans Blue, a fluorescent dye, was also injected intravenously. The Evans Blue complexed with proteins in the blood and functioned as a marker for protein extravasation. Exactly 10 minutes post-injection of the test compound, the left trigeminal ganglion was stimulated for 3 minutes at a current intensity of 1.0 mA (5 Hz, 4 msec duration) with a Model 273 potentiostat/galvanostat (EG&G Princeton Applied Research).

Fifteen minutes following stimulation, the animals were killed and exsanguinated with 20 mL of saline. The top of the skull was removed to facilitate the collection of the dural membranes. The membrane samples were removed from both hemispheres, rinsed with water, and spread flat on microscopic slides. Once dried, the tissues were coverslipped with a 70% glycerol/water solution.

A fluorescence microscope (Zeiss) equipped with a grating monochromator and a spectrophotometer was used to quantify the amount of Evans Blue dye in each sample. An excitation wavelength of approximately 535 nm was utilized and the emission intensity at 600 nm was determined. The microscope was equipped with a motorized stage and also interfaced with a personal computer. This facilitated the computer-controlled movement of the stage with fluorescence measurements at 25 points (500 µm steps) on each dural sample. The mean and standard deviation of the measurements were determined by the computer.

The extravasation induced by the electrical stimulation of the trigeminal ganglion was an ipsilateral effect (i.e. occurs only on the side of the dura in which the trigeminal ganglion was stimulated). This allows the other (unstimulated) half of the dura to be used as a control. The ratio of the amount of extravasation in the dura from the stimulated side compared to the unstimulated side was calculated. Saline controls yielded a ratio of approximately 2.0 in rats and 1.8 in guinea pigs. In contrast, a compound which effectively prevented the extravasation in the dura from the stimulated side would have a ratio of approximately 1.0. A dose-response curve was generated and the dose that inhibited the extravasation by 50% ($ID_{50}$) was approximated. Representative compounds of the present invention were assayed by the above procedure and were found to significantly inhibit neuronal protein extravasation Compounds of the present invention were efficacious in the neurogenic plasma protein extravasation migraine model.

Rabbit Saphenous Vein Contraction

Representative compounds of the present invention were tested in a rabbit saphenous vein contraction assay to measure their ability to mediate vasoconstriction.

Male New Zealand White rabbits (3-6 lbs) (Hazleton, Kalamazoo, Mich.) were sacrificed by a lethal dose of sodium pentobarbital (325 mg) injected into the ear vein. Tissues were dissected free of connective tissue, cannulated in situ with polyethylene tubing (PE50, outside diameter=0.97 mm) and placed in petri dishes containing modified Kreb's solution (described infra). The tips of two 30-gauge stainless steel hypodermic needles bent into an L-shape were slipped into the polyethylene tubing. Vessels were gently pushed from the cannula onto the needles. The needles were then separated so that the lower one was attached with thread to a stationary glass rod and the upper one was tied with thread to the transducer.

Tissues were mounted in organ baths containing 10 mL of modified Krebs' solution of the following composition: 118.2 mMol NaCl, 4.6 mMol KCl, 1.6 mMol $CaCl_2.H_2O$, 1.2 mMol $KH_2PO_4$, 1.2 mMol $MgSO_4$, 10.0 mMol dextrose and 24.8 mMol $NaHCO_3$. Tissue bath solutions were maintained at 37° C. and aerated with 95% $O_2$ and 5% $CO_2$. An initial optimum resting force of 1 gm was applied to the saphenous vein. Isometric contractions were recorded as changes in grams of force on a Beckman Dynograph with Statham UC-3 transducers and microscale accessory attachments. Tissues were allowed to equilibrate 1 to 2 hours before exposure to drugs. Cumulative agonist concentration-response curves were generated in tissues and no tissue was used to generate more than two agonist concentration-response curves. Results are expressed as a mean $EC_{50}$ and the maximal response expressed as a percentage of the maximal tissue contraction response to 67 mM KCl administered initially to each tissue.

This vasoconstriction assay measures two important parameters, saphenous vein contraction ($EC_{50}$) and maximal contraction as a % maximal KCl response (% man KCl). The saphenous vein contraction ($EC_{50}$) is a measure of the dose required to contract tissue to 50% of the maximal response that the specific compound is capable of mediating. The maximal response that the saphenous vein is capable of exhibiting is measured after administration of a high concentration (67 mM) of KCl. The % maximal KCl contraction is the ratio of the maximal response that the specific compound is capable of mediating divided by the maximal response that the tissue can produce upon stimulation with KCl. For purposes of this application, a compound may be considered to not have significant vasoconstrictive activity if it produces a maximal contraction of less than or equal to 5% of the contraction produced by the 67 mM KCl positive control at compound concentrations of up to 100 μM.

Representative compounds of the present invention were tested with the above saphenous vein assay and found to not be significantly vasoconstrictive. All compound of the present invention had a % max KCl less than or equal to 10% in this assay. This contrasts greatly with prior art compounds for the treatment of migraine targeting the neural vasoconstrictive model for migraine treatment, which compounds were selected on the basis of strong vasoconstrictive activity, as for example, sumatriptan, which has an $EC_{50}$ of 0.66 mM and a $\%_{max}$ KCl of 64.20 in this assay.

Selectivity for the 5-$HT_{1F}$ Receptor

Compounds of the prevent invention are relatively selective for the 5-$HT_{1F}$ receptor, particularly in comparison to other 5-HT receptor subtypes, specifically other receptors in the 5-$HT_1$ subclass, as for example, but without limitation, the 5-$HT_{1A}$, 5-$HT_{1B}$, 5-$HT_{1D}$, and 5-$HT_{1E}$ receptor subtypes. Affinity for these other receptor subtypes can readily be determined by slight modification of the above described radioligand receptor binding assays using cells transfected with the desired receptor subtype in place of cells transfected with the 5-$HT_{1F}$ receptor subtype. The binding affinities of representative compounds of the present invention were determined by such assays and were found to be selective for the 5-$HT_{1F}$ receptor; that is the affinity of the compounds for the 5-$HT_{1F}$ receptor was on the whole, higher than for other receptor subtypes, particular for the 5-$HT_{1B}$ and 5-$HT_{1D}$ receptor subtypes.

Specificity Index

The specificity of compounds of the present invention for 5-$HT_{1F}$ mediated inhibition of neuronal protein extravasation versus vasoconstrictive activity can be expressed with a Specificity Index, which is the ratio of vasoconstriction to efficacy in inhibiting neuronal protein extravasation:

$$\text{Specificity Index} = \frac{\text{Corrected Vasoconstriction } EC_{50}(M)}{\text{Extravasation } ID_{50}(\text{mMol/kg})}$$

The Corrected Vasoconstriction takes into consideration the maximal contraction relative to KCl for each individual compound, and is defined as the vasoconstriction $EC_{50}$ value divided by the $\%_{max}$ KCl.

For example, sumatriptan has a corrected vasoconstriction $EC_{50}$ of $1.03 \times 10^{-8}$ M (0.66 mM $EC_{50} \div 64.20\%_{max}$KCl) and an extravasation inhibition $ID_{50}$ of $2.6 \times 10-8$ mMol/Kg, giving a Specificity Index of 0.40.

Thus the procedure for determining the Specificity Index of any given compound is as follows:

1. Measure the affinity of the compound for the 5-$HT_{1F}$ receptor using the radioligand binding method described above;
2. Once affinity for the 5-$HT_{1F}$ receptor is established, determine whether the compound is an agonist, partial agonist or antagonist of the 5-$HT_{1F}$ receptor by its response in the above described cAMP assay;
3. If the compound is shown to be an agonist or partial agonist with an $E_{max}$ of at least about 50%, measure efficacy of the compound in inhibition of protein extravasation and saphenous vein contraction using the above described assays; and
4. Calculate the Specificity Index as shown above.

While compounds with a Specificity Index greater than 1 are useful for the methods and uses of the present invention, larger values for the Specificity Index are preferred. A larger Specificity Index indicates greater specificity for efficacy in inhibition of neuronal protein extravasation over vasoconstriction. Thus, preferred compounds have a Specificity Index of greater than or equal to 10 (at least 10), preferably greater than or equal to 100 (at least 100). More preferred compounds have a Specificity Index of greater than or equal to 1000 (at least 1000), and yet more preferred compounds have Specificity Indexes greater than or equal to 5000 (at least 5000).

Pharmaceutical Compositions

The type of pharmaceutical composition used for the administration of the compounds employed in the methods of the present invention may be dictated by the particular compounds selected, the type of pharmacokinetic profile desired from the route of administration, and the state of the patient.

Pharmaceutical compositions amenable to oral, sublingual, nasal or injectable administration are prepared in a manner well known in the pharmaceutical art and comprise at least one active compound. See, e.g., REMINGTON'S PHARMACEUTICAL SCIENCES, (16th ed. 1980)

In general, a pharmaceutical composition of the present invention includes an active ingredient (a compound of formula I) and is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the pharmaceutical compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and bard gelatin capsules, gels, suppositories, sterile injectable solutions, and sterile packaged powders.

In preparing a pharmaceutical composition, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the pharmaceutical composition, e.g., about 40 mesh. In one embodiment of the present invention, the particle size range is between about 0.1 µm to about 100 µm.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The pharmaceutical compositions can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compounds of the invention can be formulated so as to provide quick, sustained or delayed release of the active ingredient after administration to the patient by employing procedures known in the art.

While it is possible to administer a compound employed in the methods of this invention directly without any formulation, the compounds are usually administered in the form of pharmaceutical compositions comprising a pharmaceutically acceptable excipient and at least one active ingredient. These formulations can be administered by a variety of routes including oral, buccal, rectal, intranasal, transdermal, subcutaneous, intravenous, intramuscular, and intranasal. Many of the compounds employed in the methods of this invention are effective as both injectable and oral compositions.

In order to administer transdermally, a transdermal delivery device ("patch") is needed. Such transdermal patches may be used to provide continuous or discontinuous infusion of a compound of the present invention in controlled amounts. The construction and use of transdermal patches for the delivery of pharmaceutical agents is well known in the art. See, e.g., U.S. Pat. No. 5,023,252. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, which is herein incorporated by reference. The delivery of hydrophilic drugs may be enhanced by intra-arterial infusion of hypertonic solutions which can transiently open the blood-brain barrier.

In one preferred embodiment of the present invention, there is provided a pharmaceutical composition comprising at lest one compound as described above in a pharmaceutical composition adapted for buccal and/or sublingual, or nasal administration. This embodiment provides administration of the active compound in a manner that avoids gastric complications, such as first pass metabolism by the gastric system and/or through the liver. This administration route may also reduce adsorption times, providing more rapid onset of therapeutic benefit. The compounds of the present invention may provide particularly favorable solubility profiles to facilitate sublingual/buccal pharmaceutical compositions. Such pharmaceutical compositions typically require relatively high concentrations of active ingredients to deliver sufficient amounts of active ingredients to the limited surface area of the sublingual/buccal mucosa for the relatively short durations the pharmaceutical composition is in contact with the surface area, to allow the absorption of the active ingredient. Thus, the very high activity of the compounds of the present invention facilitate their suitability for sublingual/buccal pharmaceutical compositions.

A compound of formula I is preferably formulated in a unit dosage form, each dosage containing from about 0.001 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient as described above.

The compounds of the present invention are generally effective over a wide dosage range. For examples, dosages per day normally fall within the range of about 0.0001 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

We claim:

1. A compound of formula I:

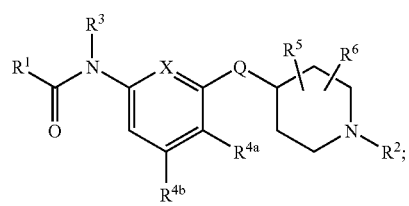

or a pharmaceutically acceptable acid addition salt thereof, where;

Q is oxygen or sulfur;

X is —C($R^{4c}$)═ or —N═;

$R^1$ is mono- di-, or tri-substituted phenyl wherein the substitutions are independently selected from halo, $C_1$-$C_2$ alkoxy, trifluoromethyl, trifluoromethoxy, and trifluoroethoxy;

$R^2$ is hydrogen or methyl;

$R^3$ hydrogen;

$R^{4a}$ and $R^{4b}$ are hydrogen

When X is —C($R^{4c}$)═, $R^{4c}$ is hydrogen $R^5$ hydrogen; and $R^6$ is hydrogen.

2. A composition comprising a compound according to claim 1 and a pharmaceutical carrier, diluent, or excipient.

3. A method for the treatment of migraine in a mammal comprising administering to a mammal in need of such treatment or prevention an effective amount of a compound of formula I:

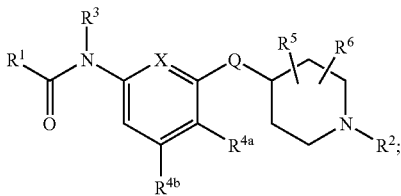

or a pharmaceutically acceptable acid addition salt thereof, where;

Q is oxygen or sulfur;
X is —C($R^{4c}$)= or —N=;
$R^1$ mono- di-, or tri-substituted phenyl wherein the substitutions are independently selected from halo, $C_1$-$C_2$ alkoxy, trifluoromethyl, trifluoromethoxy, and trifluoroethoxy;
$R^2$ is hydrogen or methyl;
$R^3$ hydrogen;
$R^{4a}$ and $R^{4b}$ are hydrogen;
When X is —C($R^{4c}$)=, $R^{4c}$ is hydrogen;
$R^5$ hydrogen; and
$R^6$ is hydrogen.

4. The method according to claim 3 wherein the mammal is a human.

5. A compound of formula I:

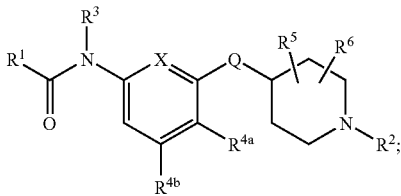

or a pharmaceutically acceptable acid addition salt thereof, where;

Q is oxygen or sulfur;
X is —C(H)= or —N=;
$R^1$ is a substituted or unsubstituted heterocycle wherein the heterocycle is selected from the group consisting of pyridinyl and thiophenyl;
$R^2$ is hydrogen or methyl;
$R^3$ is hydrogen;
$R^{4a}$ and $R^{4b}$ are hydrogen
$R^5$ hydrogen; and
$R^6$ is hydrogen.

6. A composition comprising a compound according to claim 5 and a pharmaceutical carrier, diluents, or excipient.

7. A method for the treatment of migraine in a mammal comprising administering to a mammal in need of such treatment or prevention an effective amount of a compound of formula I;

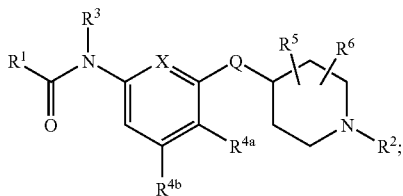

or a pharmaceutically acceptable acid addition salt thereof, where;

Q is oxygen or sulfur;
X is —C(H)= or —N=;
$R^1$ is a substituted or unsubstituted heterocycle wherein the heterocycle is selected from the group consisting of pyridinyl and thiophenyl;
$R^2$ is hydrogen or methyl;
$R^3$ hydrogen;
$R^{4a}$ and $R^{4b}$ are hydrogen
$R^5$ hydrogen; and
$R^6$ is hydrogen.

8. The method according to claim 7 wherein the mammal is human.

* * * * *

UNITED STATES PATENT AND TRADEMARK OFFICE
CERTIFICATE OF CORRECTION

| | | |
|---|---|---|
| PATENT NO. | : 7,608,629 B2 | Page 1 of 1 |
| APPLICATION NO. | : 10/552131 | |
| DATED | : October 27, 2009 | |
| INVENTOR(S) | : Blanco-Pillado et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 222 days.

Signed and Sealed this
Eleventh Day of January, 2011

David J. Kappos
*Director of the United States Patent and Trademark Office*